(12) United States Patent
Riddell et al.

(10) Patent No.: US 11,845,803 B2
(45) Date of Patent: Dec. 19, 2023

(54) COMBINATION THERAPIES FOR TREATMENT OF BCMA-RELATED CANCERS AND AUTOIMMUNE DISORDERS

(71) Applicant: Fred Hutchinson Cancer Center, Seattle, WA (US)

(72) Inventors: Stanley R. Riddell, Sammamish, WA (US); Damian Green, Seattle, WA (US); Tyler Hill, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 338 days.

(21) Appl. No.: 16/486,764

(22) PCT Filed: Feb. 16, 2018

(86) PCT No.: PCT/US2018/000050
§ 371 (c)(1),
(2) Date: Aug. 16, 2019

(87) PCT Pub. No.: WO2018/151836
PCT Pub. Date: Aug. 23, 2018

(65) Prior Publication Data
US 2019/0359727 A1 Nov. 28, 2019

Related U.S. Application Data

(60) Provisional application No. 62/582,270, filed on Nov. 6, 2017, provisional application No. 62/460,612, filed on Feb. 17, 2017.

(51) Int. Cl.
| | | |
|---|---|---|
| C07K 16/28 | (2006.01) | |
| A61P 35/00 | (2006.01) | |
| A61K 9/00 | (2006.01) | |
| A61K 31/192 | (2006.01) | |
| A61K 31/216 | (2006.01) | |
| A61K 31/417 | (2006.01) | |
| A61K 31/4245 | (2006.01) | |
| A61K 31/5513 | (2006.01) | |
| C07K 14/475 | (2006.01) | |
| C07K 14/52 | (2006.01) | |
| C07K 16/40 | (2006.01) | |
| A61K 45/06 | (2006.01) | |

(52) U.S. Cl.
CPC ........ *C07K 16/2878* (2013.01); *A61K 9/0053* (2013.01); *A61K 31/192* (2013.01); *A61K 31/216* (2013.01); *A61K 31/417* (2013.01); *A61K 31/4245* (2013.01); *A61K 31/5513* (2013.01); *A61P 35/00* (2018.01); *C07K 14/475* (2013.01); *C07K 14/52* (2013.01); *C07K 16/2887* (2013.01); *C07K 16/40* (2013.01); *A61K 45/06* (2013.01)

(58) Field of Classification Search
None
See application file for complete search history.

(56) References Cited

U.S. PATENT DOCUMENTS

| | | |
|---|---|---|
| 4,452,773 A | 6/1984 | Molday |
| 4,690,915 A | 9/1987 | Rosenberg |
| 4,795,698 A | 1/1989 | Owen et al. |
| 5,200,084 A | 4/1993 | Liberti et al. |
| 5,219,740 A | 6/1993 | Miller et al. |
| 5,283,173 A | 2/1994 | Fields et al. |
| 5,468,614 A | 11/1995 | Fields et al. |
| 6,040,177 A | 3/2000 | Riddell et al. |
| 6,207,453 B1 | 3/2001 | Maass et al. |
| 6,291,158 B1 | 9/2001 | Winter et al. |
| 6,291,161 B1 | 9/2001 | Lerner et al. |
| 6,410,319 B1 | 6/2002 | Raubitschek et al. |
| 6,423,498 B1 | 7/2002 | Markland et al. |
| 6,451,995 B1 | 9/2002 | Cheung et al. |
| 6,756,511 B2 | 6/2004 | Castro Pineiro et al. |
| 6,759,243 B2 | 7/2004 | Kranz et al. |
| 6,890,956 B2 | 5/2005 | Churcher et al. |
| 6,984,626 B2 | 1/2006 | Nadin et al. |
| 7,049,296 B2 | 5/2006 | Castro Pineiro et al. |
| 7,070,995 B2 | 7/2006 | Jensen |
| 7,101,895 B2 | 9/2006 | Churcher et al. |
| 7,138,400 B2 | 11/2006 | Collins et al. |
| 7,144,910 B2 | 12/2006 | Madin et al. |
| 7,183,303 B2 | 2/2007 | Castro Pineiro et al. |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 7,575,925 B2 | 8/2009 | Schmitt et al. |
| 7,605,236 B2 | 10/2009 | Ruben et al. |
| 7,981,632 B2 | 7/2011 | Schmidt |
| 8,119,772 B2 | 2/2012 | Yang et al. |
| 8,324,353 B2 | 12/2012 | Jensen |
| 8,361,794 B2 | 1/2013 | Jakobsen |

(Continued)

FOREIGN PATENT DOCUMENTS

| | | |
|---|---|---|
| CN | 102085372 A | 6/2011 |
| CN | 102421801 A | 4/2012 |

(Continued)

OTHER PUBLICATIONS

US 8,252,592 B2, 08/2012, Sadelain et al. (withdrawn)

(Continued)

*Primary Examiner* — Peter J Reddig
(74) *Attorney, Agent, or Firm* — Seed IP Law Group LLP

(57) ABSTRACT

The present disclosure relates to methods for using BCMA-specific binding molecules (such as a BCMA-specific chimeric antigen receptor or antibody) in combination with γ-secretase inhibitors, which can be done concurrently or sequentially, to treat or prevent a B-cell related proliferative disease, such as a cancer or autoimmune disease, or the like. A BCMA-specific binding molecule in combination with γ-secretase inhibitor can be used in, for example, adoptive immunotherapy.

33 Claims, 57 Drawing Sheets

Specification includes a Sequence Listing.

(56) References Cited

U.S. PATENT DOCUMENTS

| | | |
|---|---|---|
| 8,377,886 B2 | 2/2013 | Susztak et al. |
| 8,389,282 B2 | 3/2013 | Sadelain et al. |
| 8,399,645 B2 | 3/2013 | Campana et al. |
| 8,497,118 B2 | 7/2013 | Jensen |
| 8,569,286 B2 | 10/2013 | Hipskind et al. |
| 8,802,374 B2 | 8/2014 | Jensen |
| 8,822,647 B2 | 9/2014 | Jensen |
| 8,911,993 B2 | 12/2014 | June et al. |
| 9,034,324 B2 | 5/2015 | Kalled et al. |
| 9,765,342 B2 | 9/2017 | Kochenderfer |
| 10,126,301 B2 | 11/2018 | Berenson et al. |
| 10,555,951 B2 | 2/2020 | Benhadji et al. |
| 10,562,972 B2 | 2/2020 | Brentjens et al. |
| 10,688,104 B2 | 6/2020 | Bender et al. |
| 2002/0131960 A1 | 9/2002 | Sadelain et al. |
| 2002/0150914 A1 | 10/2002 | Andersen et al. |
| 2003/0170238 A1 | 9/2003 | Gruenberg et al. |
| 2003/0223994 A1 | 12/2003 | Hoogenboom et al. |
| 2004/0191260 A1 | 9/2004 | Reiter et al. |
| 2005/0187179 A1 | 8/2005 | Miele et al. |
| 2006/0034850 A1 | 2/2006 | Weidanz et al. |
| 2007/0065431 A1 | 3/2007 | Coia et al. |
| 2007/0092530 A1 | 4/2007 | Weidanz et al. |
| 2007/0116690 A1 | 5/2007 | Yang et al. |
| 2008/0058316 A1 | 3/2008 | Eberhart et al. |
| 2009/0169562 A1 | 7/2009 | Throsby et al. |
| 2009/0226474 A1 | 9/2009 | Weidanz et al. |
| 2009/0304679 A1 | 12/2009 | Weidanz |
| 2010/0093684 A1 | 4/2010 | Ferrando et al. |
| 2010/0222283 A1 | 9/2010 | Susztak et al. |
| 2010/0285020 A1 | 11/2010 | Aifantis et al. |
| 2011/0003380 A1 | 1/2011 | Miltenyi et al. |
| 2012/0082661 A1 | 4/2012 | Kalled et al. |
| 2012/0178669 A1 | 7/2012 | Luesch et al. |
| 2013/0029972 A1 | 1/2013 | Hipskind et al. |
| 2013/0149337 A1 | 6/2013 | Cooper et al. |
| 2013/0287748 A1 | 10/2013 | June et al. |
| 2013/0336964 A1 | 12/2013 | Rovati et al. |
| 2014/0161828 A1 | 6/2014 | Armitage et al. |
| 2014/0193433 A1 | 7/2014 | Borges et al. |
| 2014/0271635 A1 | 9/2014 | Brogdon et al. |
| 2015/0051266 A1* | 2/2015 | Kochenderfer ........ C07K 16/18 514/44 R |
| 2015/0125460 A1 | 5/2015 | Kalled et al. |
| 2016/0046724 A1* | 2/2016 | Brogdon ................ A61P 35/02 424/134.1 |
| 2017/0051035 A1 | 2/2017 | Payne et al. |
| 2018/0104254 A1 | 4/2018 | Benhadji et al. |
| 2018/0118842 A1 | 5/2018 | Brentjens et al. |
| 2018/0360880 A1 | 12/2018 | Brentjens et al. |
| 2019/0040132 A1 | 2/2019 | Balakrishnan et al. |
| 2019/0107541 A1 | 4/2019 | Berenson et al. |
| 2019/0161553 A1 | 5/2019 | Sather et al. |
| 2019/0192531 A1 | 6/2019 | Bender et al. |
| 2019/0209581 A1 | 7/2019 | Benhadji et al. |
| 2019/0231794 A1 | 8/2019 | Benhadji et al. |
| 2020/0123266 A1 | 4/2020 | Brentjens et al. |
| 2020/0276239 A1 | 9/2020 | Brentjens et al. |
| 2020/0289565 A1* | 9/2020 | Green .................... A61K 35/17 |

FOREIGN PATENT DOCUMENTS

| | | |
|---|---|---|
| CN | 103492406 A | 1/2014 |
| CN | 107827989 A | 3/2018 |
| EP | 0452342 A1 | 10/1991 |
| EP | 2537416 A1 | 12/2012 |
| JP | 2011178691 A | 9/2011 |
| JP | 2015-535002 A | 12/2015 |
| JP | 2016-538830 A | 12/2016 |
| RU | 2009138932 A | 4/2011 |
| RU | 2 624 493 C2 | 7/2017 |
| WO | WO 9208796 A1 | 5/1992 |
| WO | WO 9428143 A1 | 12/1994 |
| WO | WO 9613593 A2 | 5/1996 |
| WO | WO 9618105 A1 | 6/1996 |
| WO | WO 9828268 A2 | 7/1998 |
| WO | WO 9918129 A1 | 4/1999 |
| WO | WO 9960120 A2 | 11/1999 |
| WO | WO 0014257 A1 | 3/2000 |
| WO | 02/066516 A2 | 8/2002 |
| WO | WO 03020763 A2 | 3/2003 |
| WO | WO 03068201 A2 | 8/2003 |
| WO | WO 2004033685 A1 | 4/2004 |
| WO | WO 2006000830 A2 | 1/2006 |
| WO | WO 2006001956 A2 | 1/2006 |
| WO | WO-2006001956 A2 * | 1/2006 | ......... A61K 38/1709 |
| WO | 2006/072620 A1 | 7/2006 |
| WO | 2006/095164 A1 | 9/2006 |
| WO | WO 2006123184 A2 | 11/2006 |
| WO | WO 2007005874 A2 | 1/2007 |
| WO | 2007/062090 A2 | 5/2007 |
| WO | 2007/098934 A1 | 9/2007 |
| WO | WO 2007100895 A2 | 9/2007 |
| WO | WO 2008112249 A1 | 9/2008 |
| WO | WO 2008116149 A2 | 9/2008 |
| WO | WO 2009023453 A1 | 2/2009 |
| WO | WO 2009033765 A2 | 3/2009 |
| WO | WO 2009035522 A1 | 3/2009 |
| WO | 2009/040338 A1 | 4/2009 |
| WO | WO 2009072003 A2 | 6/2009 |
| WO | WO 2009146875 A1 | 12/2009 |
| WO | WO 2010033140 A2 | 3/2010 |
| WO | WO 2010054007 A1 | 5/2010 |
| WO | WO 2010075074 A1 | 7/2010 |
| WO | 2010/104949 A2 | 9/2010 |
| WO | WO 2011044186 A1 | 4/2011 |
| WO | WO 2011060051 A1 | 5/2011 |
| WO | WO 2011085103 A1 | 7/2011 |
| WO | 2011/108008 A2 | 9/2011 |
| WO | WO 2012066058 A1 | 5/2012 |
| WO | WO 2012079000 A1 | 6/2012 |
| WO | WO 2012097039 A1 | 7/2012 |
| WO | WO 2012129514 A1 | 9/2012 |
| WO | WO 2012143498 A1 | 10/2012 |
| WO | 2012/163805 A1 | 12/2012 |
| WO | WO 2013016081 A1 | 1/2013 |
| WO | WO 2013026837 A1 | 2/2013 |
| WO | WO 2013071154 A1 | 5/2013 |
| WO | WO 2013072406 A1 | 5/2013 |
| WO | WO 2013072415 A1 | 5/2013 |
| WO | WO 2013123061 A1 | 8/2013 |
| WO | WO 2013126726 A1 | 8/2013 |
| WO | WO 2013154760 A1 | 10/2013 |
| WO | WO 2013166321 A1 | 11/2013 |
| WO | WO 2014031687 A1 | 2/2014 |
| WO | WO 2014055668 A1 | 4/2014 |
| WO | 2014/068079 A1 | 5/2014 |
| WO | 2014/089335 A2 | 6/2014 |
| WO | WO 2014087010 A1 | 6/2014 |
| WO | 2014/122143 A1 | 8/2014 |
| WO | WO 2014124280 A1 | 8/2014 |
| WO | WO 2014134165 A1 | 9/2014 |
| WO | WO 2014191128 A1 | 12/2014 |
| WO | 2015/052538 A1 | 4/2015 |
| WO | 2015/095895 A1 | 6/2015 |
| WO | WO 2015142675 A2 | 9/2015 |
| WO | WO 2015158671 A1 | 10/2015 |
| WO | 2015/166073 A1 | 11/2015 |
| WO | WO 2015193352 A1 | 12/2015 |
| WO | 2016/014565 A2 | 1/2016 |
| WO | WO 2016014789 A2 | 1/2016 |
| WO | 2016/079177 A1 | 5/2016 |
| WO | 2016/090327 A2 | 6/2016 |
| WO | WO 2016090320 A1 | 6/2016 |
| WO | WO 2016094304 A2 | 6/2016 |
| WO | WO 2016164580 A1 | 10/2016 |
| WO | WO 2016168014 A1 | 10/2016 |
| WO | 2017/019496 A1 | 2/2017 |
| WO | WO-2017019496 A1 * | 2/2017 | ......... A61K 31/4164 |
| WO | WO 2017025038 A1 | 2/2017 |
| WO | WO 2017087547 A1 | 5/2017 |
| WO | WO 2017136607 A1 | 8/2017 |
| WO | WO 2017173256 A1 | 10/2017 |

(56) References Cited

FOREIGN PATENT DOCUMENTS

| WO | WO 2017180385 A1 | 10/2017 |
|---|---|---|
| WO | WO 2017180389 A1 | 10/2017 |
| WO | WO 2017200969 A1 | 11/2017 |
| WO | WO 2018044662 A1 | 3/2018 |
| WO | WO 2018071307 A1 | 4/2018 |
| WO | WO 2018085690 A1 | 5/2018 |
| WO | WO 2018/151836 A1 | 8/2018 |
| WO | WO 2018175988 A1 | 9/2018 |
| WO | WO 2018197675 A1 | 11/2018 |
| WO | WO 2018201056 A1 | 11/2018 |
| WO | WO 2018204427 A1 | 11/2018 |
| WO | WO 2019089969 A2 | 5/2019 |
| WO | WO 2019090003 A1 | 5/2019 |
| WO | WO 2020092848 A2 | 5/2020 |

OTHER PUBLICATIONS

Boursier et al. (J. Biol. Chem. Jan. 25, 1993 268(3): 2013-2020) (Year: 1993).*

National Center for Biotechnology Information. PubChem Compound Summary for CID 11754711, Cbz-leucinyl-leucinyl-norleucinal. https://pubchem.ncbi.nlm.nih.gov/compound/Cbz-leucinyl-leucinyl-norleucinal. Accessed Jun. 7, 2022 (Year: 2022).*

Abbas Ali et al., "T cells expressing an anti-B-cell maturation antigen chimeric antigen receptor cause remissions of multiple myeloma," *Blood* 128(13):1688-1700, Sep. 29, 2016.

Abbott, "Inhibiting γ-Secretase in Myeloma Tumor Cells to Improve Killing by Chimeric Antigen Receptor T cells," A thesis submitted in partial fulfillment of the requirements for graduation with Honors in Biology, Whitman College, May 10, 2017. (46 pages).

Alder et al., "Antibody responses of variable lymphocyte receptors in the lamprey," *Nature Immunology* 9(3):319-327, Mar. 2008.

Baral et al., "Experimental therapy of African trypanosomiasis with a nanobody-conjugated human trypanolytic factor," *Nature Medicine* 12(5):580-584, May 2006.

Barthelemy et al., "Comprehensive Analysis of the Factors Contributing to the Stability and Solubility of Autonomous Human $V_H$ Domains," *The Journal of Biological Chemistry* 283(6):3639-3654, Feb. 8, 2008.

Beavil et al., "α-Helical coiled-coil stalks in the low-affinity receptor for IgE (FcεRII/CD23) and related C-type lectins,"*Proc. Nat'l. Acad. Sci. USA* 89:753-757, Jan. 1992.

Beste et al., "Small antibody-like proteins with prescribed ligand specificities derived from the lipocalin fold," *Proc. Nat'l. Acad. Sci. USA* 96:1898-1903, Mar. 1999.

Binz et al., "Designing Repeat Proteins: Well-expressed, Soluble and Stable Proteins from Combinatorial Libraries of Consensus Ankyrin Repeat Proteins," *J. Mol. Biol.* 332:489-503, 2003.

Binz et al., "Engineering novel binding proteins from nonimmunoglobulin domains," *Nature Biotechnology* 23(10):1257-1268, Oct. 2005.

Binz et al., "High-affinity binders selected from designed ankyrin repeat protein libraries," *Nature Biotechnology* 22(5):575-582, May 2004.

Boersma et al., "DARPins and other repeat protein scaffolds: advances in engineering and applications," *Current Opinion in Biotechnology* 22:849-857, 2011.

Boyington et al., "Structure of CD94 Reveals a Novel C-Type Lectin Fold: Implications for the NK Cell-Associated CD94/NKG2 Receptors," *Immunity* 10:75-82, Jan. 1999.

Capon et al., "Designing CD4 immunoadhesins for AIDS therapy," *Nature* 337:525-531, Feb. 9, 1989.

Carpenter et al., "B-cell Maturation Antigen is a Promising Target for Adoptive T-cell Therapy of Multiple Myeloma," *Clin. Cancer Res.* 19(8):2048-2060, Apr. 15, 2013. (22 pages).

Chen et al., "Gene Expression of Gamma Secretase (GS) Complex-Related Proteins, the Enzyme That Sheds B-Cell Maturation Antigen (BCMA), Among Patients with Multiple Myeloma (MM) and Effects of the GS Inhibitor LSN424354 on Solubilized Bcma in MM and Chronic Lymphocytic Leukemia," *Blood* 128(22):5641, 2016. (7 pages).

Cortajarena et al., "Designed TPR Modules as Novel Anticancer Agents," *ACS Chemical Biology* 3(3):161-166, 2008.

Cortez-Retamozo et al., "Efficient Cancer Therapy with a Nanobody-Based Conjugate," *Cancer Research* 64:2853-2857, Apr. 15, 2004. (5 pages).

Cowan et al., "Efficacy and Safety of Fully Human Bcma CAR T Cells in Combination with a Gamma Secretase Inhibitor to Increase Bcma Surface Expression in Patients with Relapsed or Refractory Multiple Myeloma," *Blood* 134(Supplement 1):204, Nov. 13, 2019. (Abstract Only) (6 pages).

Debeb et al., "Pre-Clinical studies of Notch Signaling Inhibitor RO4929097 in Inflammatory Breast Cancer Cells," *Breast Cancer Res. Treat.* 134(2):495-510, Jul. 2012. (26 pages).

Drake et al., "Recent Developments in ADC Technology: Preclinical Studies Signal Future Clinical Trends," *BioDrugs* 37:521-531, 2017. (11 pages).

Eagar et al., "Notch 1 Signaling Regulates Peripheral T Cell Activation," *Immunity* 20:407-415, Apr. 2004.

Ebersbach et al., "Affilin-Novel Binding Molecules Based on Human γ-B-Crystallin, an All β-Sheet Protein," *J. Mol. Biol.* 372:172-185, 2007.

Engels et al., "Retroviral Vectors for High-Level Transgene Expression in T Lymphocytes," *Human Gene Therapy* 14:1155-1168, Aug. 10, 2003. (16 pages).

Figdor et al., "C-Type Lectin Receptors on Dendritic Cells and Langerhans Cells," *Nature Reviews Immunology* 2:77-84, Feb. 2002. (9 pages).

Frecha et al., "Advances in the Field of Lentivector-based Transduction of T and B Lymphocytes for Gene Therapy," *Molecular Therapy* 18(10):1748-1757, Oct. 2010.

Freeman et al., "Engagement of the PD-1 Immunoinhibitory Receptor by a Novel B7 Family Member Leads to Negative Regulation of Lymphocyte Activation," *J. Exp. Med.* 192(7):1027-1034, Oct. 2, 2000.

GenBank, "CD69 molecule [*Homo sapiens*]," Accession No. AAH07037.1, Jul. 15, 2006. (2 pages).

GenBank, "NKG2A [*Homo sapiens*]," Accession No. AAL65234.1, Jan. 17, 2002. (1 page).

GenBank, "NKG2D [*Homo sapiens*]," Accession No. CAA04925.1, Nov. 14, 2006. (2 pages).

GenBank, "B-cell differentiation antigen CD72 [*Homo sapiens*]," Accession No. NP_001773.1, Jun. 13, 2021. (3 pages).

GenBank, "low affinity immunoglobulin epsilon Fc receptor isoform a [*Homo sapiens*]," Accession No. NP_001993.2, Feb. 27, 2022. (3 pages).

Ghahroudi et al., "Selection and identification of single domain antibody fragments from camel heavy-chain antibodies," *FEBS Letter* 414:521-526, 1997.

Green et al., "CD38-bispecific antibody pretargeted radioimmunotherapy for multiple myeloma and other B-cell malignancies," *Blood* 131(6):611-620, Feb. 8, 2018.

Green et al., "Response to Bcma CAR-T Cells Correlates with Pretreatment Target Antigen Density and Is Improved By Small Molecule Inhibition of Gamma Secretase," *Blood* 134(Supplement 1):1856, Nov. 13, 2019. (Abstract Only) (6 pages).

Hackel et al., "Picomolar Affinity Fibronectin Domains Engineered Utilizing Loop Length Diversity, Recursive Mutagenesis, and Loop Shuffling," *J. Mol. Biol.* 381(5):1238-1252, Sep. 19, 2008, (27 pages).

Hamers-Casterman et al., "Naturally occurring antibodies devoid of light chains," *Nature* 363:446-448, Jun. 3, 1993.

Hedrich et al., "Antibody-Drug Conjugates: Pharmacokinetic/Pharmacodynamic Modeling, Preclinical Characterization, Clinical Studies, and Lessons Learned," *Clin. Pharmacokinet.* 57(6):687-703, Jun. 2018. (28 pages).

Herrin et al., "Structure and specificity of lamprey monoclonal antibodies," *PNAS* 105(6):2040-2045, Feb. 12, 2008.

(56) References Cited

OTHER PUBLICATIONS

Hill et al., "Gamma secretase inhibition increases recognition of multiple myeloma by BCMA-specific chimeric antigen receptor modified T-cells," *Journal for ImmunoTherapy of Cancer* 5(Suppl 2):010, 2017. (2 pages).
Hoet et al., "Generation of high-affinity human antibodies by combining donor-derived and synthetic complementarity-determining-region diversity," *Nature Biotechnology* 23(3):344-348, Mar. 2005.
Huang et al., "Scorpion-Toxin Mimics of CD4 in Complex with Human Immunodeficiency Virus gp120: Crystal Structures, Molecular Mimicry, and Neutralization Breadth," *Structure* 13:155-768, May 2005.
International Search Report and Written Opinion, dated May 14, 2018, for International Application No. PCT/US2018/000050. (19 pages).
Jespers et al., "Aggregation-resistant domain antibodies selected on phage by heat denaturation," *Nature Biotechnology* 22(9):1161-1165, Sep. 2004.
Jonnalagadda et al., "Chimeric Antigen Receptors With Mutated IgG4 Fc Spacer Avoid Fc Receptor Binding and Improve T Cell Persistence and Antitumor Efficacy," *Molecular Therapy* 23(4):757-768, April 2015.
June, "Adoptive T cell therapy for cancer in the clinic," *J. Clin. Invest.* 117(6):1466-1476, Jun. 2007. (12 pages).
Juno Therapeutics, "Juno Therapeutics Signs Licensing Agreements with Lilly, OncoTracker, and Fred Hutchinson Cancer Research Center to Advance Its BCMA-Directed Engineered T Cell Program in Multiple Myeloma with Gamma Secretase Inhibition," *Business Wire*, Dec. 6, 2017. (3 pages).
Kitchen et al., "Engineering Antigen-Specific T Cells from Genetically Modified Human Hematopoietic Stem Cells in Immunodeficient Mice," *PLoS ONE* 4(12):e8208, Dec. 2009. (9 pages).
Krisky et al., "Development of herpes simplex virus replication-defective multigene vectors for combination gene therapy applications," *Gene Therapy* 5:1517-1530, 1998. (14 pages).
Lake et al., "Construction and binding analysis of recombinant single-chain TCR derived from tumor-infiltrating lymphocytes and a cytotoxic T lymphocyte clone directed against MAGE-1," *International Immunology* 11(5):745-751, 1999.
Laurent et al., "γ-secretase directly sheds the survival receptor BCMA from plasma cells," *Nature Communications* 6:7333, Jun. 11, 2015. (12 pages).
Luo et al., "Development of genetically engineered CD4+ and CD8+ T cells expressing TCRs specific for a *M. tuberculosis* 38-kDa antigen," *J. Mol. Med.* 89:903-913, 2011.
Madhurantakam et al., "Structure-based optimization of designed Armadillo-repeat proteins," *Protein Science* 21:1015-1028, 2012.
Main et al., "Design of a Stable α-Helical Arrays from an Idealized TPR Motif," *Structure* 11:497-508, May 2003.
Martin et al., "Rational design of a CD4 mimic that inhibits HIV-1 entry and exposes cryptic neutralization epitopes," *Nature Biotechnology* 21:71-76, Jan. 2003.
Maynard et al., "High-level bacterial secretion of single-chain αβ T-cell receptors," *Journal of Immunological Methods* 306:51-67, 2005.
Meyer et al., "Click Chemistry and Radiochemistry: The First 10 Years," *Bioconjug. Chem.* 27(12):2791-2807, Dec. 21, 2016. (40 pages).
Moek et al., "Theranostics Using Antibodies and Antibody-Related Therapeutics," *The Journal of Nuclear Medicine* 58(9)(Suppl. 2):83S-90S, Sep. 2017.
Molloy et al., "Soluble T cell receptors: novel immunotherapies," *Current Opinion in Pharmacology* 5:438-443, 2005.
Morgan et al., "Cancer Regression in Patients After Transfer of Genetically Engineered Lymphocytes," *Science* 314(5796):126-129, Oct. 6, 2006. (10 pages).
Nagle et al., "The Promise of Chimeric Antigen Receptor Engineered T cells in the Treatment of Hematologic Malignancies," *Cancer J.* 22(1):27-33, 2016. (16 pages).

Nareshkumar Jain et al., "Current ADC Linker Chemistry," *Pharm. Res.* 32:3526-3540, 2015.
Nasiri et al., "Antibody-drug conjugates: Promising and efficient tools for targeted cancer therapy," *J. Cell. Physiol.* 233:6441-6457, 2018.
Nguyen et al., "Heavy-chain antibodies in *Camelidae*; a case of evolutionary innovation," *Immunogenetics* 54:39-47, 2002.
Nguyen et al., "The Specific Variable Domain of Camel Heavy-chain Antibodies is Encoded in the Germline," *J. Mol. Biol.* 275:413-418, 1998.
Nord et al., "A combinatorial library of an α-helical bacterial receptor domain," *Protein Engineering* 8(6):601-608, 1995.
Nord et al., "Binding proteins selected from combinatorial libraries of an α-helical bacterial receptor domain," *Nature Biotechnology* 15:772-777, Aug. 1997.
Nord et al., "Recombinant human factor VIII-specific affinity ligands selected from phage-displayed combinatorial libraries of protein A," *Euro. J. Biochem.* 268:4269-4277, Feb. 2001.
Parker et al., "Antibody mimics based on human fibronectin type three domain engineered for thermostability and high-affinity binding to vascular endothelial growth factor receptor two," *Protein Engineering, Design & Selection* 18(9):435-444, 2005.
Parslow et al., "Antibody-Drug Conjugates for Cancer Therapy," *Biomedicines* 4(14), 2016. (17 pages).
Pfeifer et al., "Gene Therapy: Promises and Problems," *Ann. Rev. Genomics Hum. Genet.* 2:177-211, 2001. (37 pages).
Pont et al., "γ-Secretase inhibition increases efficacy of BCMA-specific chimeric antigen receptor T cells in multiple myeloma," *Blood* 134(19):1585-1597, Nov. 7, 2019.
Richards et al., "Engineered Fibronectin Type III Domain with a RGDWXE Sequence Binds with Enhanced Affinity and Specificity to Human αvβ3 Integrin," *J. Mol. Biol.* 326:1475-1488, 2003.
Riddell et al., "The use of anti-CD3 and anti-CD28 monoclonal antibodies to clone and expand human antigen-specific T cells," *Journal of Immunological Methods* 128:189-201, 1990.
Rossi et al., "Genetic therapies against HIV," *Nature Biotechnology* 25(12):1444-1454, Dec. 2007.
Roux et al., "Structural analysis of the nurse shark (new) antigen receptor (NAR): Molecular convergence of NAR and unusual mammalian immunoglobulins," *Proc. Natl. Acad. Sci. USA* 95:11804-11809, Sep. 1998.
Ryan et al., "Antibody targeting of B-cell maturation antigen on malignant plasma cells," *Mol. Cancer Ther.* 6(11):3009-3018, Nov. 2007. (10 pages).
Sanchez et al., "Soluble B-Cell Maturation Antigen Mediates Tumor-Induced Immune Deficiency in Multiple Myeloma," *Clin. Cancer Res.* 22(13):3383-3397, Jul. 1, 2016.
Sanchez et al., "The Role of B-Cell Maturation Antigen in the Biology and Management of, and as a Potential Therapeutic Target in, Multiple Myeloma," *Targ. Oncol.* 13:39-47, 2018.
Sandberg et al., "Human T-cell lines with well-defined T-cell receptor gene rearrangements as controls for the BIOMED-2 multiplex polymerase chain reaction tubes," *Leukemia* 21:230-237, 2007.
Sato et al., "Genes encoding putative natural killer cell C-type lectin receptors in teleostean fishes," *PNAS* 100(13):7779-7784, Jun. 24, 2003.
Scatchard, "The Attractions of Proteins for Small Molecules and Ions," *Ann. N.Y. Acad. Sci.* 51:660-672, 1949.
Schmitt et al., "Induction of T cell development and establishment of T cell competence from embryonic stem cells differentiated in vitro," *Nature Immunology* 5(4):410-417, Apr. 2004.
Schmitt et al., "Induction of T Cell Development from Hematopoietic Progenitor Cells by Delta-like-1 In Vitro," *Immunity* 17:749-756, Dec. 2002.
Schmitt et al., "T Cell Receptor Gene Therapy for Cancer," *Human Gene Therapy* 20:1240-1248, Nov. 2009.
Scholten et al., "Codon modification of T cell receptors allows enhanced functional expression in transgenic human T cells," *Clinical Immunology* 119:135-145, 2006.
Schönfeld et al., "An engineered lipocalin specific for CTLA-4 reveals a combining site with structural and conformational features similar to antibodies," *PNAS* 106(20):8198-8203, May 19, 2009.

(56) References Cited

OTHER PUBLICATIONS

Shah et al., "Nicastrin Functions as a γ-Secretase-Substrate Receptor," *Cell* 122:435-447, Aug. 12, 2005.
Stumpp et al., "Designing Repeat Proteins: Modular Leucine-rich Repeat Protein Libraries Based on the Mammalian Ribonuclease Inhibitor Family," *J. Mol. Biol.* 332:471-487, 2003.
Tai et al., "Novel anti-B-cell maturation antigen antibody-drug conjugate (GSK2857916) selectively induces killing of multiple myeloma," *Blood* 123(20):3128-3138, May 15, 2014.
Takasugi et al., "The role of presenilin cofactors in the γ-secretase complex," *Nature* 422:438-441, Mar. 27, 2003.
Thachil et al., "Haematological Diseases in the Tropics," *Manson's Tropical Infectious Diseases* 65:894-932.e7, 2014. (46 pages).
Torikai et al., "A foundation for universal T-cell based immunotherapy: T cells engineered to express a CD19-specific chimeric-antigen-receptor and eliminate expression of endogenous TCR," *Blood* 119(24):5697-5705, Jun. 14, 2012.
Torikai et al., "Genetic editing of HLA expression in hematopoietic stem cells to broaden their human application," *Scientific Reports* 6:21757, 2016. (11 pages).
Torikai et al., "Toward eliminating HLA class I expression to generate universal cells from allogeneic donors," *Blood* 122(8):1341-1349, Aug. 22, 2013.
Verhoeyen et al., "Lentiviral Vector Gene Transfer into Human T Cells," *Methods in Molecular Biology, Methods and Protocols* 506:97-114, 2009.
Vincke et al., "General Strategy to Humanize a Camelid Single-domain Antibody and Identification of a Universal Humanized Nanobody Scaffold," *The Journal of Biological Chemistry* 284(5):3273-3284, Jan. 30, 2009.
Vita et al., "Scorpion toxins as natural scaffolds for protein engineering," *Proc. Natl. Acad. Sci. USA* 92:6404-6408, Jul. 1995.
Wälchli et al., "A Practical Approach to T-Cell Receptor Cloning and Expression," *PLoS ONE* 6(11):e27930, Nov. 21, 2011. (11 pages).
Walseng et al., "A TCR-based Chimeric Antigen Receptor," *Scientific Reports* 7:10713, 2017. (10 pages).
Wang et al., "A transgene-encoded cell surface polypeptide for selection, in vivo tracking, and ablation of engineered cells," *Blood* 118(5):1255-1263, Aug. 4, 2011.
Weidle et al., "The Emerging Role of New Protein Scaffold-based Agents for Treatment of Cancer," *Cancer Genomics & Proteomics* 10:155-168, 2013.
Weisel et al., "A Model for Fibrinogen: Domains and Sequence," *Science* 230(4732):1388-1390, 1985. (4 pages).
Worcester, "GSI inhibition may boost BCMA CAR T-cell therapy efficacy in myeloma," *Hematology News*, Nov. 27, 2017. (4 pages).
Worcester, "GSI may boost BCMA CAR T-cell therapy efficacy in myeloma," *Hematology and Oncology* Nov. 27, 2017. (4 pages).
Yu et al., "Targeting Strategies for Multifunctional Nanoparticles in Cancer Imaging and Therapy," *Theranostics* 2(1):3-44, 2012.
Zelensky et al., "The C-type lectin-like domain superfamily," *FEBS Journal* 272:6179-6217, 2005.
Zhang et al., "A Synthetic Antibody Fragment Targeting Nicastrin Affects Assembly and Trafficking of γ-Secretase," *The Journal of Biological Chemistry* 289(50):34851-34861, Dec. 12, 2014.
Zhang et al., "Transduction of Human T Cells with a Novel T-Cell Receptor Confers Anti-HCV Reactivity," *PLoS Pathogens* 6(7):e1001018, Jul. 2010. (13 pages).
Zhao et al., "Primary Human Lymphocytes Transduced with NY-ESO-1 Antigen-Specific TCR Genes Recognize and Kill Diverse Human Tumor Cell Lines," *The Journal of Immunology* 174:4415-4423, 2005.
"Chemotherapy of Neoplastic Diseases," in Goodmann & Gilman's Manual of Pharmacology and Therapeutics, Chapter 51, 2008. (90 pages).
"Notch Inhibitor Shows Modest Efficacy," *Cancer Discov* 7(2):OF3, Feb. 5, 2017. (Abstract Only) (5 pages).
Adams et al., "Abstract 2135: Selectivity and specificity of engineered T cells expressing KITE-585, a chimeric antigen receptor targeting B-cell maturation antigen (BCMA)," *Cancer Res* 77(13_Supplement):2135, Jul. 1, 2017. (Abstract Only) (4 pages).
Adams et al., "Abstract 4979: Development of KITE-585: A fully human BCMA CAR T-cell therapy for the treatment of multiple myeloma," *Cancer Res* 77(13_Supplement):4979, Jul. 1, 2017. (Abstract Only) (5 pages).
Al-Hujaily et al., "Development of novel immunotherapies for multiple myeloma," *Int J Mol Sci* 17:1506, 2016. (26 pages).
Ali et al., "T cells expressing an anti-B-cell maturation antigen chimeric antigen receptor cause remissions of multiple myeloma," *Blood* 128(13): 1688-1700, 2016. (13 pages).
Al-Lazikani et al., "Standard conformations for the canonical structures of immunoglobulins," *JMB* 273:927-948, 1997. (22 pages).
Alonso-Camino et al., "CARbodies: Human Antibodies Against Cell Surface Tumor Antigens Selected From Repertoires Displayed on T Cell Chimeric Antigen Receptors," *Mol Ther Nucl Acids* 2:e93, 2013. (11 pages).
Alyea et al., "Toxicity and efficacy of defined doses of CD4(+) donor lymphocytes for treatment of relapse after allogeneic bone marrow transplant," *Blood* 91(10):3671-3680, 1998. (10 pages).
Anderson, "Oncogenomics to target myeloma in the bone marrow microenvironment," *Clin Cancer Res* 17(6): 1225-1233, 2011. (9 pages).
Anderson, "Progress and paradigms in multiple myeloma" *Clin Cancer Res* 22(22); 5419-27, 2016. (9 pages).
Andersson et al., "Therapeutic modulation of Notch signalling—are we there yet?," *Nat Rev Drug Discov* 13:357-378, 2014. (22 pages).
Attal et al., "A Prospective, Randomized Trial of Autologous Bone Marrow Transplantation and Chemotherapy in Multiple Myeloma," *The New England Journal of Medicine* 335(2):91-97, Jul. 11, 1996. (7 pages).
Avery et al., "BAFF selectively enhances the survival of plasmablasts generated from human memory B cells," *The Journal of Clinical Investigation* 112(2):286-297, Jul. 2003. (12 pages).
Aviva Systems Biology, "Product Data sheet: ARP63925 P050—RORI Antibody—C-terminal region (ARP63925_P050)," Retrieved from the internet: URL:http://www.avivasysbio.com/sd/tds/html_datasheet.php?sku=ARP63925_P050, Retrieved on on Oct. 7, 2022. (2 pages).
Barlogie et al., "Standard Chemotherapy Compared With High-Dose Chemoradiotherapy for Multiple Myeloma: Final Results of Phase III US Intergroup Trial S9321," *Journal of Clinical Oncology* 24(6):929-936, Feb. 20, 2006. (8 pages).
Barrett et al., "Chimeric Antigen Receptor Therapy for Cancer," *Annu Rev Med.* 65:333-347, 2014. (NIH Public Access, Author Manuscript, available in PMC Aug. 4, 2014) (18 pages).
Bender et al., "Abstract 1131: Novel inhibitor of Notch signaling for the treatment of cancer," *Cancer Res* 73:1131, Apr. 15, 2013. (Abstract Only) (4 pages).
Berdeja et al., "First-in-human multicenter study of bb2121 anti-BCMA CAR T-cell therapy for relapsed/refractory multiple myeloma: updated results," *Journal of Clinical Oncology* 35(15_suppl):3010, May 20, 2017. (Abstract Only) (4 pages).
Best et al., "The Novel y Secretase TnhibitorN-[cis-4-[(4-Chlorophenyl)sulfonyl]-4-(2,5-difluorophenyl)cyclohexyl]-1, 1, 1-trifluoromethanesulfonamide (MRK-560) Reduces Amyloid Plaque Deposition without Evidence of Notch-Related Pathology in the Tg2576 Mouse," *The Journal of Pharmacology and Experimental Therapeutics* 320(2): 552-558, 2007. (7 pages).
Bihel et al., "Discovery of a Subnanomolar Helical D-Tridecapeptide Inhibitor of y-Secretase." *J. Med. Chem.* 47:3931-3933, 2004. (3 pages).
Blade et al., "Hematopoietic stem cell transplantation for multiple myeloma beyond 2010," *Blood* 115(18):3655-3663, 2010. (9 pages).
Bluebird Bio, "EORTC-NCI-AACR Molecular Targets and Cancer Therapies Symposium," Presentation, Dec. 1, 2016. (23 pages).
Bluebirdbio, "Corporate Overview," Oct. 2017. (81 pages).
Boris-Lawrie et al., "Recent advances in retrovirus vector technology," *Cur. Opin. Genet. Develop.* 3:102-109, 1993. (8 pages).
Brentjens et al., "CD19-targeted T cells rapidly induce molecular remissions in adults with chemotherapy-refractory acute lymphoblastic leukemia," *Sci Transl Med.* 5(177), 2013. (NIH Public Access, Author Manuscript, available in PMC Sep. 20, 2013) (19 pages).

(56) References Cited

OTHER PUBLICATIONS

Brentjens et al., "CD19-targeted T cells rapidly induce molecular remissions in adults with chemotherapy-refractory acute lymphoblastic leukemia," *Sci. Transl. Med.* 5(177):177ra38, Mar. 20, 2013. (NIH Public Access, Author Manuscript, available in PMC Sep. 20, 2013) (19 pages).

Brentjens et al., "Safety and persistence of adoptively transferred autologous CD19-targeted T cells in patients with relapsed or chemotherapy refractory B-cell leukemias," *Blood* 118(18):4817-4828, 2011. (12 pages).

Brown et al., "Tolerance of single, but not multiple, amino acid replacements in antibody VH CDR2: a means of minimizing B cells wastage from somatic hypermutation?" *J. Immunol.* 156(9):3285-3291, 1996. (8 pages).

Brudno et al. "T cells Genetically Modified to Express an Anti-B-Cell Maturation Antigen Chimeric Antigen Receptor Cause Remissions of Poor-Prognosis Relapsed Multiple Myeloma," *Journal of Clinical Oncology* 36(22):2261-2280, Aug. 1, 2018. (16 pages).

Burns et al., "Vesicular stomatitis virus G glycoprotein pseudotyped retroviral vectors: concentration to very high titer and efficient gene transfer into mammalian and nonmammalian cells," *Proc. Natl. Acad. Sci. USA* 90:8033-8037, 1993. (5 pages).

Carlens et al., "Ex vivo T lymphocyte expansion for retroviral transduction: influence of serum-free media on variations in cell expansion rates and lymphocyte subset distribution," *Exp Hematol* 28(10): 1137-46, 2000. (10 pages).

Caron et al., "Engineered Humanized Dimeric Forms of IgG are More Effective Antibodies," *J Exp. Med* 176: 1191-1195, 1992. (5 pages).

Carpenter et al., "B-cell maturation antigen is a promising target for adoptive T-cell therapy of multiple myeloma," *Clin Cancer Res* 19(8):2048-2060, 2013. (14 pages).

Carrillo et al., "The Multiple Sequence Alignment Problem in Biology," *SIAM Journal on Applied Mathematics* 48(5):1073-1082, Oct. 1988. (11 pages).

Casset et al., "A peptide mimetic of an anti-CD4 monoclonal antibody by rational design." *BBRC* 307:198-205, 2003. (8 pages).

Cavalieri et al., "Human T lymphocytes transduced by lentiviral vectors in the absence of TCR activation maintain an intact immune competence," *Blood* 102(2):497-505, 2003. (9 pages).

Challita et al., "Multiple modifications in cis elements of the long terminal repeat of retroviral vectors lead to increased expression and decreased DNA methylation in embryonic carcinoma cells," *J Virol.* 69(2):748-55, 1995. (8 pages).

Cheadle et al., "Chimeric antigen receptors for T-cell based therapy," *Methods Mol Biol.* 907:645-66, 2012. (22 pages).

Cheever et al., "The Prioritization of Cancer Antigens: A National Cancer Institute Pilot Project for the Acceleration of Translational Research." *Clin Cancer Res* 15(17):5323-5331, 2009. (HHS Public Access, Author Manuscript, available in PMC Jan. 23, 2018) (31 pages).

Chekmasova et al., "A Novel and Highly Potent CAR T Cell Drug Product for Treatment of BCMA-Expressing Hematological Malignances," *Blood* 126(23):3094, Dec. 3, 2015. (Abstract Only) (2 pages).

Chen et al., "Gamma-secretase inhibitor enhances that cytotoxic effect of bortezomib in multiple myeloma," *Cell Oncol. (DORDR)* 34(6):545-551, Dec. 2011. (NIH Public Access, Author Manuscript, available in PMC Dec. 1, 2012) (12 pages).

Chen et al., "Gamma-secretase inhibitor enhances that cytotoxic effect of bortezomib in multiple myeloma," *Cell Oncol.* 34:545-551, 2011. (7 pages).

Chen et al., "Selection and Analysis of an Optimized Anti-VEGF Antibody: Crystal Structure of an Affinity-matured Fab in Complex with Antigen," *J. Mol. Bio.* 293:865-881, 1999. (17 pages).

Chen et al., "Serum B-cell maturation antigen (BCMA) reduces binding of anti-BCMA antibody to multiple myeloma cells." *Leukemia Research* 81:62-66, Jun. 2019. (5 pages).

Chervin et al., "Engineering higher affinity T cell receptors using a T cell display system," *J Immunol Methods* 339(2):175-184, Dec. 31, 2008. (NIH Public Access, Author Manuscript, available in PMC Dec. 31, 2009) (21 pages).

Chicaybam et al., "An efficient low cost method for gene transfer to T lymphocytes," *PLoS ONE* 8(3):e60298, 2013. (11 pages).

Child et al., "High-Dose Chemotherapy with Hematopoietic Stem-Cell Rescue for Multiple Myeloma," *The New England Journal of Medicine* 348(19):1875-1883, May 8, 2003. (9 pages).

Chim et al., "Management of relapsed and refractory multiple myeloma: novel agents, antibodies, immunotherapies and beyond," *Leukemia* 32:252-262, 2018. (11 pages).

Cho et al., "Human mammalian cell sorting using a highly integrated micro-fabricated fluorescence-activated cell sorter (μFACS)," *Lab Chip* 10(12):1567-1573, Jun. 21, 2010. (NIH Public Access, Author Manuscript, available in PMC Jun. 19, 2011) (17 pages).

Chothia et al., "The outline structure of the T-cell $\alpha\beta$ receptor," *EMBO J.* 7:3745-3755, 1988. (11 pages).

Chung, "Role of Immunotherapy in Targeting the Bone Marrow Microenvironment in Multiple Myeloma: An Evolving Therapeutic Strategy," *Pharmacotherapy* 37(1):129-143, 2017. (15 pages).

Clackson et al., "Making antibody fragments using phage display libraries," *Nature* 352:624-628, 1991. (5 pages).

Claudio et al., "A molecular compendium of genes expressed in multiple myeloma," *Blood* 100(6):2175-2186, 2002. (12 pages).

Clinical Trial Identifier NCT02079636, "A Study of Abemaciclib (LY2835219) in Combination With Another Anti-cancer Drug in Participants With Lung Cancer (NSCLC)," Retrieved from https://clinicaltrials.gov/archive/NCT02079636/2016_02_03, Retrieved on Oct. 7, 2022. (13 pages).

Clinical Trial Identifier NCT02215967, "Study of T Cells Targeting B-Cell Maturation Antigen for Previously Treated Multiple Myeloma," Retrieved on https://clinicaltrials.gov/ct2/show/NCT02215967, Retrieved on Oct. 7, 2022. (12 pages).

Clinical Trial Identifier NCT02546167, "CART-BCMA Cells for Multiple Myeloma," Retrieved on https://clinicaltrials.gov/ct2/show/NCT02546167, Retrieved on Oct. 7, 2022. (8 pages).

Clinical Trial Identifier NCT02658929, "Study of bb2121 in Multiple Myeloma," Retrieved on https://clinicaltrials.gov/ct2/show/NCT02658929, Retrieved on Oct. 7, 2022. (8 pages).

Clinical Trial Identifier NCT02784795. "A Study of LY3039478 in Participants with Advanced or Metastatic Solid Tumors," Retrieved from https://clinicaltrials.gov/archive/NCT02784795/2016_05_26, Retrieved on Oct. 7, 2022. (9 pages).

Clinical Trial Identifier NCT03070327, "BCMA Targeted CART Cells With or Without Lenalidomide for the Treatment of Multiple Myeloma," Retrieved on https://clinicaltrials.gov/ct2/show/NCT03070327, Retrieved on Oct. 6, 2022. (9 pages).

Clinical Trial Identifier NCT03430011, "Study Evaluating the Safety and Efficacy of JCARH125 in Subjects With Relapsed and/or Refractory Multiple Myeloma (EVOLVE)," Retrieved on https://clinicaltrials.gov/ct2/show/NCT03430011, Retrieved on Oct. 7, 2022. (10 pages).

Clinical Trial Identifier NCT03436771, "Long-term Follow-up Study for Patients Previously Treated With a Juno CAR T-Cell Product," Retrieved on https://clinicaltrials.gov/ct2/show/NCT03436771, Retrieved on Oct. 7, 2022. (6 pages).

Clinical Trial Identifier NCT03502577, "BCMA-Specific CART-Cells Combined With a Gamma Secretase Inhibitor (JSMD194) to Treat Relapsed or Persistent Multiple Myeloma," Retrieved on https://clinicaltrials.gov/ct2/show/NCT03502577, Retrieved on Oct. 7, 2022. (11 pages).

Clinical Trial Identifier NCT04855136, "Safety and Efficacy of bb2121 (Ide-cel) Combinations in Multiple Myeloma (KarMMa-7)," Retrieved on https://clinicaltrials.gov/ct2/show/study/NCT04855136, Retrieved on Oct. 7, 2022. (12 pages).

Cohen et al., "B cell maturation antigen-specific CAR T cells are clinically active in multiple myeloma," *The Journal of Clinical Investigation* 129(6):2210-2221, Jun. 2019. (12 pages).

Cohen et al., "B-cell Maturation Antigen (BMCA)-specific chimeric antigen receptor T cells (CART-BCMA) for multiple myeloma (MM): initial safety and efficacy from a phase I study," *Blood* 128:1147, 2016. (4 pages).

(56) References Cited

OTHER PUBLICATIONS

Cohen et al., "CAR-T Cell Therapy for Myeloma: State of the Art and Perspective on a Possible Cure," Lymphoma and Myeloma 2018. Presentation. Presented on Oct. 18, 2018. (23 pages).
Cohen et al., "Recognition of Fresh Human Tumor by Human Peripheral Blood Lymphocytes Transduced with a Bicistronic Retroviral Vector Encoding a Murine Anti-p5 3 TCR," *J. Immunol.* 175(9):5799-5808, Nov. 1, 2005. (11 pages).
Cohen et al., "Recombinant antibodies with MHC-restricted, peptide-specific, T-cell receptor-like specificity: new tools to study antigen presentation and TCR-peptide-MHC interactions," *J Mol. Recogn.* 16:324-332, 2003. (9 pages).
Cohen et al., "Safety and efficacy of B-Cell maturation antigen (BCMA)-specific chimeric antigen receptor T cells (CART-BCMA) with Cyclosphamide conditioning for refractory multiple myeloma (MM)," *Blood* 130(supplement 1):505, 2017. (Abstract Only) (3 pages).
Cooper et al., "T-cell clones can be rendered specific for CD19: toward the selective augmentation of the graft-versus-B-lineage leukemia effect," *Blood* 101:1637-1644, 2003. (8 pages).
Coquery et al., "Regulatory roles of the tumor necrosis factor receptor BCMA," *Crit Rev Immunol* 32(4):287-305, 2012. (NIH Public Access, Author Manuscript, available in PMC Jan. 18, 2013) (19 pages).
Cornell et al., "Evolving paradigms in the treatment of relapsed/refractory multiple myeloma: increased options and increased complexity," *Bone Marrow Transplant* 51(4):479-491, 2016. (13 pages).
Cowan et al., "Gamma secretase inhibitor improves responses to BCMA CAR T cells in myeloma," Jan. 14, 2020. (32 pages).
Cullion et al., "Targeting the Notchl and mTOR pathways in a mouse T-ALL model," *Blood* 113:6172-6181, 2009. (10 pages).
Daneshmanesh et al., "Rorl, a cell surface receptor tyrosine kinase is expressed in chronic lymphocytic leukemia and may serve as a putative target for therapy," *International Journal of Cancer* 123:1190-1195, 2008. (6 pages).
Davies, et al., "Novel Crystallization-Induced Diastereomeric Transformation Based on a Reversible Carbon-Sulfur Bond Formation. Application to the Synthesis of a γ-Secretase Inhibitor," *J. Org. Chem.* 72:4864-4871, 2007. (8 pages).
Davila et al., "CD19 CAR-targeted T cells induce long-term remission and B Cell Aplasia in an immunocompetent mouse model of B cell acute lymphoblastic leukemia," *PLoS ONE* 8(4):e61338, 2013. (14 pages).
Davila et al., "How do CARs work?: Early insights from recent clinical studies targeting CD19," *Oncoimmunology* 1(9):1577-1583, 2012. (7 pages).
De Felipe et al., "Skipping the co-expression problem: the new 2A "Chysel" technology," *Genetics Vaccines and Therapy* 2:13, 2004. (6 pages).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084, 2002. (10 pages).
Dimopoulos et al., "Current treatment landscape for relapsed and/or refractory multiple myeloma," *Nat Rev Clin Oncol* 12:42-54, 2015. (13 pages).
Dondelinger et al., "Understanding the Significance and Implications of Antibody Numbering and Antigen-Binding Surface/Residue Definition," *Fronts. Immunol.* 9:1-15, 2018. (15 pages).
Dudley et al., "Cancer regression and autoimmunity in patients after clonal repopulation with antitumor lymphocytes," *Science* 298(5594):850-854, Oct. 25, 2002. (NIH Public Access, Author Manuscript, available in PMC Jan. 5, 2007) (10 pages).
El-Gendy et al., "Membrane permeability related physicochemical properties of a novel γ-secretase inhibitor," *International Journal of Pharmaceutics* 280:41-55, 2004. (9 pages).
EP Application No. 16831120.7, Extended European Search Report dated Jun. 4, 2019, 26 pages.

EP Application No. 16831120.7, Partial Supplementary Search Report dated Mar. 1, 2019, 30 pages.
EP Application No. 19218389.5, Extended European Search Report dated May 7, 2020, 16 pages.
Fan et al., "Durable remissions with BCMA specific chimeric antigen receptor (CAR)-modified T cells in patients with refractory/relapsed multiple myeloma," *Journal of Clinical Oncology* 35(18_suppl), Jun. 13, 2017. (Abstract Only) (4 pages).
Fedorov et al., "PD-1- and CTLA-4-based inhibitory chimeric antigen receptors (iCARs) divert off-target immunotherapy responses," *Sci. Transl. Medicine* 5(215):215ra172, Dec. 11, 2013. (NIH Public Access, Author Manuscript, available in PMC Nov. 20, 2014) (25 pages).
Fonseca et al., "International Myeloma Working Group molecular classification of multiple myeloma: spotlight review," *Leukemia* 23(12):2210-2221, Dec. 2009. (NIH Public Access, Author Manuscript, available in PMC Oct. 26, 2010) (27 pages).
Food and Drug Administration, "Guidance for Industry: Considerations for the Design of Early-Phase Clinical Trials of Cellular and Gene Therapy Products," Dated Jun. 2015. (27 pages).
Frigyesi et al., "Robust isolation of malignant plasma cells in multiple myeloma," *Blood* 723(9):1336-1340, Feb. 27, 2014. (5 pages).
Fry et al., "CD22-CAR T Cells Induce Remissions in CD19-CAR Naive and Resistant B-ALL," *Nat. Med.* 24(1):20-28, Jan. 2018. (HHS Public Access, Author Manuscript, available in PMC May 20, 2018) (28 pages).
Gadducci et al., "Pharmacological treatment for uterine leiomyosarcomas," *Expert Opin Pharmacother* 16(3):335-346, 2015. (13 pages).
Gantke et al., "AFM26 is a novel and highly potent BCMA CD16A directed bispecific antibody for high affinity NK-cell engagement in multiple myeloma," ASCO 2017. Abstract 8045. Presented Jun. 5, 2017. (21 pages).
Garfall et al., "Immunotherapy with chimeric antigen receptors for multiple myeloma," *Discov Med* 17(91):37-46, 2014. (9 pages).
Gerecke et al., "The Diagnosis and Treatment of Multiple Myeloma," *Dtsch Arztebl Int* 113(27-28):470-476, 2016. (8 pages).
Gershoni et al., "Epitope mapping—The first step in developing epitope-based vaccines," *Biodrugs* 21(3):145-156, 2007. (12 pages).
Geyer et al., "Review: Current clinical applications of chimeric antigen receptor (CAR) modified T cells," *Cytotherapy* 18(11):1393-1409, Nov. 2016. (HHS Public Access, Author Manuscript, available in PMC Nov. 1, 2017) (25 pages).
Ghermezi et al., "Serum B-cell maturation antigen: a novel biomarker to predict outcomes for multiple myeloma patients," *Haematologica* 102(4):785-795, 2017. (11 pages).
Giavridis et al., "Car T cell-induced cytokine release syndrome is mediated by macrophages and abated by IL-1 blockade," *Nat. Med.* 24(6):731-738, Jun. 2018. (HHS Public Access, Author Manuscript, available in PMC Mar. 11, 2019) (19 pages).
Gieseler et al., "Cellular resistance mechanisms with impact on the therapy of multiple myeloma," *Leukemia* 12(7):1009-1012, 1998. (4 pages).
Godin et al., "Microfluidics and photonics for Bio-System-on-a-Chip: a review of advancements in technology towards a microfluidic flow cytometry chip," *J Biophoton.* 1(5):355-376, Oct. 2008. (NIH Public Access, Author Manuscript, available in PMC Sep. 17, 2009) (43 pages).
Gogishvili et al., "SLAMF7-CAR T cells eliminate myeloma and confer selective fratricide of SLAMF7+ normal lymphocytes," *Blood* 130(26):2838-2847, Dec. 28, 2017. (10 pages).
Golde et al., "γ-Gamma-Secretase Inhibitors and Modulators," *Biochim. Biophys. Acta.* 1828(12):2898-2907, Dec. 2013. (NIH Public Access, Author Manuscript, available in PMC Dec. 1, 2014) (27 pages).
Grabher et al., "Notch 1 activation in the molecular pathogenesis of T-cell acute lymphoblastic leukaemia," *Nature Reviews Cancer* 6:347-359, 2006. (13 pages).
Granell et al., "Prognostic impact of circulating plasma cells in patients with multiple myeloma: implications for plasma cell leukemia definition," *Haematologica* 102(6):1099-1104, 2017. (6 pages).

(56) References Cited

OTHER PUBLICATIONS

Green et al., "Fully Human BCMA Targeted Chimeric Antigen Receptor T Cells Administered in a Defined Composition Demonstrate Clinical Potency at Low Doses in Advanced Stage High Risk Multiple Myeloma," *Blood* 132(Supplement 1):1011, Nov. 29, 2018. (Abstract Only) (4 pages).
Grupp et al., "Chimeric Antigen Receptor-Modified T Cells for Acute Lymphoid Leukemia," *N. Engl. J. Med.* 368(16):1509-1518, Apr. 18, 2013. (NIH Public Access, Author Manuscript, available in PMC Jun. 16, 2014) (16 pages).
Gu et al., "Notch signaling: its roles and therapeutic potential in hematological malignancies," *Oncotarget* 7(20):29804-29823, May 17, 2016. (20 pages).
Han et al.,"Chimeric antigen receptor-engineered T cells for cancer immunotherapy: progress and challenges," *Journal of Hematology & Oncology* 6:47, 2013. (7 pages).
Harousseau et al., "Autologous Stem Cell Transplantation After First Remission Induction Treatment in Multiple Myeloma: A Report of the French Registry on Autologous Transplantation in Multiple Myeloma," *Blood* 85(11):3077-3085, Jun. 1, 1995. (9 pages).
Harrington et al., "Development of JCARH125: Optimization of a Fully Human Anti-Bcma CAR for Use in the Treatment of Multiple Myeloma," *Blood* 130(Suppl_1):1813, Dec. 7, 2017. (Abstract Only) (3 pages).
Hermans et al., "The VITAL assay: a versatile fluorometric technique for assessing CTL- and NKT-mediated cytotoxicity against multiple targets in vitro and in vivo," *J. Immunological Methods* 285(1):25-40, 2004. (16 pages).
Hettle et al., "The assessment and appraisal of regenerative medicine and cell therapy products: an exploration of methods for review, economic evaluation and appraisal," *Health Technology Assessment* 21(7):1-204, Feb. 1, 2017. (238 pages).
Hipp et al., "A novel BCMA/CD3 bispecific T-cell engager for the treatment of multiple myeloma induces selective lysis in vitro and in vivo," *Leukemia* 31(8):1743-1751, Aug. 2017. (9 pages).
Holler et al., "In vitro evolution of a T cell receptor with high affinity for peptide/MHC," *PNAS* 97(10):5387-5392, 2000. (6 pages).
Holler et al., "TCRs with high affinity for foreign pMHC show self-reactivity," *Nat Immunol* 4(1):55-62, 2003. (8 pages).
Holliger et al., "Specific killing of lymphoma cells by cytotoxic T-cells mediated by a bispecific diabody," *Protein Engineering* 9(3):299-305, 1996. (7 pages).
Holthof et al., "Challenges for Immunotherapy in Multiple Myeloma: Bone Marrow Microenvironment-Mediated Immune Suppression and Immune Resistance," *Cancers* 12(4):988, Apr. 17, 2020. (15 pages).
Honegger et al., "Yet another numbering scheme for immunoglobulin variable domains: an automatic modeling and analysis tool," *J Mol Biol* 309(3):657-70, 2001. (14 pages).
Hu et al., "Antiproliferative Effects of γ-Secretase Inhibitor, a Notch Signalling Inhibitor, in Multiple Myeloma Cells and Its Molecular Mechanism of Action," *J Int Med Res.* 41(4):1017-1026, 2013. (10 pages).
Huang et al., "DNA transposons for modification of human primary T lymphocytes," *Methods Mol Biol* 506:115-126, 2009. (12 pages).
Hudecek et al., "Receptor affinity and extracellular domain modifications affect tumor recognition by ROR1-specific chimeric antigen receptor T cells," *Clin. Cancer Res.* 19(12):3153-3164, Jun. 15, 2013. (NIH Public Access, Author Manuscript, available in PMC Oct. 21, 2013) (22 pages).
Hudecek et al., "The non-signaling extracellular spacer domain of chimeric antigen receptors is decisive for in vivo antitumor activity," *Cancer Immunol. Res.* 3(2):125-135, Feb. 2015. (HHS Public Access, Author Manuscript, available in PMC Feb. 1, 2016) (20 pages).
International Preliminary Report on Patentability for International Application No. PCT/US2016/043536, dated Jan. 30, 2018, 5 pages.
International Search Report and Written Opinion for International Application No. PCT/US2016/043536, dated Oct. 7, 2016, 7 pages.

Janeway et al., "Structure of the Antibody Molecule and Immunoglobulin Genes," Immunology 3rd Edition p,3:1-3:11, 1997. (14 pages).
Jelinek et al., "Human B Lymphocyte Malignancies: Exploitation of BLyS and APRIL and Their Receptors," *Curr. Dir. Autoimmun.* 8:266-288, 2005. (23 pages).
Jensen et al., "Anti-transgene Rejection Responses Contribute to Attenuated Persistence of Adoptively Transferred CD20/CD19-specific Chimeric Antigen Receptor Redirected T Cells in Humans," *Biol Blood Marrow Transplant* 16(9):1245-1256, Sep. 2010. (NIH Public Access, Author Manuscript, available in PMC Jun. 26, 2012) (19 pages).
Jensen et al., "Design and implementation of adoptive therapy with chimeric antigen receptor-modified T cells," *Immunological Reviews* 257(1):127-144, Jan. 2014. (NIH Public Access, Author Manuscript, available in PMC Jan. 1, 2015) (32 pages).
Jiang et al., "T-cell exhaustion in the tumor microenvironment," *Cell Death & Disease* 6:e1792, 2015. (9 pages).
Johnston et al., "Biolistic transformation: microbes to mice," *Nature* 346:776-777, 1990. (2 pages).
Jores et al., "Resolution of hypervariable regions in T-cell receptor β chains by a modified Wu-Kabat index of amino acid diversity," *PNAS* 87(23):9138-9142, 1990. (5 pages).
Jundt et al., "Activated Notch 1 signaling promotes tumor cell proliferation and survival in Hodgkin and anaplastic large cell lymphoma," *Blood* 99:3398-3403, 2002. (6 pages).
Juno Corporate Presentation, Aug. 31, 2017, Retrieved on http://ir.junotherapeutics.com. (2 pages).
Juno Corporate Presentation, Jan. 22, 2018, Retrieved on http://ir.junotherapeutics.com. (23 pages).
Kalos et al., "T Cells with Chimeric Antigen Receptors Have Potent Antitumor Effects and Can Establish Memory in Patients with Advanced Leukemia," *Sci. Transl. Med.* 3(95):95ra73, Aug. 10, 2011. (NIH Public Access, Author Manuscript, available in PMC Aug. 10, 2012) (21 pages).
Kandoth et al., "Mutational landscape and significance across 12 major cancer types," *Nature* 502(747 1):333-339, 2013. (20 pages).
Kapustin et al., "Cryptic splice sites and split genes," *Nucleic Acids Res.* 39(14):5837-5844, 2011. (8 pages).
Kipriyanov et al., "Bispecific tandem diabody for tumor therapy with improved antigen binding and pharmacokinetics," *J Mol Biol* 293(1):41-56, 1999. (16 pages).
Klebanoff et al., "Sorting through subsets: which T-cell populations mediate highly effective adoptive immunotherapy?," *J Immunother.* 35(9):651-660, Nov. 2012. (NIH Public Access, Author Manuscript, available in PMC Nov. 1, 2013) (18 pages).
Kochenderfer et al., "Adoptive transfer of syngeneic T cells transduced with a chimeric antigen receptor that recognizes murine CD19 can eradicate lymphoma and normal B cells", *Blood* 116(19):3875-3886, 2010. (12 pages).
Kochenderfer et al., "B-cell depletion and remissions of malignancy along with cytokine-associated toxicity in a clinical trial of anti-CD19 chimeric-antigen-receptor-transduced T cells," *Blood* 119(12):2709-2720, Mar. 22, 2012. (12 pages).
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," *Journal of Clinical Oncology* 33(6):540-549, Feb. 20, 2015. (11 pages).
Kochenderfer et al., "Construction and preclinical evaluation of an anti-CD19 chimeric antigen receptor," *J. Immunotherapy* 32(7):689-702, Sep. 2009. (NIH Public Access, Author Manuscript, available in PMC Sep. 1, 2010) (26 pages).
Kochenderfer et al., "Treating B-cell cancer with T cells expressing anti-CD19 chimeric antigen receptors," *Nature Reviews Clinical Oncology* 10(5):267-276, May 2013. (HHS Public Access, Author Manuscript, available in PMC Jan. 7, 2019) (24 pages).
Kogoshi et al., "γ-Secretase inhibitors suppress the growth of leukemia and lymphoma cells." Oncol Rep. 18(1):77-80, Jul. 2007. (4 pages).
Koste et al., "T-cell receptor transfer into human T cells with ecotropic retroviral vectors," *Gene Therapy* 21:533-538, 2014. (6 pages).

(56) References Cited

OTHER PUBLICATIONS

Kotb, "Bacterial pyrogenic exotoxins as superantigens," *Clinical Microbiology Reviews* 8(3):411-426, 1995. (16 pages).

Krämer et al., "Lenalidomide enhances myeloma-specific T-cell responses in vivo and in vitro," *Oncoimmunology* 5(5):e1139662, 2016. (9 pages).

Kumar et al., "Immunophenotyping in multiple myeloma and related plasma cell disorders," *Best Pract Res Clin Haematol.* 23(3):433-451, Sep. 2010. (NIH Public Access, Author Manuscript, available in PMC Sep. 1, 2011) (23 pages).

Kumar et al., "Risk of Progression and Survival in Multiple Myeloma Relapsing After Therapy with IMiDs and Bortezomib: A Multicenter International Myeloma Working Group Study," *Leukemia.* 26(1):149-157, Jan. 2012. (NIH Public Access, Author Manuscript, available in PMC Jul. 24, 2014) (30 pages).

Kurucz et al., "A bacterially expressed single-chain Fv construct from the 2B4 T-cell receptor," *PNAS* 90(9):3830-3834, 1993. (5 pages).

Laabi et al., "The BCMA gene, preferentially expressed during B lymphoid maturation, is bidirectionally transcribed," *Nucleic Acids Research* 22(7):1147-1154, 1994. (8 pages).

Lamers et al., "Immune Responses to Transgene and Retroviral Vector in Patients Treated With Ex Vivo-Engineered T Cells," *Blood* 117(1):72-82, 2011. (11 pages).

Lamminmäki et al., "Crystal Structure of a Recombinant Anti-estradiol Fab Fragment in Complex with 17β-Estradiol," *JBC* 276(39):36687-36694, 2001. (8 pages).

Laras et al., "Substituted thiazolamide coupled to a redox delivery system: a new γ-secretase inhibitor with enhanced pharmacokinetic profile," *Org. Biomol. Chem.* 3:612-618, 2005. (7 pages).

Laurent, "γ-secretase directly sheds the survival receptor BCMA from plasma cells," Dissertation der Graduate School of Systemic Neurosciences der Ludwig-Maximilians-Universitat Munchen, 2015, XP055688798, Jun. 1, 2015 (Jun. 1, 2015). (113 pages) Retrieved from the Internet: URL:https://d-nb.info/1078852014/34 [retrieved on Oct. 21, 2022].

Lee et al., "An APRIL-based chimeric antigen receptor for dual targeting of BCMA and TACI in multiple mveloma," *Blood* 131(7):746-758, Feb. 15, 2018. (14 pages).

Lee et al., "Evaluation of B cell maturation antigen as a target for antibody drug conjugate mediated cytotoxicity in multiple myeloma." *BJH* 174:911-922, 2016. (12 pages).

Lee et al., "T cells expressing CD19 chimeric antigen receptors for acute lymphoblastic leukaemia in children and yound adults: a phase 1 dose escalation trial," *The Lancet* 385:517-528, 2015. (12 pages).

Lefranc et al., "IMGT unique numbering for immunoglobulin and T cell receptor variable domains and Ig superfamily V-like domains," *Dev Comp Immunol* 27:55-77, 2003. (23 pages).

Leukemia & Lymphoma Society, "Peripheral T-Cell Lymphoma Facts: No. 25 in a series providing the latest information for patients, caregivers and healthcare professionals," Retrieved https://www.lls.org/sites/default/files/file_assets/peripheraltcelllymphomafacts.pdf, (2014) (8 pages).

Lewis et al., "Catalytic site-directed γ-secretase complex inhibitors do not discriminate pharmacologically between Notch S3 and β-APP cleavages," *Biochemistry* 42(24):7580-7586, 2003. (7 pages).

Li et al., "Combined inhibition of Notch signaling and Bcl-2/Bcl-xL results in synergistic antimyeloma effect," *Mol Cancer Ther.* 9(12):3200-3209, Dec. 2010. (11 pages).

Li et al., "Directed evolution of human T-cell receptors with picomolar affinities by phage display," *Nature Biotechnology* 23(3):349-354, 2005. (6 pages).

Li et al., "Notch Signaling in T-Cell Development and T-ALL," *ISRN Hematology 2011*(Article ID 921706):1-9, 2011. (10 pages).

Lipson et al., "Durable cancer regression off-treatment and effective reinduction therapy with an anti-PD-1 antibody," *Clin Cancer Res* 19(2):462-468, 2013. (7 pages).

Liu et al., "Inclusion of Strep-tag II in design of antigen receptors for T-cell immunotherapy," *Nat Biotechnol* 34(4):430-434, Apr. 2016. (7 pages).

Liu et al., "Inclusion of Strep-Tag II in design of antigen receptors for T-cell immunotherapy," *Nat. Biotechnol.* 34(4):430-434, Apr. 2016. (HHS Public Access, Author Manuscript, available in PMC Aug. 22, 2016) (16 pages).

Liu et al., "Silencing of Receptor Tyrosine Kinase RORI Inhibits Tumor-Cell Proliferation via P13K/AKT/mTOR Signaling Pathway in Lung Adenocarcinoma," *PLoS One* 10(5):e0127092, 2015. (14 pages).

Lonial et al., "How I treat high-risk myeloma," *Blood* 126(13):1536-1543, Sep. 24, 2015. (8 pages).

Lupton et al., "Dominant positive and negative selection using a hygromycin phosphotransferase-thymidine kinase fusion gene," *Mol. and Cell Biol.* 11(6):3374-3378, Jun. 1991. (5 pages).

Lyu et al., "The rGel/BLyS fusion toxin specifically targets malignant B cells expressing the BLyS receptors BAFF-R, TACI, and BCMA," *Mol. Cancer Ther.* 6(2):460-470, Feb. 2007. (11 pages).

Maccallum et al., "Antibody-antigen interactions: Contact analysis and binding site topography," *J. Mol. Biol.* 262:732-745, 1996. (14 pages).

Mailankody et al., "JCARH125, Anti-BCMA CART-cell Therapy for Relapsed/Refractory Multiple Myeloma_Initial Proof of Concept Results from a Phase 1/2 Multicenter Study (EVOLVE)," *Blood* 132(Suppl_1):957, Nov. 29, 2018. (Abstract Only) (3 pages).

Manuri et al., "piggyBac transposon/transposase system to generate CD19-specific T cells for the treatment of B-lineage malignancies," *Hum Gene Ther* 21(4):427-437, 2010. (12 pages).

Martin et al., "Modeling antibody hypervariable loops: a combined algorithm," *Proc Natl Acad Sci USA* 86(23):9268-72, Dec. 1989. (5 pages).

Martin-Liberal, "Leiomyosarcoma: Principles of management," *Intractable & Rare Disease Research* 2(4):127-129, 2013. (3 pages).

Massard et al., "First-in-human study of LY3039478, an oral Notch signaling inhibitor in advanced or metastatic cancer," *Annals of Oncology* 29(9):1911-1917, 2018. (7 pages).

Mathieu et al., "Notch signaling regulates PD-1 expression during CD8+ T-cell activation," *Immunology and Cell Biology* 91(1):82-88, 2013. (19 pages).

Maude et al., "Chimeric Antigen Receptor T Cells for Sustained Remissions in Leukemia," *N Engl J Med.* 371(16):1507-1517, 2014. (11 pages).

Maude et al., "Chimeric Antigen Receptor T Cells for Sustained Remissions in Leukemia," *N. Engl. J. Med.* 371(16):1507-1517, Oct. 16, 2014. (NIH Public Access, Author Manuscript, available in PMC Apr. 16, 2015) (17 pages).

Maus et al., "Making Better Chimeric Antigen Receptors for Adoptive T-cell Therapy." *Clin Cancer Res.* 22(8):1875-1884, Apr. 15, 2016. (11 pages).

Maus et al., "Zoom zoom: racing CARs for multiple myeloma," *Clinical Cancer Research* 19(8):1917-1919, Apr. 15, 2013. (NIH Public Access, Author Manuscript, available in PMC Apr. 15, 2014) (4 pages).

McLendon et al., "Cell-free assays for γ-secretase activity," *The FASEB Journal* 14(15):2383-2386, 2000. (21 pages).

Meibohm, Pharmacokinetics and Pharmacodynamics of Biotech Drugs, Wiley-VHC, Chapter 3:45-91, 2006. (25 pages).

Melkova et al., "Classification of Conditioning Regimens for Bone Marrow Transplantation: Historical Background and Current Perspectives," *Clinical oncohematology* 10(4):494-500, 2017. (English Abstract) (7 pages).

Miller et al., "Improved retroviral vectors for gene transfer and expression," *BioTechniques* 7(9):980-990, Oct. 1989. (NIH Public Access, Author Manuscript, available in PMC Feb. 3, 2006) (14 pages).

Miller, "Retrovirus packaging cells," *Human Gene Therapy* 1:5-14, 1990. (10 pages).

Moreaux et al., "BAFF and APRIL protect myeloma cells from apoptosis induced by interleukin 6 deprivation and dexamethasone," *Blood* 103(8):3148-3157, Apr. 15, 2004. (10 pages).

(56) References Cited

OTHER PUBLICATIONS

Mullen et al., "Transfer of the bacterial gene for cytosine deaminase to mammalian cells confers lethal sensitivity to 5-fluorocytosine: a negative selection system," *Proc. Natl. Acad. Sci. USA* 89:33-37, Jan. 1992. (5 pages).
Muranski et al., "Increased intensity lymphodepletion and adoptive immunotherapy—how far can we go?," *Nat Clin Pract Oncol.* 3(12):668-681, Dec. 2006. (NIH Public Access, Author Manuscript, available in PMC Jan. 17, 2007) (21 pages).
Nagoresen et al., "Immunomodulatory therapy of cancer with T cell-engaging BiTE antibody blinatumomab," *Exp Cell Res* 317(9):1255-1260, 2011. (6 pages).
Nasonov et al., "Belimumab: progress in treatment systemic lupus erythematosus," *Nauch-praktich revmatol* 54(5):13-19, 2012. (7 pages).
Naymagon et al., "Novel agents in the treatment of multiple myeloma: a review about the future," *J Hematol Oncol* 9:52, 2016. (20 pages).
Neelapu et al., "Chimeric antigen receptor T-cell therapy—assessment and management of toxicities," *Nat Rev Clin Oncol* 15(1):47-62, Jan. 2018. (HHS Public Access, Author Manuscript, available in PMC Sep. 9, 2019) (37 pages).
Nefedova et al., "Inhibition of Notch signaling induces apoptosis of myeloma cells and enhances sensitivity to chemotherapy," *Blood* 111(4):2220-2229, Feb. 2008. (11 pages).
Norelli et al., "Monocyte-derived IL-1 and IL-6 are differentially required for cytokine-release syndrome and neurotoxicity due to CAR T cells," *Nature Medicine* 24:739-748, Jun. 1, 2018. (16 pages).
Novak et al., "Expression of BCMA, TACI, and BAFF-R in multiple myeloma: a mechanism for growth and survival," *Blood* 103(2):689-694, Jan. 15, 2004. (6 pages).
O'Connor et al., "BCMA is Essential for the Survival of Long-lived Bone Marrow Plasma Cells," *J. Exp. Med.* 199(1):91-97, Jan. 5, 2004. (7 pages).
Okuhashi et al., "Effects of γ-Secretase Inhibitors on the Growth of Leukemia Cells," *Anticancer Res.* 30(2):495-498, Feb. 2010. (4 pages).
O'Rourke et al., "A single dose of peripherally infused EGFRvIII-directed CAR T cells mediates antigen loss and induces adaptive resistance in patients with recurrent glioblastoma," *Sci. Transl. Med.* 9(399), Jul. 19, 2017. (HHS Public Access, Author Manuscript, available in PMC Jan. 19, 2018) (30 pages).
Padlan et al. "Structure of an antibody-antigen complex: crystal structure of the HyHEL-10 Fab-lysozyme complex," *PNAS* 86:5938-5942, 1989. (5 pages).
Paiva et al., "New criteria for response assessment: role of minimal residual disease in multiple myeloma," *Blood* 125(20):3059-3068, 2015. (10 pages).
Palumbo et al., "Multiple Myeloma," *The New England Journal of Medicine* 364(11):1046-1060, Mar. 17, 2011. (15 pages).
Pardoll, "The blockade of immune checkpoints in cancer immunotherapy," *Nature* 12:252-264, 2012. (13 pages).
Park et al., "Adoptive transfer of chimeric antigen receptor re-directed cytolytic T lymphocyte clones in patients with neuroblastoma," *Molecular Therapy* 15(4):825-833, 2007. (9 pages).
Park et al., "Treating cancer with genetically engineered T cells," *Trends Biotechnol.* 29(11):550-557, Nov. 2011. (NIH Public Access, Author Manuscript, available in PMC Nov. 1, 2012) (15 pages).
Parkhurst et al., "Characterization of Genetically Modified T-Cell Receptors that Recognize the CEA:691-699 Peptide in the Context of HLA-A2.1 on Human Colorectal Cancer Cells," *Clin. Cancer Res.* 15(1):169-180, Jan. 1, 2009. (NIH Public Access, Author Manuscript, available in PMC Oct. 17, 2012) (23 pages).
Pisklakova et al., "Anti-myeloma effect of pharmacological inhibition of Notch/gamma-secretase with Ro4929097 is mediated by modulation of tumor microenvironment," *Cancer Biology Therapy* 17(5):477-485, 2016. (9 pages).
Porter et al., "Chimeric antigen receptor T cells persist and induce sustained remissions in relapsed refractory chronic lymphocytic leukemia," *Sci Trans. Med.* 7(303):303ra139, Sep. 2, 2015. (HHS Public Access, Author Manuscript, available in PMC Apr. 20, 2018) (25 pages).
Portolano et al., "Lack of promiscuity in autoantigen-specific H and L chain combinations as revealed by human H and L chain "roulette"," *J. Immunol.* 150:880-887, 1993. (9 pages).
Prasad et al., "Discovery of (S)-2-((S)-2-(3,5-difluorophenyl)-2-hydroxyacetamido)-A-((S,Z)-3-methyl-4-oxo-4,5-dihydro-3H-benzo[d][1,2]diazepin-5-yl)propanamide (BMS-433796): A γ-secretase inhibitor with Aβ lowering activity in a transgenic mouse model of Alzheimer's disease," *Bioorganic & Medicinal Chemistry Letters* 17:4006-4011, 2007. (6 pages).
Quinn et al., "APRIL promotes cell-cycle progression in primary multiple myeloma cells: influence of D-type cyclin group and translocation status," *Blood* 117(3):890-901, Jan. 20, 2011. (12 pages).
Raje et al., "Anti-BCMA CAR T-Cell Therapy bb2121 in Relapsed or Refractory Multiple Myeloma," *N. Engl. J. Med.* 380(18):1726-1737, May 2, 2019. (HHS Public Access, Author Manuscript, available in PMC Jun. 14, 2021) (21 pages).
Rajkumar et al., "Guidelines for determination of the number of prior lines of therapy in multiple myeloma," *Blood* 126(7):921-922, 2015. (2 pages).
Rajkumar, "Multiple myeloma: 2012 update on diagnosis, risk-stratification, and management," *Am J Hematol* 87(1):78-88, Jan. 2012. (NIH Public Access, Author Manuscript, available in PMC Apr. 18, 2013) (23 pages).
Rajkumar, "Updated Diagnostic criteria and staging for multiple myeloma," *ASCO Educational Book* e418-e423, 2016. (6 pages).
Ramadoss et al., "An anti-B cell maturation antigen bispecific antibody for multiple myeloma: Supplemental Information," *J. Am. Chem. Soc.* 137(16):5288-5291, 2015. (12 pages).
Ramadoss et al., "An Anti-B Cell Maturation Antigen Bispecific Antibody for Multiple Myeloma," *J. Am. Chem. Soc.* 137:5288-5291, 2015. (4 pages).
Ramakrishnan et al., "MRK003, a gamma secretase inhibitor exhibits promising in vitro pre-clinical activity in multiple myeloma and non hodgkin's lymphoma," *Leukemia* 26(2):340-348, Feb. 2012. (HHS Public Access, Author Manuscript, available in PMC Apr. 3, 2015) (20 pages).
Rapoport et al., "NY-ESO-1-specific TCR-engineered T-cells mediate sustained antigen-specific antitumor effects in myeloma," *Nat. Med.* 21(8):914-921, Aug. 2015. (HHS Public Access, Author Manuscript, available in PMC Feb. 1, 2016) (23 pages).
Raza et al., "Optimizing current and emerging therapies in multiple myeloma: a guide for the hematologist," *Ther Adv Hematol* 8(2):55-70, 2017. (16 pages).
Rennert et al., "A Soluble Form of B Cell Maturation Antigen, a Receptor for the Tumor Necrosis Factor Family Member APRIL, Inhibits Tumor Cell Growth," *J. Exp. Med.* 192(11):1677-1683, Dec. 4, 2000. (7 pages).
Richardson et al., "A Phase 2 Study of Bortezomib in Relapsed, Refractory Myeloma." *N Engl J Med.* 348(26):2609-2617, Jun. 26, 2003. (21 pages).
Riddell et al., "Phase I study of cellular adoptive immunotherapy using genetically modified CD8+ HIV-specific T cells for HIV seropositive patients undergoing allogeneic bone marrow transplant," *Human Gene Therapy* 3:319-338, 1992. (20 pages).
Rosati et al., "γ-Secretase inhibitor I induces apoptosis in chronic lymphocytic leukemia cells by proteasome inhibition, endoplasmic reticulum stress increase and notch down-regulation," *Int J Cancer.* 132:1940-1953, Apr. 2013. (14 pages).
Rosenberg et al., "Cell transfer immunotherapy for metastatic solid cancer—what clinicians need to know," *Nat Rev Clin Oncol.* 8(10):577-85, 2011. (HHS Public Access, Author Manuscript, available in PMC Dec. 13, 2018) (23 pages).
Rosenberg et al., "Durable complete responses in heavily pretreated patients with metastatic melanoma using T-cell transfer immunotherapy," *Clin Cancer Res* 17(13):4550-4557, Jul. 1, 2011. (NIH Public Access, Author Manuscript, available in PMC Jul. 1, 2012) (16 pages).
Rudikoff et al., "Single amino acid substitution altering antigen-binding specificity," *PNAS* 79:1979-1983, 1982. (5 pages).

(56) References Cited

OTHER PUBLICATIONS

Ryan et al., "Antibody targeting of B-cell maturation antigen on malignant plasma cells," *Molecular Cancer Therapeutics, American Association for Cancer Research* 6(11):3009-3018, Nov. 2007. (10 pages).
Sadelain et al., "The basic principles of chimeric antigen receptor (CAR) design," *Cancer Discov.* 3(4):388-398, Apr. 2013. (NIH Public Access, Author Manuscript, available in PMC Apr. 2, 2014) (21 pages).
Sahebjam et al., "A Phase I study of the combination of ro4929097 and cediranib in patients with advanced solid tumors (PJC-004/NCI 8503)," *Brit J of Cancer* 109:943-949, 2013. (7 pages).
Salem et al., "Quantification of B-cell maturation antigen, a target for novel chimeric antigen receptor T-cell therapy in Myeloma," *Leuk. Res.* 71:106-111, Aug. 2018. (HHS Public Access, Author Manuscript, available in PMC Apr. 23, 2021) (17 pages).
Salter et al., "Phosphoproteomic analysis of chimeric antigen receptor signaling reveals kinetic and quantitative differences that affect cell function," *Sci. Signal* 11(544), 2018. (HHS Public Access, Author Manuscript, available in PMC Feb. 21, 2019) (35 pages).
Sanchez et al., "Serum B-cell maturation antigen is elevated in multiple myeloma and correlates with disease status and survival," *Br J Haematol* 158(6):727-38, 2012. (25 pages).
Sanchez et al., "Soluble BCMA in myeloma serum binds its ligands BAFF and prevents normal antibody production in multiple myeloma patients," *Blood* 126(23):1799, 2015. (3 pages).
Savoldo et al., "CD28 costimulation improves expansion and persistence of chimeric antigen receptor-modified T cells in lymphoma patients," *JCI* 121(5):1822-1826, 2011. (6 pages).
Scarpa et al., "Characterization of recombinant helper retroviruses from Moloney-based vectors in ecotropic and amphotropic packaging cell lines," *Virology* 180:849-852, 1991. (4 pages).
Scatchard, "The attractions of proteins for small molecules and ions," *Annals of the New York Academy of Sciences* 51(4):660-672, 1949. (13 pages).
Schlueter et al., "Specificity and Binding Properties of a Single-chain T Cell Receptor," *J. Mol. Biol.* 256(5):859-869, 1996. (11 pages).
Schuler et al., "SYFPEITHI: Database for Searching and T-Cell Epitope Prediction," *Immunoinformatics Methods in Molecular Biology* 409(1):75-93, 2007. (19 pages).
Scott et al., "Post-transplant outcomes in high-risk compared to non-high risk multiple myeloma, a CIBMIR analysis," *Biol. Blood Marrow Transplant.* 22(10):1893-1899, Oct. 2016. (HHS Public Access, Author Manuscript, available in PMC Oct. 1, 2017) (17 pages).
Seckinger et al., "Target Expression, Generation, Preclinical Activity, and Pharmacokinetics of the BCMA-T Cell Bispecific Antibody EM801 for Multiple Myeloma Treatment," *Cancer Cell* 31(3):396-410, Mar. 13, 2017. (16 pages).
Seimetz et al., "Development and approval of the trifunctional antibody catumaxomab (anti-EpCAM x anti-CD3) as a targeted cancer immunotherapy," *Cancer Treat Rev* 36:458-467, 2010. (10 pages).
Seow et al., "Advances in Targeted and immunobased Therapies for Colorectal Cancer in the Genomic Era," *OncoTargets and Therapy* 9:1899-1920, 2016. (22 pages).
Sharma et al., "Efficient sleeping beauty DNA transposition from DNA minicircles," *Molec Ther Nucl Acids* 2:e74, 2013. (10 pages).
Shearman et al., "L-685,458, an Aspartyl Protease Transition State Mimic, Is a Potent Inhibitor of Amyloid β-Protein Precursor γ-Secretase Activity," *Biochemistry* 39:8698-8704, 2000. (7 pages).
Shih et al., "Notch Signaling, γ-Secretase Inhibitors, and Cancer Therapy," *Cancer Res* 67(5):1879-1882, Mar. 1, 2007. (5 pages).
Singh et al., "ProPred: prediction of HLA-DR binding sites," *Bioinformatics* 17(12):1236-1237, 2001. (2 pages).
Smith et al., "A phase I dose escalation and expansion study of the anticancer stem cell agent demcizumab (Anti-DLL4) in patients with previously treated solid tumors," *Clin Cancer Res.* 20(24):6295-303, 2014. (9 pages).
Smith et al., "Development and Evaluation of a Human Single Chain Variable Fragment (scFv) Derived BCMA Targeted CAR T Cell Vector Leads to a High Objective Response Rate in Patients with Advanced MM," *Blood* 130(Suppl_1):742, Dec. 7, 2017. (Abstract Only) (4 pages).
Sommermeyer et al., "Fully human CD19-specific chimeric antigen receptors for T-cell therapy," *Leukemia* 31(10):2191-2199, Oct. 2017. (HHS Public Access, Author Manuscript, available in PMC Sep. 22, 2017) (21 pages).
Sonneveld et al., "Treatment of multiple myeloma with high-risk cytogenetics: a consensus of the International Myeloma Working Group," *Blood* 127(24):2955-2962, Jun. 16, 2016. (8 pages).
Soo Hoo et al., "Characterization of a single-chain T-cell receptor expressed in *Escherichia coli*," *Proc Natl Acad Sci USA* 89(10):4759-4763, 1992. (5 pages).
Sotillo et al., "Convergence of Acquired Mutations and Alternative Splicing of CD19 Enables Resistance to CART-19 Immunotherapy," *Cancer Discov.* 5(12):1282-1295, Dec. 2015. (HHS Public Access, Author Manuscript, available in PMC Jun. 1, 2016) (25 pages).
Stewart et al., "Carfilzomib, Lenalidomide, and Dexamethasone vs Lenalidomide and Dexamethasone in Patients (Pts) with Relapsed Multiple Myeloma: Interim Results from ASPIRE, a Randomized, Open-Label, Multicenter Phase 3 Study," *Blood* 124(21):79, Dec. 6, 2014. (4 pages).
Tai et al., "B cell maturation antigen (BCMA)-based immunotherapy for multiple myeloma," *Expert Opinion on Biological Therapy* 19(11):1143-1156, Nov. 2019. (14 pages).
Tai et al., "Novel anti-B-cell maturation antigen antibody-drug conjugate (GSK2857916) selectively induces killing of multiple myeloma," *Blood* 123(20):3128-3138, 2014. (12 pages).
Tai et al., "Targeting B-cell maturation antigen in multiple myeloma," *Immunotherapy* 7(11):1187-1199, 2015. (13 pages).
Takebe et al., "Targeting Notch signaling pathway in cancer: Clinical development advances and challenges," *Pharmacol Ther* 141(2):140-149, Feb. 2014. (NIH Public Access, Author Manuscript, available in PMC Feb. 1, 2015) (21 pages).
Tejada et al., "The challenge of targeting Notch in hematologic malignancies," *Frontiers in Pediatrics* 2:1-8, 2014. (8 pages).
Terakura et al., "Generation of CD19-chimeric antigen receptor modified CD8+ T cells derived from virus-specific central memory T cells," *Blood* 119(1):72-82, Jan. 5, 2012. (11 pages).
Themeli et al., "Generation of tumor-targeted human T lymphocytes from induced pluripotent stem cells for cancer therapy," *Nat Biotechnol.* 31(10):928-933, 2013. (HHS Public Access, Author Manuscript, available in PMC Dec. 8, 2017) (20 pages).
Thompson et al., "BAFF Binds to the Tumor Necrosis Factor Receptor-like Molecule B Cell Maturation Antigen and Is Important for Maintaining the Peripheral B Cell Population," *J. Exp. Med.* 192(1):129-135, Jul. 3, 2000. (7 pages).
Tolcher et al., "Phase I Study of RO4929097, a Gamma Secretase Inhibitor of Notch Signaling, in Patients With Refractory Metastatic or Locally Advanced Solid Tumors," *Journal of Clinical Oncology* 30(19):2348-2353, July 1, 2012. (6 pages).
Tomita et al., "The Inhibition of γ-Secretase as a Therapeutic Approach to Alzheimer's Disease," *Drugs News Perspect* 17(5):321-325, 2004. (5 pages).
Tsukahara et al., "CD19 target-engineered T-cells accumulate at tumor lesions in human B-cell lymphoma xenograft mouse models," *Biochem Biophys Res Commun* 438(1):84-9, Aug. 16, 2013. (HHS Public Access, Author Manuscript, available in PMC Aug. 14, 2017) (13 pages).
Turtle et al., "Durable Molecular Remissions in Chronic Lymphocytic Leukemia Treated With CD19-Specific Chimeric Antigen Receptor-Modified T Cells After Failure of Ibrutinib," *Journal of Clinical Oncology* 35(26):3010-3020, Sep. 10, 2017. (15 pages).
Turtle et al., "Engineered T cells for anti-cancer therapy," *Curr. Opin. Immunol.* 24(5):633-39, Oct. 2012. (NIH Public Access, Author Manuscript, available in PMC Oct. 1, 2013) (12 pages).
Turtle et al., "Immunotherapy of non-Hodgkin lymphoma with a defined ratio of CD8+ and CD4+ CD19-specific chimeric antigen receptor-modified T cells," *Sci. Transl. Med.* 8(355):355ra116, Sep. 7, 2016. (HHS Public Access, Author Manuscript, available in PMC Mar. 7, 2017) (24 pages).

(56) References Cited

OTHER PUBLICATIONS

Vajdos et al. "Comprehensive functional maps of the antigen-binding site of an anti-ErbB2 antibody obtained with shotgun scanning mutagenesis," *J. Mol. Biol.* 320:415-428, 2002. (14 pages).
Van Tendeloo et al., "High-level transgene expression in primary human T lymphocytes and adult bone marrow CD34⁺ cells via electroporation-mediated gene delivery," *Gene Therapy* 7:1431-1437, 2000. (7 pages).
Varela-Rohena et al., "Control of HIV-1 immune escape by CD8 T-cells expressing enhanced T-cell receptor," *Nat. Med.* 14(12):1390-1395, Dec. 2008. (Europe PMC Funders Group, Author Manuscript, available in PMC Dec. 22, 2010) (12 pages).
Varga et al., "Investigational agents in immunotherapy: a new horizon for the treatment of multiple myeloma," *British Journal of Haematology* 181:433-446, 2018. (14 pages).
Walker et al., "Tumor Antigen and Receptor Densities Regulate Efficacy of a Chimeric Antigen Receptor Targeting Anaplastic Lymphoma Kinase," *Molecular Therapy* 25(9):2189-2201, Sep. 2017. (13 pages).
Wang et al., "Phenotypic and functional attributes of lentivirus-modified CD19-specific human CD8⁺ central memory T cells manufactured at clinical scale," *J Immunother.* 35(9):689-701, Nov. 2012. (NIH Public Access, Author Manuscript, available in PMC Nov. 1, 2013) (28 pages).
Watanabe et al., "Target Antigen Density Governs the Efficacy of Anti-CD20-CD28-CD3ζ Chimeric Antigen Receptor-Modified Effector CD8⁺ T Cells," *The Journal of Immunology* 194:911-920, 2015. (11 pages).
Weng et al., "Activating mutations of NOTCH1 in human T cell acute lymphoblastic leukemia," *Science* 306(5694):269-271, 2004. (4 pages).
White et al., "Antibody-Targeted Immunotherapy for Treatment of Malignancy," *Ann. Rev. Med.* 52:125-145, 2001. (23 pages).
Wigler et al., "Transfer of purified herpes virus thymidine kinase gene to cultured mouse cells," *Cell* 11:223-232, 1997. (10 pages).
Wilson, "Tech Sight: Analyzing Biomolecular Interactions," *Science* 295(5562):2103-2105, 2002. (3 pages).
Wolff et al., "Monoclonal Antibody Homodimers: Enhanced Antitumor Activity in Nude Mice," *Can Res* 53:2560-2565, 1993. (6 pages).
Wooldridge et al., "Corticosteroids in Advanced Cancer," *Oncology* 15(2):225-236, 2001. (14 pages) https://www.cancernetwork.com/view/corticosteroids-advanced-cancer.
Works et al., "Lenalidomide Enhances Anti-BCMA Chimeric Antigen Receptor T Cell Function Against Multiple Myeloma," *Blood* 130:1794, Dec. 7, 2017. (Abstract Only) (3 pages).
Works et al., "Lenalidomide Enhances Anti-BCMA Chimeric Antigen Receptor T Cell Function Against Multiple Myeloma," *Blood* 130:1794, Dec. 7, 2017. (Abstract Only) (6 pages).
Wu et al., "Adoptive T-cell therapy using autologous tumor-infiltrating lymphocytes for metastatic melanoma: current status and future outlook," *Cancer* 18(2):160-75, Mar. 2012. (NIH Public Access, Author Manuscript, available in PMC Mar. 1, 2013) (32 pages).
Wu et al., "Humanization of a murine monoclonal antibody by simultaneous optimization of framework and CDR residues," *J. Mol. Biol.* 294:151-162, 1999. (12 pages).
Wulfing et al., "Correctly Folded T-cell Receptor Fragments in the Periplasm of *Escherichia coli*: Influence of Folding Catalysts," *J. Mol. Biol.* 242(5):655-669, 1994. (15 pages).
Yong et al., "Evaluation Of Bcma As a Therapeutic Target In Multiple Myeloma Using An Antibody-Drug Conjugate," *Blood* 122(21):4447, 2013. (3 pages).
Yuan et al., "Notch signaling: An emerging therapeutic target for cancer treatment," *Cancer Letters* 369:20-27, 2015. (8 pages).
Yuen et al., "Abstract CT048: Population pharmacokinetics and pharmacodynamics for an oral Notch inhibitor, LY3039478, in the first-in-man study," *Cancer Research* 76(14):CT048, Jul. 15, 2016. (Abstract Only) (4 pages).
Zhang et al., "ROR1 expression correlated with poor clinical outcome in human ovarian cancer," *Scientific Reports* 4:5811, 2014. (7 pages).
Zhang et al., "ROR1 Is Expressed in Human Breast Cancer and Associated with Enhanced Tumor-Cell Growth," *PloS One* 7(3):e31127, 2012. (12 pages).
Zhang et al., "The onco-embryonic antigen ROR1 is expressed by a variety of human cancers," *The American Journal of Pathology* 181(6):1903-1910, 2012. (8 pages).
Zhao et al., "Structural Design of Engineered Costimulation Determines Tumor Rejection Kinetics and Persistence of CAR T Cells," *Cancer Cell* 28(4):415-428, Oct. 12, 2015. (HHS Public Access, Author Manuscript, available in PMC Oct. 12, 2016) (27 pages).
Filipovic et al., "Anti-nicastrin monoclonal antibodies elicit pleiotropic anti-tumour pharmacological effects in invasive breast cancer cells," *Breast Cancer Res Treat* 148:455-462, 2014 [Published Online Sep. 24, 2014] (8 pages).
Hayashi et al., "Neutralization of the γ-secretase activity by monoclonal antibody against extracellular domain of nicastrin," *Oncogene* 31(6):787-798, Feb. 9, 2012 (NIH Public Access Author Manuscript, available in PMC Jun. 1, 20146) (21 pages).
National Cancer Institute dictionary entry for RO4929097, excerpt of what is available at URL: https://www.cancer.gov/publications/dictionaries/cancer-terms/def/ro4929097, generated Jul. 19, 2023 (1 page).
NCBI MeSH listing of gamma-secretase inhibitor or modulator compounds, excerpt of what is available at URL: https://www.nobi.nlm.nih.gov/pccompound?Db=pccompound&DbFrom=mesh&Cmd=Link&LinkName=mesh_pccompound&IdsFromResult=2101240y, generated Jul. 19, 2023 (9 pages).
PubChem CID 9843750, Semagacestat, excerpt of what is available at URL: https://pubchem.nebi.nlm.nih.gov/compound/Semagacestat, Oct. 25, 2006, generated Jul. 19, 2023 (3 pages).
"Small molecule versus biological drugs," Generics and Biosimilar Initiatve, https://www.gabionline.net/biosimilars/research/Small-molecule-versus-b, Jun. 29, 2012. (5 pages).
Buvailo, "Will Biologics Surpass Small Molecules In The Pharma Race?," *Bio Pharma Trend* , Jul. 11, 2018. (8 pages).
Camacho et al., "Biosimilars 101: considerations for U.S. oncologists in clinical practice," *Cancer Medicine* 3(4):889-899, Aug. 2014. (11 pages).
Downing et al., "Regulatory Review of Novel Therapeutics—Comparison of Three Regulatory Agencies," *The New England Journal of Medicine* 366(24):2284-93, Jun. 14, 2012. (Published Online May 16, 2012) (10 pages).
Giannis et al., "Peptidomimetics for Receptor Ligands-Discovery, Development, and Medical Perspectives," *Angewandte Chemie International Edition in English* 32(9):1244-1267, Sep. 1993. (Abstract Only) (3 pages).
Luistro et al., "Preclinical Profile of a Potent γ-Secretase Inhibitor Targeting Notch Signaling with In vivo Efficacy and Pharmacodynamic Properties," *Cancer Res* 69(19):7672-7680, Oct. 1, 2009. (Published Online Sep. 22, 2009) (11 pages).
Melkova et al., "Classification of Conditioning Regimens for Bone Marrow Transplantation: Historical Background and Current Perspectives," *Clinical Oncohematology* 10(4):494-500, Oct. 1, 2017. (English Abstract) (7 pages).
Pelay-Gimeno et al., "Structure-Based Design of Inhibitors of Protein-Protein Interactions: Mimicking Peptide Binding Epitopes," *Angew. Chem. Int. Ed.* 54:8896-8927, 2015. (Published Online Jun. 26, 2015) (32 pages).
Pont et al., "γ-Secretase inhibition increases efficacy of BCMA-specific chimeric antigen receptor T cells in multiple myeloma," *Blood* 134(19):1585-1597, Nov. 7, 2019. (with Supplemental Methods and Figure Legends) (28 pages).
Vagner et al., "Peptidomimetics, a synthetic tool of drug discovery," *Curr Opin Chem Biol.* 12(3):292-296, Jun. 2008. (NIH Public Access, available in PMC Jun. 1, 2009) (10 pages).

\* cited by examiner patient MM

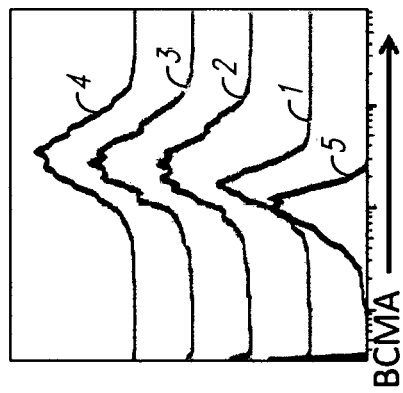
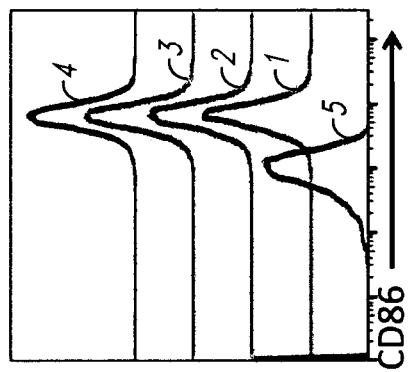
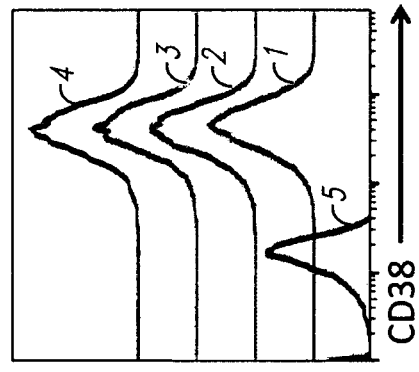
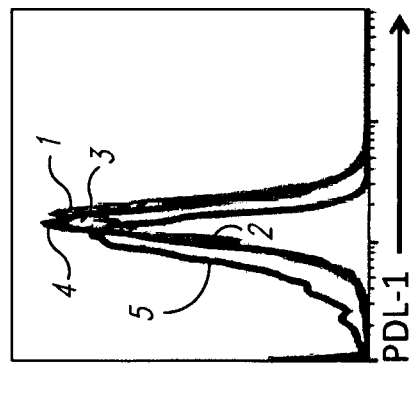
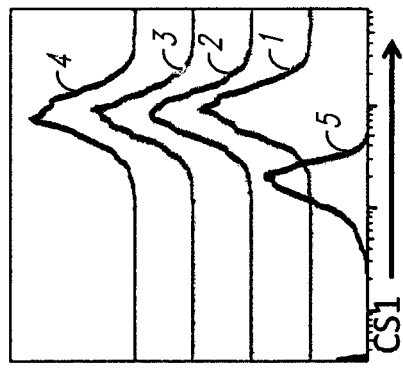
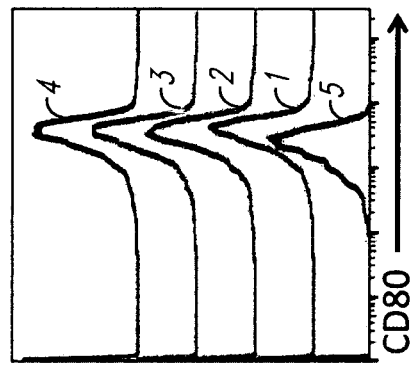
FIG. 30

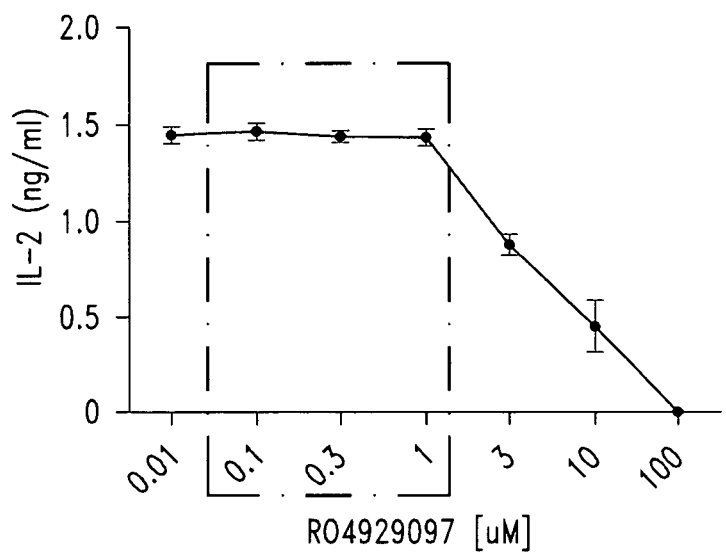
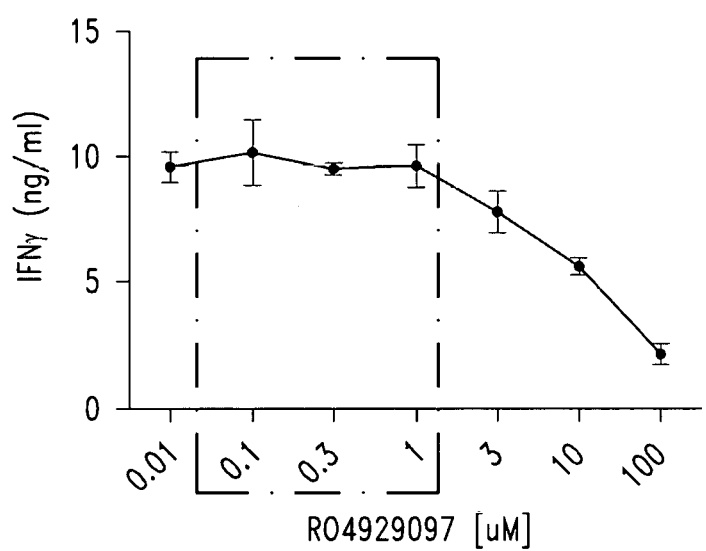
FIG. 5C

SEQUENCE LISTING

```
<160> NUMBER OF SEQ ID NOS: 34

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence

<400> SEQUENCE: 1

Gly Gly Gly Gly Ser
1               5

<210> SEQ ID NO 2
<211> LENGTH: 4
<212> TYPE: PRT
```

```
<213> ORGANISM: Artificial Sequence
<220> FEATURE:
<223> OTHER INFORMATION: Synthetic sequence

<400> SEQUENCE: 2

Gly Gly Gly Ser
1

<210> SEQ ID NO 3
<211> LENGTH: 25
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (5)...(20)
<223> OTHER INFORMATION: any one or all of amino acids 5-20  can either
      be present or absent

<400> SEQUENCE: 3

Gly Gly Gly Ser Gly Gly Gly Ser Gly Gly Gly Ser Gly Gly Gly Ser
1               5                   10                  15

Gly Gly Gly Ser Gly Gly Gly Gly Ser
            20                  25

<210> SEQ ID NO 4
<211> LENGTH: 45
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (5)...(0)
<223> OTHER INFORMATION: any one or all of amino acids 5-20 can either
      be present or absent.
<220> FEATURE:
<221> NAME/KEY: VARIANT
<222> LOCATION: (26)...(45)
<223> OTHER INFORMATION: any one or all of amino acids 26-45 can either
      be present or absent.

<400> SEQUENCE: 4

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Gly Ser
        35                  40                  45

<210> SEQ ID NO 5
<211> LENGTH: 25
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (6)...(20)
<223> OTHER INFORMATION: any one or all of amino acids 6-20 can either
      be present or absent.

<400> SEQUENCE: 5

Gly Gly Gly Gly Ser Gly Gly Gly Gly Ser Gly Gly Gly Ser Gly
1               5                   10                  15

Gly Gly Gly Ser Gly Gly Gly Gly Ser
            20                  25
```

<210> SEQ ID NO 6
<211> LENGTH: 6
<212> TYPE: PRT
<213> ORGANISM: Artificial Sequence
<220> FEATURE:
<223> OTHER INFORMATION: Synthetic sequence

<400> SEQUENCE: 6

His Gly Gly His His Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic sequence

<400> SEQUENCE: 7

Trp Ser His Pro Gln Phe Glu Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic sequence

<400> SEQUENCE: 8

Trp Arg His Pro Gln Phe Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic sequence

<400> SEQUENCE: 9

Cys Pro Pro Cys Pro
1               5

<210> SEQ ID NO 10
<211> LENGTH: 29
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (10)...(29)
<223> OTHER INFORMATION: any one or all of amino acids 10-29 can either
      be present or absent.

<400> SEQUENCE: 10

Gly Gly Gly Ser Gly Gly Gly Gly Ser Gly Gly Gly Gly Ser Gly Gly
1               5                   10                  15

Gly Gly Ser Gly Gly Gly Gly Ser Gly Gly Gly Gly Ser
            20                  25

<210> SEQ ID NO 11
<211> LENGTH: 3
<212> TYPE: PRT
<213> ORGANISM: Artificial Sequence

```
<220> FEATURE:
<223> OTHER INFORMATION: Synthetic sequence

<400> SEQUENCE: 11

Gly Gly Gly
1

<210> SEQ ID NO 12
<211> LENGTH: 15
<212> TYPE: PRT
<213> ORGANISM: Artificial Sequence
<220> FEATURE:
<223> OTHER INFORMATION: Synthetic sequence

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic sequence

<400> SEQUENCE: 13

Gly Gly Gly Ser Gly Gly Gly Ser Gly Gly Gly Ser Gly Gly Gly Ser
1               5                   10                  15

<210> SEQ ID NO 14
<211> LENGTH: 111
<212> TYPE: PRT
<213> ORGANISM: Artificial Sequence
<220> FEATURE:
<223> OTHER INFORMATION: Synthetic sequence

<400> SEQUENCE: 14

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys
            100                 105                 110

<210> SEQ ID NO 15
<211> LENGTH: 111
<212> TYPE: PRT
<213> ORGANISM: Artificial Sequence
<220> FEATURE:
<223> OTHER INFORMATION: Synthetic sequence

<400> SEQUENCE: 15

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
```

```
            20                  25                  30

Gly Ala His Leu Ile His Trp Tyr Gln Gln Lys Pro Gly Gln Pro Pro
            35                  40                  45

Lys Leu Leu Ile Tyr Leu Ala Ser Asn Leu Glu Thr Gly Val Pro Ala
        50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Ser Cys Leu Gln Ser Arg
                85                  90                  95

Ile Phe Pro Arg Thr Phe Gly Gln Gly Thr Lys Leu Glu Ile Lys
            100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Synthetic sequence

<400> SEQUENCE: 16

Asp Ile Val Leu Thr Gln Ser Pro Ala Ser Leu Ala Met Ser Leu Gly
1               5                   10                  15

Glu Arg Ala Thr Ile Ser Cys Arg Ala Ser Glu Ser Val Ser Val Ile
            20                  25                  30

Gly Ala His Leu Ile His Trp Tyr Gln Gln Lys Pro Gly Gln Pro Pro
            35                  40                  45

Lys Leu Leu Ile Tyr Leu Ala Ser Asn Leu Glu Thr Gly Val Pro Ala
        50                  55                  60

Arg Phe Ser Gly Ser Gly Ser Gly Thr Asp Phe Thr Leu Thr Ile Ser
65                  70                  75                  80

Arg Val Gln Ala Glu Asp Ala Ala Ile Tyr Ser Cys Leu Gln Ser Arg
                85                  90                  95

Ile Phe Pro Arg Thr Phe Gly Gln Gly Thr Lys Leu Glu Ile Lys
            100                 105                 110

<210> SEQ ID NO 17
<211> LENGTH: 117
<212> TYPE: PRT
<213> ORGANISM: Artificial Sequence
<220> FEATURE:
<223> OTHER INFORMATION: Synthetic sequence

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
            35                  40                  45

Gly Trp Ile Asn Thr Glu Thr Arg Glu Pro Ala Tyr Ala Tyr Asp Phe
        50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Ser Tyr Ala Met Asp Tyr Trp Gly Gln Gly Thr Leu
            100                 105                 110
```

Val Thr Val Ser Ser
        115

<210> SEQ ID NO 18
<211> LENGTH: 117
<212> TYPE: PRT
<213> ORGANISM: Artificial Sequence
<220> FEATURE:
<223> OTHER INFORMATION: Synthetic sequence

<400> SEQUENCE: 18

Gln Val Gln Leu Val Gln Ser Gly Ser Glu Leu Lys Lys Pro Gly Glu
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Trp Ile Asn Thr Glu Thr Arg Glu Pro Ala Tyr Ala Tyr Asp Phe
    50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Leu Asp Tyr Ser Tyr Ala Met Asp Tyr Trp Gly Gln Gly Thr Leu
            100                 105                 110

Val Thr Val Ser Ser
        115

<210> SEQ ID NO 19
<211> LENGTH: 117
<212> TYPE: PRT
<213> ORGANISM: Artificial Sequence
<220> FEATURE:
<223> OTHER INFORMATION: Synthetic sequence

<400> SEQUENCE: 19

Gln Val Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Trp Ile Asn Thr Glu Thr Arg Glu Pro Ala Tyr Ala Tyr Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Leu Asp Tyr Ser Tyr Ala Met Asp Tyr Trp Gly Gln Gly Thr Leu
            100                 105                 110

Val Thr Val Ser Ser
        115

<210> SEQ ID NO 20
<211> LENGTH: 117
<212> TYPE: PRT
<213> ORGANISM: Artificial Sequence
<220> FEATURE:
<223> OTHER INFORMATION: Synthetic sequence

<400> SEQUENCE: 20

Gln Val Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Ile Asn Trp Val Lys Gln Ala Pro Gly Gln Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Leu Asp Tyr Ser Tyr Ala Met Asp Tyr Trp Gly Gln Gly Thr Leu
            100                 105                 110

Val Thr Val Ser Ser
        115

<210> SEQ ID NO 21
<211> LENGTH: 117
<212> TYPE: PRT
<213> ORGANISM: Artificial Sequence
<220> FEATURE:
<223> OTHER INFORMATION: Synthetic sequence

<400> SEQUENCE: 21

Gln Ile Gln Leu Val Gln Ser Gly Ser Glu Leu Lys Lys Pro Gly Glu
1               5                   10                  15

Ser Val Lys Ile Ser Cys Lys Ala Ser Gly Tyr Thr Phe Thr Asp Tyr
            20                  25                  30

Ser Ile Asn Trp Val Lys Gln Ala Pro Gly Gln Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Leu Asp Tyr Ser Tyr Ala Met Asp Tyr Trp Gly Gln Gly Thr Leu
            100                 105                 110

Val Thr Val Ser Ser
        115

<210> SEQ ID NO 22
<211> LENGTH: 25
<212> TYPE: DNA
<213> ORGANISM: Artificial Sequence
<220> FEATURE:
<223> OTHER INFORMATION: Synthetic sequence

<400> SEQUENCE: 22
caccggagaa tcaaaatcgg tgaat                                       25

<210> SEQ ID NO 23
<211> LENGTH: 25
<212> TYPE: DNA
<213> ORGANISM: Artificial Sequence
<220> FEATURE:
<223> OTHER INFORMATION: Synthetic sequence

<400> SEQUENCE: 23
aaacattcac cgattttgat tctcc                                              25

<210> SEQ ID NO 24
<211> LENGTH: 24
<212> TYPE: DNA
<213> ORGANISM: Artificial Sequence
<220> FEATURE:
<223> OTHER INFORMATION: Synthetic sequence

<400> SEQUENCE: 24
caccgcagtt gtgtgacacg gaag                                               24

<210> SEQ ID NO 25
<211> LENGTH: 24
<212> TYPE: DNA
<213> ORGANISM: Artificial Sequence
<220> FEATURE:
<223> OTHER INFORMATION: Synthetic sequence

<400> SEQUENCE: 25
aaaccttccg tgtcacacaa ctgc                                               24

<210> SEQ ID NO 26
<211> LENGTH: 25
<212> TYPE: DNA
<213> ORGANISM: Artificial Sequence
<220> FEATURE:
<223> OTHER INFORMATION: Synthetic sequence

<400> SEQUENCE: 26
caccggcaaa ggtgagtgag acttt                                              25

<210> SEQ ID NO 27
<211> LENGTH: 25
<212> TYPE: DNA
<213> ORGANISM: Artificial Sequence
<220> FEATURE:
<223> OTHER INFORMATION: Synthetic sequence

<400> SEQUENCE: 27
aaacaaagtc tcactcacct ttgcc                                              25

<210> SEQ ID NO 28
<211> LENGTH: 25
<212> TYPE: DNA
<213> ORGANISM: Artificial Sequence
<220> FEATURE:
<223> OTHER INFORMATION: Synthetic sequence

<400> SEQUENCE: 28
caccggtttc tgcagccgct ttggg                                              25

<210> SEQ ID NO 29
<211> LENGTH: 25
<212> TYPE: DNA
<213> ORGANISM: Artificial Sequence
<220> FEATURE:
<223> OTHER INFORMATION: Synthetic sequence

<400> SEQUENCE: 29
aaaccccaaa gcggctgcag aaacc                                              25

<210> SEQ ID NO 30

```
<211> LENGTH: 5
<212> TYPE: PRT
<213> ORGANISM: Artificial Sequence
<220> FEATURE:
<223> OTHER INFORMATION: Synthetic sequence G4S linker

<400> SEQUENCE: 30

Gly Gly Gly Gly Ser
1               5

<210> SEQ ID NO 31
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)...(20)
<223> OTHER INFORMATION: any one of amino acids 1-2 can be absent or
      can be present up 10 times, provided that amino acids 1
      and 2 are not both absent

<400> SEQUENCE: 31

Gly Gly Gly Gly Gly Gly Gly Gly Gly Gly Ser Ser Ser Ser Ser
1               5                   10                  15

Ser Ser Ser Ser
            20

<210> SEQ ID NO 32
<211> LENGTH: 10
<212> TYPE: PRT
<213> ORGANISM: Artificial Sequence
<220> FEATURE:
<223> OTHER INFORMATION: Synthetic sequence

<400> SEQUENCE: 32

Gly Gly Gly Gly Ser Gly Gly Gly Gly Ser
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Synthetic sequence

<400> SEQUENCE: 33

Gly Gly Gly Ser Gly Gly Gly Ser
1               5

<210> SEQ ID NO 34
<211> LENGTH: 11
<212> TYPE: PRT
<213> ORGANISM: Artificial Sequence
<220> FEATURE:
<223> OTHER INFORMATION: Synthetic sequence

<400> SEQUENCE: 34

Gly Gly Gly Ser Gly Gly Gly Ser Gly Gly Ser
1               5                   10
```

COMBINATION THERAPIES FOR TREATMENT OF BCMA-RELATED CANCERS AND AUTOIMMUNE DISORDERS

STATEMENT OF GOVERNMENT INTEREST

This invention was made with government support under CA136551 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_445USPC_SEQUENCE_LISTING.txt. The text file is 14.3 KB, was created on Aug. 16, 2019, and is being submitted electronically via EFS-Web.

BACKGROUND

The human immune system generally protects the body from invading foreign substances and pathogens. B lymphocytes, also referred to as B-cells and a component of the immune system, produce antibodies that bind to, and in some cases mediate destruction of, the foreign substance or pathogen. In some instances, however, the immune system may be dysregulated and result in diseases that involve uncontrolled proliferation of B-cells, such cancer, autoimmune disease and inflammatory disease.

Mature B cells and their differentiated progeny can be identified by molecules on their cell surface, such as B cell maturation antigen (BCMA, also known as tumor necrosis factor receptor superfamily member 17 (TNFRSF17), TNFRSF13A, and CD269), which is expressed on plasma cells and some mature B cells. BCMA has been shown to specifically bind to B cell activating factor (BAFF, also known as TNFSF138, TALL-1, and CD257) and a proliferation-inducing ligand (APRIL, also known as TNFSF13, TALL-2, and CD256), which can lead to NF-κB activation. BCMA-targeted therapies, including adoptive transfer of BCMA-specific chimeric antigen receptor (CAR) modified T cells, naked-BCMA specific antibodies or the administration of BCMA-specific antibodies conjugated to a therapeutic moiety (antibody drug conjugate, ADC, such as a radiolabel) can be used to treat some types of B cell malignancies, such as multiple myeloma, but may be limited in efficacy by the number of BCMA molecules expressed on the tumor cell surface and/or the presence of soluble BCMA in the circulation. Low BCMA surface expression on the cancer cells or soluble BCMA can limit and prevent the efficacy of therapeutic agents due to inadequate binding to the BCMA present on the surface of the tumor cells. Low levels of other target molecules on tumor cells (e.g., CD19, CD20) that are targeted with antibody, antibody drug conjugates or chimeric antigen receptor T cells has been shown to limit the efficacy of these therapies, and enable cancer cells that express low levels of the target molecule to escape elimination. In the case of BCMA, the short extracellular portion of the molecule is cleaved from the cell surface and shed through the action of gamma-secretase (γ-secretase), a membrane-localized cellular enzyme involved in protein cleavage. This cleavage lowers the density of BCMA on cells such as myeloma cancer cells that express the molecule and results in elevated levels of soluble BCMA (sBCMA) in the serum of patients with certain autoimmune diseases (e.g., systemic lupus erythomatosis) and cancer (e.g., multiple myeloma).

Currently, there remains a need in the immunotherapy field for alternative or improved compositions and methods for more efficiently treating autoimmune disease and cancer.

(A) Illustrations of exemplary CARs having an extracellular component comprised of a BCMA-specific scFv derived from A7D12.2 antibody ("A7") or C11D5.3 antibody ("C11") and a spacer region (comprised of an IgG4 hinge region), a hydrophobic portion (comprised of a CD28 transmembrane domain), and an intracellular component comprised of a CD3ζ effector domain and a 4-1BB costimulatory domain. The scFvs were constructed with the C-terminal end of the $V_H$ region linked ("G$_4$S" variable region linker (SEQ ID NO:30)) to the N-terminal end of the $V_L$ region ("HL" orientation) or the C-terminal end of the $V_L$ region linked to the N-terminal end of the $V_H$ region ("LH" orientation).

Figure 1A:
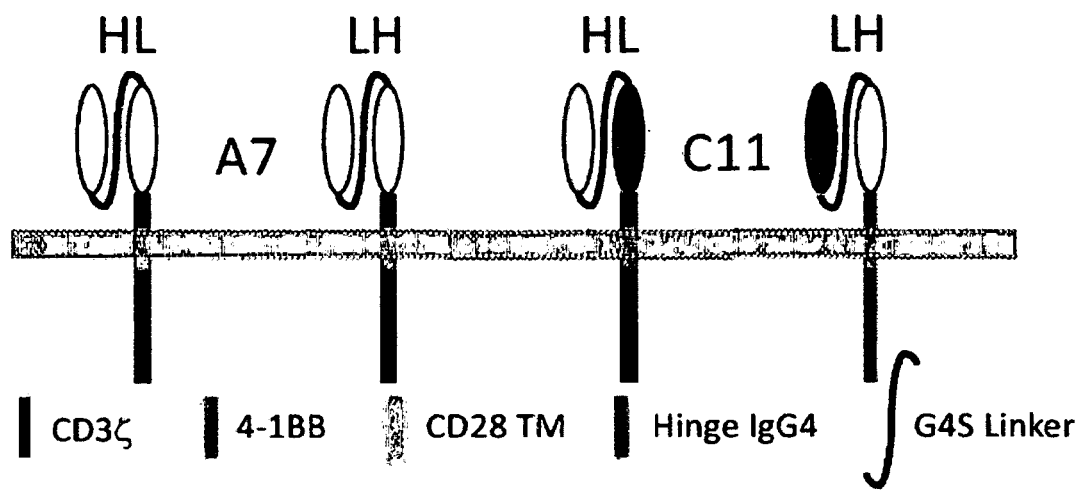
FIGS. 1A-1P show design and functional testing of exemplary chimeric antigen receptor (CAR) molecules of this disclosure.

(B) Flow cytometry data (carboxyfluorescein succinimidyl ester (CFSE) staining) showing proliferation of human T cells expressing the CARs shown in FIG. 1A and control T cells not containing a CAR in response to BCMA-expressing tumor cells.

Figure 1B:
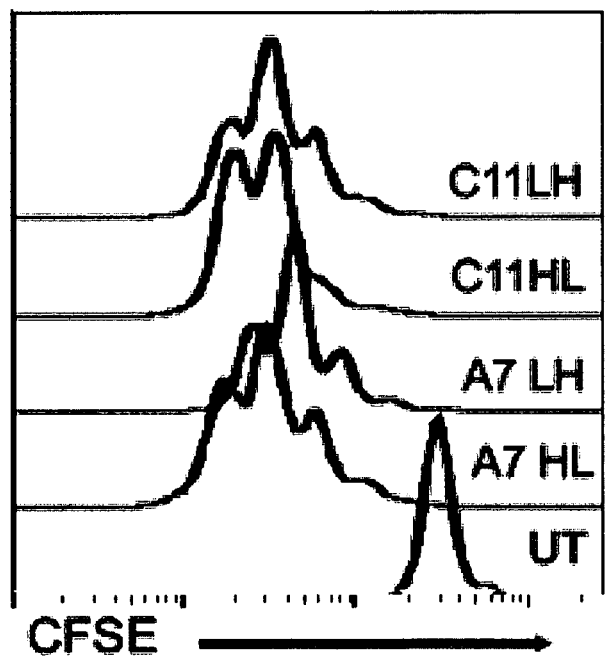

(C) Cytokine production (IFN-γ) by the CAR-transduced T cells shown in FIG. 1B when cultured in vitro with the indicated BCMA (K562) or BCMA$^+$ (K562 BCMA, U266, MM1.S) tumor cell lines.

(D) Specific lysis of the indicated target cell lines by the BCMA CAR-T cells.

(E) Illustration of two exemplary CARs of this disclosure, wherein the spacer region (Spacer +) can include a tag cassette, a linker module, a hinge, spacer amino acid and any combination thereof. If the CAR contains one or more tag in the spacer region, it would be referred to as a T-ChARM as described herein. The upper CAR contains an extracellular component (comprised of a BCMA-specific scFv and a spacer region that optionally contains other elements, such as a tag or linker), hydrophobic portion (comprised of a CD28 transmembrane domain), and an intracellular component (comprised of a CD3ζ effector domain and a 4-1BB costimulatory domain). The lower CAR contains an extracellular component (comprised of a BCMA-specific scFv and a spacer region that optionally contains other elements, such as a tag or linker), hydrophobic portion (comprised of a CD28 transmembrane domain), and an intracellular component (comprised of a CD3ζ effector domain and a CD28 costimulatory domain). Both BCMA-specific CAR/T-ChARM constructs contain a gene marker for transduction comprising a truncated human EGFR (EGFRt), which separated from the BCMA-specific CAR/T-ChARM constructs by a self-cleaving *Thoseaasigna* virus 2A (T2A) peptide sequence. Other known self-cleaving peptides can be used as well, such as porcine teschovirus-1 2A (P2A), equine rhinitis A virus (ERAV) 2A (E2A), and foot-and-mouth disease virus (FMDV) 2A (F2A).

(F) Exemplary CAR/T-ChARM constructs having different length spacer regions. sh=12 amino acid Short spacer; 2ST=48 amino acid spacer with two Strep tag cassettes; 3ST=66 amino acid spacer with three Strep tag cassettes; 2ST Int=157 amino acid intermediate length spacer with two Strep tag cassettes; and Lo=228 amino acid spacer Long spacer. The Short and Long spacer can optionally contain a tag cassette, such as a Strep tag.

(G) Additional illustrations of exemplary CAR/T-ChARM constructs with a C11 or A7 HL scFv and having different spacer regions, optionally including STII tags.

(H) The ability of human T cells modified with BCMA-specific CARs to recognize BCMA and proliferate is measured by labeling the T cells with carboxyfluoroscein (CFSE), culturing the CAR-T cells or control untransduced CFSE labeled T cells with K562 cells transduced with a polynucleotide encoding full-length BCMA (KS62/BCMA), and using flow cytometry to measure the dilution of CFSE with each cell division. CFSE-labeled T cells containing different BCMA-specific CARs with different spacer lengths, but not control untransduced T cells (UT), diluted CFSE after co-culture with K562/BCMA cells. The CAR-T cells containing the 2 ST or longer spacers proliferated better than CAR-T cells expressing the short spacer.

(I, J) Cytokine release (IFN-γ, I; IL-2, J) by anti-BCMA CAR T cells with different spacer lengths in response to BCMA-expressing U266 and 8266 myeloma cells.

(K) Cell surface EGFRt and STII expression on CD8+ T cells transduced with anti-BCMA C11 T-ChARM or BCMA-2 CAR constructs after isolation and expansion.

(L, M) Cytokine release (IFNγ, L; IL-2, M) by human CD4 (top panels) and CD8 (bottom panels) T cells engineered to express C11 T-ChARMs of this disclosure that include a 41BB costimulatory domain or a CD28 costimulatory domain, or by a previously disclosed anti-BCMA CAR ("BCMA-2"; see Carpenter et al. *Clin. Cancer Res.* 19:2048, 2013).

(N) Proliferation of human T cells engineered to express the disclosed C11 T-ChARMs or the BCMA-2 CAR when co-cultured with the indicated BCMA-expressing cell lines.

(O) Lysis of K562 BCMA-negative cells by CD8 T cells engineered to express C11 T-ChARMs of this disclosure (circle=41BB costimulatory domain, square=CD28 costimulatory domain) or BCMA-2 CAR (triangle) at the indicated E:T ratios.

Figure 1C:
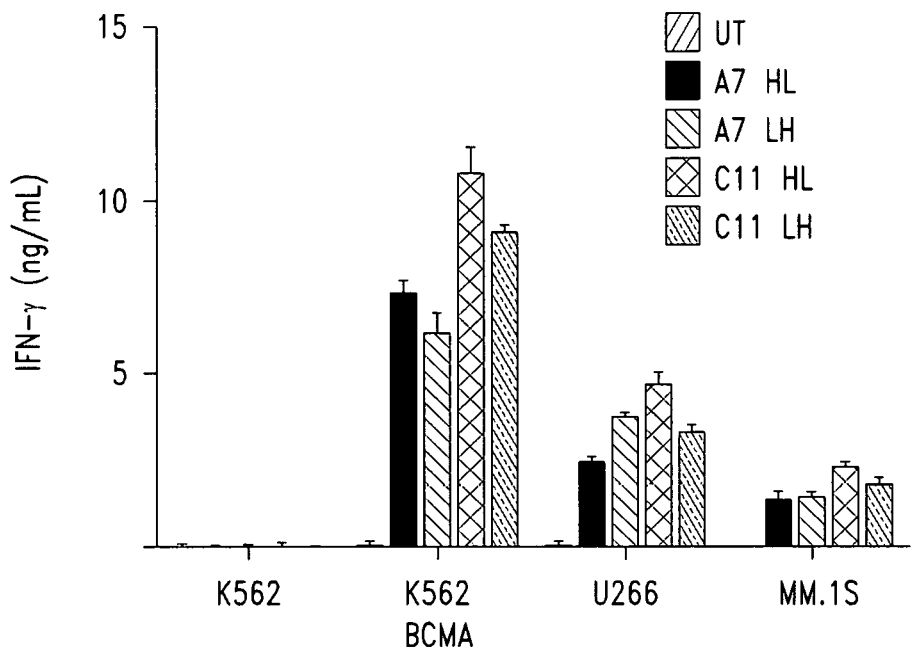
Figure 1D:
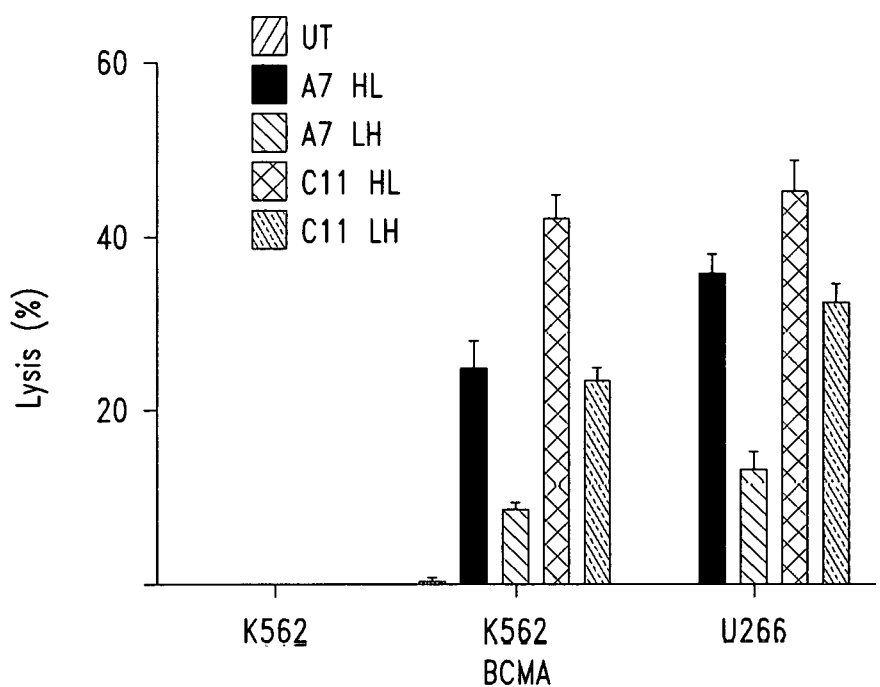
Figure 1E:
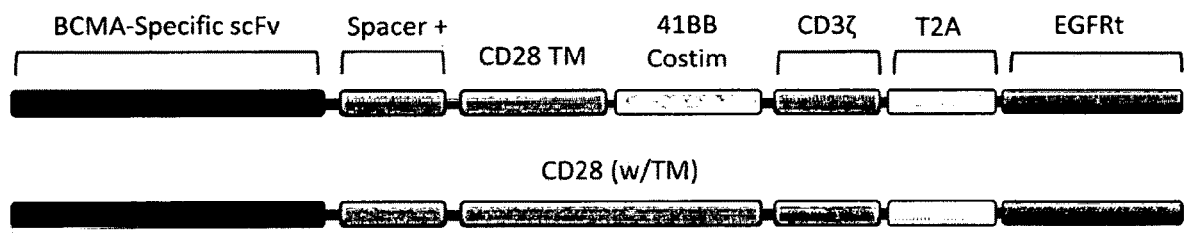
Figure 1F:
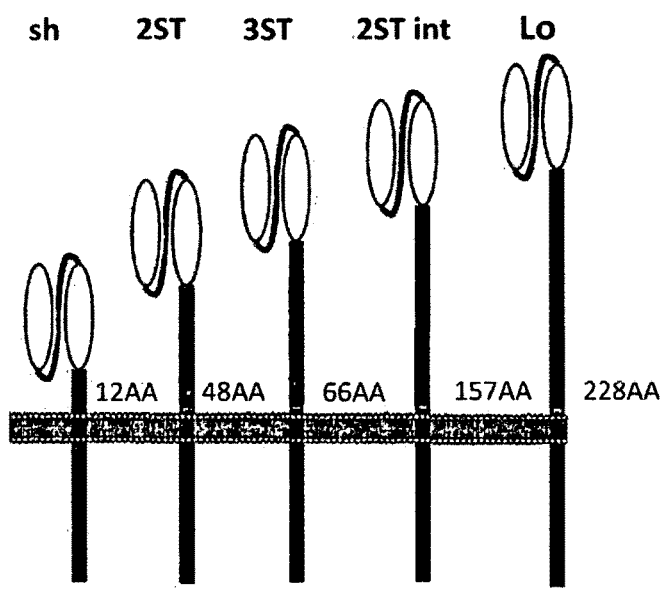
Figure 1G:
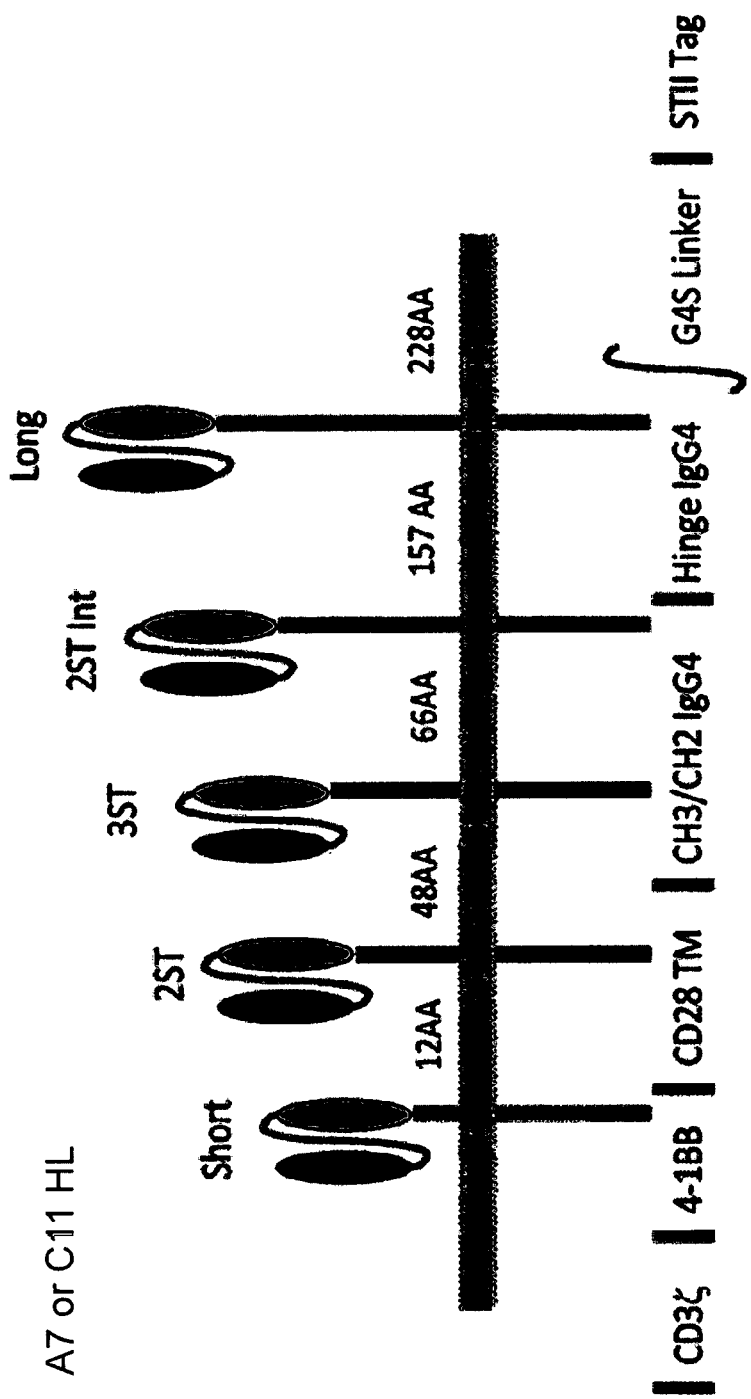
Figure 1H:
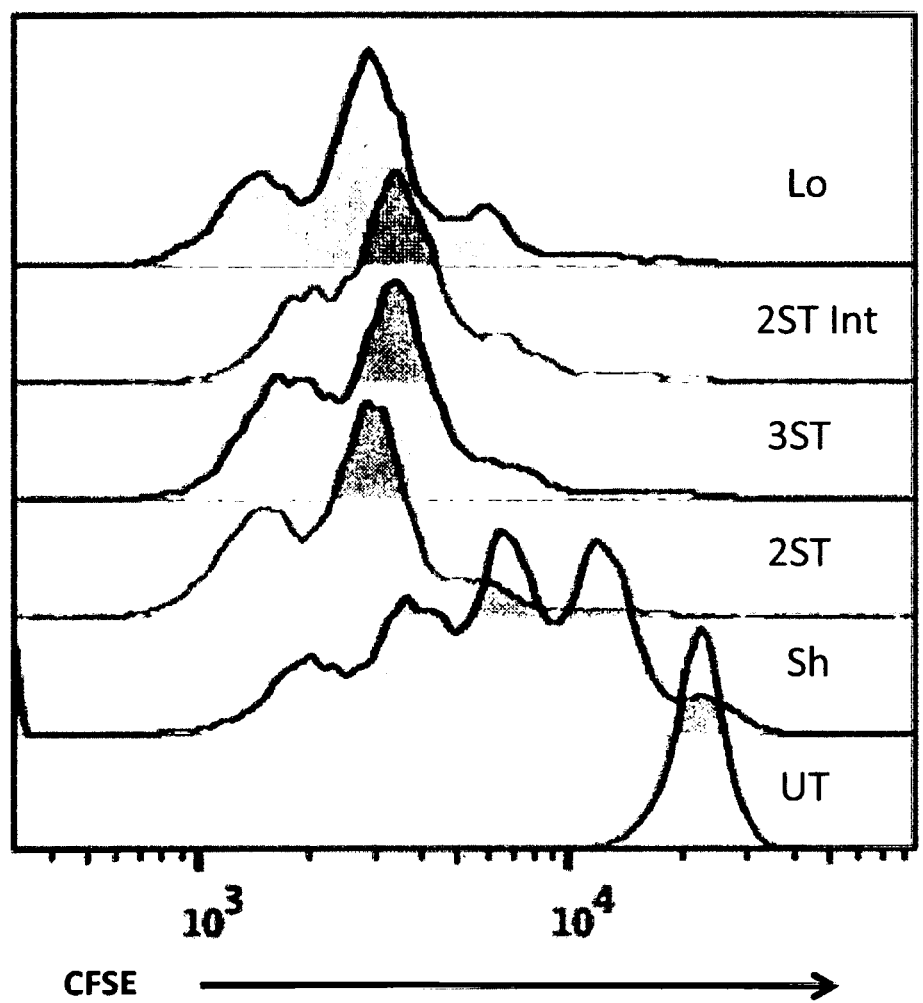
Figure 1I:
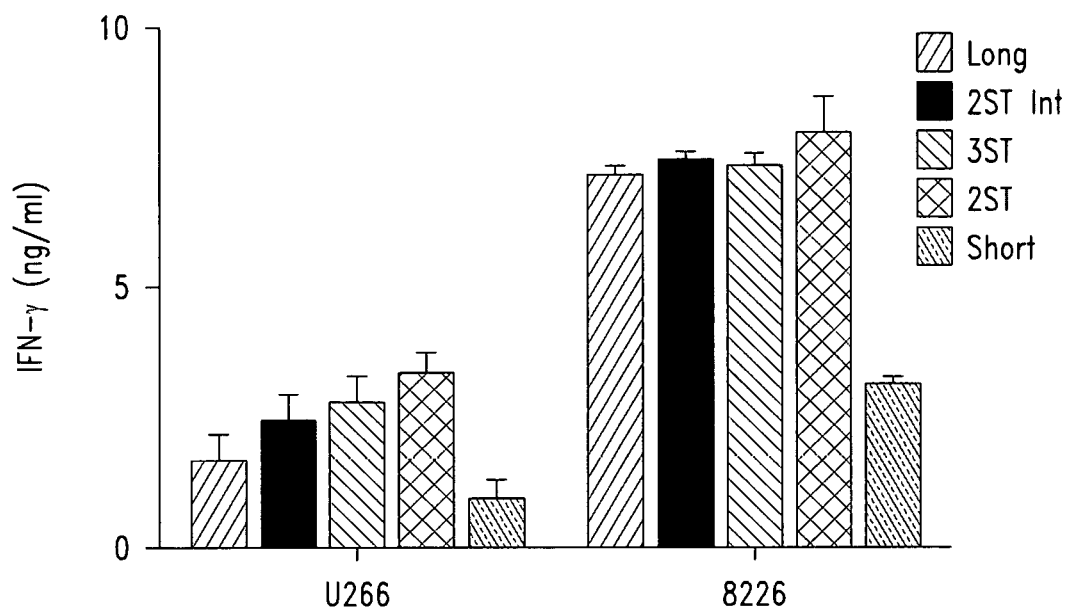
Figure 1J:
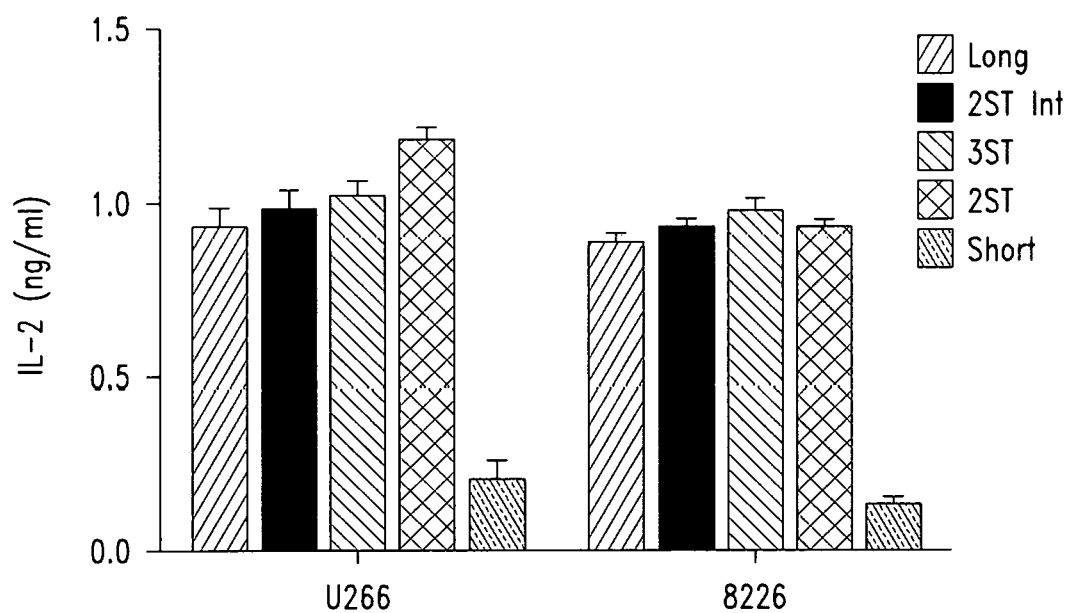
Figure 1K:
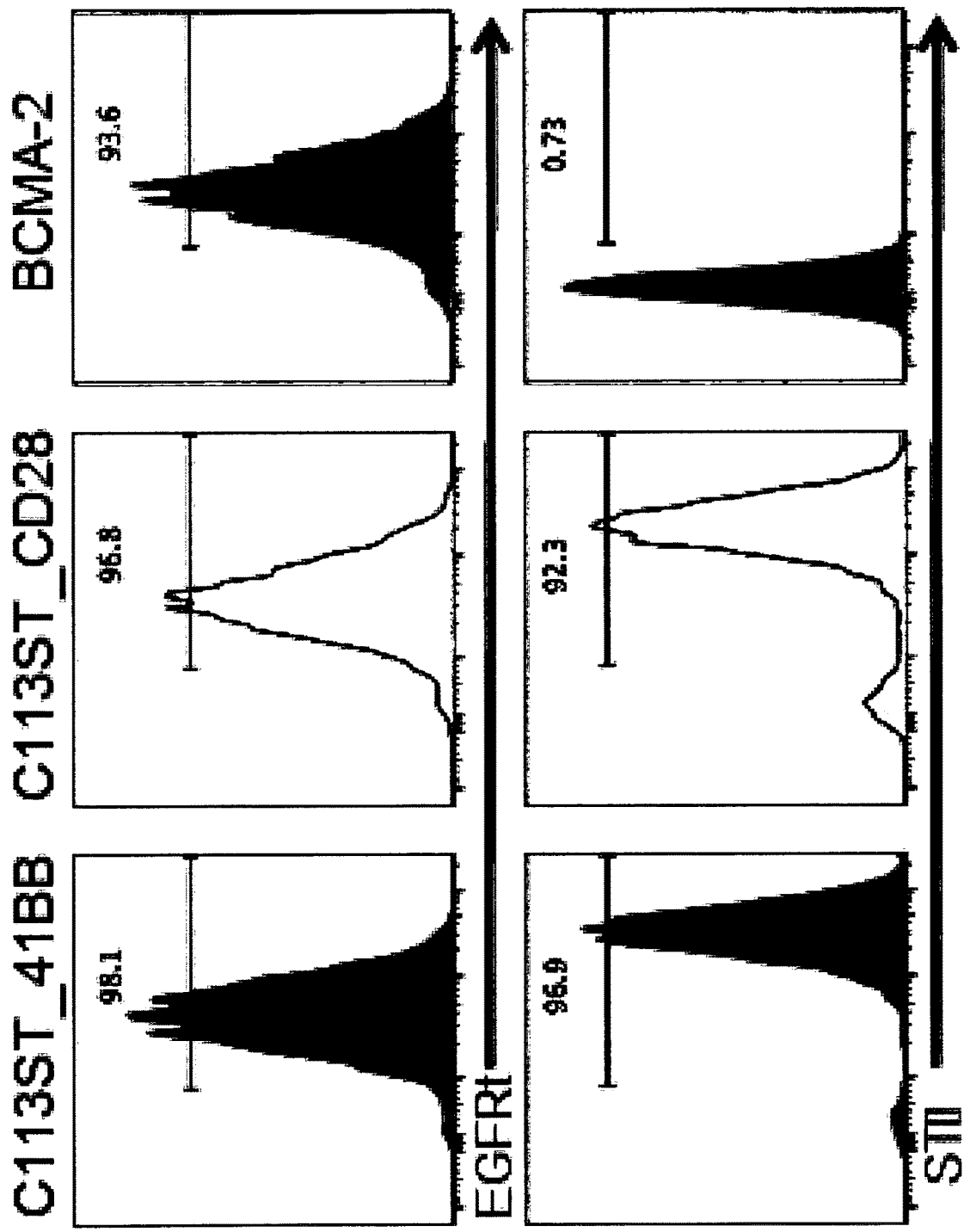
Figure 1L:
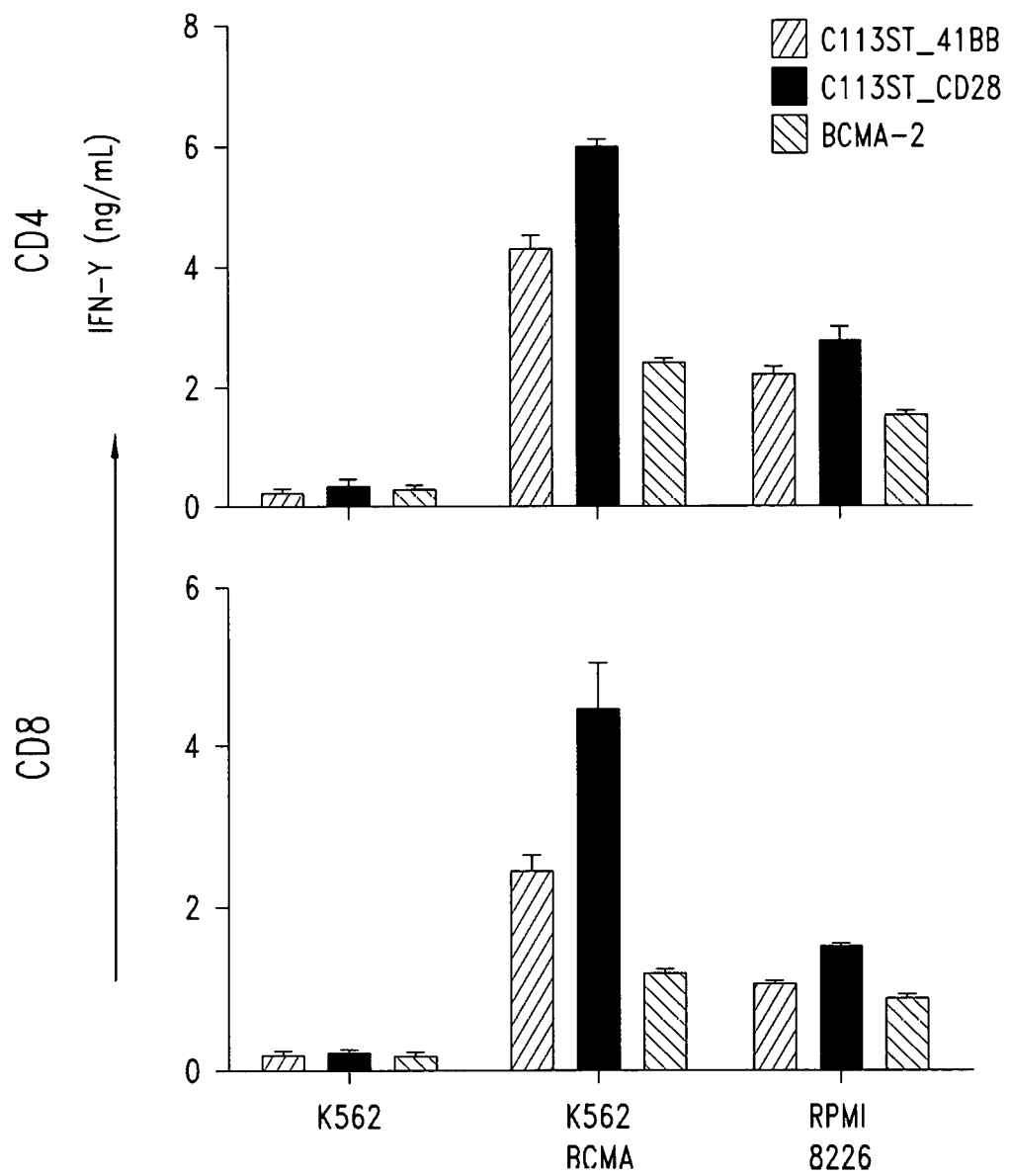
Figure 1M:
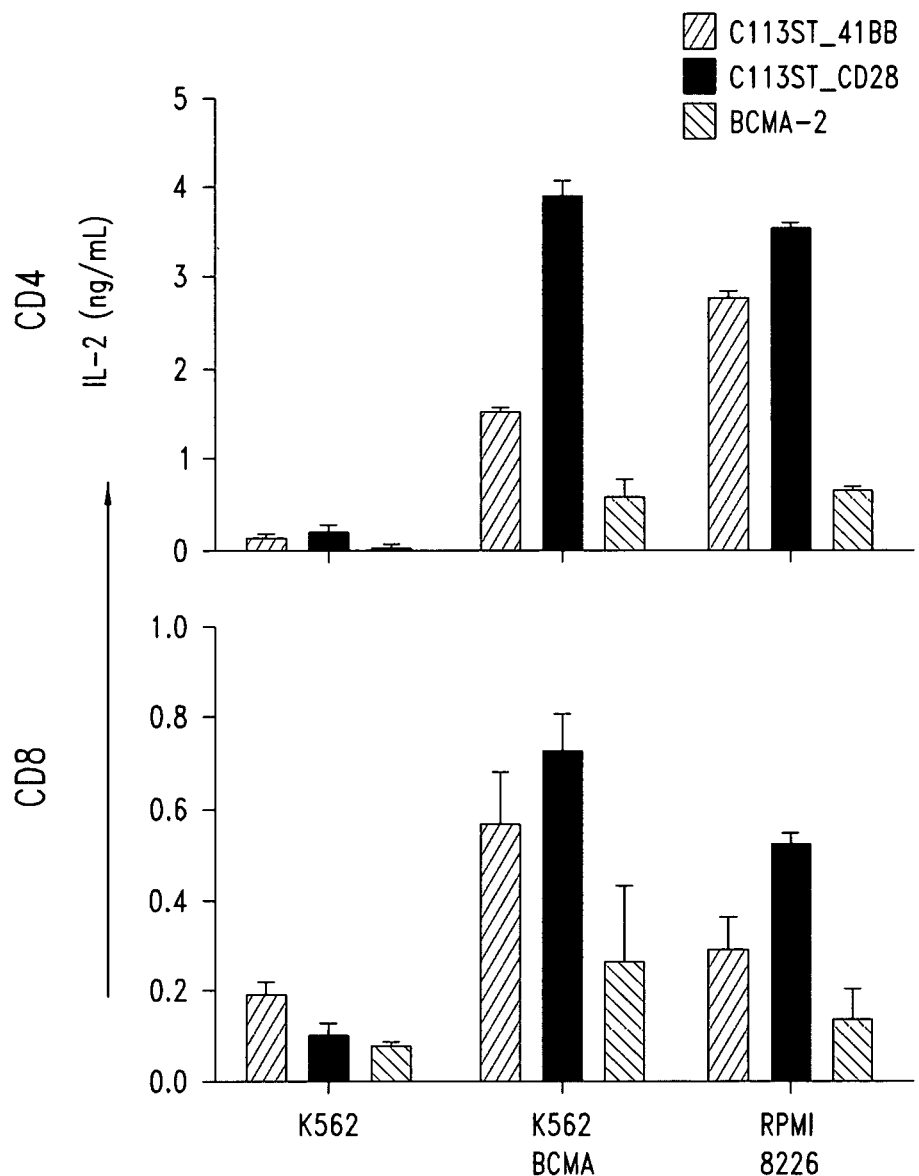
Figure 1N:
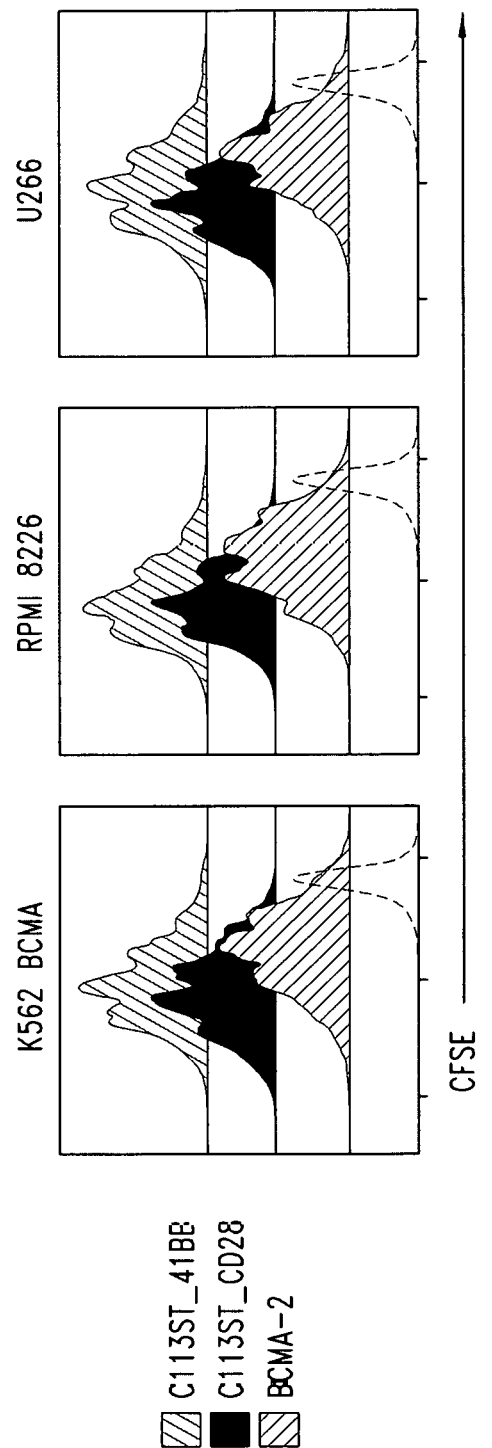
Figure 1O:
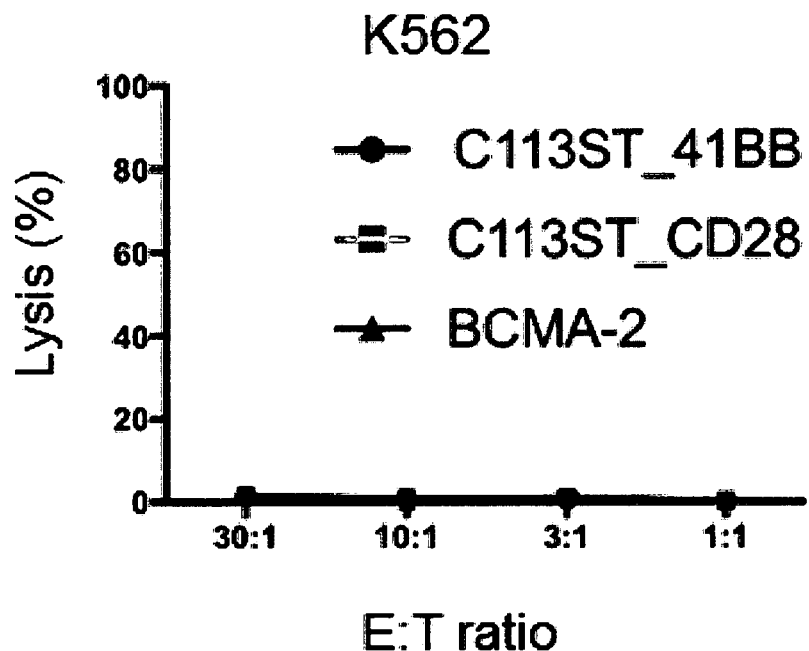

(P) Lysis of K562 cells transduced to express BCMA, by the engineered CD8 T cells indicated in FIG. 1O, at various E:T ratios (x-axis).

Figure 2A:
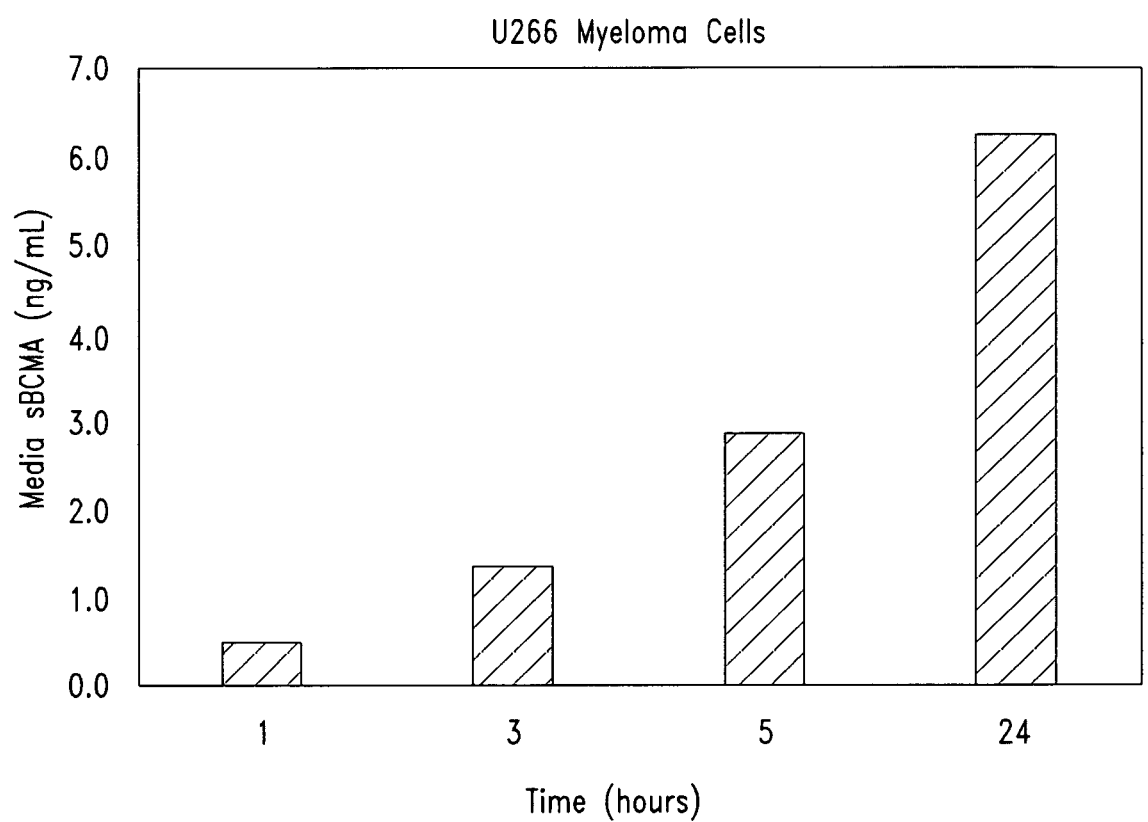
Figure 2B:
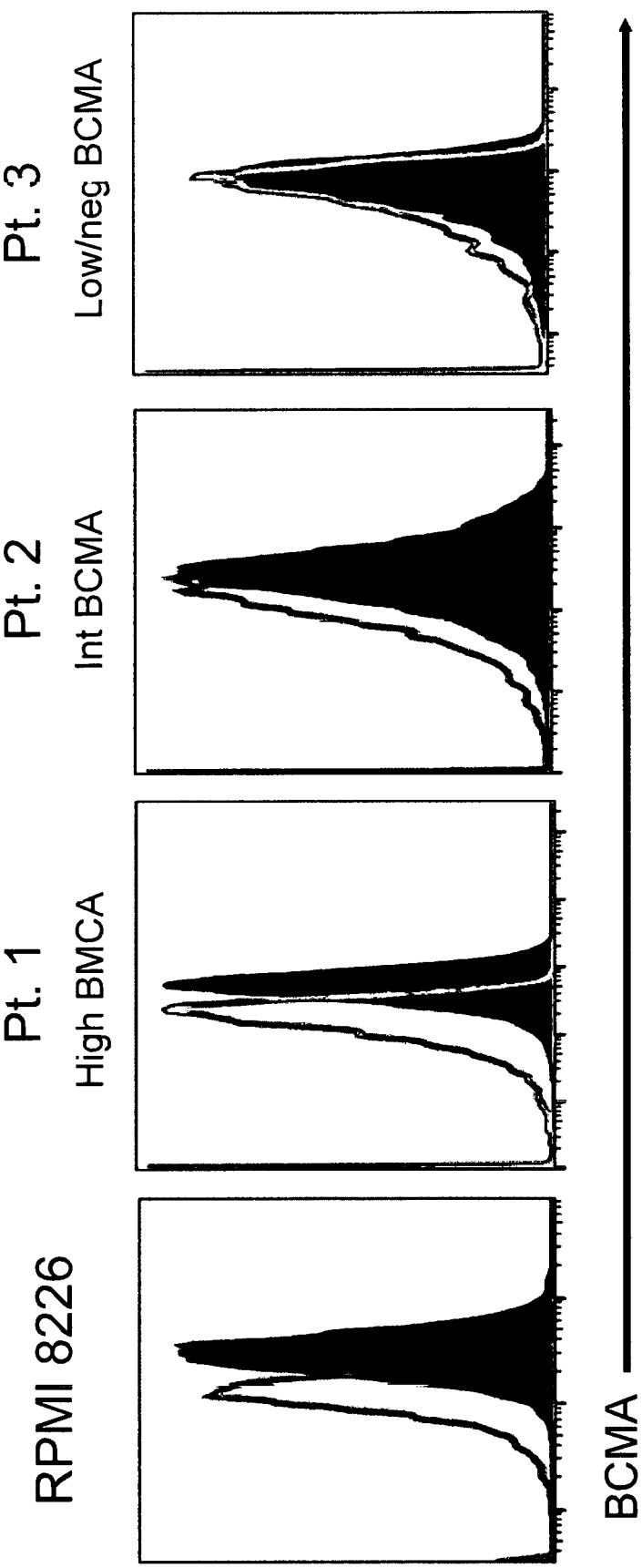
Figure 2C:
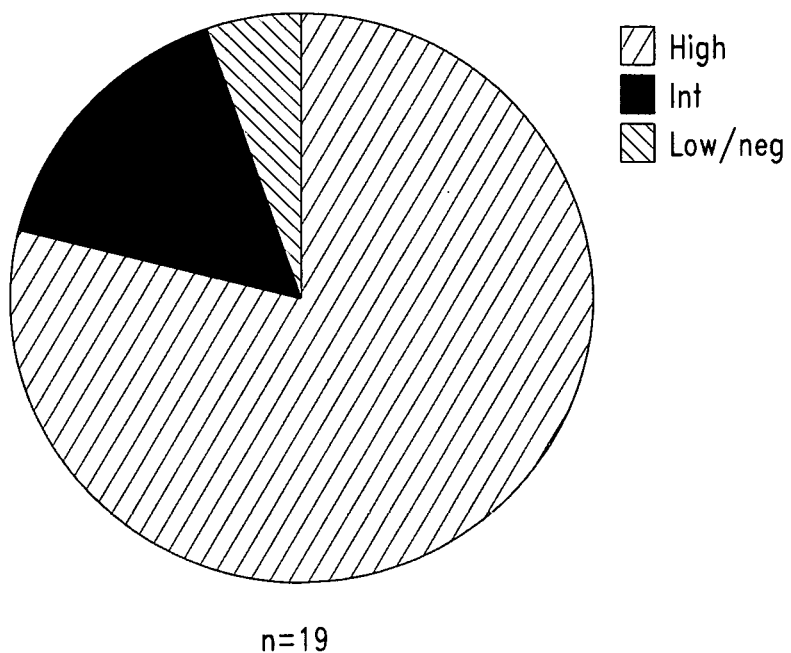
Figure 2D:
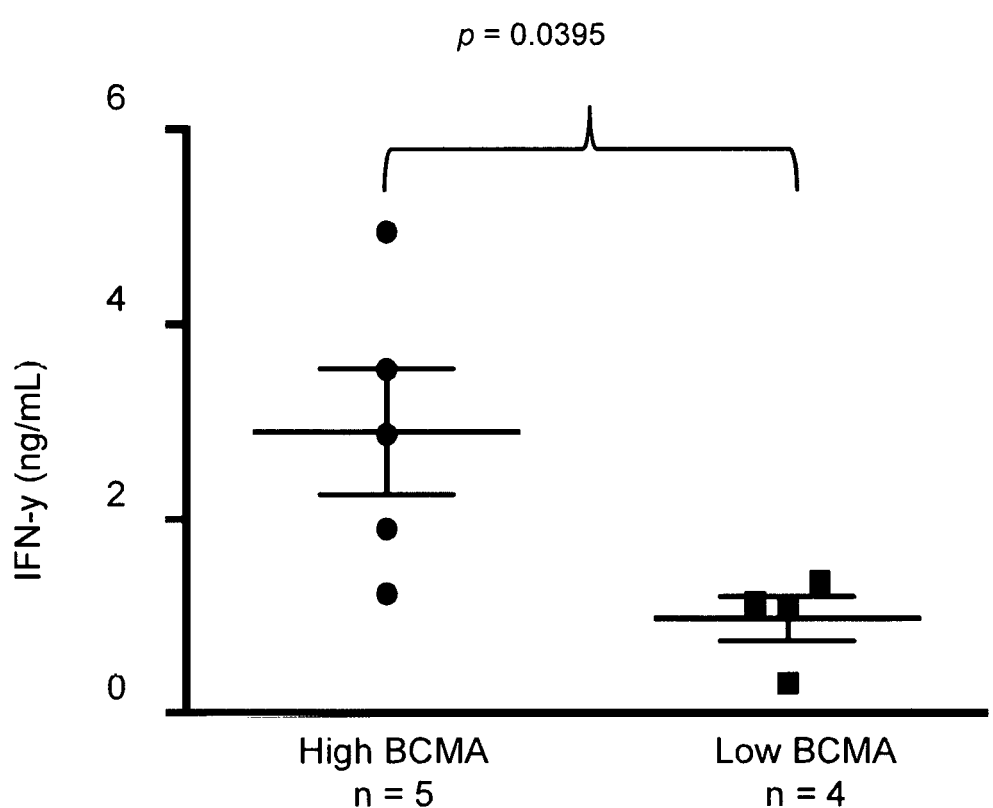
Figure 2E:
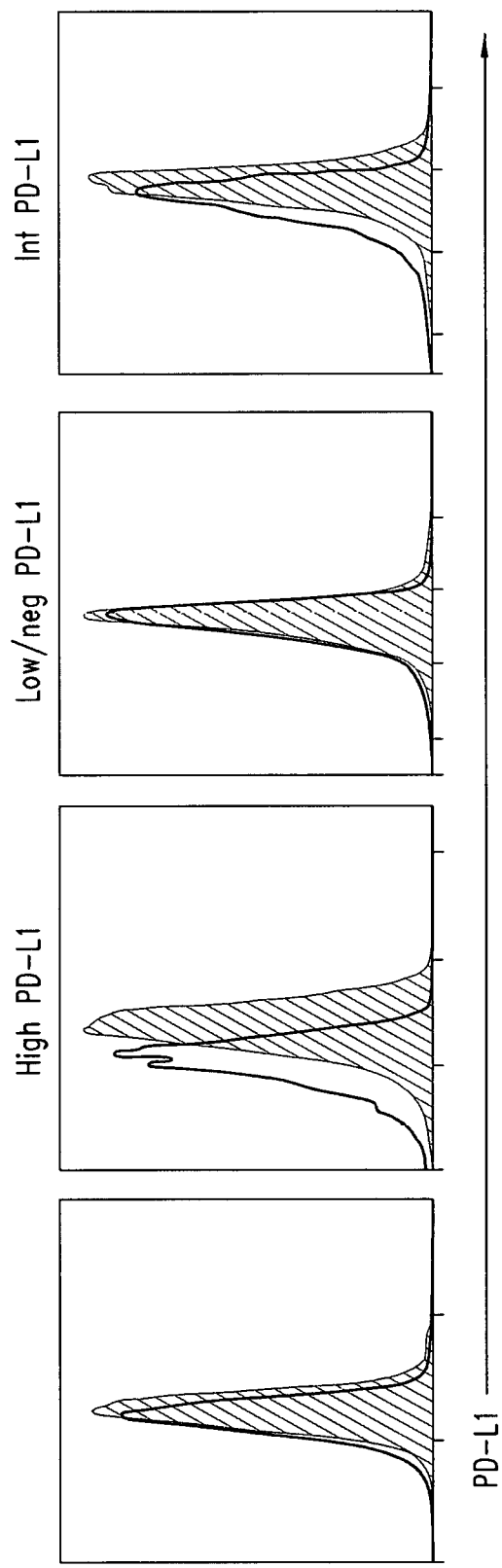
Figure 2F:
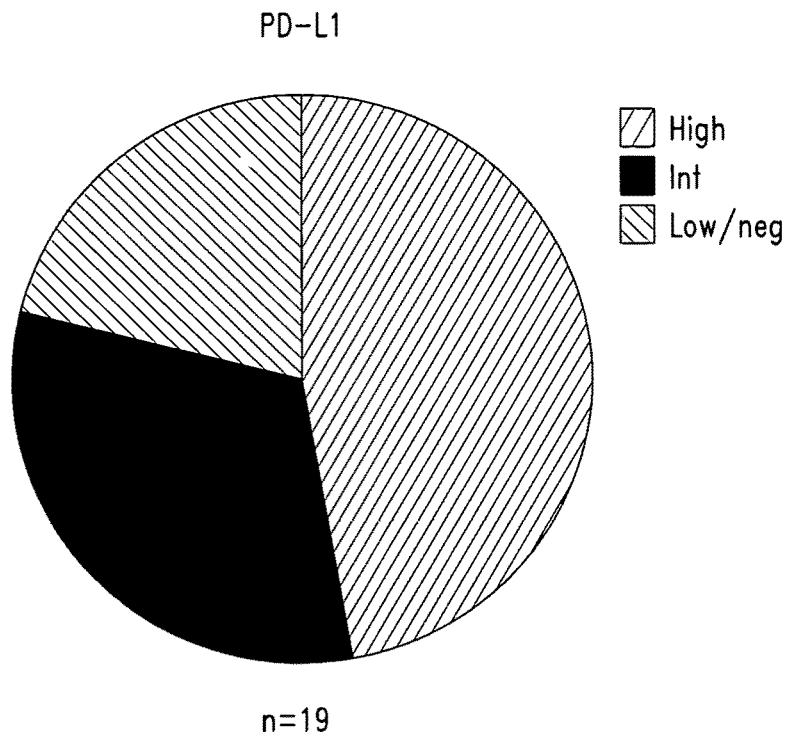
Figure 2G:
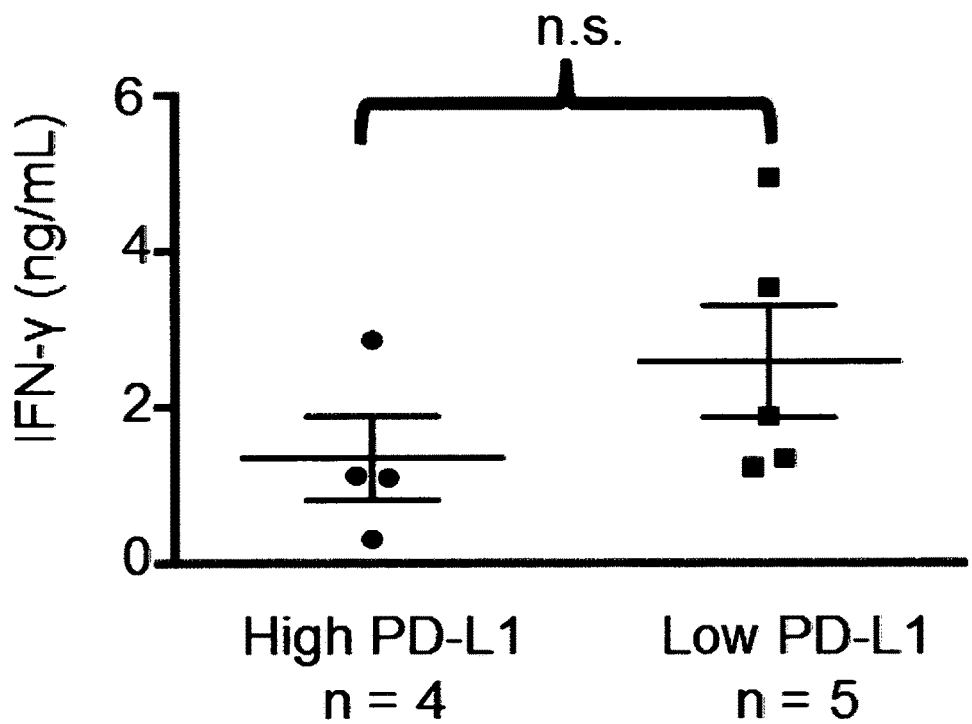
Figure 2H:
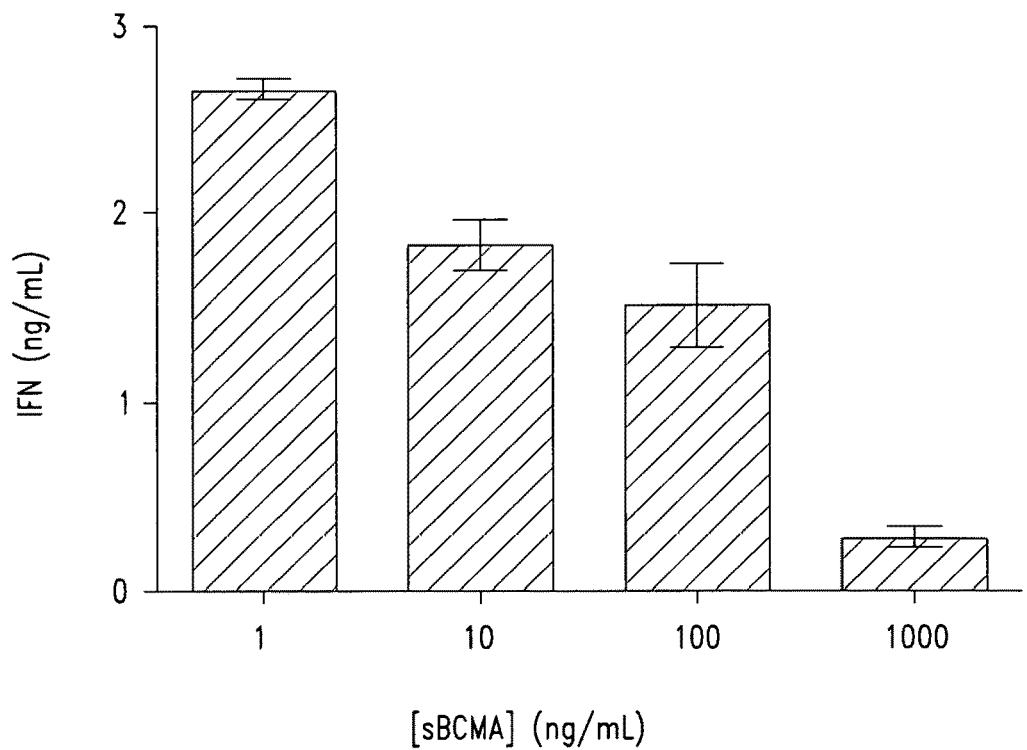
Figure 2I:
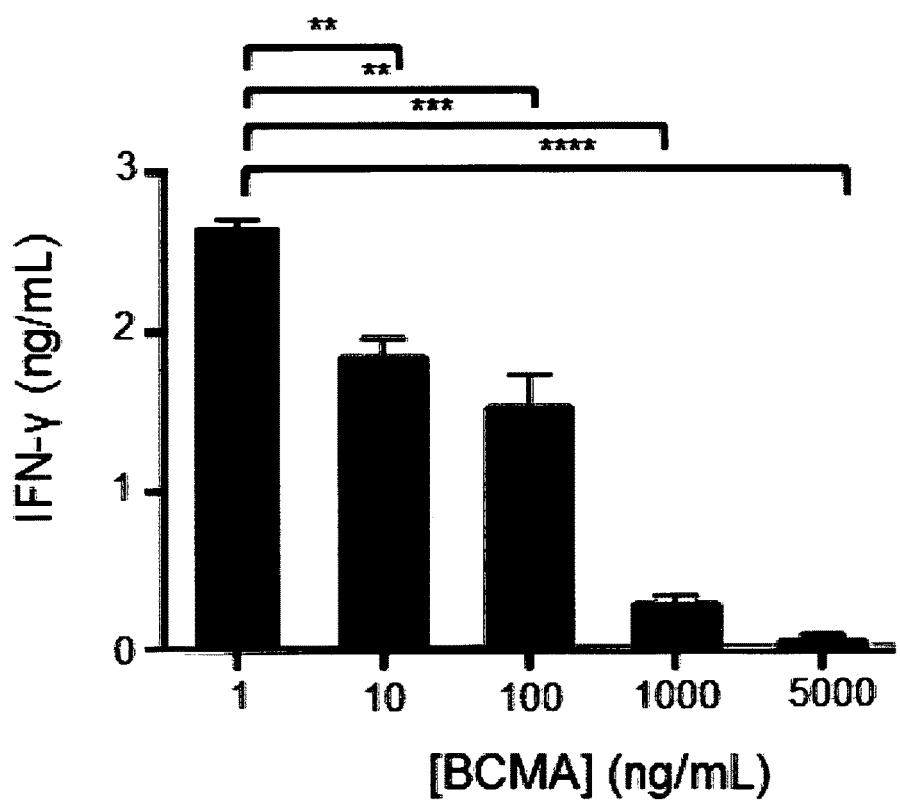
Figure 2J:
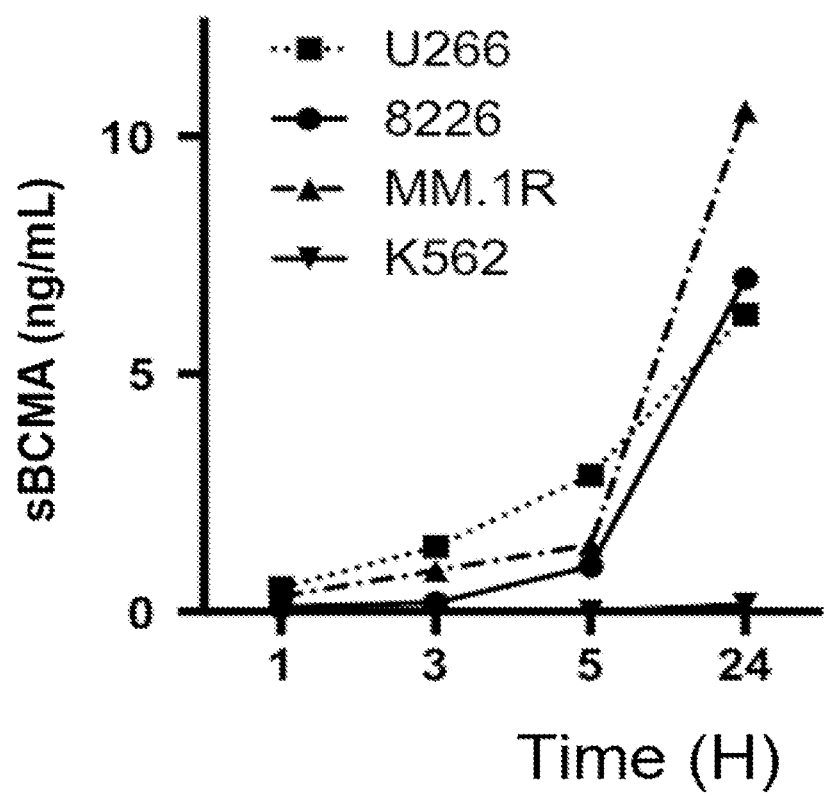
Figure 2K:
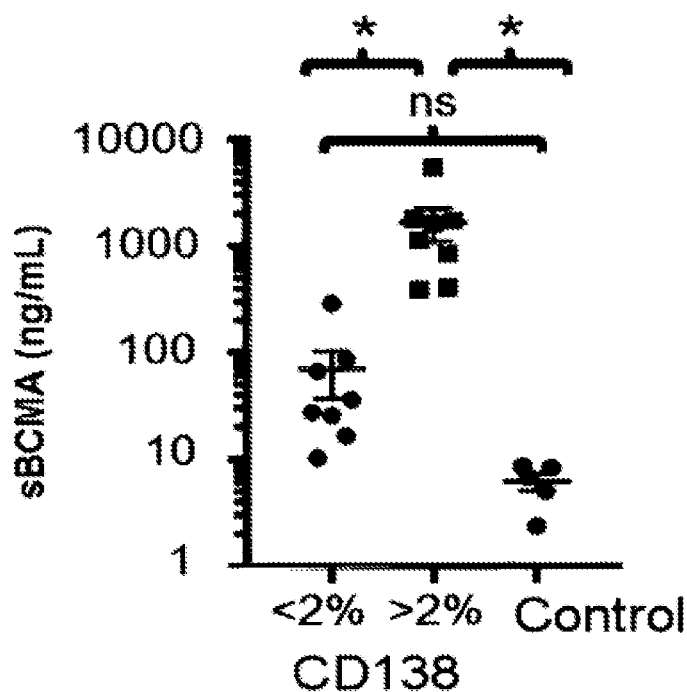
Figure 2L:
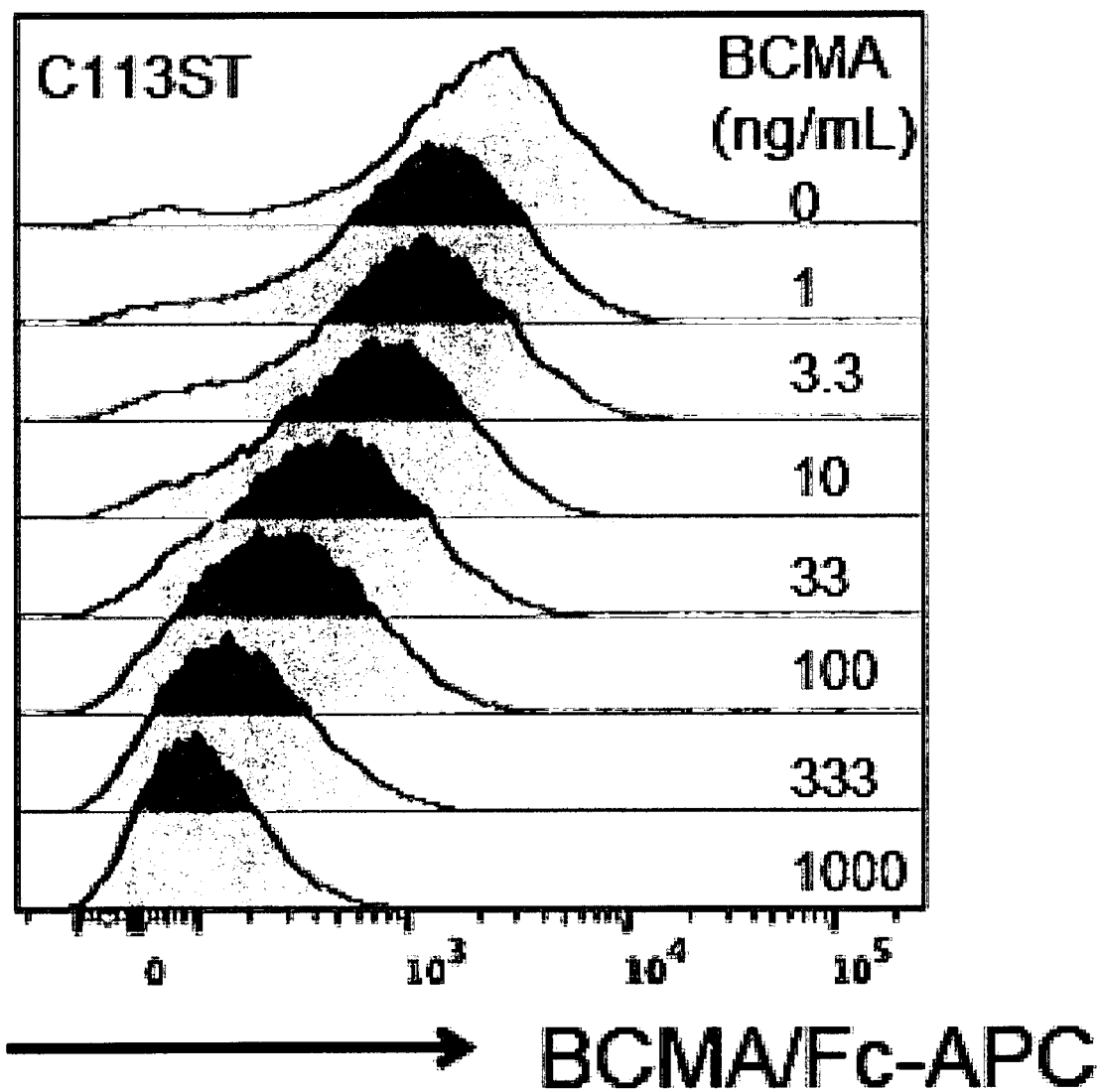
Figure 2M:
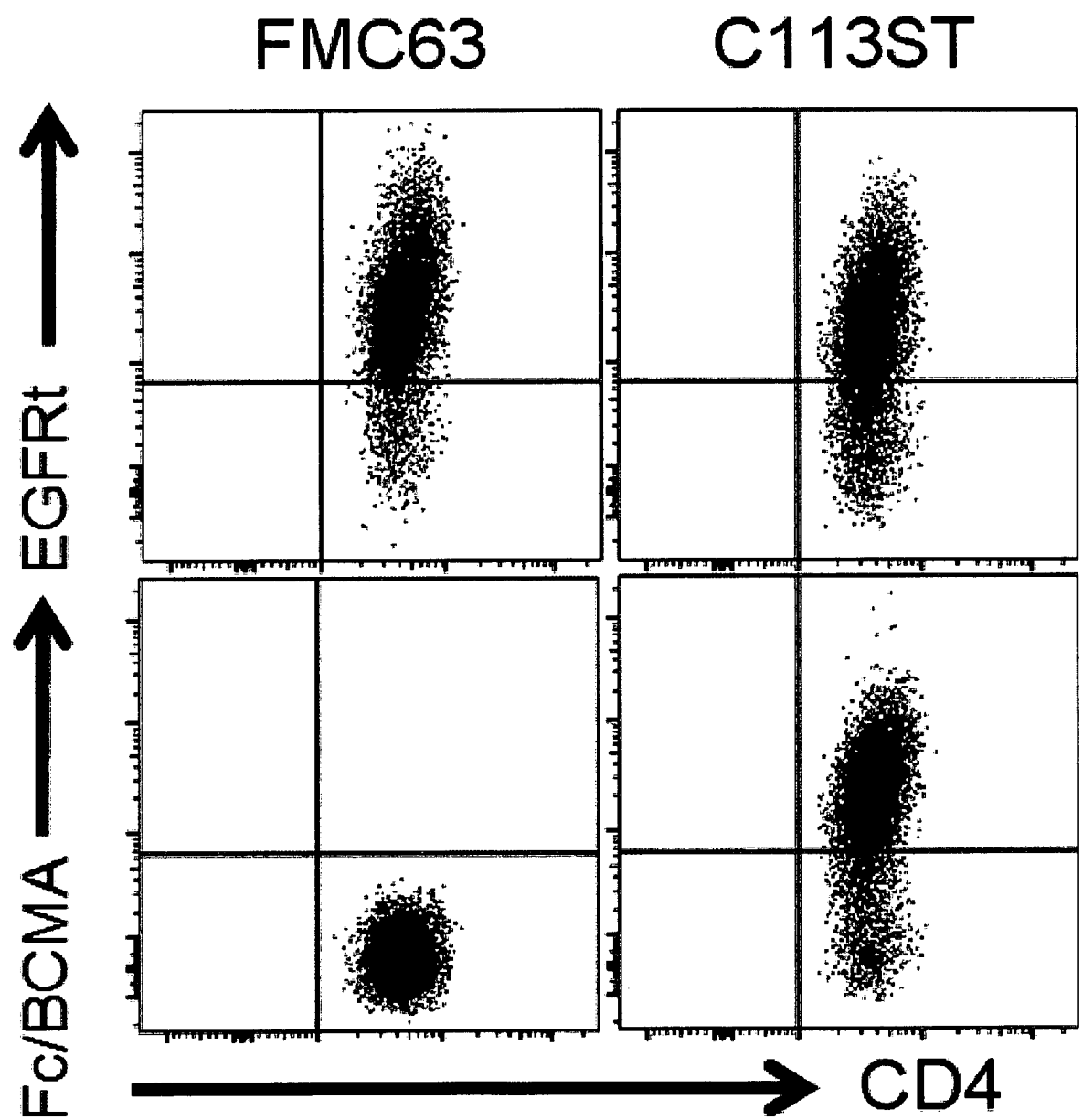
Figure 2N:
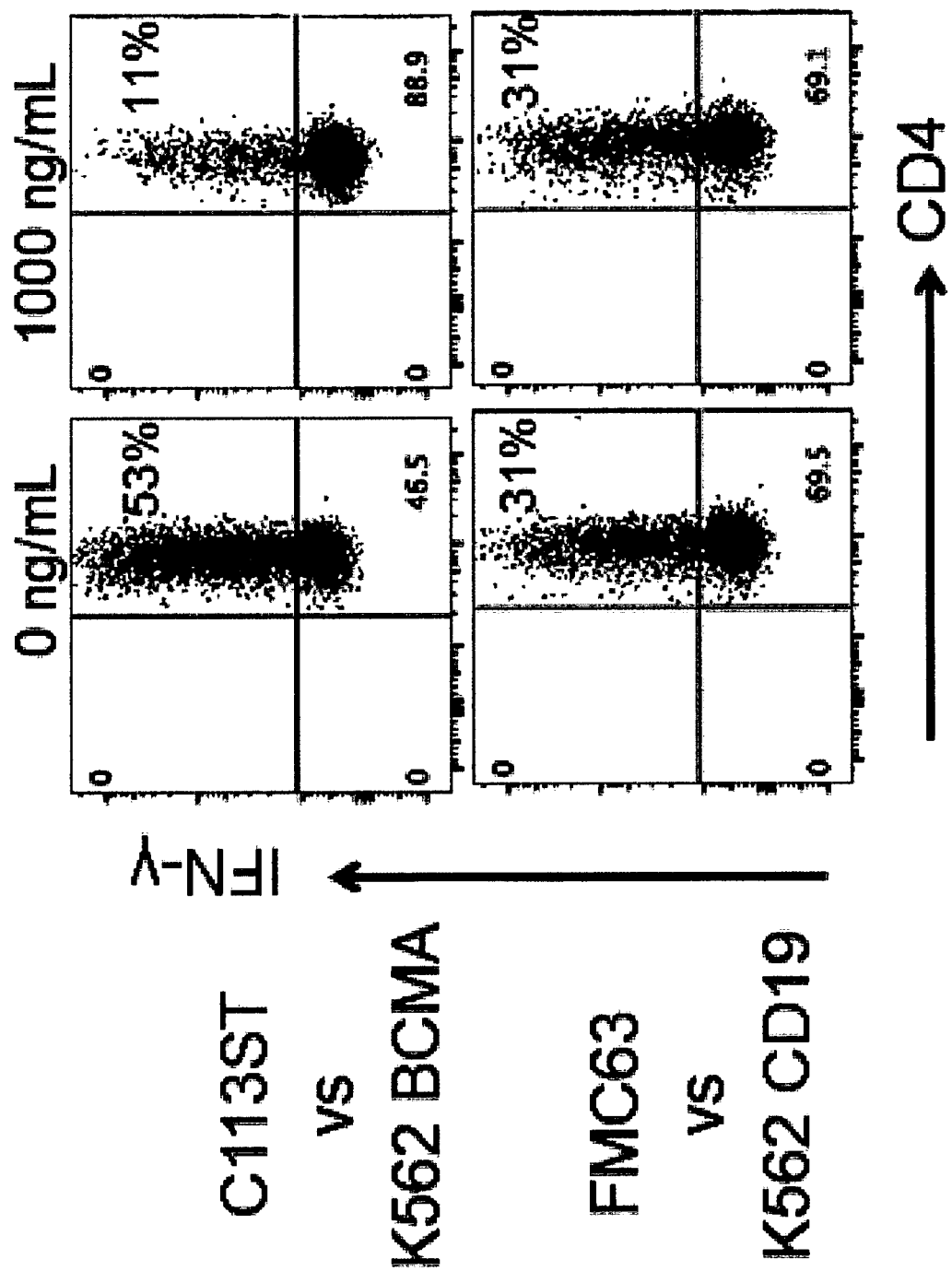
Figure 2O:
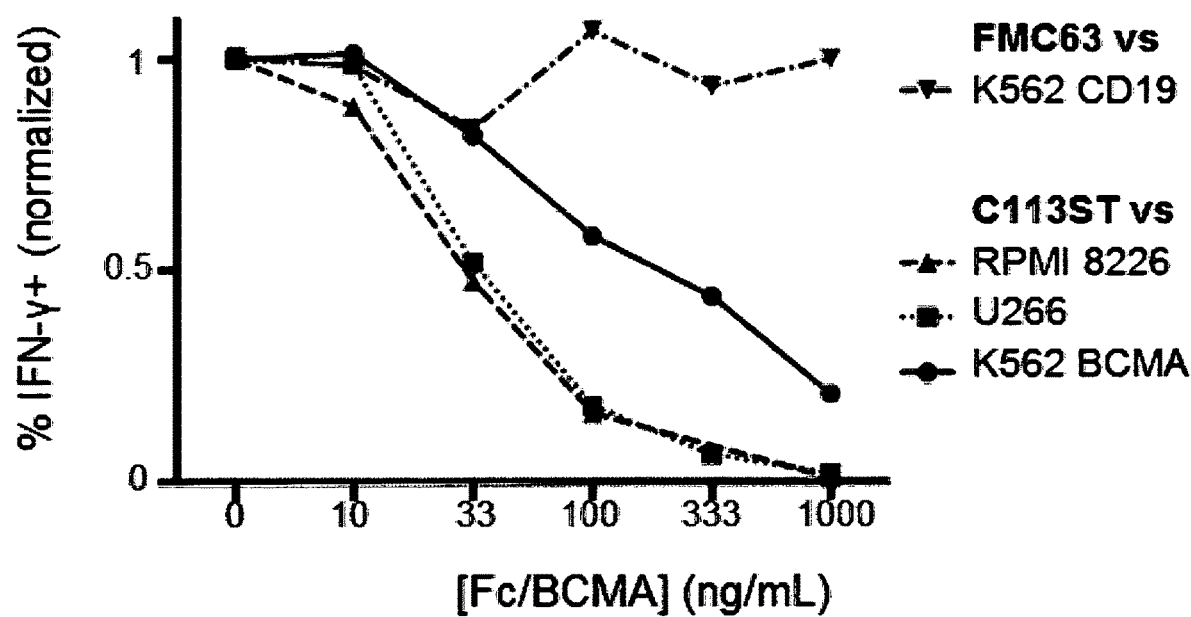
Figure 2P:
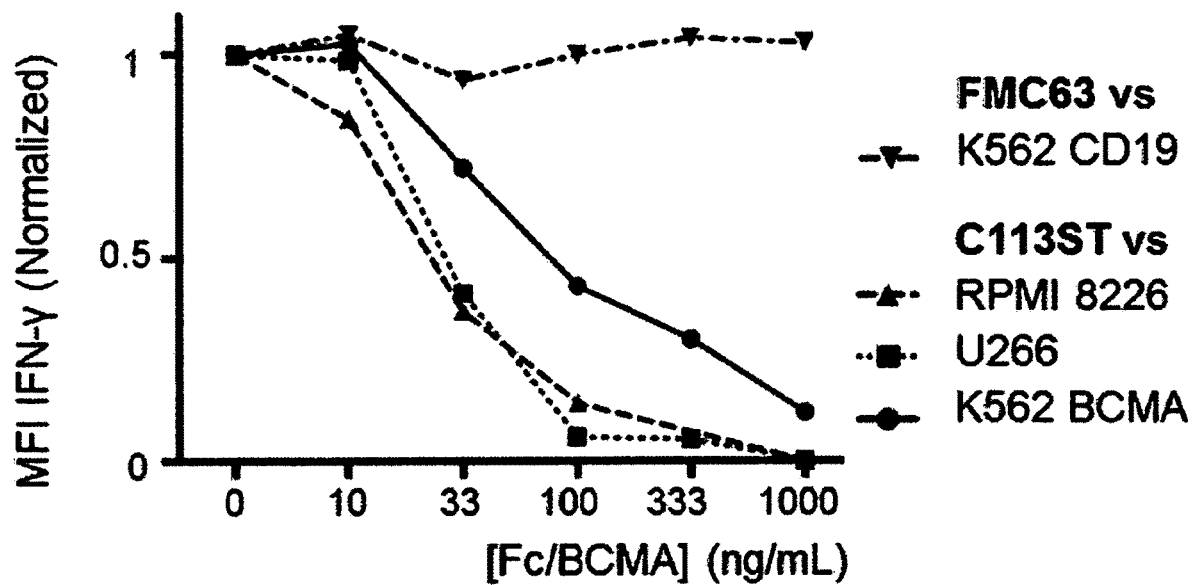
Figure 2Q:
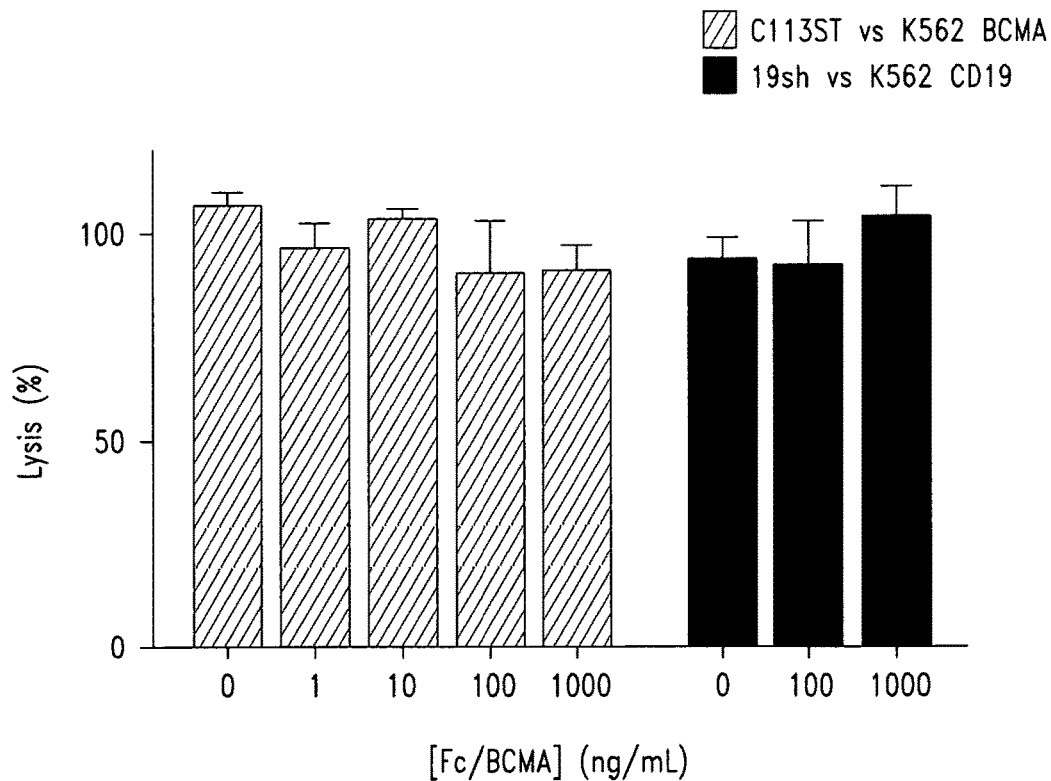

FIGS. 2A-2Q show the production of BCMA and PD-L1 by multiple myeloma (MM) cells in culture and the effect of soluble BCMA, surface-bound BCMA, and surface-bound PD-L1 on the ability of anti-BCMA T-ChARM-T cells to recognize the tumor cells and produce IFN-γ.

(A) U266 myeloma cells were washed and plated in culture media for 1, 3, 5 and 24 hours. The media supernatant was harvested and assayed for soluble BCMA by ELISA. The data shows a time dependent increase in soluble BCMA (sBCMA) levels in the supernatant.

(B) Histograms showing BCMA expression by reference MM cells (RPMI 8226) or by exemplary patient primary MM cells having high (Pt. 1), intermediate (Pt. 2), or low/negative expression (Pt. 3) as measured by ELISA (black=anti-BCMA antibody; grey line=isotype control).

(C) Chart showing percentages of myeloma patients (n=19) having high, intermediate, or low/negative BCMA expression in MM cells.

(D) IFN-γ production by anti-BCMA C11 T-ChARM+ CD8+ T cells in response to stimulation with patient MM cells with high (left, n=5) or low (right, n=4) BCMA expression (24 h at 2:1 E:T (ELISA)). Significance was tested using an unpaired two-tailed T test and bars represent average IFN-γ production+SEM.

(E) Histograms showing PD-L1 expression by RPMI 8226 myeloma cells (left-most panel) and primary MM cells from 3 patients having high, low/negative, or intermediate PD-L expression, as measured by ELISA (diagonal shading=staining with anti-PD-L1 antibody; empty histogram=isotype control).

(F) Chart showing percentage of patients (n=19) having high, intermediate, or low/negative PD-L1 expression in MM cells.

(G) IFN-γ production by anti-BCMA C11 T-ChARM+ CD8+ cells of this disclosure in response to patient MM cells with high (left, n=4) or low (right, n=5) PD-L1 expression (24 h at 2:1 E:T (ELISA)). Significance was tested using an unpaired two-tailed T test and bars represent average IFN-γ production+SEM.

(H) IFN-γ production by BCMA-specific T-ChARM T cells in the presence of exogenous soluble BCMA. sBCMA was added to co-cultures of T cells expressing a BCMA-specific T-ChARM and K562 cells transduced with a polynucleotide encoding full-length BCMA (K562/BCMA+). There is a dose-dependent inhibition of BCMA-specific T-ChARM T cell effector function as measured by IFN-γ release into the media supernatant.

(I) Data from another dose-titration experiment showing the effect of sBCMA on IFN-γ production by BCMA-specific T-ChARM T cells recognizing K562 BCMA+ cells, which included adding sBCMA to culture at another, higher concentration (5000 ng/mL).

(J) Shedding of BCMA by the indicated MM cells cultured in vitro.

(K) sBCMA measured in bone marrow (BM) sera from patients with lower (<2% CD138+ cells) or higher (>2% CD138+ cells) disease burden.

(L) sBCMA binding to C113ST-ChARM T cells of this disclosure. T cells were incubated with the indicated levels of recombinant sBCMA (right side of diagram) and then stained with a BCMA-Fc fusion that was conjugated to APC.

(M) Flow cytometry data showing surface staining (APC-conjugated BCMA-Fc and anti-EGFRt antibody) and CD4 expression of C113ST T-ChARM and FMC63 CAR-T cells.

(N) Flow cytometry data showing IFN-γ production (y-axis) and CD4 expression (x-axis) by T cells expressing either a C113ST-ChARM ("C113ST") of this disclosure or a control anti-CD19 CAR ("FMC632"), in co-culture with target-expressing K562 cells and administered the BCMA-Fc fusion protein (left panels: 0 ng/ml BCMA-Fc; right panels: 1000 ng/ml BCMA-Fc.

(O) Dose titration showing IFN-γ release by CAR T cells in response to target cell lines as indicated in the presence or absence of exogenous recombinant BCMA (BCMA-Fc fusion). FMC63 (anti-CD19) vs. K562 CD19+ (control; downward-facing triangle); C113ST T-ChARM T cells vs. RPMI 8226 (upward-facing triangle), U266 (square), and K562 BCMA+ cells (circle). Data is representative of 2 independent experiments. Bars represent mean+SEM. P-value=<0.05, as determined by one-way ANOVA with post-test. MFI=mean fluorescence intensity.

(P) IFN-γ production (normalized Mean Fluorescence Intensity, MFI) by the T cells shown in FIG. 2O in co-culture with indicated antigen-expressing cells and in the presence or absence of BCMA-Fc (x-axis).

(Q) Cytolytic activity of CD8+ C113ST T-ChARM T cells against K562 BCMA+ target cells and of FMC63 CAR-T cells against K562 CD19+ target cells at varying concentrations of recombinant BCMA, analyzed by a 4 h CRA at E:T ratio of 10:1. Data is representative of 2 independent experiments. Bars represent mean+SEM. P-value=<0.05, as determined by one way ANOVA with post-test. MFI=mean fluorescence intensity.

Figure 3A:
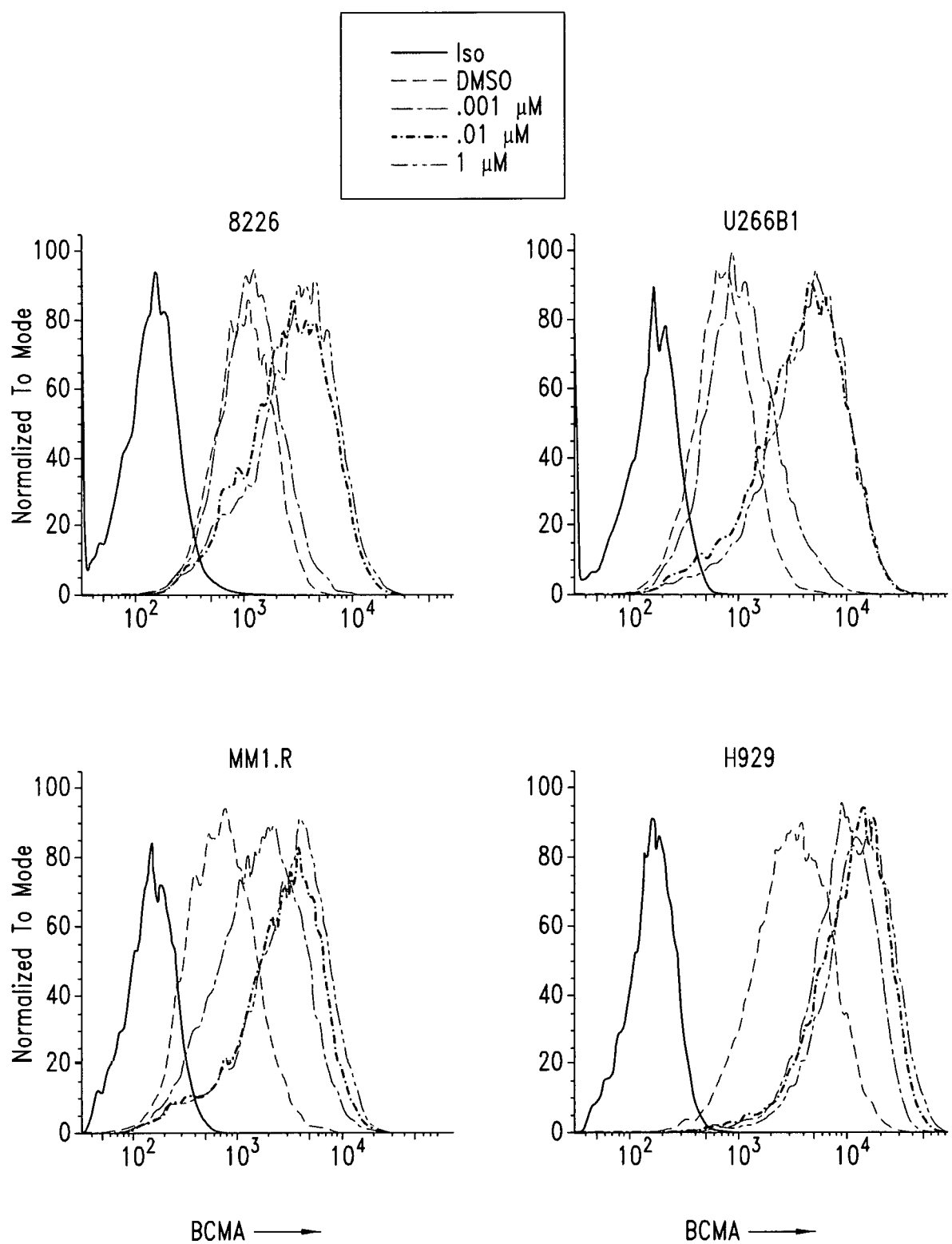
Figure 3B:
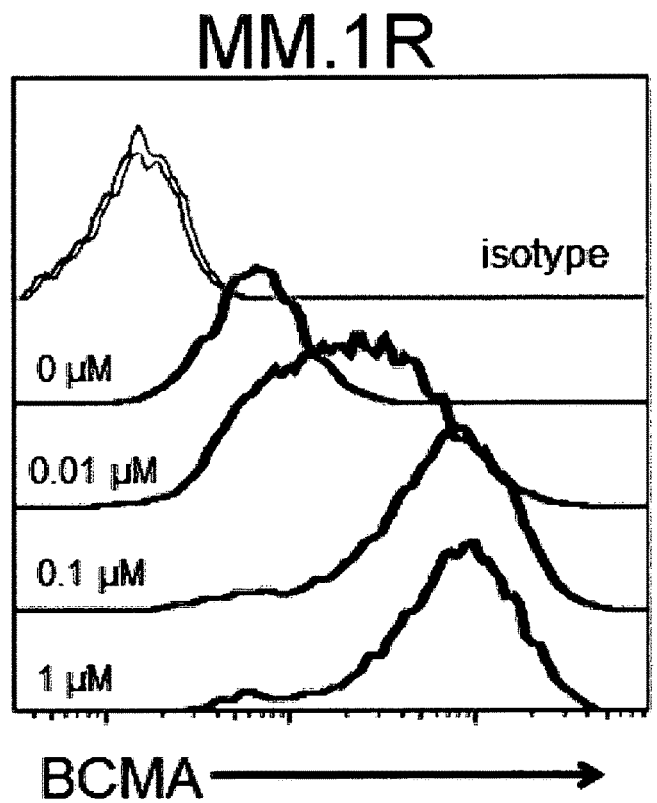
Figure 3C:
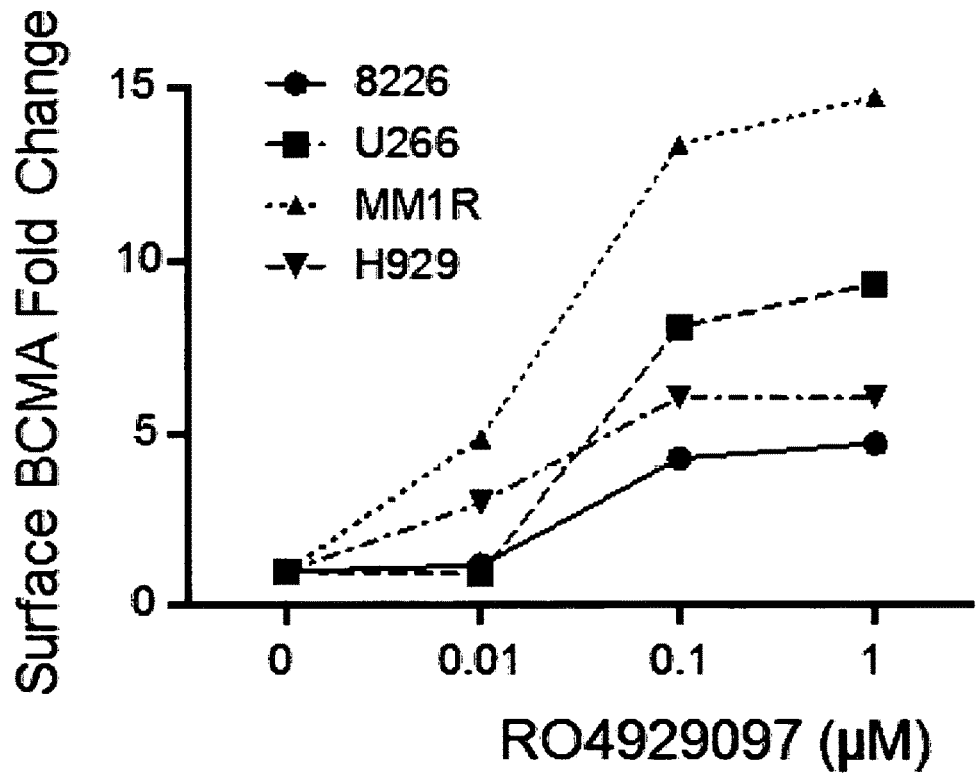
Figure 3D:
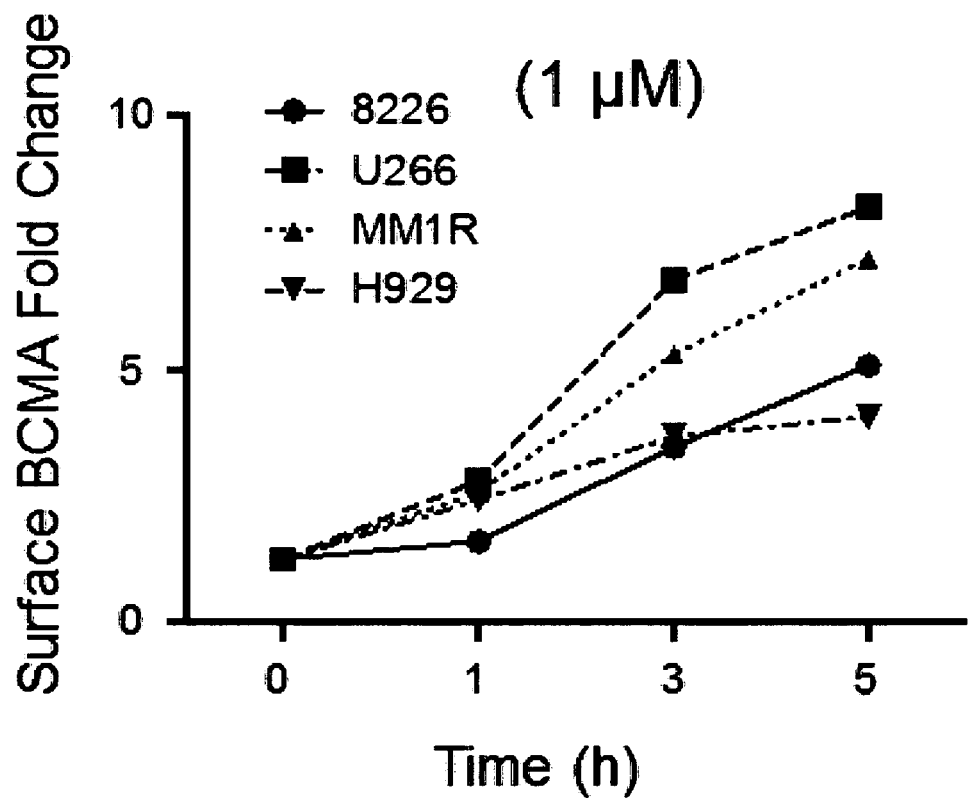
Figure 3E:
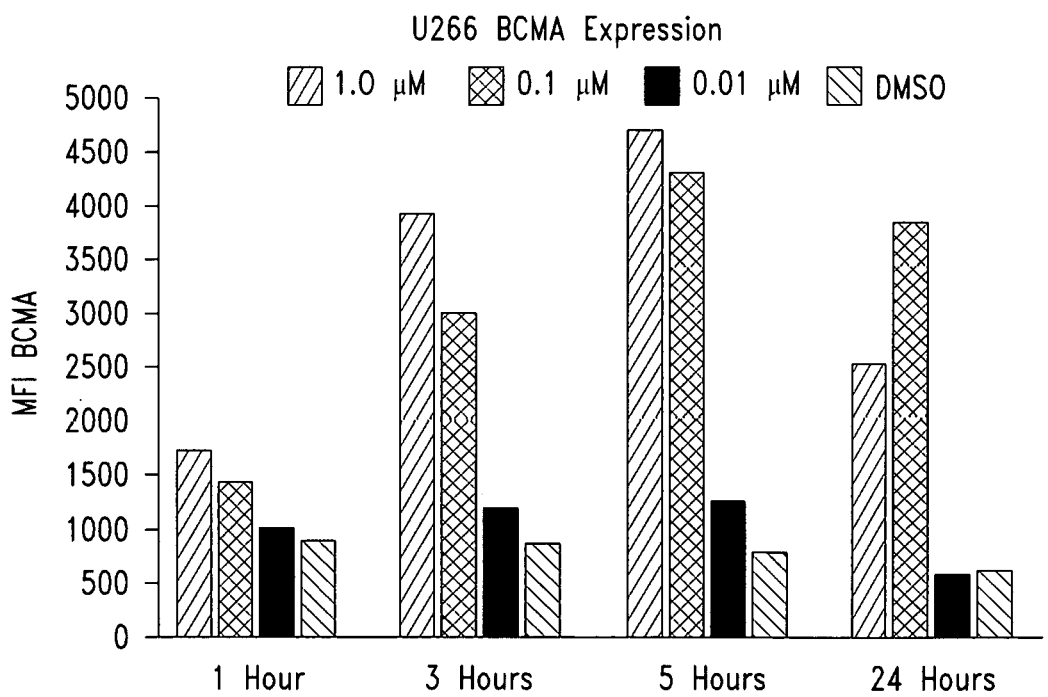
Figure 3F:
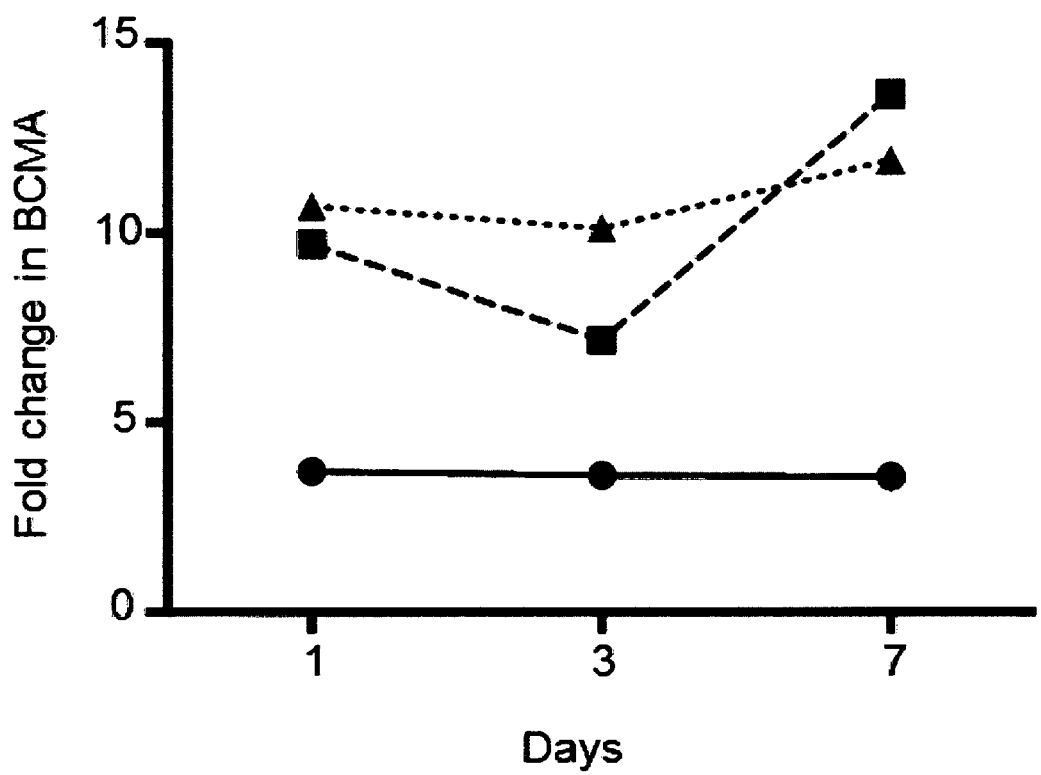
Figure 3G:
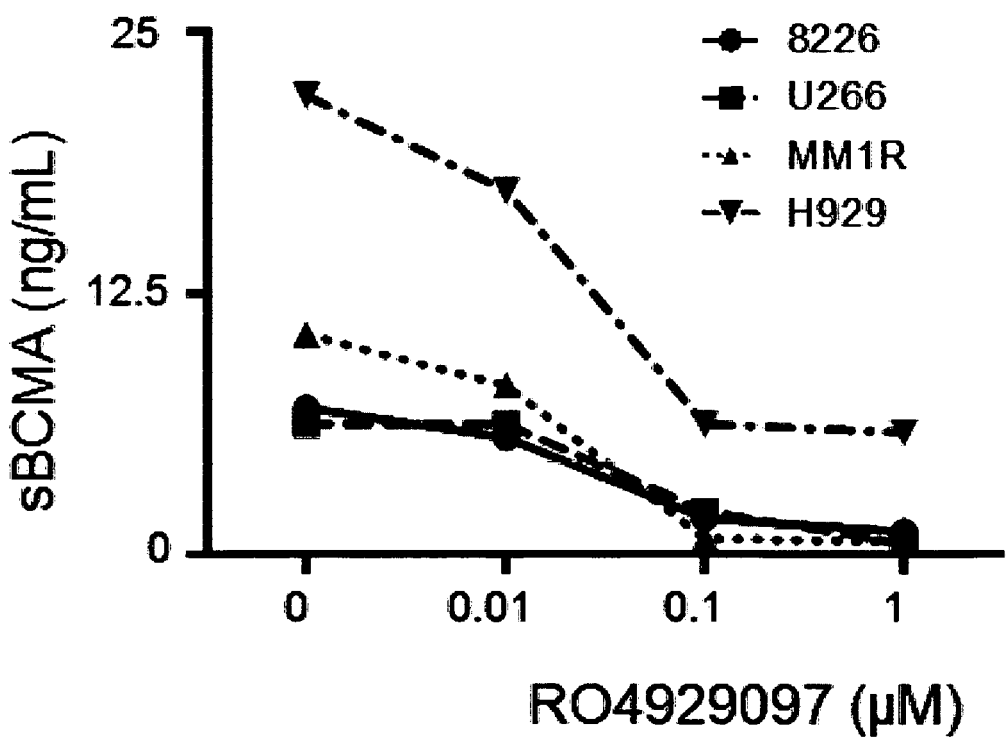
Figure 3H:
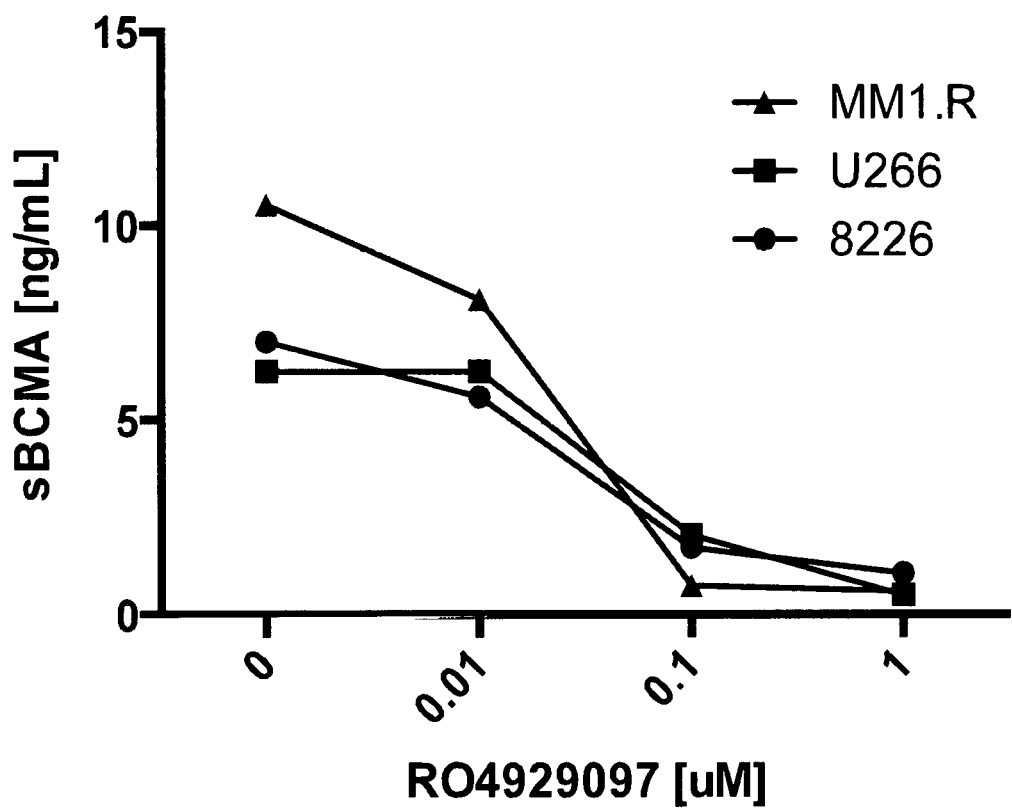
Figure 3I:
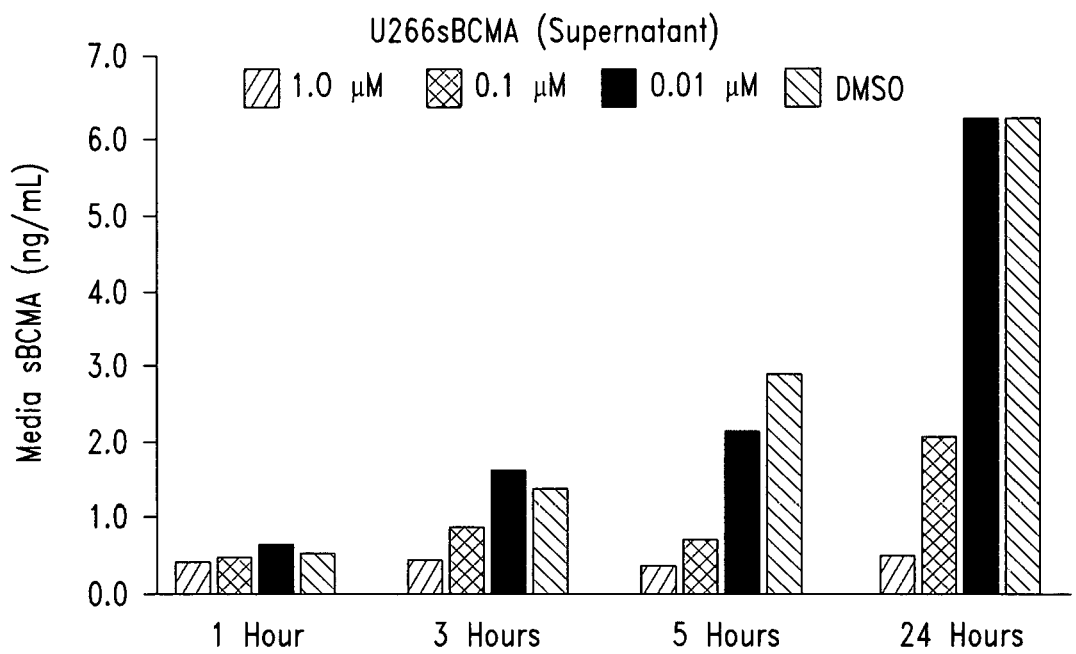
Figure 3J:
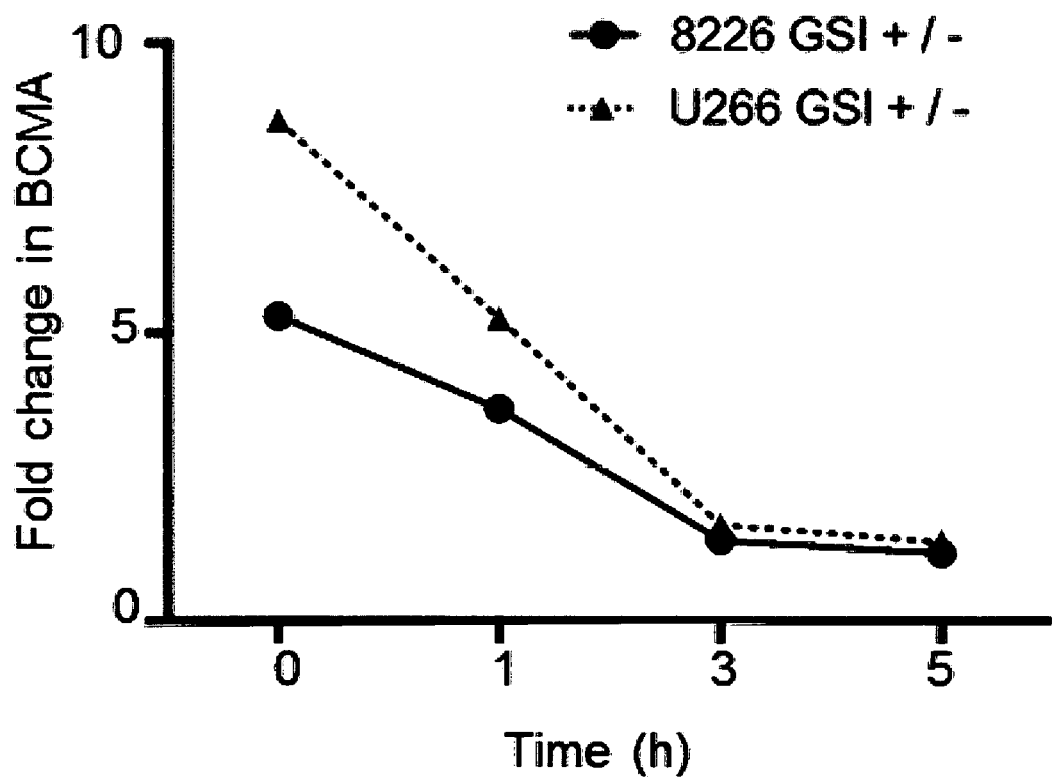
Figure 3K:
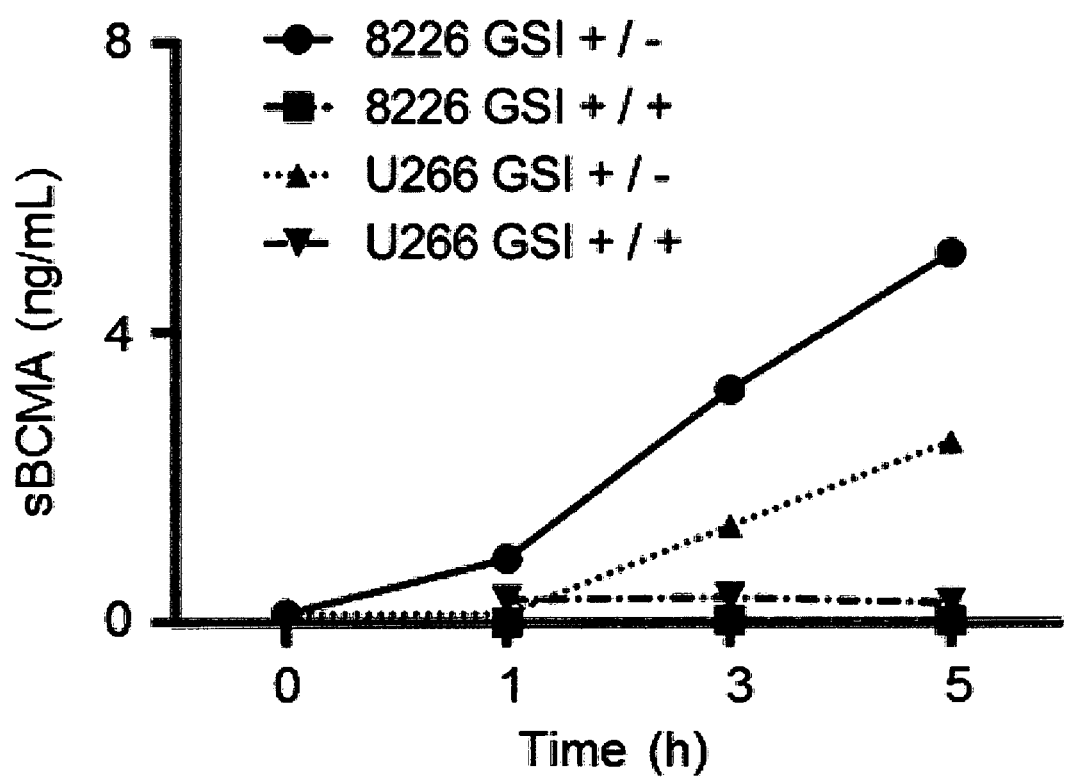
Figure 3L:
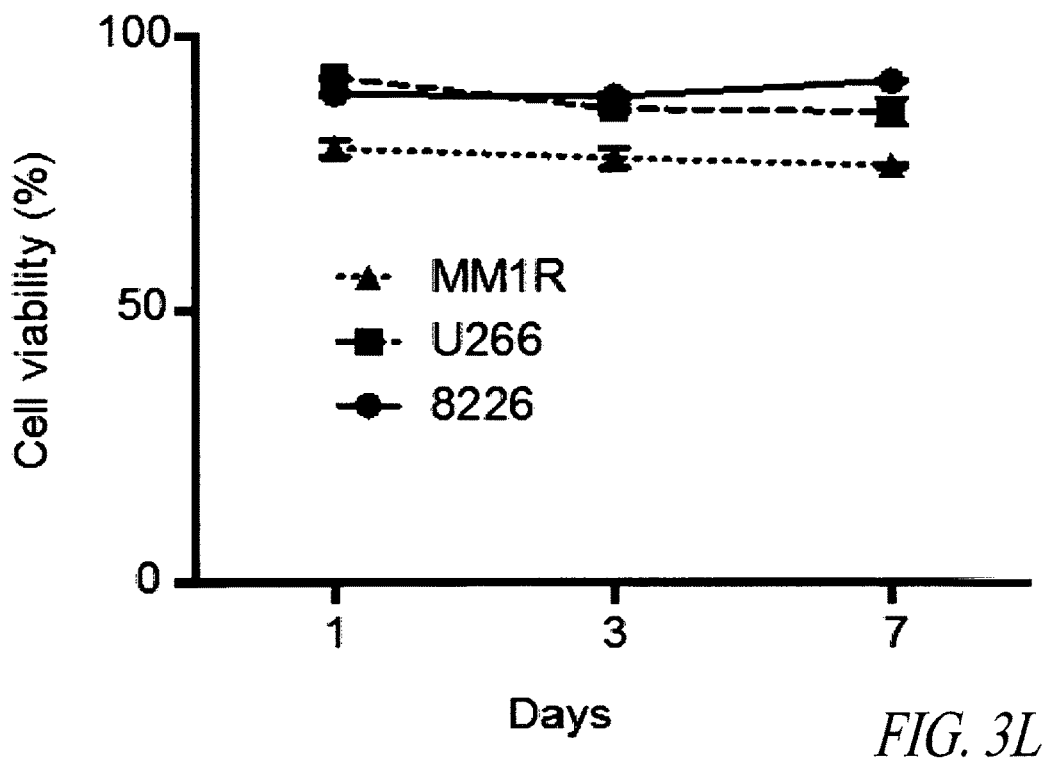
Figure 3M:
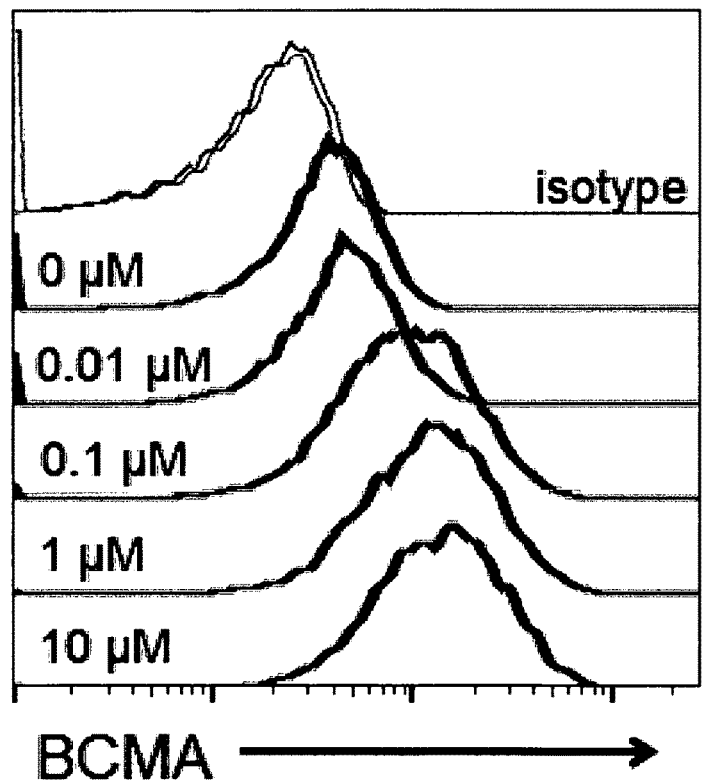
Figure 3N:
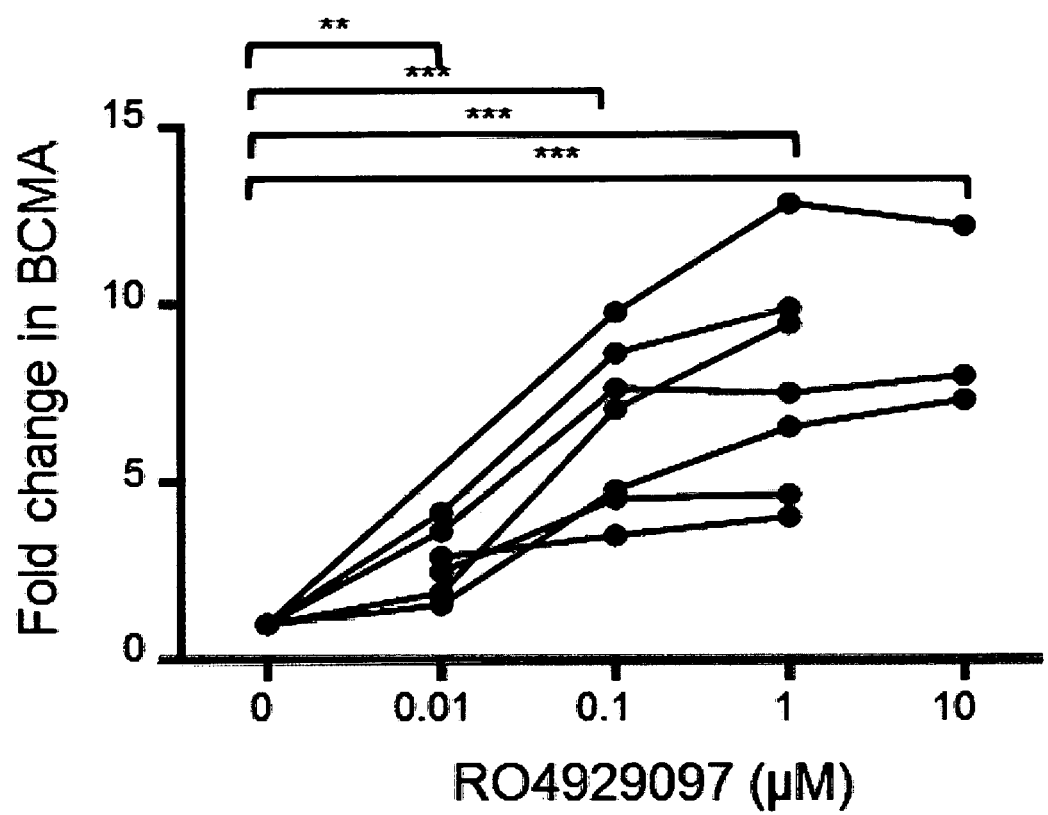
Figure 3P:
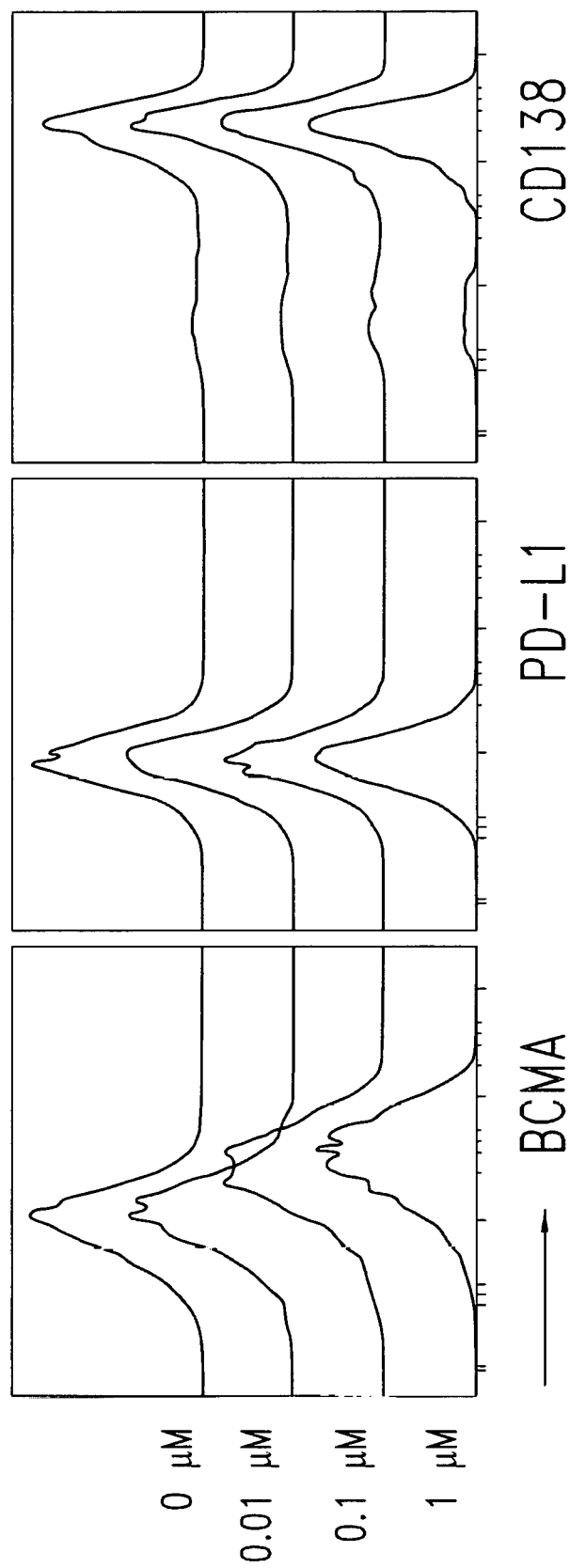
Figure 3Q:
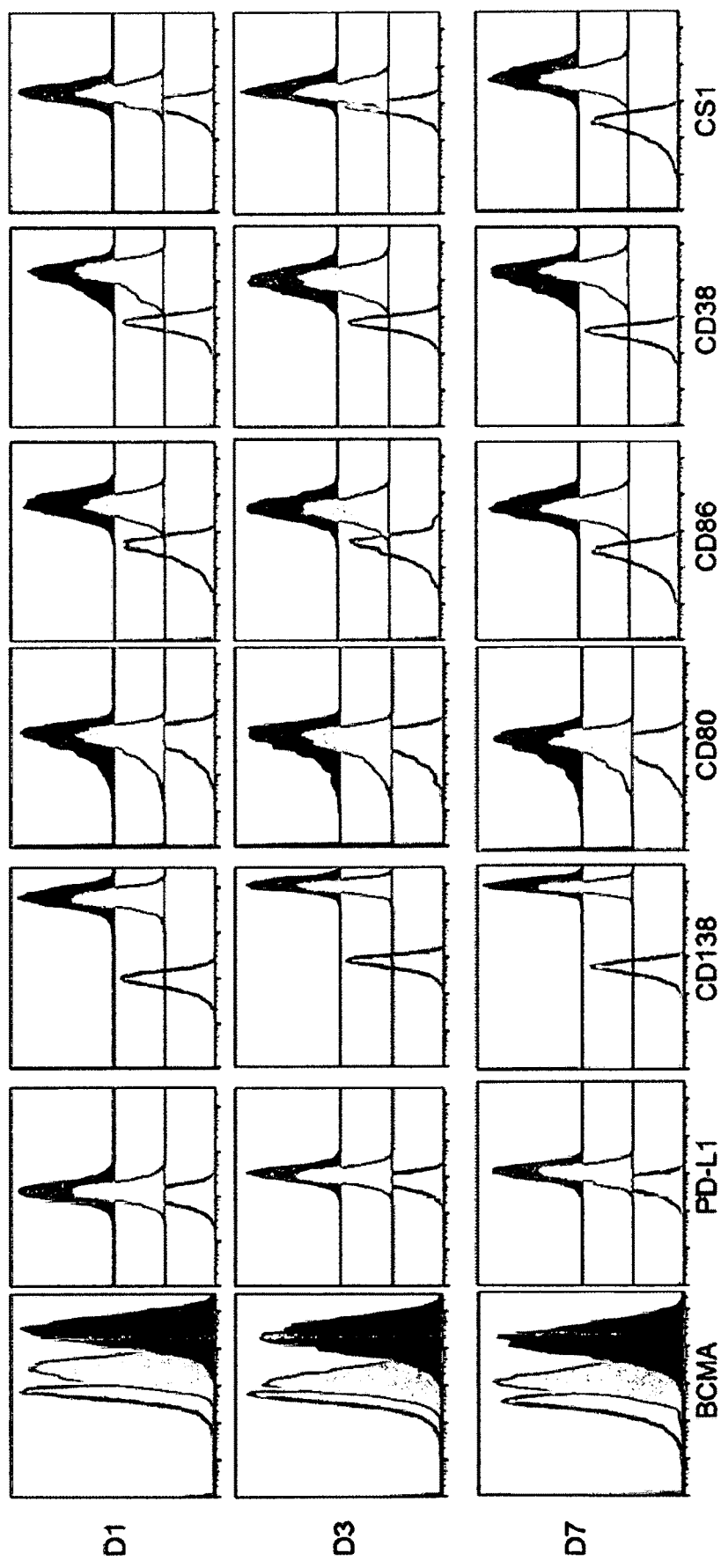
Figure 3R:
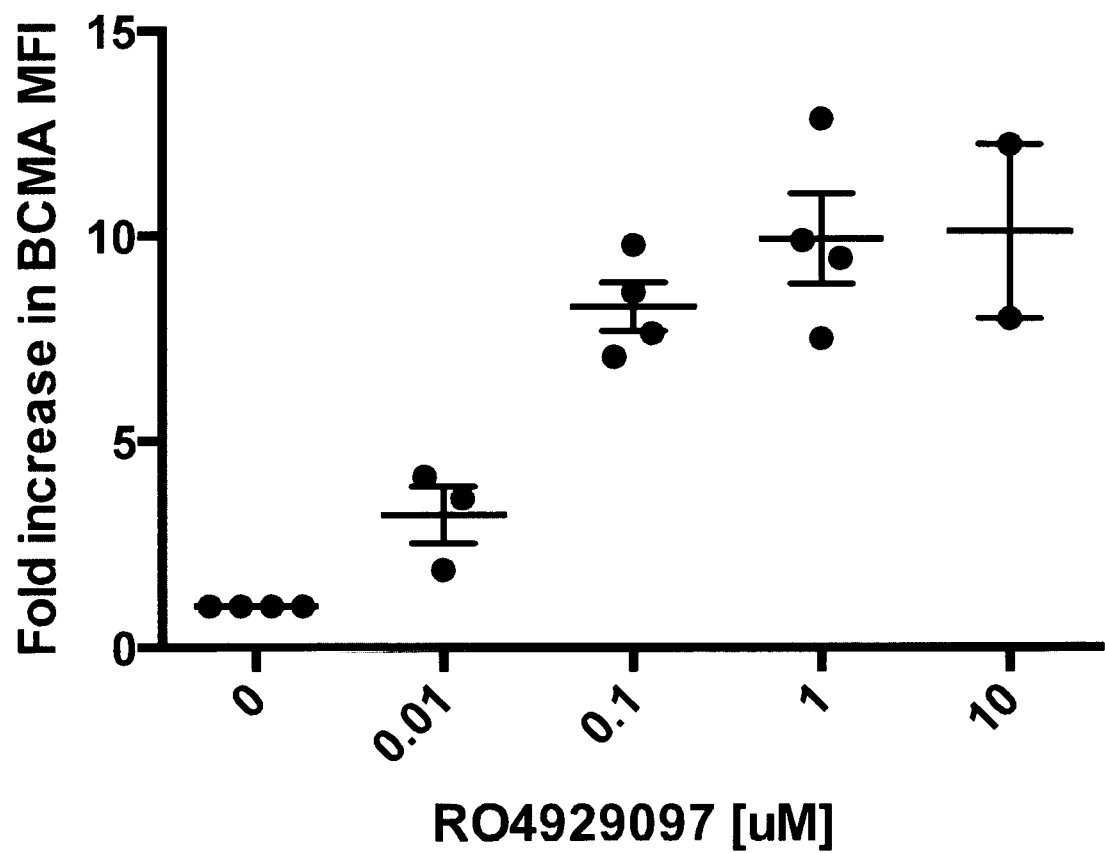

FIGS. 3A-3R show the effect of γ-secretase inhibitor (GSI) RO4929097 on levels of cell surface BCMA and other cell surface molecules on myeloma cell lines or primary myeloma cells.

(A) Cell surface BCMA was measured on four myeloma cell lines (8226, U266B1, MM1.R, H929) by flow cytometry with an anti-BCMA monoclonal antibody before, and 5 hours after (see diagrams), incubation of the myeloma cell lines with GSI RO4929097 in a range of concentrations from 0 µM (DMSO control) to 1.0 µM.

(B) Surface BCMA expression by MM.1R cells cultured with the indicated concentrations of RO4929097; staining with anti-BCMA antibody (black lines) compared to isotype control (grey line).

(C) Fold-change in surface BCMA expression by MM cell lines when cultured with the indicated concentrations of RO4929097; fold change indicated relative to untreated MM cells of the same line.

(D) Fold-change kinetics of surface BCMA expression over time by the indicated MM cells in culture with 1 µM RO4929097.

(E) U266 myeloma cells were incubated for 1, 3, 5 and 24 hours in the presence of various concentrations of GSI RO429097 (0.01 µM, 0.1 µM and 1.0 µM) and evaluated for surface BCMA expression by flow cytometry. BCMA expression increased in a dose-dependent manner in the presence of the GSI with the peak increase observed after 5 hours of exposure.

(F) Fold change of surface BCMA expression on cell lines (MM1R=triangle; U266=square; 8226=circle) cultured in 1 µM GSI over time. GSI was re-administered as a half media change every 2 days. Fold change in BCMA is defined as Treated (MFIBCMA-MFIiso)/Control (MFIBCMA-MFIiso). Data is representative of at least 2 independent experiments.

(G, H) Culture supernatant concentration of sBCMA in MM cell line cells cultured in the presence of indicated concentrations of RO4929097.

(I) U266 myeloma cells were washed and plated in culture media in the presence of various concentrations of GSI RO429097 (0.01 µM, 0.1 µM and 1.0 µM). The media supernatant was harvested after 1, 3, 5 and 24 hours and assayed for soluble BCMA (sBCMA) by ELISA. The data shows that the amount of BCMA released from the tumor cells into the supernatant over time was decreased when a GSI was present at a concentration of at least about 0.01 µM.

(J, K) Fold change in BCMA expression (J) and supernatant sBCMA concentrations (K) at various time points after 1 µM GSI had been removed from myeloma cell line cultures (GSI +/−) as compared to cultures with continued presence of GSI (GSI +/+).

(L) Viability of indicated MM-expressing cells as measured by propidium iodide staining of cell lines cultured in 1 µM GSI.

(M) Surface BCMA expression by primary patient MM cells cultured with the indicated concentrations of RO4929097. Staining was as described in regard to FIG. 3B.

(N) Fold change in BCMA on primary myeloma cells (n=7) cultured with vary amounts of GSI for 4 h. Primary and cell lines were cultured at 0.5×106 cells/mL. Fold change in BCMA is defined as Treated (MFIBCMA-MFIiso)/Control (MFIBCMA-MFIiso). Data is representative of 3 independent experiments with T cells derived from different donors.

(O, P) Co-culture of primary myeloma cells with various concentrations of GSI for 4 hours does not affect the levels of several other cell surface molecules on tumor cells, including CS1, CD86, PD-L1, CD80 and CD38.

(Q) Staining of various surface markers on MM1R cells in the presence (black) or absence (gray) of 1 µM GSI in culture media. Isotype staining is shown as open plot.

(R) CD138+ primary myeloma cells were enriched from patient bone marrow samples, incubated for 3 hours in the presence of various concentrations of GSI RO429097 (0.01 µM to 10 µM) and evaluated for surface BCMA expression by flow cytometry. BCMA mean fluorescence intensity (MFI) on tumor cells is presented as fold increase over that observed on tumor cells incubated without RO429097. There is an observed dose dependent upregulation of BCMA.

Figure 4A:
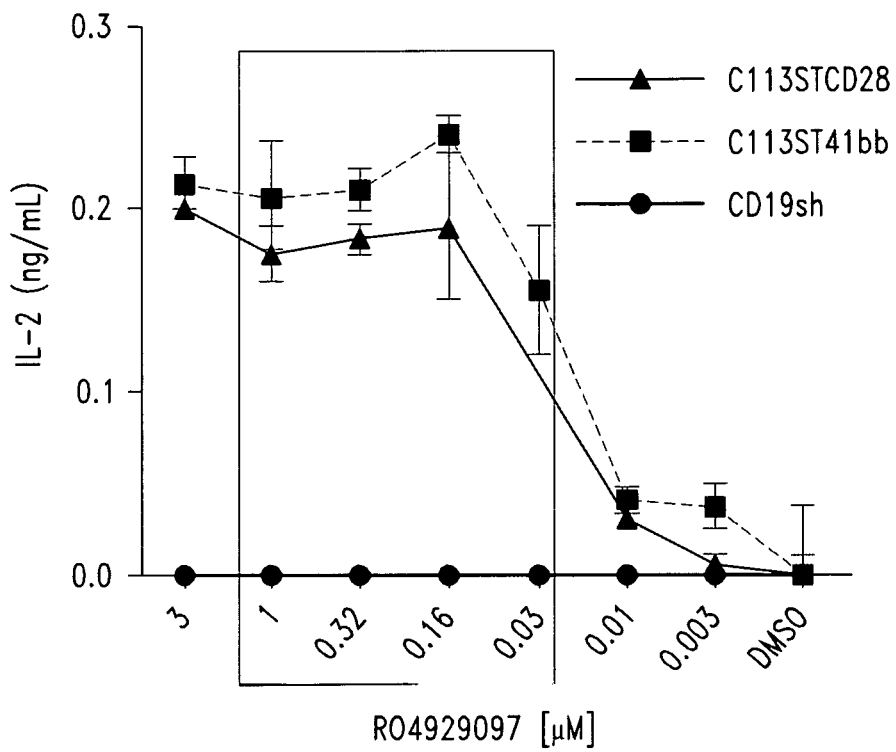
Figure 4B:
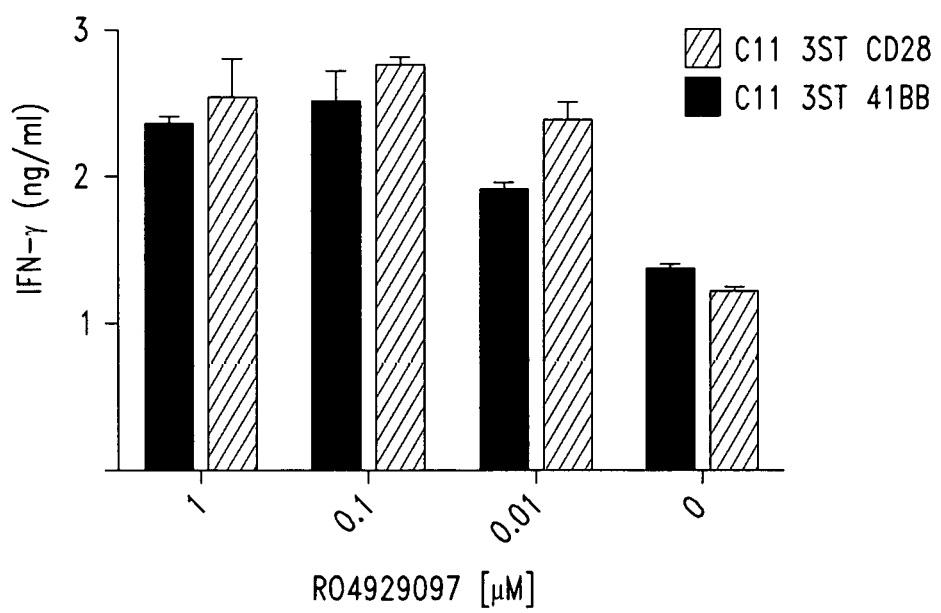
Figure 4C:
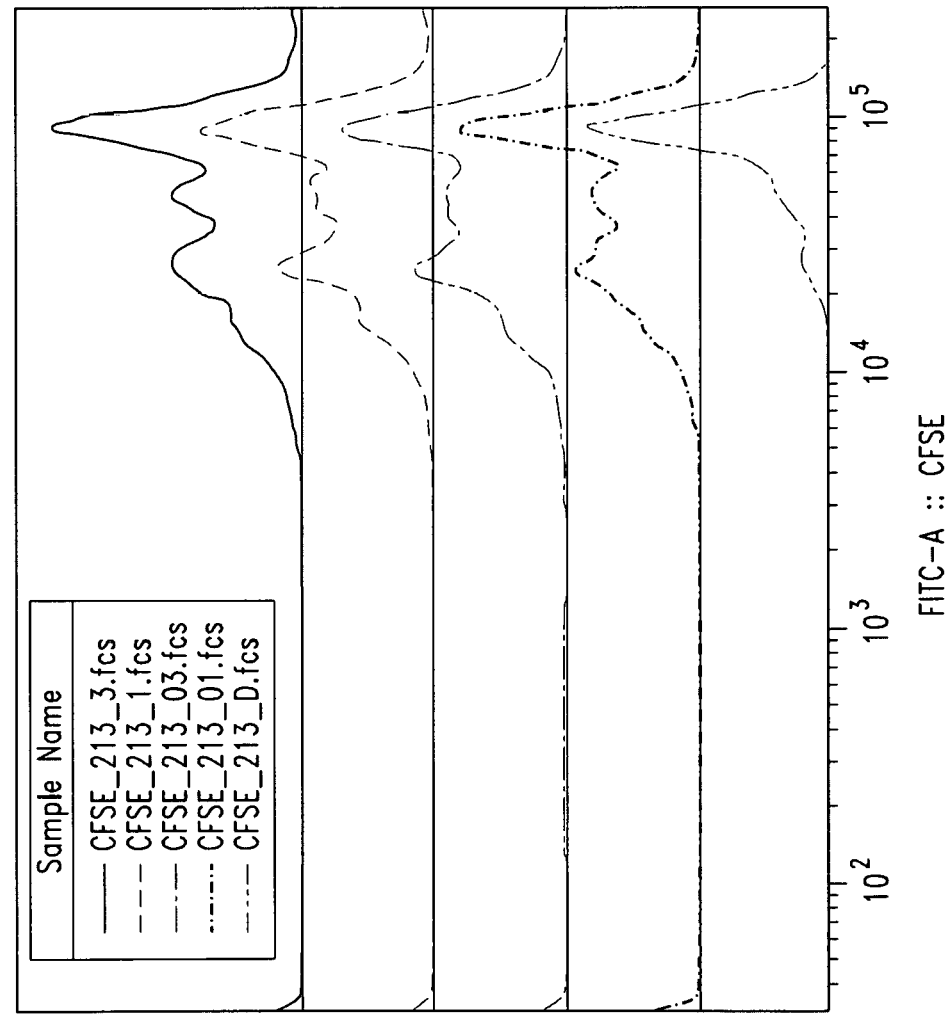

FIGS. 4A-4C show that cytokine release following recognition of primary myeloma cells by BCMA-specific CAR-T cells is increased when the myeloma cells are pre-treated with a GSI.

(A) IL-2 production by BCMA CAR-T cells (BCMA-specific T-ChARM C11 3ST-CD28 and BCMA-specific T-ChARM C11 3ST-41BB) or control CD19sh CAR (short spacer)-T cells co-cultured with primary human myeloma tumor cells for 24 hours alone or with various concentrations of GSI RO429097 (0.003 µM to 3.0 µM).

(B) IFN-γ production by BMCA T-ChARM T cells co-cultured with myeloma cells at various concentrations of RO429097.

(C) Proliferation of CFSE-labeled BCMA-specific T-ChARM T cells increased in a dose-dependent manner after co-culture for 3 days with primary human myeloma tumor cells in media alone or in media containing GSI RO492097 at the indicated concentrations.

Figure 5A:
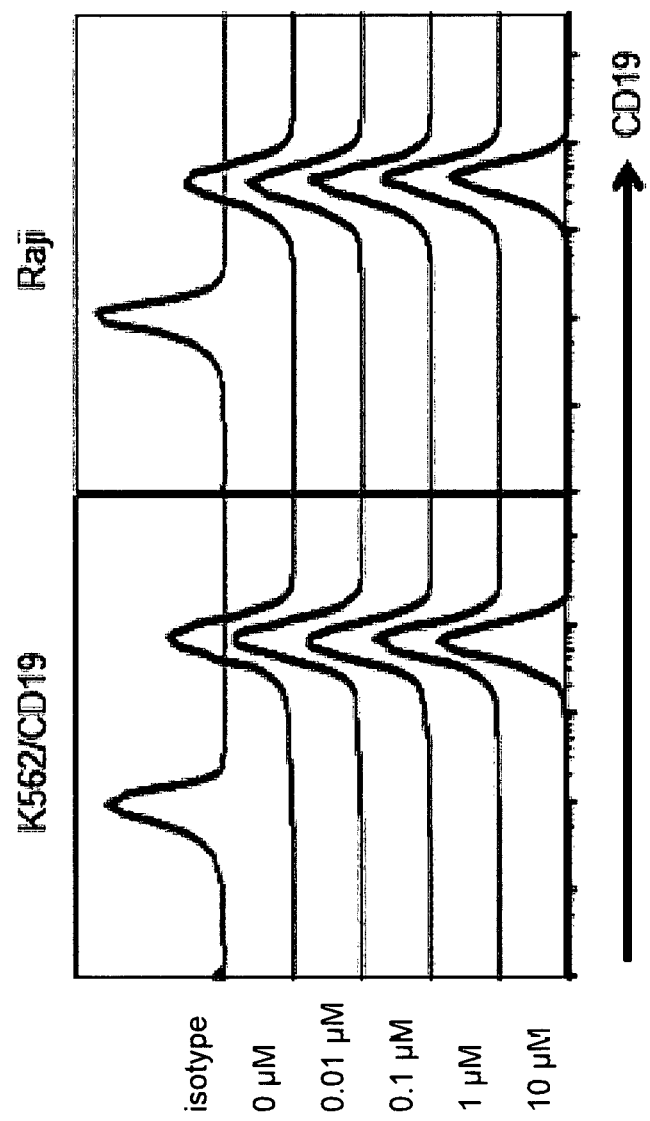
Figure 5B:
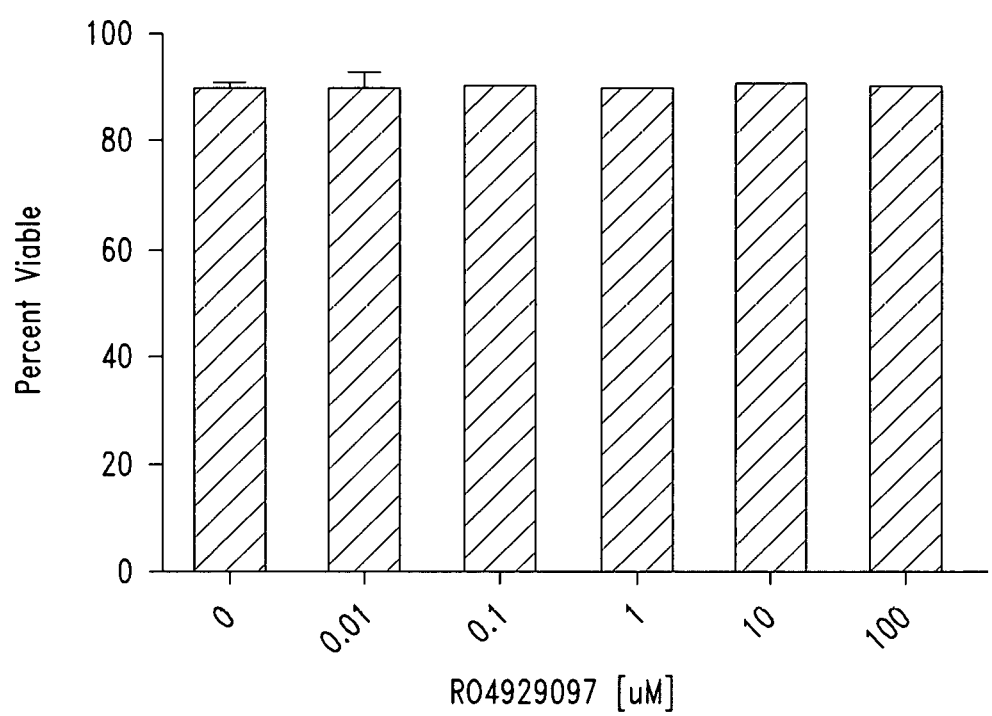
Figure 5D:
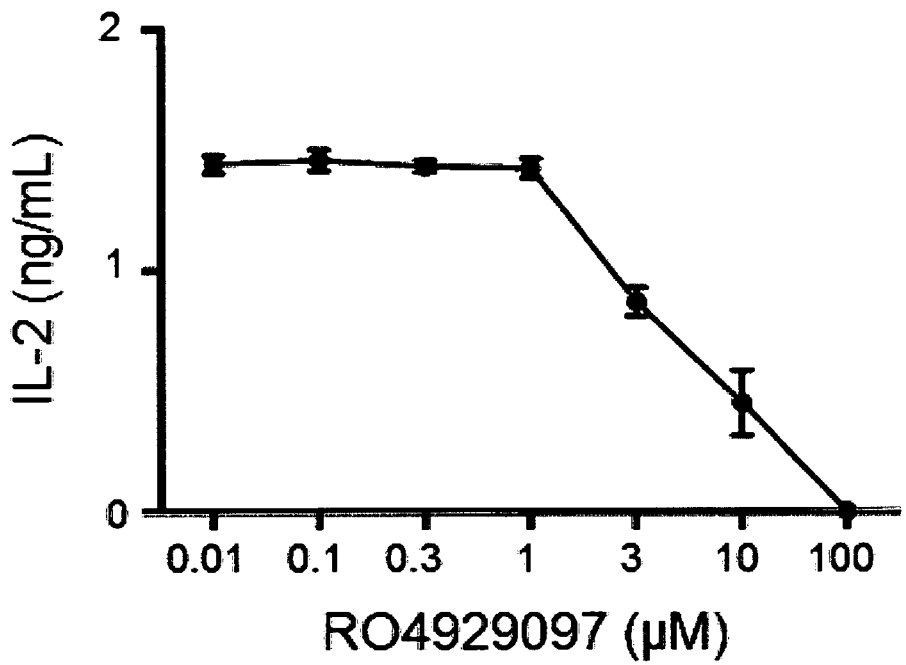
Figure 5E:
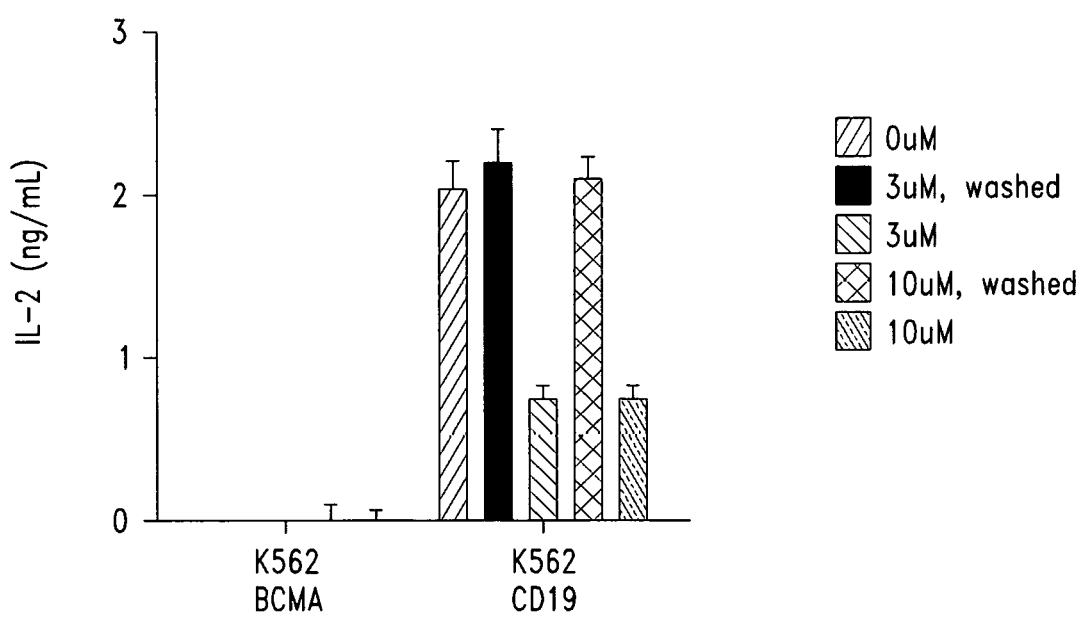
Figure 5F:
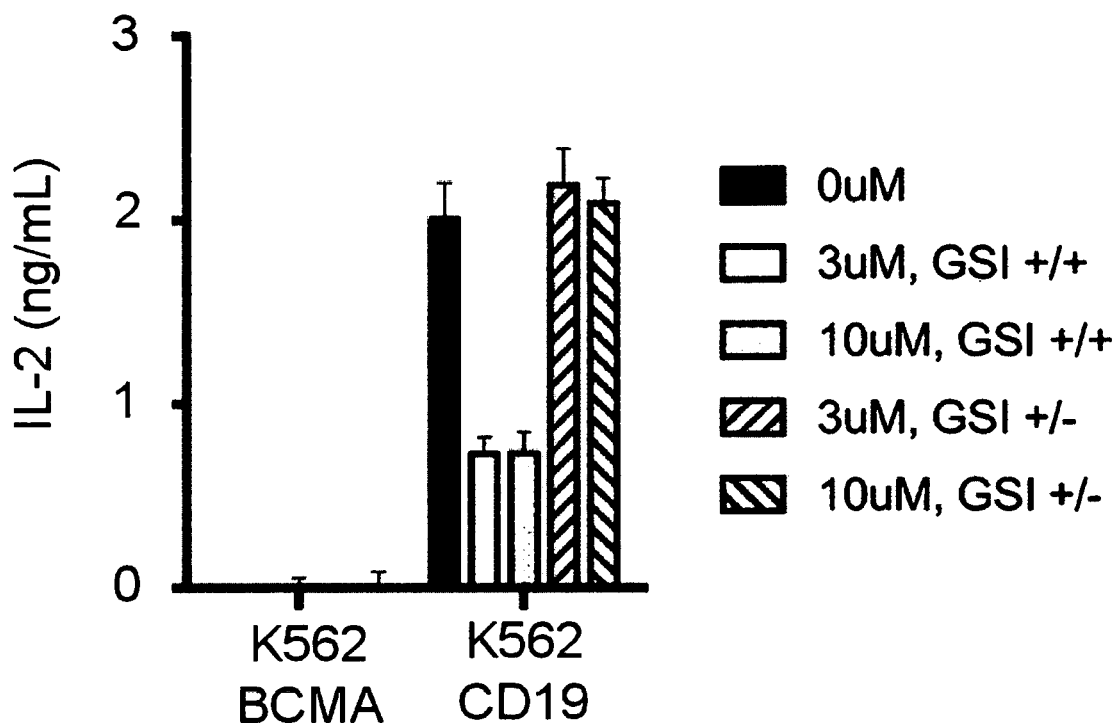
Figure 5G:
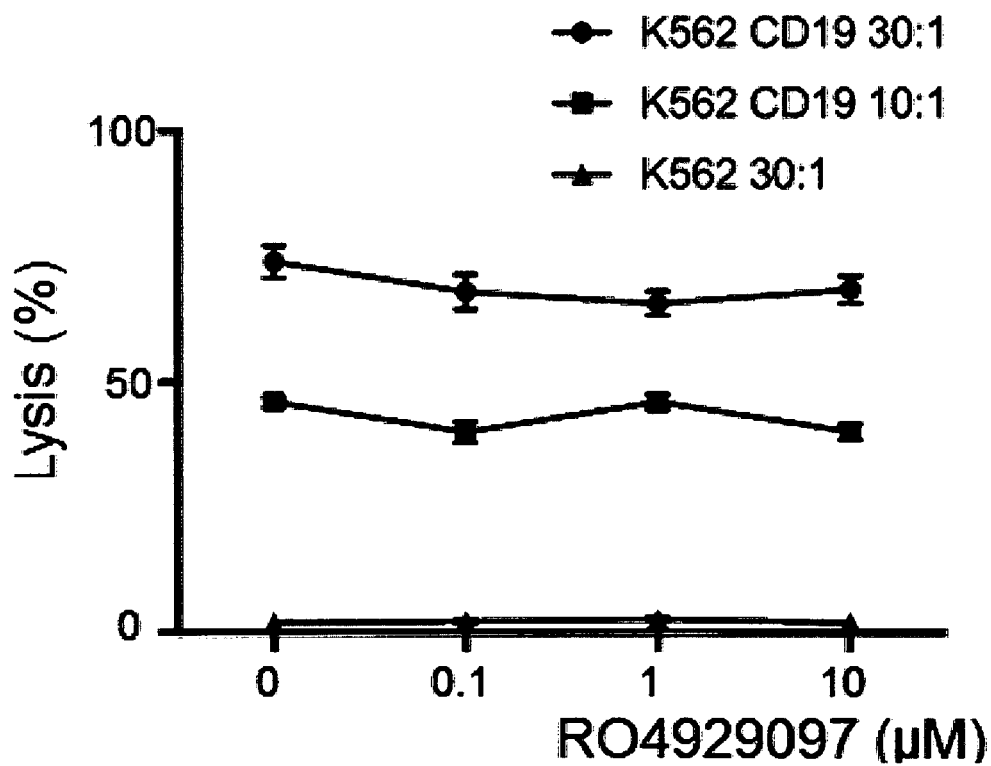
Figure 5H:
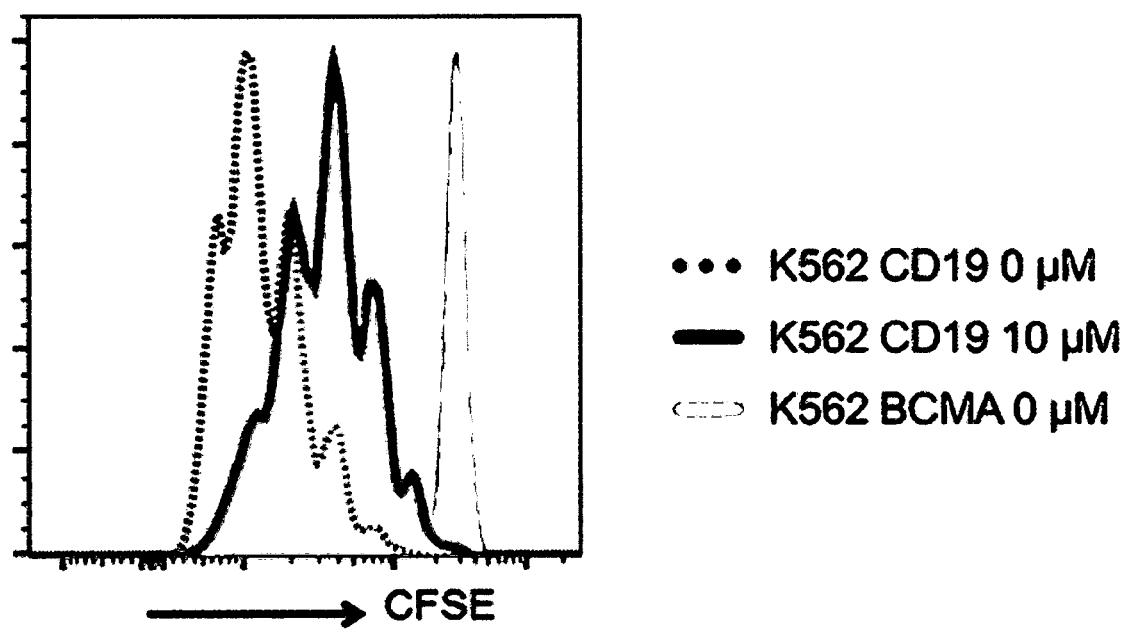
Figure 5I:
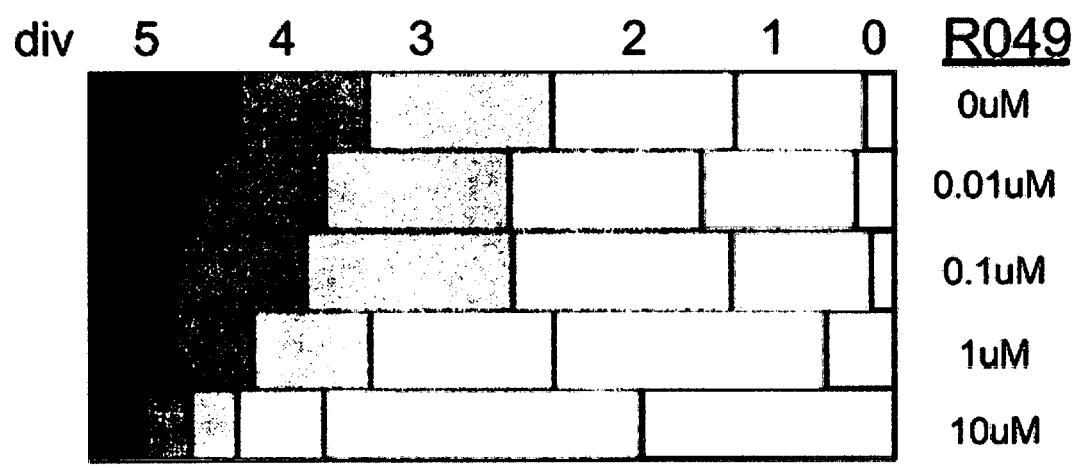
Figure 5J:
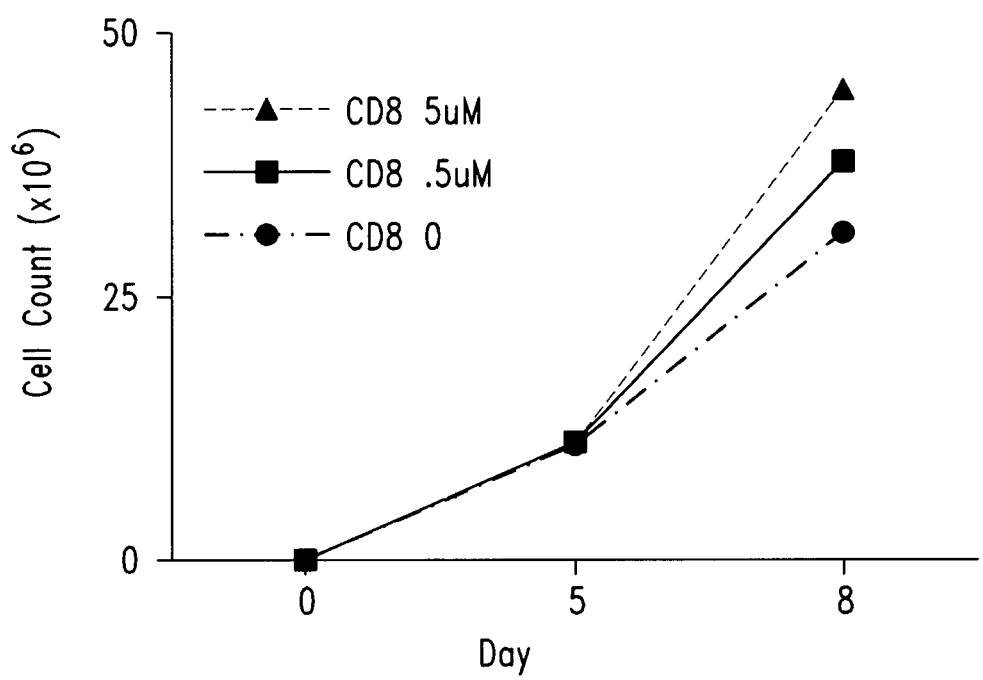
Figure 5K:
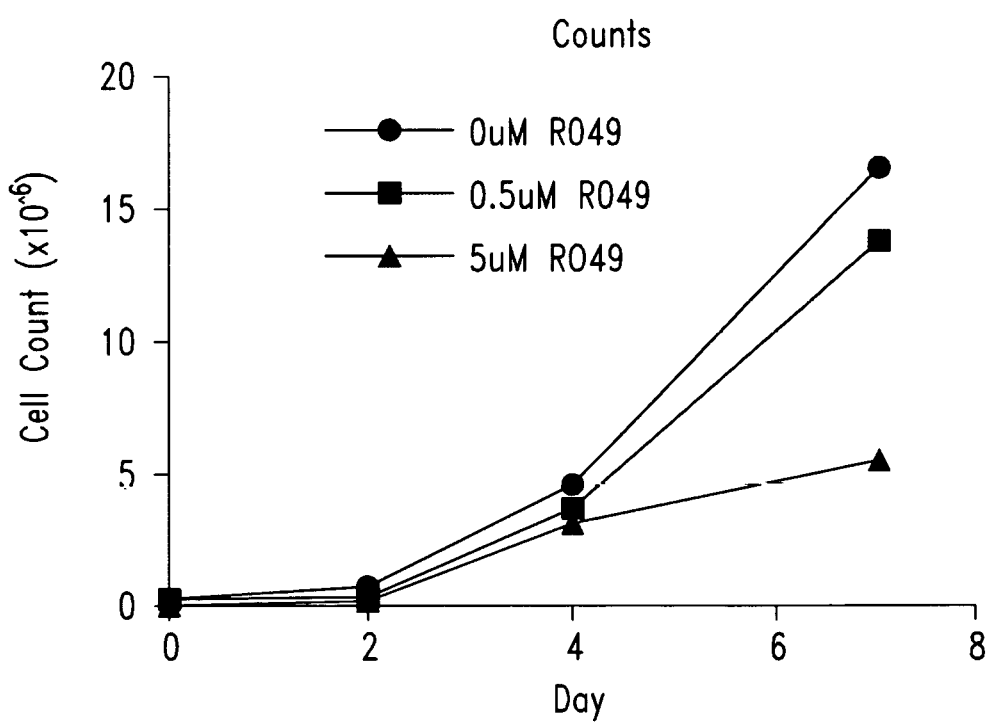
Figure 5L:
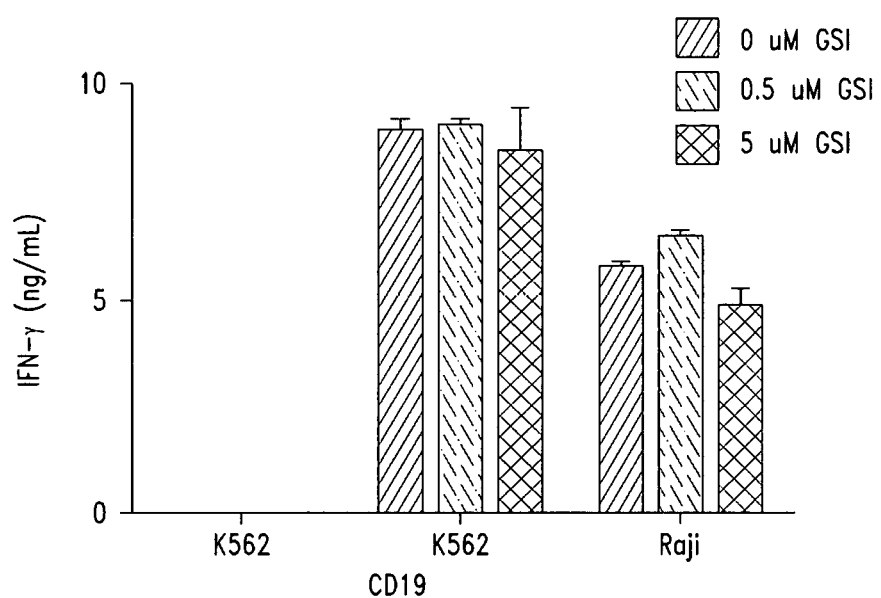
Figure 5M:
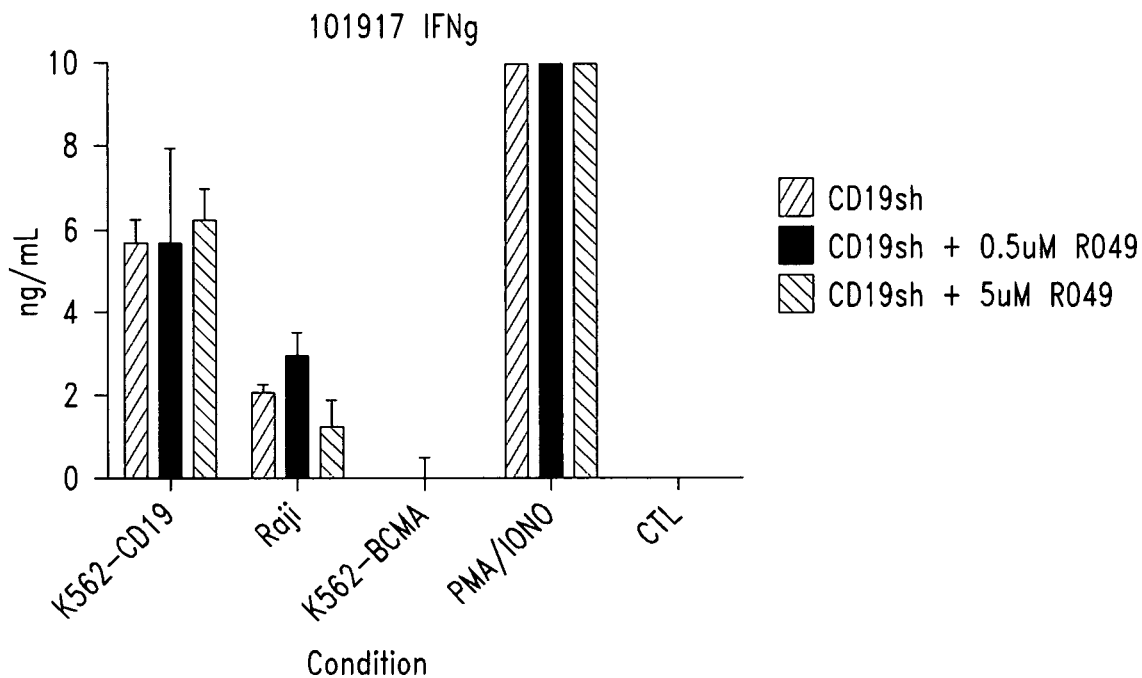
Figure 5N:
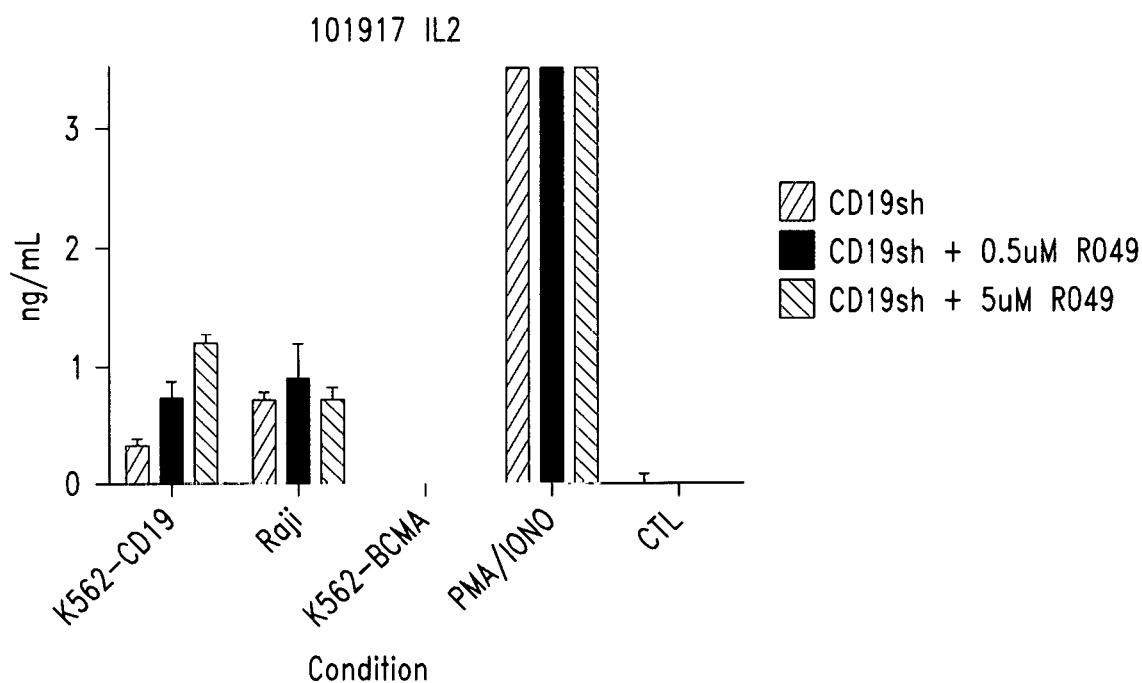
Figure 50:
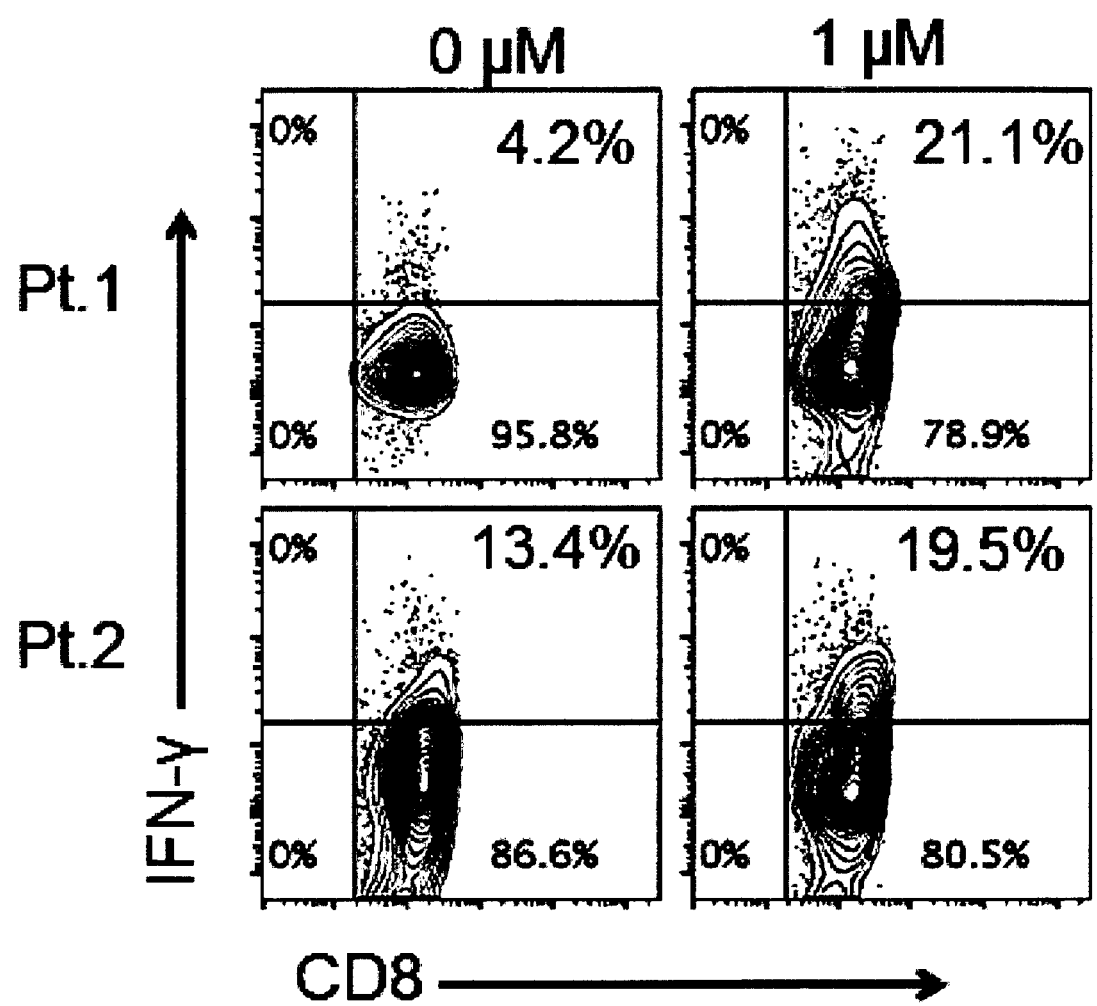
Figure 5P:
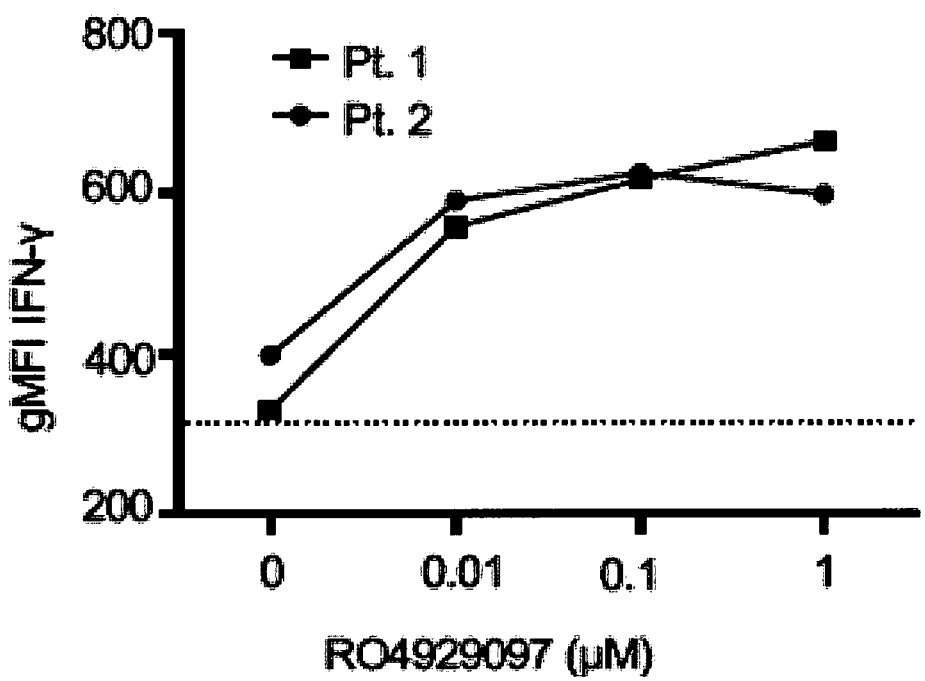
Figure 5Q:
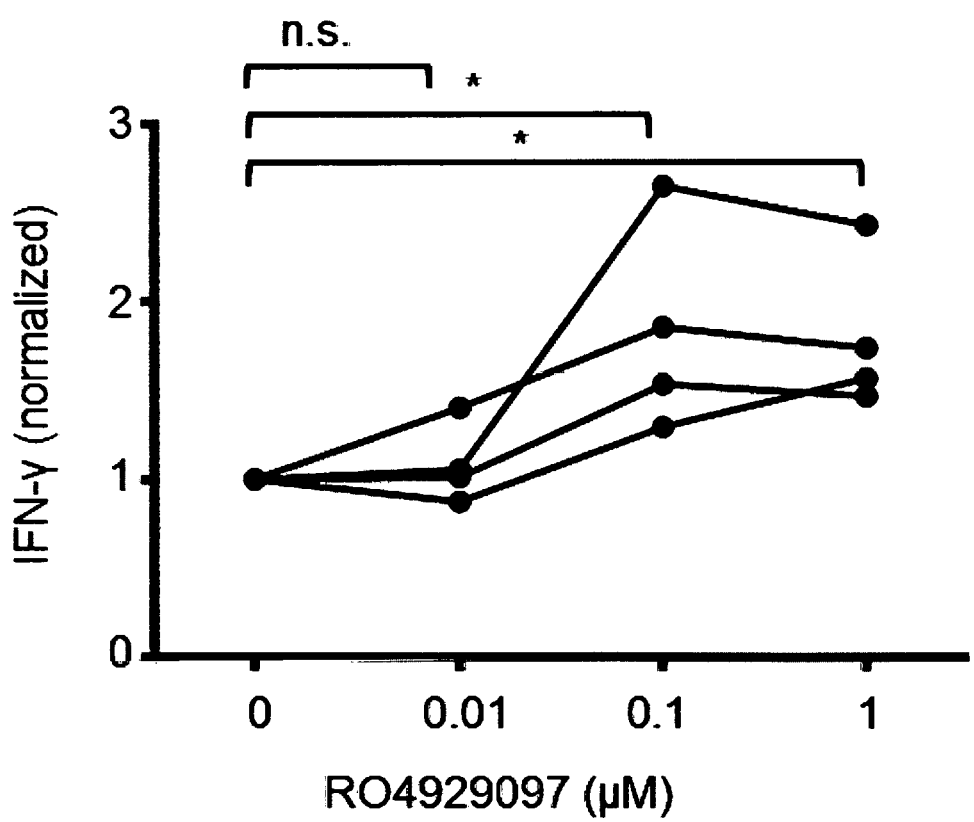
Figure 5R:
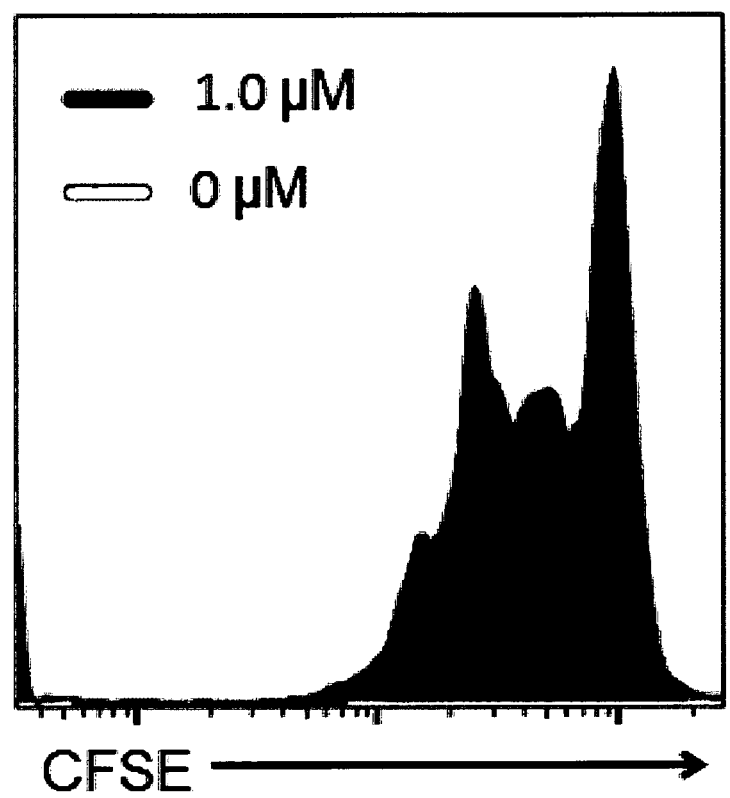

FIGS. 5A-5R show the effect of various concentrations of GSI on CAR-T cell viability, growth, and functional activity.

(A) CD19 staining of K562 CD19+ and Raji cells that were cultured with or without GSI for ±12-16 h. Isotype control shown as gray line.

(B) Primary human T cells were cultured in GSI RO4929097 at concentrations ranging from 0.01 µM to 100 µM and viability was measured by trypan blue dye exclusion after 24 hours. There was no effect of GSI, at any concentration, on T cell viability.

(C) CD19 CAR-T cells were co-cultured with K562/CD19 target cells in media containing various concentrations of RO4929097. RO4929097 inhibits CD19 CAR-T cell effector function at concentrations of 3 µM when co-cultured, as determined by measuring IL-2 (upper panel) and IFNγ (lower panel) production. Box shows the relevant therapeutic window of drug that does not inhibit CAR-T cell effector function.

(D) IL-2 production by CD19 CAR-T cells cultured with target cells in the presence of increasing concentrations of GSI RO4929097.

(E) IL-2 production by CD19 CAR-T cells cultured with target cells ("K562 CD19") or control cells ("KS562 BCMA") in the presence of increasing concentrations of GSI RO4929097. Cells were administered the indicated amounts of the GSI and then washed (empty bars) or not (filled bars).

(F) Data from another experiment showing IL-2 production by CD19 CAR-T cells after overnight co-culture with K562 BCMA+ or K562 CD19+ cells following pre-incubation with varying concentrations of GSI. After washing, GSI was either added back in (+/+) or left out of the co-culture (+/−) to assess the reversibility of cytokine production.

(G) Specific lysis, by CD19 CAR-T cells, of the indicated target or control cells in the presence of GSI RO4929097.

(H) Proliferation of CD19 CAR-T cells cultured with CD19-expressing target cells in the presence or absence of GSI or with control cells in the absence of GSI. Cells were stained with CFSE and proliferation was measured by flow cytometry.

(I) Graphic representation of the number of cell divisions of CD19 CAR-T cells in the presence of the indicated concentrations of GSI RO4929097. The width of the horizontal bars represents the proportion of CAR-T cells in culture that divided the indicated number of generations (i.e., 5, 4, 3, 2, 1, or 0 generations) over the course of the experiment.

(3) Cell counts (CD8 staining) during expansion of CD19-specific CAR-T cells with $CD19^+$ TM LCL cells and exogenous IL-2 in the absence of GSI (circle) or the presence of GSI at 0.5 μM (square) or 5 μM (triangle).

(K) Cell counts of CD19-specific CAR-T cells (CD4:CD8 (1:1) expanded with $CD19^+$ TM. LCL cells in the absence or presence of GSI as indicated, but without the addition of exogenous IL-2.

(L) IFN-γ concentrations in supernatants of GSI-expanded anti-CD19 CAR $CD8^+$ T cells following re-stimulation with K562 cells (no antigen), K562 $CD19^+$ cells, or Raji cells.

(M, N) Production of IFN-γ (M) and IL-2 (N) by the CD4:CD8 anti-CD19 CAR-T cell mixture following re-stimulation with the indicated cell lines in the absence of GSI or the presence of either 0.5 μM or 5 μM GSI.

(O) Intracellular staining showing IFN-γ production (y-axis) and CD8 expression (x-axis) by T-ChARM T cells of the present disclosure cultured with primary MM cells from 2 patients in the absence (0 μM; left panels) or presence (1 μM; right panels) of GSI RO4929097.

(P) IFN-γ production (geometric mean fluorescence intensity (gMFI)) by T-ChARM T cells of the present disclosure cultured with primary MM cells in the presence of the indicated concentration of RO4929097 (x-axis).

(Q) IFN-γ production (normalized MFI; y-axis) by T-ChARM T cells of the present disclosure cultured with primary MM cells in the presence of the indicated concentration of RO4929097 (x-axis).

(R) Proliferation of T-ChARM T cells of the present disclosure in the presence of primary MM cells that were untreated (grey shading) or treated with 1.0 μM GSI RO4929097.

Figure 6A:
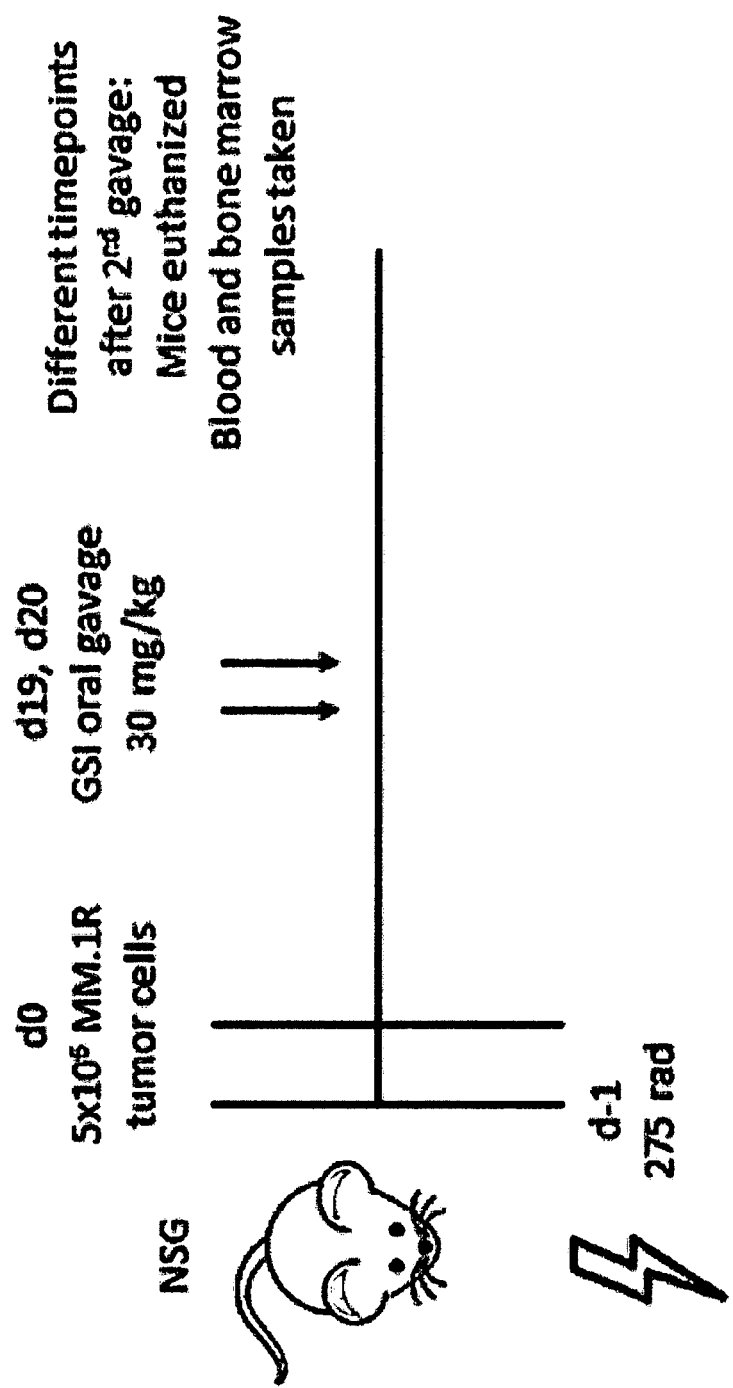
Figure 6B:
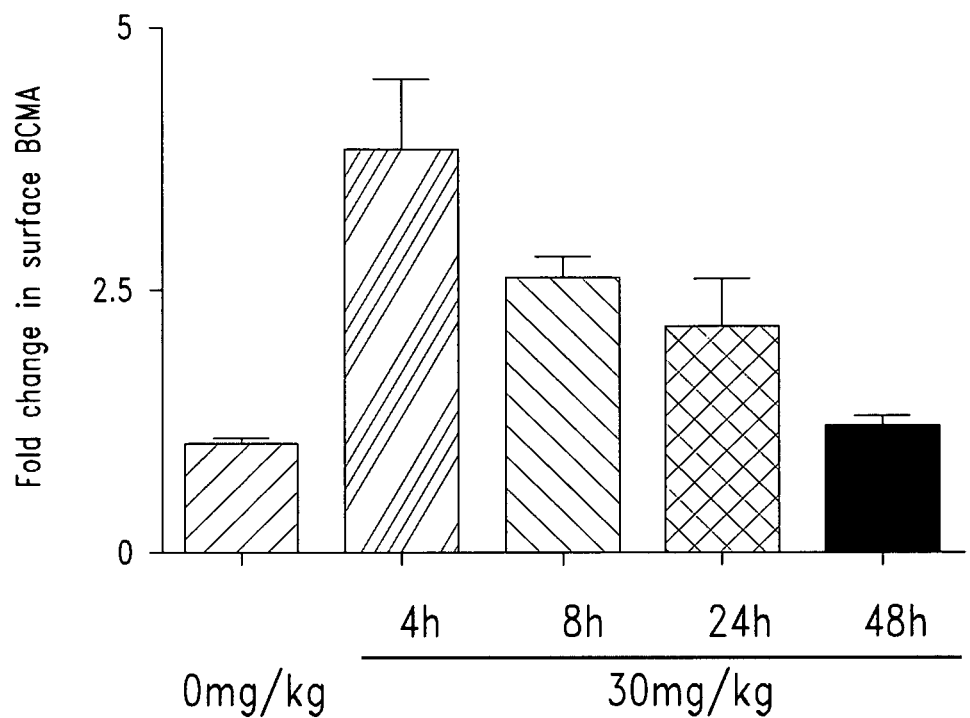
Figure 6C:
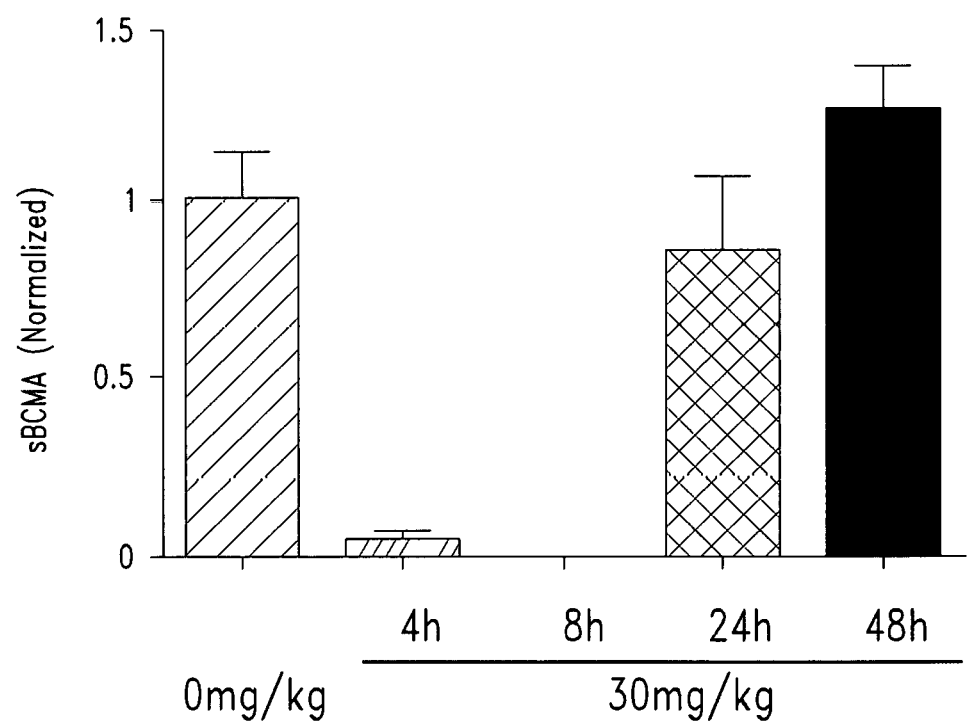

FIGS. 6A-6C show the effects of GSI RO4929097 on BCMA expression in a preclinical in vivo model of multiple myeloma.

(A) Experimental scheme for a disseminated xenograft murine myeloma model. NSG mice were irradiated (275 rad) to facilitate tumor engraftment and received human MM tumor cells ($5 \times 10^6$ MM.1R) followed by GSI treatment (30 mg/kg). Subsequently, mice were euthanized and blood and BM samples were taken to determine if GSI had upregulated BCMA expression on myeloma cells in vivo.

(B) Fold change in surface BCMA expression on myeloma cells in mice euthanized at the indicated timepoints following the second GSI administration.

(C) Levels of sBCMA in sera from mouse sacrificed at the indicated timepoints after administration of RO4929097.

FIGS. 7A-7E show the effects of GSI RO4929097 on anti-BCMA CAR T cell therapy in the preclinical mouse MM model.

(A) Experimental scheme in which the mice received radiation followed by human MM tumor cells ($5 \times 10^6$ MM.1R expressing firefly luciferase). Twenty days thereafter, mice were administered GSI (30 mg/kg) at the indicated timepoints and a single suboptimal dose of anti-BCMA T-ChARM T cells ($0.33 \times 10^6$ cells, 1:1 CD4:CD8) at day 0. Bioluminescence (BLI) imaging and survival were monitored throughout.

(B) BLI images of mice taken at days 2, 17, and 16 following treatment with C113ST T-ChARM T cells (0 mg/kg $0.33 \times 106$ cells, 1:1 CD4:CD8, left-panels; 30 mg/kg, middle panels) or control FM63 anti-CD19 CAR T cells ($0.33 \times 10^6$ cells, 1:1 CD4:CD8, 30 mg/kg, right-hand panels).

Figure 7A:
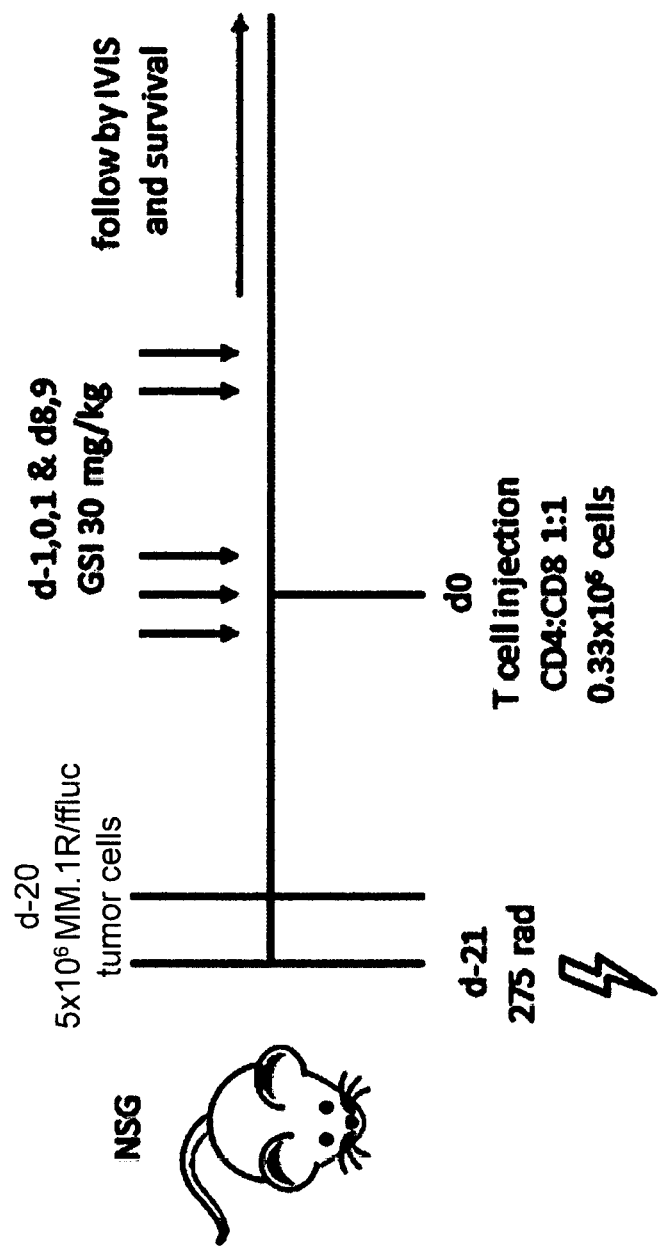
Figure 7B:
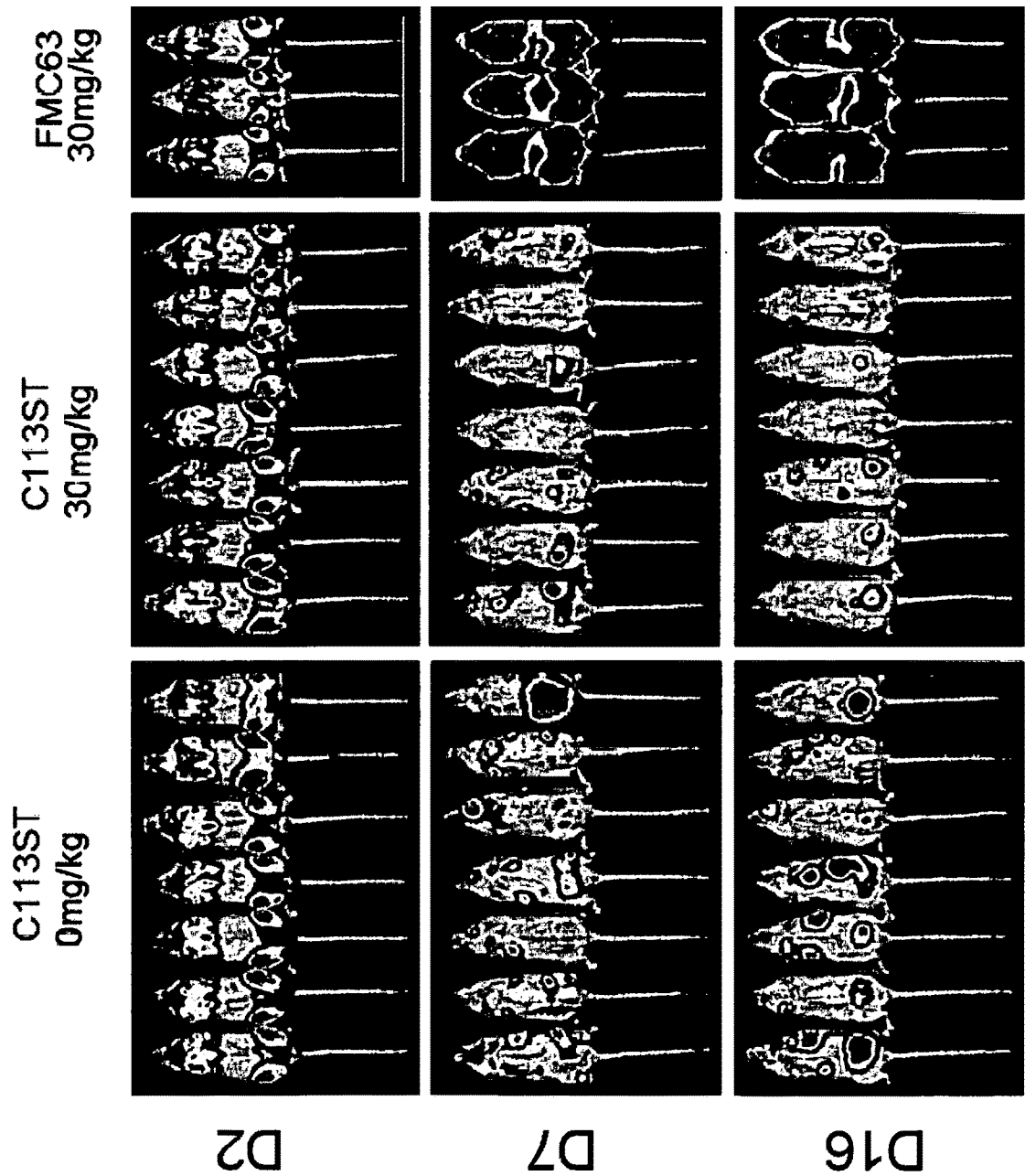

(C) Quantified luminescence data from the BLI shown in FIG. 7B.

(D) Percent survival of the mice shown in FIG. 7B following administration of the T-ChARM T cells.

(E) (left) Quantified luminescence data from the BLI shown in FIG. 7B; (right) percent survival of the mice following administration of the T-ChARM T cells.

Figure 8:
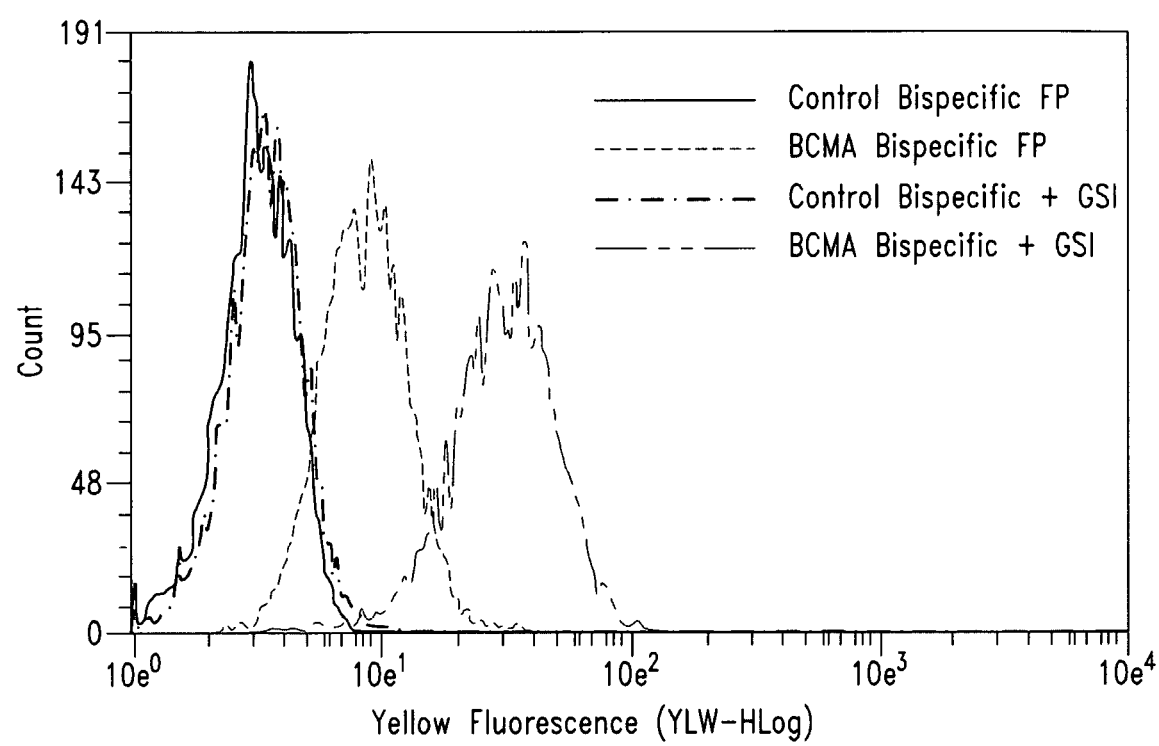

FIG. 8 shows flow cytometric analysis of binding, by a bispecific fusion molecule with specificity for BCMA, to H929 MM cells in the presence or absence of GSI. A control bispecific fusion molecule not targeting BCMA was also tested.

DETAILED DESCRIPTION

The instant disclosure provides compositions and methods for treating autoimmune disease and cancer through the combined use of a B cell maturation antigen (BCMA)-specific binding protein, in soluble form or expressed on a cytotoxic or other cell, and a γ-secretase inhibitor (GSI). Polynucleotides encoding such BCMA-specific binding proteins can be used to generate modified host immune cells (e.g., T cells) for use in, for example, adoptive immunotherapy. In certain aspects, the instant disclosure is directed to the use of such a therapy in a subject in need of treatment in combination with a GSI, which latter treatment may be administered prior to, concurrently with, or subsequent to adoptive immunotherapy (i.e., immunotherapy with a modified immune cell expressing a BCMA-specific binding protein on the cell surface). Also provided herein are immunotherapy methods comprising administering a GSI in combination with a BCMA-specific binding protein that comprises an antibody or antigen-binding portion thereof, which may in certain embodiments be conjugated or otherwise coupled to a cytotoxic drug, e.g., forming an antibody-drug conjugate (ADC). The useful therapeutic applications include the treatment of a proliferative disease or disorder (such as cancer), an autoimmune disease, or aging-associated disease or disorder in the subject in which BCMA-positive cells are pathogenic.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, module or cassette (e.g., a binding domain, hinge region, linker module, tag cassette) or a protein (which may have one or more domains, regions, modules or cassettes) "consists essentially of" a particular amino acid sequence when the amino acid sequence of a domain, region, module, cassette or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, cassette or protein and do not substantially affect (i.e., do not reduce the activity by more than 50%, such as no more than 40%, 30%, 25%, 20%, 15%, 10%, 5%, or 1%) the activity of the domain(s), region(s), module(s), cassette(s) or protein (e.g., the target binding affinity of a binding protein or tag cassette).

As used herein, "proliferative disorder" refers to excessive or otherwise abnormal growth or proliferation as compared to a normal or undiseased cell. Excessive or abnormal growth includes, for example, dysregulated growth or proliferation that can occur rapidly (e.g., hyperproliferation) or can occur more slowly or progressively over time (e.g., multiple myeloma), within a native tissue (e.g., plasmacytoma growth within bone marrow), as well as spread to/grow within a distal tissue or body site that is non-native to the diseased cell. Exemplary proliferative disorders include tumors, cancers, neoplastic tissue, carcinoma, sarcoma, malignant cells, pre malignant cells, as well as non-neoplastic or non-malignant proliferative disorders (e.g., adenoma, fibroma, lipoma, leiomyoma, hemangioma, fibrosis, restenosis), or autoimmune diseases (such as rheumatoid arthritis, osteoarthritis, psoriasis, inflammatory bowel disease, or the like).

A "binding protein" (also referred to as a "binding domain," "binding region" or "binding moiety"), as used herein, refers to a molecule, such as a peptide, oligopeptide, polypeptide, or protein that possesses the ability to specifically and non-covalently associate, unite, or combine with a target molecule (e.g., BCMA). A binding protein includes any naturally occurring, synthetic, semi-synthetic, or recombinantly produced binding partner for a biological molecule, compound or other target of interest. In some embodiments, a binding protein is from an immunoglobulin or immunoglobulin-like molecule, such as an antibody or T cell receptor (TCR), which includes a functional binding domain or antigen-binding fragment thereof. Exemplary binding proteins include single chain antibody variable regions (e.g., domain antibodies, sFv, scFv, Fab), BCMA ligands (e.g., BAFF, APRIL and binding fragments thereof), antigen-binding regions of T cell receptors (TCRs), such as single chain TCRs (scTCRs), or synthetic polypeptides selected for the specific ability to bind to a biological molecule.

As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample. Binding domains (or fusion proteins thereof) may be classified as "high affinity" binding domains (or fusion proteins thereof) or "low affinity" binding domains (or fusion proteins thereof). "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^8$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a Ka (equilibrium association constant) for the target antigen that is higher than the wild type binding domain, or due to a $K_d$ (dissociation constant) for the target antigen that is less than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and Biacore® analysis (see also, e.g., Scatchard et al., Ann. N.Y. Acad. Sci. 51:660, 1949; and U.S. Pat. Nos. 5,283,173, 5,468,614, or the equivalent).

As used herein, "heterologous" or "non-endogenous" or "exogenous" refers to any gene, protein, compound, molecule or activity that is not native to a host cell or a subject, or is any gene, protein, compound, molecule or activity native to a host or host cell but has been altered or mutated such that the structure, activity or both is different as between the native and mutated molecules. In certain embodiments, heterologous, non-endogenous or exogenous molecules (e.g., receptors, ligands) may not be endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extrachromosomal genetic material (e.g., as a plasmid or other self-replicating vector). The term "homologous" or "homolog" refers to a molecule or activity found in or derived from a host cell, species or strain. For example, a heterologous or exogenous molecule or gene encoding the molecule may be homologous to a native host or host cell molecule or gene that encodes the molecule, respectively, but may have an altered structure, sequence, expression level or combinations thereof. A non-endogenous molecule may be from the same species, a different species or a combination thereof.

As used herein, the term "endogenous" or "native" refers to a gene, protein, compound, molecule or activity that is normally present in a host or host cell.

As used herein, "tag cassette" refers to a unique peptide sequence affixed to, fused to, or that is part of a protein of interest, to which a heterologous or non-endogenous cognate binding molecule (e.g., receptor, ligand, antibody, or other binding partner) is capable of specifically binding where the binding property can be used to detect, identify, isolate or purify, track, enrich for, or target a tagged protein or cells expressing a tagged protein, particularly when a tagged protein is part of a heterogeneous population of proteins or other material, or when cells expressing a tagged protein are part of a heterogeneous population of cells (e.g., a biological sample like peripheral blood). In certain embodiments, a cell expressing a tagged protein can be contacted with a heterologous or non-endogenous cognate binding molecule and induce a biological response, such as promote cell activation, cell proliferation or cell death. In the provided fusion proteins, the ability of the tag cassette(s) to be specifically bound by the cognate binding molecule(s) is distinct from or in addition to the ability of the binding domain(s) to specifically bind to the target molecule(s). The tag cassette generally is not an antigen-binding molecule, for example, is not an antibody or TCR or an antigen-binding portion thereof.

As used herein, a "hinge region" or a "hinge" refers to (a) an immunoglobulin hinge sequence (made up of, for example, upper and core regions) or a functional fragment or variant thereof, (b) a type II C-lectin interdomain (stalk) region or a functional fragment or variant thereof, or (c) a cluster of differentiation (CD) molecule stalk region or a functional variant thereof. As used herein, a "wild type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a hinge region is human, and in particular embodiments, comprises a human IgG hinge region.

As used herein, a "spacer region" refers to one or more proteins, polypeptides, oligopeptides, peptides, domains, regions, modules, cassettes, motifs or any combination thereof that join two or more proteins, polypeptides, oligopeptides, peptides, domains, regions, modules, cassettes, motifs or any combination thereof in a fusion protein. For example, a spacer region may provide a separation or spacing function to facilitate the interaction of two single chain fusion proteins, or positioning of one or more binding domains, so that the resulting polypeptide structure maintains a specific binding affinity to a target molecule or maintains signaling activity (e.g., effector domain activity) or both. In certain embodiments, a spacer region may comprise a "linker module" that is an amino acid sequence having from about to two up to about 500 amino acids, which can provide flexibility and room for conformational movement between two regions, domains, motifs, cassettes or modules connected by a linker. Exemplary linker modules include those having from one to about ten repeats of $Gly_xSer_y$ (SEQ ID NO:31), wherein x and y are independently an integer from 0 to 10 provided that x and y are not both 0 (e.g., $(Gly_4Ser)_2$ (SEQ ID NO:32), $(Gly_3Ser)_2$ (SEQ ID NO:33), $Gly_2Ser$, or a combination thereof such as $(Gly_3Ser)_2Gly_2Ser)$) (SEQ ID NO:34). In certain other embodiments, a spacer region may have a linker module that comprises one or more immunoglobulin heavy chain constant regions, such as a CH3 alone or a CH2CH3. In further embodiments, a spacer region may comprise a hinge region or a tag cassette. Each such connector component is not mutually exclusive. For example, a spacer region may comprise a hinge and one or more linker modules, or a spacer region may comprise a hinge, one or more linker modules, and one or more tag cassettes. Exemplary spacer regions can vary in length, for instance, from about five to about 500 amino acids, or from about ten to about 350 amino acids, or from about 15 to about 100 amino acids, or from about 20 to about 75 amino acids, or from about 25 to about 35 amino acids. Exemplary short spacers range from about five to about 100 amino acids (e.g., 12 amino acids, 15 amino acids, 48 amino acids, 50 amino acids, 66 amino acids, 70 amino acids), intermediate spacers range from about 100 to about 200 amino acids (e.g., 110 amino acids, 120 amino acids, 130 amino acids, 140 amino acids, 150 amino acids, 157 amino acids, 175 amino acids), and long spacers range from about 200 to about 500 amino acids (e.g., 200 amino acids, 210 amino acids, 220 amino acids, 228 amino acids, 230 amino acids, 250 amino acids, 300 amino acids, 350 amino acids, 400 amino acids, 450 amino acids).

A "hydrophobic portion," as used herein, means any amino acid sequence having a three-dimensional structure that is thermodynamically stable in a cell membrane, and generally ranges in length from about 15 amino acids to about 30 amino acids. The structure of a hydrophobic domain may comprise an alpha helix, a beta barrel, a beta sheet, a beta helix, or any combination thereof.

As used herein, an "effector domain" is an intracellular portion of a fusion protein or receptor that can directly or indirectly promote a biological or physiological response in a cell when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM), and such a cellular response can be aided or improved with a costimulatory domain or functional portion thereof. An exemplary protein having an effector domain is CD3ζ. In other embodiments, an effector domain will indirectly promote a cellular response by associating with one or more other proteins that directly promote a cellular response.

A "costimulatory domain," as the term is used herein refers to a signaling moiety that provides T cells a signal which, in addition to the primary (effector) signal provided by, for instance, a CD3ζ chain of the TCR/CD3 complex, mediates a T cell response, including activation, proliferation, differentiation, cytokine secretion, or the like. In certain embodiments, an intracellular component comprises an effector domain or functional portion thereof, a costimulatory domain or functional portion thereof, or any combination thereof.

A "variable region linker" specifically refers to a five to about 35 amino acid sequence that connects a heavy chain immunoglobulin variable region to a light chain immunoglobulin variable region or connects T cell receptor $V_{\alpha/\beta}$ and $C_{\alpha/\beta}$ chains (e.g., $V_\alpha$-$C_\beta$, $V_\beta$-$C_\beta$, $V_\alpha$-$V_\beta$) or connects each $V_\alpha$-$C_\beta$, $V_\beta$-$C_\beta$, $V_\alpha$-$V_\beta$ pair to a hinge or hydrophobic domain, which provides a spacer function and flexibility sufficient for interaction of the two sub-binding domains so that the resulting single chain polypeptide retains a specific binding affinity to the same target molecule as an antibody or T cell receptor. In certain embodiments, a variable region linker comprises from about ten to about 30 amino acids or from about 15 to about 25 amino acids. In particular embodiments, a variable region linker peptide comprises from one to ten repeats of $Gly_xSer_y$, wherein x and y are independently an integer from 1 to 5 (e.g., Gly$_4$Ser (SEQ ID NO:1), Gly$_3$Ser (SEQ ID NO:2), Gly$_2$Ser, or (Gly$_3$Ser)$_n$ (Gly$_4$Ser)$_1$ (SEQ ID NO:3), (Gly$_3$Ser)$_n$(Gly$_4$Ser)$_n$ (SEQ ID NO:4), or (Gly$_4$Ser)$_n$ (SEQ ID NO:5), wherein n is an integer of 1, 2, 3, 4, or 5) and wherein linked variable regions form a functional binding domain (e.g., scFv, scTCR).

"Junction amino acids" or "junction amino acid residues" refer to one or more (e.g., about 2-20) amino acid residues between two adjacent motifs, regions or domains of a polypeptide, such as between a binding domain and an adjacent linker region or between a hydrophobic domain and an adjacent effector domain or on one or both ends of a linker region that links two motifs, regions or domains (e.g., between a linker and an adjacent binding domain and/or between a linker and an adjacent hinge). Junction amino acids may result from the construct design of a fusion protein (e.g., amino acid residues resulting from the use of a restriction enzyme site during the construction of a nucleic acid molecule encoding a fusion protein).

Terms understood by those in the art of antibody technology are each given the meaning acquired in the art, unless expressly defined differently herein. The term "antibody" refers to an intact antibody comprising at least two heavy (H) chains and two light (L) chains inter-connected by disulfide bonds, as well as an antigen-binding portion of an intact antibody that has or retains the capacity to bind a target molecule. A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988).

For example, the terms "$V_L$" and "$V_H$" refer to the variable binding region from an antibody light and heavy chain, respectively. The variable binding regions are made up of discrete, well-defined sub-regions known as "complementarity determining regions" (CDRs) and "framework regions" (FRs). The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 of the heavy chain linked to the light chain via an inter-chain disulfide bond.

As used herein, "Fc region portion" refers to the heavy chain constant region segment of the Fc fragment (the "fragment crystallizable" region or Fc region) from an antibody, which can in include one or more constant domains, such as CH2, CH3, CH4, or any combination thereof. In certain embodiments, an Fc region portion includes the CH2 and CH3 domains of an IgG, IgA, or IgD antibody or any combination thereof, or the CH3 and CH4 domains of an IgM or IgE antibody and any combination thereof. In other embodiments, a CH2CH3 or a CH3CH4 structure has sub-region domains from the same antibody isotype and are human, such as human IgG1, IgG2, IgG3, IgG4, IgA1, IgA2, IgD, IgE, or IgM (e.g., CH2CH3 from human IgG1). By way of background, an Fc region is responsible for the effector functions of an immunoglobulin, such as ADCC (antibody-dependent cell-mediated cytotoxicity), CDC (complement-dependent cytotoxicity) and complement fixation, binding to Fc receptors (e.g., CD16, CD32, FcRn), greater half-life in vivo relative to a polypeptide lacking an Fc region, protein A binding, and perhaps even placental transfer (see Capon et al., Nature 337:525, 1989). In certain embodiments, an Fc region portion found in fusion proteins of the present disclosure will be capable of mediating one or more of these effector functions, or will lack one or more or all of these activities by way of, for example, one or more mutations known in the art.

In addition, antibodies have a hinge sequence that is typically situated between the Fab and Fc region (but a lower section of the hinge may include an amino-terminal portion of the Fc region). By way of background, an immunoglobulin hinge acts as a flexible spacer to allow the Fab portion to move freely in space. In contrast to the constant regions, hinges are structurally diverse, varying in both sequence and length between immunoglobulin classes and even among subclasses. For example, a human IgG1 hinge region is freely flexible, which allows the Fab fragments to rotate about their axes of symmetry and move within a sphere centered at the first of two inter-heavy chain disulfide bridges. By comparison, a human IgG2 hinge is relatively short and contains a rigid poly-proline double helix stabilized by four inter-heavy chain disulfide bridges, which restricts the flexibility. A human IgG3 hinge differs from the other subclasses by its unique extended hinge region (about four times as long as the IgG1 hinge), containing 62 amino acids (including 21 prolines and 11 cysteines), forming an inflexible poly-proline double helix and providing greater flexibility because the Fab fragments are relatively far away from the Fc fragment. A human IgG4 hinge is shorter than IgG1 but has the same length as IgG2, and its flexibility is intermediate between that of IgG1 and IgG2.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease*, 3$^{rd}$ Ed., Current Biology Publications, p. 4:33, 1997). TCR, as used in the present disclosure, may be from various animal species, including human, mouse, rat, cat, dog, goat, horse, or other mammals. TCRs may be cell-bound (i.e., have a transmembrane region or domain) or in soluble form.

"Major histocompatibility complex molecules" (MHC molecules) refer to glycoproteins that deliver peptide antigens to a cell surface. MHC class I molecules are heterodimers consisting of a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where peptide:MHC complex is recognized by CD8$^+$ T cells. MHC class II molecules deliver peptides originating in the vesicular system to the cell surface, where they are recognized by CD4$^+$ T cells. An MHC molecule may be from various animal species, including human, mouse, rat, or other mammals.

A "vector" is a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

"T cells" or "cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 lineage commitment; thymocyte progenitor cells that are $CD4^+$ $CD8^+$ double positive; single positive $CD4^+$ or $CD8^+$; TCR$\alpha\beta$ or TCR $\gamma\delta$; or mature and functional or activated T cells.

"Nucleic acid molecule", or "polynucleotide," may be in the form of RNA or DNA, which includes cDNA, genomic DNA, and synthetic DNA. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

"Treat" or "treatment" or "ameliorate" refers to medical management of a disease, disorder, or condition of a subject (e.g., a human or non-human mammal, such as a primate, horse, dog, mouse, rat). For example, an appropriate dose or treatment regimen comprising BCMA-specific binding protein or a host cell expressing a BCMA-specific binding protein used in combination with a γ-secretase inhibitor (GSI) of this disclosure, and optionally an adjuvant or pre-conditioning regimen, is administered to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount" of a BCMA-specific binding protein (also referred to as a BCMA-specific or BCMA-targeted immunotherapy), a γ-secretase inhibitor, a host cell expressing a BCMA-specific binding protein, or a host cell expressing a γ-secretase inhibitor of this disclosure (e.g., BCMA-specific CAR, anti-secretase antibody) refers to that amount of compound or cells sufficient to result in amelioration of one or more symptoms of the disease being treated in a statistically significant manner. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially, concurrently or simultaneously. Another combination may be a cell expressing more than one active ingredient, such as two or more different BCMA-specific binding proteins or the like.

Additional definitions are provided throughout the present disclosure.

B Cell Maturation Antigen (BCMA) Binding Proteins or Molecules

In certain aspects, the present disclosure provides methods for treating a proliferative or autoimmune disease or disorder in a subject having or suspected having the disease or disorder, comprising administering to the subject a therapeutically effective amount of a BCMA-specific binding protein (or BCMA-targeted immunotherapy) and a therapeutically effective amount of a γ-secretase inhibitor. An exemplary BCMA-specific binding protein is a chimeric antigen receptor comprising an extracellular component and an intracellular component connected by a hydrophobic portion, wherein the extracellular component comprises a BCMA-specific binding domain (e.g., BCMA-specific scFv, BCMA ligand or binding portion thereof, such as BAFF or APRIL) and optionally comprises a spacer region or hinge, and wherein the intracellular component comprises an effector domain and optionally a costimulatory domain.

In certain embodiments, the present disclosure provides a BCMA-targeted immunotherapy, for use with a γ-secretase inhibitor to treat a proliferative or autoimmune disease or disorder, comprising a BCMA-specific antibody or antigen-binding portion thereof, a chimeric antigen receptor (CAR), or a tagged chimeric antigen receptor molecule (T-ChARM). In certain embodiments, a BCMA-specific antibody or antigen-binding portion thereof is human or humanized.

Exemplary BCMA-specific antibodies include antibodies J22.0-xi, J22.9-xi, J6M0, J6M1, J6M2, J9M0, J9M1, J9M2, 1 D5-3, CA8, A7D12.2, C11 D5.3, C12A3.2, C13F12.1, 13C2, 17A5, 83A10, 13A4, 13D2, 14B11, 14E1, 29B11, 29F3, 13A7, CA7, SG1, S307118G03, S332121F02, S332126E04, S322110D07, S336105A07, S335115G01, S335122F05, ET140-3, ET140-24, ET140-37, ET140-40, ET140-54, TBL-CLN1, C4.E2.1, Vicky-1, pSCHLI333, pSCHLI372, and pSCHLI373, and antigen-binding portions thereof. Various embodiments of BCMA-specific antibodies and antigen-binding portions thereof, including humanized versions, are disclosed in, for example, PCT Publication Nos. WO 2002/066516, WO 2007/062090, WO 2010/104949, WO 2011/108008, WO 2012/163805, WO 2014/068079, WO 2015/166073, WO 2014/122143, WO 2014/089335, WO 2016/090327, and WO 2016/079177; Ryan et al., *Mol. Cancer. Ther.* 6(11):3009, 2007; and Abbas et al., *Blood* 128:1688, 2016, which BCMA-specific antibodies, antigen-binding portions thereof and humanized versions are all incorporated herein by reference in their entirety. Variable domains and scFv molecules from these BCMA-specific antibodies can be used as a binding domain in any of the T-ChARM and CAR proteins mentioned herein.

Antigen binding portions or domains obtained from BCMA-specific antibodies of present disclosure and useful in the methods disclosed herein include, for example, domain antibodies, sFvs, single chain Fv fragments (scFvs), Fabs, F(ab')$_2$, nanobodies, tandem scFvs, scFv-Fcs, scFv dimers, scFv zippers, diabodies, minibodies, triabodies, tetrabodoes, Fabs, F(ab)'2s, scFabs, miniantibodies, nanobodies, nanobody-HSAs, Bispecific T cell Engagers (BiTEs), DARs, scDiabodies, scDiabody-CH3s, or scFv-CH3 Knobs-Into-Holes (KIH) assemblies.

In certain embodiments, a BCMA-specific binding protein comprises a bispecific or multispecific antibody (or an antigen-binding portion thereof) comprising a first binding region (e.g., a heavy chain variable region, a light chain variable region, or both) that is specific for BCMA and at least one other binding region that is specific for a second target (e.g., a BCMA epitope that is different from the epitope of the first binding region, or an epitope of a non-BCMA target, such as, for example, a tumor-associated antigen that is not BCMA (for example, CD19 (e.g., blinatumomab, MOR-208, SGN-19A, SAR3419, coltuximabravtansine, denituzumabmafodotin, taplitumomabpaptox, XmAb 5574, MDI-551, Merck patent anti-CD19 aka B4 aka DI-B4, XmAb 5871, MDX-1342, AFM11), CD20 (e.g., rituximab, ofatumumab, ocrelizumab), CD38 (e.g., daratumumab or isatuximab (SAR650984)), CD45, or a cell surface protein expressed on an immune effector cell, such as a T cell (e.g., CD3), an NK cell (e.g., CD56), or an NK-T cell (e.g., NK1.1), or another non-tumor-associated antigen or target.

In particular embodiments, the present disclosure provides a BCMA-specific binding protein alone or expressed as a T-ChARM in a cell, for use with a γ-secretase inhibitor (GSI). An exemplary T-ChARM comprises an extracellular component and an intracellular component connected by a hydrophobic portion, wherein the extracellular component comprises a binding domain that specifically binds BCMA, an optional spacer region, a tag cassette, and a hinge region, and wherein the intracellular component comprises an effector domain and optionally a costimulatory domain (e.g., a functional domain or portion from 4-1BB, a functional domain or portion from CD28, or both). In certain embodiments, a T-ChARM binding domain comprises a BCMA-specific scFv, a BCMA-specific scTCR, or a BCMA ligand or binding portion thereof (e.g., BAFF, APRIL), optionally wherein the BCMA-specific scFv is human or humanized. Various embodiments of the T-ChARMs are disclosed in PCT Publication No. WO 2015/095895, which T-ChARM scaffolds are incorporated herein by reference in their entirety.

Exemplary tag cassettes include Strep tag (which refers to the original Strep® tag, Strep® tag II, or any variant thereof; see, e.g., U.S. Pat. No. 7,981,632, which Strep tags are incorporated herein by reference), His tag, Flag tag, Xpress tag, Avi tag, Calmodulin tag, Polyglutamate tag, HA tag, Myc tag, Nus tag, S tag, SBP tag, Softag 1, Softag 3, V5 tag, CREB-binding protein (CBP), glutathione S-transferase (GST), maltose binding protein (MBP), green fluorescent protein (GFP), Thioredoxin tag, or any combination thereof. In some embodiments, a tag cassette may be a genetically engineered affinity site, such as a minimal chelation site (e.g., HGGHHG, SEQ ID NO.:6). In certain embodiments, a tag cassette is a Strep tag having an amino acid sequence of Trp-Ser-His-Pro-Gln-Phe-Glu-Lys (SEQ ID NO.:7) or Trp-Arg-His-Pro-Gln-Phe-Gly-Gly (SEQ ID NO.:8).

Tag cassettes may be present in single or multiple copies in fusion proteins of this disclosure. For example, a BCMA-specific binding protein of this disclosure can have one, two, three, four or five tag cassettes (e.g., Strep tag). In certain embodiments, an extracellular component of a BCMA-specific T-ChARM includes one tag cassette, two tag cassettes, three tag cassettes, four tag cassettes, or five tag cassettes. Each of the plurality of tag cassettes may be the same or different.

In certain embodiments, a tag cassette comprises from about five to about 500 amino acids, or from about six to about 100 amino acids, or from about seven to about 50 amino acids, or from about eight to about 20 amino acids. In some embodiments, a tag cassette has seven to ten amino acids. Preferably, a tag cassette is non-immunogenic or minimally immunogenic. Essentially, a tag cassette can function as a handle or beacon to allow for the identification, enrichment, isolation, promotion of proliferation, activation, tracking, or elimination of cells expressing a BCMA-specific T-ChARM.

In further embodiments, the present disclosure provides a BCMA-specific binding protein, for use with a γ-secretase inhibitor, that is a chimeric antigen receptor (CAR), which comprises an extracellular component and an intracellular component connected by a hydrophobic portion, wherein the extracellular component comprises a binding domain that specifically binds BCMA and a hinge region, and wherein the intracellular component comprises an effector domain and optionally a costimulatory domain. In certain embodiments, a CAR binding domain comprises a BCMA-specific scFv, a BCMA-specific scTCR, a BCMA-specific TCR binding domain (see, e.g., Walseng et al., *Scientific Reports* 7:10713 (2017), the TCR CAR constructs of which are hereby incorporated by reference in their entirety), or a BCMA ligand or binding portion thereof (e.g., BAFF, APRIL), optionally wherein the BCMA-specific scFv is human or humanized. In any of these embodiments, a BCMA-specific binding protein in the form of a CAR may be expressed on the surface of a cell, such as an immune system cell (e.g., T cell).

A BCMA-specific T-ChARM or CAR may be cell-bound (e.g., expressed on a cell surface) or in soluble form. In certain embodiments, polynucleotides encoding BCMA-specific T-ChARM or CAR proteins may be codon optimized to enhance or maximize expression in a host cell, such as a T cell (Scholten et al., *Clin. Immunol.* 119:135, 2006).

In certain embodiments, a hinge present in a BCMA-specific T-ChARM or CAR of this disclosure may be an immunoglobulin hinge region, such as a wild type immunoglobulin hinge region or an altered immunoglobulin hinge region thereof. In certain embodiments, a hinge is a wild type human immunoglobulin hinge region. In certain other embodiments, one or more amino acid residues may be added at the amino- or carboxy-terminus of a wild type immunoglobulin hinge region as part of a fusion protein construct design. For example, one, two or three additional junction amino acid residues may be present at the hinge amino-terminus or carboxy-terminus, or a hinge may contain a terminal or internal deletion and have added back one, two or three additional junction amino acid residues.

In certain embodiments, a hinge is an altered immunoglobulin hinge in which one or more cysteine residues in a wild type immunoglobulin hinge region is substituted with one or more other amino acid residues. Exemplary altered immunoglobulin hinges include an immunoglobulin human IgG1, IgG2 or IgG4 hinge region having one, two or three cysteine residues found in a wild type human IgG1, IgG2 or IgG4 hinge substituted by one, two or three different amino acid residues (e.g., serine or alanine). In certain embodiments, a hinge polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% identical to a wild type immunoglobulin hinge region, such as a wild type human IgG1 hinge, a wild type human IgG2 hinge, or a wild type human IgG4 hinge.

In further embodiments, a hinge present in a BCMA-specific T-ChARM or CAR of this disclosure may be a hinge that is not based on or derived from an immunoglobulin hinge (i.e., not a wild type immunoglobulin hinge or an altered immunoglobulin hinge). Examples of such hinges include peptides of about five to about 150 amino acids of the stalk region of type II C-lectins or CD molecules, including peptides of about eight to about 25 amino acids or peptides of about seven to about 18 amino acids, or variants thereof.

A "stalk region" of a type II C-lectin or CD molecule refers to the portion of the extracellular domain of the type II C-lectin or CD molecule that is located between the C-type lectin-like domain (CTLD; e.g., similar to CTLD of natural killer cell receptors) and the hydrophobic portion (transmembrane domain). For example, the extracellular domain of human CD94 (GenBank Accession No. AAC50291.1) corresponds to amino acid residues 34-179, but the CTLD corresponds to amino acid residues 61-176, so the stalk region of the human CD94 molecule comprises amino acid residues 34-60, which are located between the hydrophobic portion (transmembrane domain) and CTLD (see Boyington et al., *Immunity* 10:75, 1999; for descriptions of other stalk regions, see also Beavil et al., *Proc. Nat'l. Acad. Sci. USA* 89:753, 1992; and Figdor et al., *Nat. Rev. Immunol.* 2:77, 2002). These type II C-lectin or CD molecules may also have junction amino acids between the stalk region and the transmembrane region or the CTLD. In another example, the 233 amino acid human NKG2A protein (GenBank Accession No. P26715.1) has a hydrophobic portion (transmembrane domain) ranging from amino acids 71-93 and an extracellular domain ranging from amino acids 94-233. The CTLD comprises amino acids 119-231, and the stalk region comprises amino acids 99-116, which may be flanked by additional junction amino acids. Other type II C-lectin or CD molecules, as well as their extracellular ligand-binding domains, stalk regions, and CTLDs are known in the art (see, e.g., GenBank Accession Nos. NP_001993.2; AAH07037.1; NP_001773.1; AAL65234.1; CAA04925.1; for the sequences of human CD23, CD69, CD72, NKG2A and NKG2D and their descriptions, respectively).

A "derivative" of a stalk region hinge, or fragment thereof, of a type II C-lectin or CD molecule includes about an eight to about 150 amino acid sequence in which one, two, or three amino acids of the stalk region of a wild type type II C-lectin or CD molecule have a deletion, insertion, substitution, or any combination thereof. For instance, a derivative can comprise one or more amino acid substitutions and/or an amino acid deletion. In certain embodiments, a derivative of a stalk region is more resistant to proteolytic cleavage as compared to the wild-type stalk region sequence, such as those derived from about eight to about 20 amino acids of NKG2A, NKG2D, CD23, CD64, CD72, or CD94.

In certain embodiments, stalk region hinges may comprise from about seven to about 18 amino acids and can form an α-helical coiled coil structure. In certain embodiments, stalk region hinges contain 0, 1, 2, 3, or 4 cysteines. Exemplary stalk region hinges include fragments of the stalk regions, such as those portions comprising from about ten to about 150 amino acids from the stalk regions of CD69, CD72, CD94, NKG2A and NKG2D.

Alternative hinges that can be used in BCMA-specific T-ChARMs and CARs of this disclosure are from portions of cell surface receptors (interdomain regions) that connect immunoglobulin V-like or immunoglobulin C-like domains. Regions between Ig V-like domains where the cell surface receptor contains multiple Ig V-like domains in tandem and between Ig C-like domains where the cell surface receptor contains multiple tandem Ig C-like regions are also contemplated as hinges useful in BCMA-specific T-ChARMs and CARs of this disclosure. In certain embodiments, hinge sequences comprised of cell surface receptor interdomain regions may further contain a naturally occurring or added motif, such as an IgG core hinge sequence to provide one or more disulfide bonds to stabilize the BCMA-specific T-ChARM or CAR dimer formation. Examples of hinges include interdomain regions between the Ig V-like and Ig C-like regions of CD2, CD4, CD22, CD33, CD48, CD58, CD66, CD80, CD86, CD150, CD166, or CD244.

In certain embodiments, hinge sequences have from about 5 to about 150 amino acids, about 5 to about 10 amino acids, about 10 to about 20 amino acids, about 20 to about 30 amino acids, about 30 to about 40 amino acids, about 40 to about 50 amino acids, about 50 to about 60 amino acids, about 5 to about 60 amino acids, about 5 to about 40 amino acids, for instance, about 8 to about 20 amino acids or about 10 to about 15 amino acids. The hinges may be primarily flexible, but may also provide more rigid characteristics or may contain primarily α-helical structure with minimal n-sheet structure.

In certain embodiments, a hinge sequence is stable in plasma and serum, and is resistant to proteolytic cleavage. For example, the first lysine in an IgG1 upper hinge region may be mutated or deleted to minimize proteolytic cleavage, and hinges may include junction amino acids. In some embodiments, a hinge sequence may contain a naturally occurring or added motif, such as an immunoglobulin hinge core structure CPPCP (SEQ ID NO.:9) that confers the capacity to form a disulfide bond or multiple disulfide bonds to stabilize dimer formation.

A hydrophobic portion contained in a BCMA-specific binding protein of the present disclosure (e.g., BCMA-specific T-ChARM or CAR) will allow a BCMA-specific binding protein of this disclosure to associate with a cellular membrane such that a portion of the binding protein will be located extracellularly (e.g., tag cassette, binding domain) and a portion will be located intracellularly (e.g., effector domain, costimulatory domain). A hydrophobic portion will generally be disposed within the cellular membrane phospholipid bilayer. In certain embodiments, one or more junction amino acids may be disposed between and connecting a hydrophobic portion with an effector domain, or disposed between and connecting a hydrophobic portion with a spacer region, or disposed between and connecting a hydrophobic portion with a tag cassette.

In certain embodiments, a hydrophobic domain is a transmembrane domain, such as one derived from an integral membrane protein (e.g., receptor, cluster of differentiation (CD) molecule, enzyme, transporter, cell adhesion molecule, or the like). In particular embodiments, a hydrophobic portion is a transmembrane domain from CD4, CD8, CD27, or CD28.

An intracellular component contained on a BCMA-specific binding protein of the present disclosure (e.g., BCMA-specific T-ChARM or CAR) will be capable of transmitting functional signals to a cell. In certain embodiments, a BCMA-specific T-ChARM or CAR will dimerize with a second single chain T-ChARM or CAR, respectively, wherein the dimerization allows the intracellular component comprising an effector domain and optionally a costimulatory domain to be in close proximity and promote signal transduction when exposed to the proper signal. In addition to forming such dimer protein complexes, the effector domains and optional costimulatory domains may further associate with other signaling factors, such as costimulatory factors, to form multiprotein complexes that produce an intracellular signal. In certain embodiments, an effector domain will indirectly promote a cellular response by associating with one or more other proteins that directly promote a cellular response. An intracellular component may include one, two, three or more receptor signaling domains (e.g., effector domains), costimulatory domains, or combinations thereof. Any intracellular component comprising an effector domain or functional portion thereof, a costimulatory domain or functional portion thereof, or any combination thereof from any of a variety of signaling molecules (e.g., signal transduction receptors) may be used in the BCMA-specific binding proteins of this disclosure.

An intracellular component may have an effector or costimulatory domain useful in the BCMA-specific binding proteins of this disclosure, which may be based on or from a protein of a Wnt signaling pathway (e.g., LRP, Ryk, ROR2), NOTCH signaling pathway (e.g., NOTCH1, NOTCH2, NOTCH3, NOTCH4), Hedgehog signaling pathway (e.g., PTCH, SMO), receptor tyrosine kinases (RTKs) (e.g., epidermal growth factor (EGF) receptor family, fibroblast growth factor (FGF) receptor family, hepatocyte growth factor (HGF) receptor family, Insulin receptor (IR) family, platelet-derived growth factor (PDGF) receptor family, vascular endothelial growth factor (VEGF) receptor family, tropomycin receptor kinase (Trk) receptor family, ephrin (Eph) receptor family, AXL receptor family, leukocyte tyrosine kinase (LTK) receptor family, tyrosine kinase with immunoglobulin-like and EGF-like domains 1 (TIE) receptor family, receptor tyrosine kinase-like orphan (ROR) receptor family, discoidin domain (DDR) receptor family, rearranged during transfection (RET) receptor family, tyrosine-protein kinase-like (PTK7) receptor family, related to receptor tyrosine kinase (RYK) receptor family, muscle specific kinase (MuSK) receptor family); G-protein-coupled receptors, GPCRs (Frizzled, Smoothened); serine/threonine kinase receptors (BMPR, TGFR); or cytokine receptors (IL-1R, IL-2R, IL-7R, IL-15R).

In certain embodiments, an effector domain comprises a lymphocyte receptor signaling domain or comprises an amino acid sequences having one or a plurality of immunoreceptor tyrosine-based activation motifs (ITAMs). In still further embodiments, an effector domain comprises a cytoplasmic portion that associates with a cytoplasmic signaling protein, wherein the cytoplasmic signaling protein is a lymphocyte receptor or signaling domain thereof, a protein comprising a plurality of ITAMs, a costimulatory factor, or any combination thereof.

Exemplary effector and costimulatory domains include those based on or derived from 4-1BB, CD3ε, CD3δ, CD3ζ, CD27, CD28, CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, Slp76, pTα, TCRα, TCRβ, TRIM, Zap70, PTCH2, or any combination thereof.

In particular embodiments, BCMA-specific binding proteins of this disclosure comprise (a) an effector domain from CD3ζ or functional portion thereof and a costimulatory domain from CD28 or functional portion thereof, (b) an effector domain from CD3ζ or functional portion thereof and a costimulatory domain from 4-1BB or functional portion thereof, or (c) (a) an effector domain from CD3ζ or a functional portion thereof and a costimulatory domain from CD28 and 4-1BB or functional portions thereof.

γ-Secretase Inhibitors (GSI)

By way of background, γ-secretase is a multi-subunit integral membrane protease complex, including presenilin (PS), nicastrin (NCT), anterior pharynx-defective 1 (APH-1), and presenilin enhancer 2 (PEN-2). PS is the catalytic subunit that is an aspartate protease capable of forming a hydrophilic catalytic pore buried within the membrane (Takasugi et al., *Nature* 422:438-41, 2003), which cleaves single pass transmembrane proteins within the transmembrane domain. NCT is a type I membrane glycoprotein with a large extracellular domain (ECD), which ECD captures the amino-terminus of the substrate as a primary substrate receptor for γ-secretase (Shah et al., *Cell* 122:435-47, 2005). The γ-secretase complex plays a role in a processing of a variety of substrates, including Notch, CD44, Cadherins, and ephrin B2, as well as cleaving amyloid precursor protein into amyloid beta peptide that is implicated in Alzheimer's disease. The γ-secretase complex is also known to cleave B-cell maturation antigen (BCMA) (Laurent et al., *Nature Communications* 6, 2015), which is a therapeutic target in various cancers, including multiple myeloma.

Exemplary γ-secretase inhibitors (GSIs) include small molecules, peptidomimetic compounds or γ-secretase-specific binding proteins. A GSI can target any one or more of the γ-secretase complex proteins, including presenilin 1 (PS1), presenilin 2 (PS2), nicastrin (NCT), anterior pharynx-defective 1 (APH-1), and presenilin enhancer 2 (PEN-2), provided that the γ-secretase cleavage activity is reduced compared to uninhibited γ-secretase. In certain embodiments, the γ-secretase activity is reduced at least about 50%, at least about 60%, at least about 70%, at least about 75%, at least about 80%, at least about 85%, at least about 90%, at least about 95%, or 100%. Assays for measuring γ-secretase activity are known in the art (see, e.g., Laurent et al., 2015). For example, the level of soluble BCMA can be a surrogate measure for γ-secretase activity. Representative small molecule GSIs, for use with a BCMA-targeted immunotherapy to treat a proliferative or autoimmune disease or disorder, include avagacestat, DAPT, BMS-906024, BMS-986115, LY411575, MK-0752, PF-03084014, RO4929097, semagacestat, YO-01027, and any combination thereof.

Other GSIs are γ-secretase-specific binding proteins, such as antibodies or antigen binding portions thereof that a γ-secretase complex or a γ-secretase complex protein, such as presenilin 1 (PS1), presenilin 2 (PS2), nicastrin (NCT), anterior pharynx-defective 1 (APH-1), and presenilin enhancer 2 (PEN-2). An exemplary γ-secretase-specific binding protein is a nicastrin-specific binding protein, such as antibodies scFvG9, A5226A, 2H6, 10C11, and antigen binding fragments thereof.

Binding Domains

A binding domain may be any peptide that specifically binds BCMA or specifically inhibits γ-secretase activity as described herein. Sources of binding domains include antibody variable regions from various species (which can be in the form of antibodies, sFvs, scFvs, Fabs, scFv-based grababody, or soluble VH domain or domain antibodies), including human, rodent, avian, or ovine. Additional sources of binding domains include variable regions of antibodies from other species, such as camelid (from camels, dromedaries, or llamas; Ghahroudi et al., *FEBS Lett.* 414:521, 1997; Vincke et al., *J. Biol. Chem.* 284:3273, 2009; Hamers-Casterman et al., *Nature* 363:446, 1993 and Nguyen et al., *J. Mol. Biol.* 275:413, 1998), nurse sharks (Roux et al., *Proc. Nat'l. Acad. Sci. (USA)* 95:11804, 1998), spotted ratfish (Nguyen et al., *Immunogen.* 54:39, 2002), or lamprey (Herrin et al., *Proc. Nat'l. Acad. Sci. (USA)* 105:2040, 2008 and Alder et al. *Nat. Immunol.* 9:319, 2008). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008).

An alternative source of binding domains of this disclosure includes sequences that encode random peptide libraries or sequences that encode an engineered diversity of amino acids in loop regions of alternative non-antibody scaffolds, such as scTCR (see, e.g., Lake et al., *Int. Immunol.* 11:745, 1999; Maynard et al., *J. Immunol. Methods* 306:51, 2005; U.S. Pat. No. 8,361,794), fibrinogen domains (see, e.g., Weisel et al., *Science* 230:1388, 1985), Kunitz domains (see, e.g., U.S. Pat. No. 6,423,498), designed ankyrin repeat proteins (DARPins) (Binz et al., *J. Mol. Biol.* 332:489, 2003 and Binz et al., *Nat. Biotechnol.* 22:575, 2004), fibronectin binding domains (adnectins or monobodies) (Richards et al., *J. Mol. Biol.* 326:1475, 2003; Parker et al., *Protein Eng. Des. Selec.* 18:435, 2005 and Hackel et al. (2008) *J. Mol. Biol.* 381:1238-1252), cysteine-knot miniproteins (Vita et. al. (1995) *Proc. Nat'l. Acad. Sci. (USA)* 92:6404-6408; Martin et al. (2002) *Nat. Biotechnol.* 21:71, 2002 and Huang et al. (2005) *Structure* 13:755, 2005), tetratricopeptide repeat domains (Main et al., *Structure* 11:497, 2003 and Cortajarena et al., *ACS Chem. Biol.* 3:161, 2008), leucine-rich repeat domains (Stumpp et al., *J. Mol. Biol.* 332:471, 2003), lipocalin domains (see, e.g., WO 2006/095164, Beste et al., *Proc. Nat'l. Acad. Sci. (USA)* 96:1898, 1999 and Schönfeld et al., *Proc. Nat'l. Acad. Sci. (USA)* 106:8198, 2009), V-like domains (see, e.g., US Patent Application Publication No. 2007/0065431), C-type lectin domains (Zelensky and Gready, *FEBS J.* 272:6179, 2005; Beavil et al., *Proc. Nat'l. Acad. Sci. (USA)* 89:753, 1992 and Sato et al., *Proc. Nat'l. Acad. Sci. (USA)* 100:7779, 2003), mAb$^2$ or Fcab™ (see, e.g., PCT Patent Application Publication Nos. WO 2007/098934; WO 2006/072620), armadillo repeat proteins (see, e.g., Madhurantakam et al., *Protein Sci.* 21: 1015, 2012; PCT Patent Application Publication No. WO 2009/040338), affilin (Ebersbach et al., *J. Mol. Biol.* 372: 172, 2007), affibody, avimers, knottins, fynomers, atrimers, cytotoxic T-lymphocyte associated protein-4 (Weidle et al., *Cancer Gen. Proteo.* 10:155, 2013) or the like (Nord et al., *Protein Eng.* 8:601, 1995; Nord et al., *Nat. Biotechnol.* 15:772, 1997; Nord et al., *Euro. J. Biochem.* 268:4269, 2001; Binz et al., *Nat. Biotechnol.* 23:1257, 2005; Boersma and Plückthun, *Curr. Opin. Biotechnol.* 22:849, 2011).

Binding domains of this disclosure can be generated as described herein or by a variety of methods known in the art (see, e.g., U.S. Pat. Nos. 6,291,161 and 6,291,158). For example, binding domains of this disclosure may be identified by screening a Fab phage library for Fab fragments that specifically bind to a target of interest (e.g., BCMA, γ-secretase complex component such as presenilin or nicastrin) (see Hoet et al., *Nat. Biotechnol.* 23:344, 2005). Additionally, traditional strategies for hybridoma development using a target of interest (e.g., BCMA, γ-secretase complex component such as presenilin or nicastrin) as an immunogen in convenient systems (e.g., mice, HuMAb Mouse®, TC Mouse™, KM-Mouse®, llamas, chicken, rats, hamsters, rabbits, etc.) can be used to develop binding domains of this disclosure.

In some embodiments, a binding domain is a single chain Fv fragment (scFv) that comprises VH and VL regions specific for a target of interest (e.g., BCMA, γ-secretase complex component such as presenilin or nicastrin). In certain embodiments, the $V_H$ and $V_L$ regions are human. Exemplary $V_H$ and $V_L$ regions include the segments of anti-BCMA specific antibodies J22.0-xi, J22.9-xi, J6M0, J6M1, J6M2, J9M0, J9M1, J9M2, 11D5-3, CA8, A7D12.2, C11 D5.3, C12A3.2, C13F12.1, 13C2, 17A5, 83A10, 13A4, 13D2, 14B11, 14E1, 29B11, 29F3, 13A7, CA7, SG1, S307118G03, S332121F02, S332126E04, S322110D07, S336105A07, S335115G01, S335122F05, ET140-3, ET140-24, ET140-37, ET140-40, ET140-54, TBL-CLN1, C4.E2.1, Vicky-1, pSCHLI333, pSCHLI372, or pSCHLI373. Other exemplary $V_H$ and $V_L$ regions include the segments of anti-nicastrin specific antibodies or antigen binding fragments thereof from scFvG9, A5226A, 2H6, or 10C11.

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region ($V_L$) (e.g., from anti-BCMA J22.0-xi, J22.9-xi, J6M0, J6M1, J6M2, J9M0, J9M1, J9M2, 110D5-3, CA8, A7D12.2, C11 D5.3, C12A3.2, or C13F12.1, 13C2, 17A5, 83A10, 13A4, 13D2, 14B11, 14E1, 29B11, 29F3, 13A7, CA7, S307118G03, S332121F02, S332126E04, S322110D07, S336105A07, S335115G01, S335122F05, ET140-3, ET140-24, ET140-37, ET140-40, ET140-54, TBL-CLN1, C4.E2.1, Vicky-1, pSCHLI333, pSCHLI372, or pSCHLI373; or from anti-nicastrin scFvG9, A5226A, 2H6, or 10C11) or to a heavy chain variable region ($V_H$) (e.g., from anti-BCMA J22.0-xi, J22.9-xi, J6M0, J6M1, J6M2, J9M0, J9M1, J9M2, 11D5-3, CA8, A7D12.2, C11 D5.3, C12A3.2, C13F12.1, 13C2, 17A5, 83A10, 13A4, 13D2, 14B11, 14E1, 29B11, 29F3, 13A7, CA7, SG1, S307118G03, S332121F02, S332126E04, S322110D07, S336105A07, S335115G01, S335122F05, ET140-3, ET140-24, ET140-37, ET140-40, ET140-54, TBL-CLN1, C4.E2.1, Vicky-1, pSCHLI333, pSCHLI372, or pSCHLI373; or from anti-nicastrin scFvG9, A5226A, 2H6, or 10C11), or both, wherein each CDR comprises zero changes or at most one, two, or three changes, from a monoclonal antibody or fragment or derivative thereof that specifically binds to target of interest (e.g., BCMA, γ-secretase complex component such as presenilin or nicastrin).

In certain embodiments, a binding domain $V_H$ region of the present disclosure can be derived from or based on a $V_H$ of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_H$ of a known monoclonal antibody. An insertion, deletion or substitution may be anywhere in the $V_H$ region, including at the amino- or carboxy-terminus or both ends of this region, provided that each CDR comprises zero changes or at most one, two, or three changes and provided a binding domain containing the modified $V_H$ region can still specifically bind its target with an affinity similar to the wild type binding domain.

In further embodiments, a $V_L$ region in a binding domain of the present disclosure is derived from or based on a $V_L$ of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the $V_L$ of the known monoclonal antibody. An insertion, deletion or substitution may be anywhere in the $V_L$ region, including at the amino- or carboxy-terminus or both ends of this region, provided that each CDR comprises zero changes or at most one, two, or three changes and provided a binding domain containing the modified $V_L$ region can still specifically bind its target with an affinity similar to the wild type binding domain.

The $V_H$ and $V_L$ domains may be arranged in either orientation (i.e., from amino-terminus to carboxyl terminus, $V_H$-$V_L$ or $V_L$-$V_H$) and may be joined by an amino acid sequence (e.g., having a length of about five to about 35 amino acids) capable of providing a spacer function such that the two sub-binding domains can interact to form a functional binding domain. In certain embodiments, a variable region linker that joins the $V_H$ and $V_L$ domains includes those belonging to the (Gly$_n$Ser) family, such as (Gly$_3$Ser)$_n$(Gly$_4$Ser)$_1$ (SEQ ID NO:3), (Gly$_3$Ser)$_1$(Gly$_4$Ser)$_n$ (SEQ ID NO:10), (Gly$_3$Ser)$_n$(Gly$_4$Ser)$_n$ (SEQ ID NO:4), or (Gly$_4$Ser)$_n$ (SEQ ID NO: 5), wherein n is an integer of 1 to 5. In certain embodiments, the linker is (Gly-Gly-Gly-Gly-Ser)$_3$ (SEQ ID NO.:12) or (Gly-Gly-Gly-Ser)$_4$ (SEQ ID NO.:13). In certain embodiments, these (Gly$_n$Ser)-based linkers are used to link the $V_H$ and $V_L$ domains in a binding domain, and these linkers may also be used to link the binding domain to a tag cassette, or to link a tag cassette to a hydrophobic portion or intracellular component.

In some embodiments, a binding domain is a single chain T cell receptor (scTCR) comprising $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or comprising $V_\alpha$-$C_\alpha$, $V_\beta$-$C_\beta$, $V_\alpha$-$V_\beta$ pair specific for a target of interest (e.g., peptide-MHC complex).

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a TCR $V_\alpha$, $V_\beta$, $C_\alpha$, or $C_\beta$, wherein each CDR comprises zero changes or at most one, two, or three changes, from a TCR or fragment or derivative thereof that specifically binds to a target of interest (e.g., BCMA, γ-secretase complex component such as presenilin or nicastrin).

In certain embodiments, a binding domain $V_\alpha$, $V_\beta$, $C_\alpha$, or $C_\beta$ region of the present disclosure can be derived from or based on a $V_\alpha$, $V_\beta$, $C_\alpha$, or $C_\beta$ of a known TCR (e.g., a high-affinity TCR) and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a $V_\alpha$, $V_\beta$, $C_\alpha$, or $C_\beta$ region, including at the amino- or carboxy-terminus or both ends of these regions, provided that each CDR comprises zero changes or at most one, two, or three changes and provided a binding domain containing a modified $V_\alpha$, $V_\beta$, $C_\alpha$, or $C_\beta$ region can still specifically bind its target with an affinity similar to wild type.

BCMA, γ-secretase, or both may be found on or in association with a cell of interest ("target cell"). Exemplary target cells include a cancer cell, a cell associated with an autoimmune disease or disorder or with an inflammatory disease or disorder, and an infectious organism or cell (e.g., bacteria, virus, virus-infected cell).

Cytotoxic Conjugates

Antibody-drug conjugates are used for selectively delivering a cytotoxic element to a target cell, e.g., a tumor or cancer cell. Antibody-drug conjugates and related techniques and chemistries are described in, for example, Nasiri et al., *J. Cell. Physiol.* (2018), Hedrich et al., *Clin. Pharmacokinet.* (2017), Drake and Rabuka, *BioDrugs* 31(6):521 (2017), Meyer et al., *Bioconj. Chem.* 27(12):2791 (2016), Mock et al., *J. Nucl. Med.* 58:83S (2017), Nareshkumar et al., *Pharm. Res.* 32:3526 (2015), Parslow et al., *Biomedicines* 4:14 (2016), and Green et al., *Blood* 131:611 (2018), of which the antibody formats, cytotoxic payloads, linker and conjugation chemistries, dosing regimens, treatment methods, pharmacokinetics, and principles of ADC design are incorporated herein by reference in their entirety.

In certain embodiments of the methods provided herein, a BCMA-specific antibody or antigen-binding portion thereof, chimeric antigen receptor (CAR), or tagged chimeric antigen receptor molecule (T-ChARM) is conjugated or otherwise coupled to a cytotoxic agent, such as a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamincoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

An exemplary ADC that specifically binds to BCMA is J6M0-mcMMAF (GSK2857916), described in Tai et al., *Blood* 123(20):3128-3138 (2014), which ADC and methods of using the same are hereby incorporated by reference in their entirety. Another BCMA-specific ADC (SG1-MMAF) was described by Ryan et al. (*Mol. Cancer Ther.,* 6(11): 3009-3018, 2007), which ADC is incorporated herein by reference.

Host Cells and Nucleic Acids

In certain aspects, the present disclosure provides nucleic acid molecules that encode any one or more of the BCMA-specific binding proteins (including multispecific and bispecific binding proteins comprising at least one BCMA binding domain) or γ-secretase inhibitors described herein. Such nucleic acid molecules can be inserted into an appropriate vector (e.g., viral vector or non-viral plasmid vector) for introduction in a host cell of interest (e.g., T cell).

As used herein, the term "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, fusion proteins or enzymes, or other nucleic acid molecule additions, deletions, substitutions, or other functional disruption of a cell's genetic material. Additional modifications include, for example, non-coding regulatory regions in which the modifications alter expression of a gene or operon. In certain embodiments, a cell, such as a T cell, obtained from a subject may be converted into a non-natural or recombinant cell (e.g., a non-natural or recombinant T cell) by introducing a nucleic acid that encodes a BCMA-specific binding protein or γ-secretase inhibitor of this disclosure (e.g., BCMA-specific T-ChARM or CAR; or anti-γ-secretase) as described herein and whereby the cell expresses a cell surface located BCMA specific binding protein.

A vector that encodes a core virus is referred to herein as a "viral vector." There are a large number of available viral vectors suitable for use with the compositions of the instant disclosure, including those identified for human gene therapy applications (see Pfeifer and Verma, *Ann. Rev. Genomics Hum. Genet.* 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric antigen receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous polynucleotide encoding a BCMA-specific binding protein or γ-secretase inhibitor. A viral vector may be a retroviral vector or a lentiviral vector. A viral vector may also include polynucleotides encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising green fluorescent protein, an extracellular domain of human CD2, or a truncated human EGFR (huEGFRt; see Wang et al., *Blood* 118:1255, 2011). When a viral vector genome comprises a plurality of nucleic acid sequences to be expressed in a host cell as separate transcripts, the viral vector may also comprise additional sequences between the two (or more) transcripts allowing bicistronic or multicistronic expression. Examples of such sequences used in viral vectors include internal ribosome entry sites (IRES), furin cleavage sites, viral 2A peptide (e.g., P2A, T2A, E2A, F2A), or any combination thereof.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other vectors recently developed for gene therapy uses can also be used with the compositions and methods of this disclosure. Such vectors include those derived from baculoviruses and α-viruses. (Jolly, D J. 1999. *Emerging Viral Vectors*. p. 209-40 in Friedmann T. ed. The Development of Human Gene Therapy. New York: Cold Spring Harbor Lab), or plasmid vectors (such as sleeping beauty or other transposon vectors). In some embodiments, a viral or plasmid vector further comprises a gene marker for transduction (e.g. green fluorescent protein, huEGFRt).

In certain embodiments, hematopoietic progenitor cells or embryonic stem cells are modified to comprise a non-endogenous polynucleotide that encodes a BCMA-specific binding protein (e.g., BCMA-specific T-ChARM or CAR) of this disclosure. Hematopoietic progenitor cells may comprise thymocyte progenitor cells or induced pluripotent stem cells, which may be derived or originate from fetal liver tissue, bone marrow, cord blood, or peripheral blood. The hematopoietic progenitor cells may be from human, mouse, rat, or other mammals. In particular embodiments, $CD24^{lo}$ $Lin^-$ $CD117^+$ thymocyte progenitor cells are used.

In certain embodiments, culture conditions entail culturing hematopoietic progenitor cells expressing fusion proteins of this disclosure for a sufficient time to induce proliferation or differentiation. The cells are maintained in culture generally for about 3 days to about 5 days, or about 4 to about 10 days, or about 5 to about 20 days. It will be appreciated that the cells may be maintained for an appropriate amount of time required to achieve a desired result, i.e., a desired cellular composition or level of proliferation. For example, to generate a cellular composition comprising primarily immature and inactivated T cells, cells may be maintained in culture for about 5 to about 20 days. Cells may be maintained in culture for about 20 to about 30 days to generate a cellular composition comprising primarily mature T cells. Non-adherent cells may also be collected from culture at various time points, such as from about several days to about 25 days. In certain embodiments, hematopoietic stem cells are co-cultured on stromal cells lines (U.S. Pat. No. 7,575,925; Schmitt et al., *Nat. Immunol.* 5:410, 2004; Schmitt et al., *Immunity* 17:749, 2002).

One or more cytokines that promote commitment or differentiation of hematopoietic progenitor cells may be added to the culture. The cytokines may be human or non-human. Representative examples of cytokines that may be used include all members of the FGF family, including FGF-4 and FGF-2; Flt-3-ligand, stem cell factor (SCF), thrombopoietin (TPO), and IL-7. Cytokines may be used in combination with a glycosaminoglycan, such as heparin sulfate.

In some embodiments, host cells capable of expressing a BCMA-specific binding protein of this disclosure on the cell surface are T cells, including primary cells or cell lines derived from human, mouse, rat, or other mammals. If obtained from a mammal, a T cell can be obtained from numerous sources, including blood, bone marrow, lymph node, thymus, or other tissues or fluids. A T cell or subpopulations thereof (e.g., naïve, central memory, effector memory) may be enriched or purified. T cell lines are well known in the art, some of which are described in Sandberg et al., *Leukemia* 21:230, 2000. In certain embodiments, T cells that lack endogenous expression of TCRα and β chains are used. Such T cells may naturally lack endogenous expression of TCRα and β chains or may have been modified to block expression (e.g., T cells from a transgenic mouse that does not express TCR α and β chains or cells that have been manipulated to inhibit expression of TCR α and β chains) or to knockout TCRα chain, TCRβ chain, or both genes. In certain embodiments, cells capable of expressing a BCMA-specific binding protein of this disclosure on the cell surface are not T cells or cells of a T cell lineage, but cells that are progenitor cells, stem cells or cells that have been modified to express cell surface anti-CD3.

In any of the embodiments provided herein, a host cell can be a "universal donor" cell that is modified to reduce or eliminate expression of one or more endogenous genes involved in an immune response. For example, a T cell may be modified to reduce or eliminate expression of one or more polypeptides selected from PD-1, LAG-3, CTLA4, TIGIT, TIM3, an HLA complex component, or a TCR or TCR complex component. Without wishing to be bound by theory, certain endogenously expressed immune cell proteins may be recognized as foreign by an allogeneic host that receives the modified immune cells, which may result in elimination of the modified immune cells (e.g., an HLA allele), or may downregulate the immune activity of the modified immune cells (e.g., PD-1, LAG-3, CTLA4, TIGIT), or may interfere with the binding activity of a heterologously expressed binding protein of the present disclosure (e.g., an endogenous TCR that binds to a non-tumor-associated antigen and interferes with the antigen-specific receptor of the modified immune cell specifically binding to the tumor-associated antigen). Accordingly, decreasing or eliminating expression or activity of such endogenous genes or proteins can improve the activity, tolerance, and persistence of the modified immune cells in an allogeneic host setting, and can allow universal administration of the cells (e.g., to any recipient regardless of HLA type).

In certain embodiments, a host cell (e.g., modified immune cell) of this disclosure comprises a chromosomal gene knockout of one or more genes encoding a PD-1, LAG-3, CTLA4, TIM3, TIGIT, an HLA complex component (e.g., a gene that encodes an α1 macroglobulin, an α2 macroglobulin, an α3 macroglobulin, a β1 microglobulin, or a β2 microglobulin), a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013) the gene editing techniques, compositions, and adoptive cell therapies of which are herein incorporated by reference in their entirety). For example, in some embodiments, a chromosomal gene knockout is produced using a CRISPR/Cas9 system, and may involve transfection of the modified immune cell with a lentivirus (e.g., pLentiCRISPRv2; Torikai et al., *Blood* (2016)) expressing a CRISPR/Cas9 system targeting PD-1, LAG-3, CTLA4, an HLA component, or a TCR component, or any combination thereof. Primers useful for designing a lentivirus that expresses a CRISPR/Cas9 system for inhibiting an endogenously expressed immune cell protein include for example, primer pairs comprising forward and reverse primers having the nucleotide sequences set forth in SEQ ID NOS:22 and 23, 24 and 25, 26 and 27, and 28 and 29.

In certain embodiments, a host T cell transfected to express a BCMA-specific binding protein (e.g., T-ChARM, CAR, multispecific binding proteins comprising at least one BCMA binding domain, bispecific binding proteins comprising at least one BCMA binding domain) of this disclosure is a functional T cell, such as a virus-specific T cell, a tumor antigen specific cytotoxic T cell, a naïve T cell, a memory stem T cell, a central or effector memory T cell, or a CD4+ CD25+ regulatory T cell.

One or more growth factor cytokines that promote proliferation of T cells expressing a BCMA-specific binding protein of this disclosure may be added to the culture. The cytokines may be human or non-human. Exemplary growth factor cytokines that may be used promote T cell proliferation include IL-2, IL-15, IL-21, or the like.

Uses

Diseases that may be treated with a BCMA-targeted immunotherapy or cells expressing a BCMA-specific binding protein in combination with a γ-secretase inhibitor (GSI) as described in the present disclosure include cancer (e.g., cancers that express BCMA), immune diseases (e.g., autoimmune), or aging-related diseases (e.g., senescence). Adoptive immune and gene therapy are promising treatments for various types of cancer (Morgan et al., Science 314:126, 2006; Schmitt et al., Hum. Gene Ther. 20:1240, 2009; June, J. Clin. Invest. 117:1466, 2007) and infectious disease (Kitchen et al., PLoS One 4:38208, 2009; Rossi et al., Nat. Biotechnol. 25:1444, 2007; Zhang et al., PLoS Pathog. 6:e 1001018, 2010; Luo et al., J. Mol. Med. 89:903, 2011).

Cancers that are amenable to the compositions and methods disclosed herein are those that express, or are capable of expressing, BCMA on their cell surface. Exemplary types of cancer that may be treated include myelomas (such as multiple myeloma), leukemias (such as plasma cell leukemia), lymphomas (such as lymphoplasmacytic lymphoma), plasmacytomas, Waldenström's macroglobulinemia. Other cancers that may express BCMA include adenocarcinoma of the breast and bronchogenic carcinoma of the lung. In certain embodiments, proliferative disorders amenable to a combination therapy of a BCMA-specific binding protein and a GSI are certain types of B-cell cancer, including plasma cell disorders (such as, for example, multiple myeloma).

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-Barré Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In particular embodiments, a method of treating a subject with the BCMA-binding protein in combination with a γ-secretase inhibitor as disclosed herein include treating multiple myeloma, plasmacytoma, plasma cell leukemia, Waldenström's macroglobulinemia, B cell lymphoma, and lymphoplasmactyic lymphoma.

A BCMA-specific binding protein, such as a CAR or T-ChARM, of this disclosure may be administered to a subject in cell-bound form (e.g., gene therapy of target cell population (mature T cells (e.g., CD8$^+$ or CD4$^+$ T cells) or other cells of T cell lineage)). In a particular embodiment, cells of T cell lineage expressing BCMA-specific binding protein (e.g., BCMA specific CAR or T-ChARM) administered to a subject are syngeneic, allogeneic, or autologous cells.

A method of the present disclosure includes steps of administering a BCMA-specific binding molecule expressed on an immune cell surface (e.g., T cell) and administering a γ-secretase inhibitor (GSI). In certain embodiments, the combination may be administered concurrently, together in the same pharmaceutically acceptable carrier, or in separate formulations (but concurrently). Concurrent administration means the each component is administered at the same time or within 8-12 hours of each other. Administration of a second component more than 12 hours after the first component will be considered a sequential administration. In other embodiments, a BCMA-specific immunotherapeutic and GSI can be administered sequentially (e.g., one, two, three, four, five, six, seven, eight, or nine days apart; one, two, three, or four weeks apart; one, two, three, four, five, six, seven, eight, or nine weeks apart; or one, two, three, four, five, six, or more years apart; or the like), in any order and in any combination. In particular embodiments, when administered sequentially, the GSI is administered first and the BCMA-targeted immunotherapy (soluble or cell form) is administered second. In other embodiments, a BCMA-targeted immunotherapy (soluble or cell form) is administered first and the GSI is administered second. In particular embodiments, a BCMA-targeted immunotherapy comprising a modified immune cell that specifically binds to BCMA (e.g., a BCMA-specific T cell, such as a CAR-T, T-ChARM, bispecific, multispecific T cell) is administered first and a GSI is administered second (e.g., within hours, days, weeks, months, or years of the BCMA immunotherapy). In further embodiments, a BCMA-targeted immunotherapy comprising a modified immune cell comprising a binding protein that specifically binds to BCMA (e.g., a BCMA-specific T cell, such as a CAR-T, T-ChARM, bispecific, multispecific T cell) is (a) administered to a subject; (b) after a period of time (e.g., about 5 days to about one week, about one week to about two weeks, about two weeks to about three weeks, about one week to about one month, about one month to about six months, about three months to about one year, or the longer as needed), the subject or a tissue from the subject is probed or examined for the presence or persistence of the previously administered modified immune cell comprising a binding protein that specifically binds to BCMA, and (c) administering a GSI second after the presence or persistence of the BCMA immunotherapy is detected.

In some embodiments, a GSI is administered to a subject at least once before, simultaneous with, and at least once (e.g., at least two, three, or four times) after, the BCMA-targeted immunotherapy. In particular embodiments, a combination therapy of this disclosure comprises a BCMA-targeted immunotherapy and administration of from about 0.01 μM GSI to about 5 μM GSI, from about 0.03 μM GSI to about 1.5 μM GSI, from about 0.05 μM GSI to about 2.5 μM GSI, or from about 0.1 μM GSI to about 1.0 μM GSI. In certain embodiments, a combination therapy comprising a modified immune cell that specifically binds BCMA and a GSI comprises a lower amount of the immune cell that specifically binds BCMA, the GSI, or both as compared to administration of these therapies individually.

For example, by way of background and not wishing to be bound by theory, during adoptive immunotherapy engraftment of administered cells expressing the BCMA-specific binding protein may be facilitated by prior immunosuppressive conditioning with one or more chemotherapeutic agents or treatments. In any of the embodiments described herein, the method further comprises pre-conditioning a subject concurrent with or prior to administering a BCMA-targeted immunotherapy or an immune cell expressing a BCMA-specific binding protein and a GSI. In particular embodiments, a pre-conditioning regimen is an immunosuppressive conditioning comprising depleting endogenous lymphocytes (also referred to as lymphodepletion, which may be non-myeloablative or myeloablative). Exemplary lymphodepletion may be achieved with cyclophosphamide alone, cyclophosphamide in combination with fludarabine, by use of other agents or treatments that are cytotoxic to lymphocytes (e.g., total body irradiation), or any combination thereof.

The binding molecule, inhibitor or combination compositions may be administered orally, topically, transdermally, parenterally, by inhalation spray, vaginally, rectally, or by intracranial injection, or any combination thereof. When administered separately, a BCMA-targeted immunotherapy and a GSI may be administered by the same route or by different routes. For example, in certain embodiments, the BCMA-targeted immunotherapy is administered parenterally and the GSI is administered orally, which can be concurrently or sequentially. The term "parenteral," as used herein, includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient. Injection or infusion, especially intravenous, is preferred for administering a BCMA-targeted immunotherapy.

In other embodiments, BCMA-specific binding protein, GSI or both may be administered to a subject in soluble form (e.g., antibody). Soluble TCRs are also known in the art (see, e.g., Molloy et al., Curr. Opin. Pharmacol. 5:438, 2005; U.S. Pat. No. 6,759,243).

Pharmaceutical compositions including a combination therapy of a BCMA-targeted immunotherapy and a γ-secretase inhibitor of this disclosure may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration. The present disclosure provides pharmaceutical compositions comprising cells expressing a BCMA-specific binding protein, such as a CAR or T-ChARM, and a pharmaceutically acceptable carrier, diluents, or excipient. Suitable excipients include water, saline, dextrose, glycerol, or the like and combinations thereof.

An advantage of the instant disclosure is that BCMA-specific binding protein, such as a CAR or T-ChARM, expressing cells administered to a patient can be depleted using the cognate binding partner to a tag cassette. In certain embodiments, the present disclosure provides a method for depleting a T cell expressing a BCMA-specific T-ChARM by using an antibody specific for the tag cassette, using a cognate binding partner specific for the tag cassette, or by using a second T cell expressing a CAR and having specificity for the tag cassette. In certain embodiments, a tag cassette allows for immunodepletion of a T cell expressing a BCMA-specific T-ChARM of this disclosure. Elimination of engineered T cells may be accomplished using depletion agents specific for a tag cassette. For example, if a Strep tag is used, then an anti-Strep tag antibody, anti-Strep tag scFv, or Streptactin each fused to or conjugated to a cell-toxic reagent (such as a toxin, radiometal) may be used, or an anti-Strep tag/anti-CD3 bispecific scFv, or an anti-Strep tag CAR T cell may be used.

In another aspect, the present disclosure provides a method for selectively promoting proliferation of a recombinant T cell expressing a BCMA-specific T-ChARM of this disclosure. In certain embodiments, the method comprises selective ex vivo proliferation of T cells expressing a BCMA-specific T-ChARM using a tag binding partner, such as an antibody. In further embodiments, the method comprises expanding functional T cells (e.g., virus-specific, TAA (tumor-associated antigen) specific CTL, or specific T cell subsets, such as naïve T cells, memory stem T cells, central or effector memory T cells, CD4+ CD25+ regulatory T cells) with a tag binding partner, such as an antibody, which may optionally be done in the presence of a costimulatory molecule binding partner (such as an anti-CD27 or antiCD28 antibody).

In still further embodiments, a BCMA-specific T-ChARM allows for selective promotion of T cell proliferation in vivo when expressing a BCMA-specific T-ChARM of this disclosure. In certain embodiments, a T cell expressing a CAR comprising a tag cassette allows for expansion of the CAR T cells in vivo when contacting cells expressing a ligand (e.g., including T cell suppressor cell ligands PD-L1, PD-L2). Such expanded T cells are useful in the disease treatment methods described herein. In certain embodiments, proliferation or expansion of cells expressing BCMA-specific T-ChARM as disclosed herein is induced in vivo, which may be induced with a tag cassette binding partner (such as an anti-tag antibody) and optionally a costimulatory molecule binding partner (such as an anti-CD27 or anti-CD28 antibody).

In certain further embodiments, cells expressing BCMA-specific T-ChARM as disclosed herein are activated in vivo, such as at the site of a tumor. For example, a composition (e.g., alginate, basement membrane matrix (Matrigel®), biopolymer, or other matrix) or a carrier (e.g., microbead, nanoparticle, or other solid surface) comprising a tag cassette binding partner (such as an anti-tag antibody) and a costimulatory molecule binding partner (such as an anti-CD27 or antiCD28 antibody) may be used to locally activate at the site of a tumor (e.g., a solid tumor) a T cell expressing a BCMA-specific T-ChARM as disclosed herein.

In certain embodiments, recombinant cells expressing a BCMA-specific T-ChARM may be detected or tracked in vivo by using antibodies that bind with specificity to a tag cassette (e.g., anti-Tag antibodies), or by other cognate binding proteins that specifically bind the tag cassette sequence (e.g., Streptactin binding to Strep tag), which binding partners for the tag cassette are conjugated to a fluorescent dye, radio-tracer, iron-oxide nanoparticle or other imaging agent known in the art for detection by X-ray, CT-scan, MRI-scan, PET-scan, ultrasound, flow-cytometry, near infrared imaging systems, or other imaging modalities (see, e.g., Yu et al., *Theranostics* 2:3, 2012).

In further embodiments, cells expressing BCMA-specific T-ChARM of the instant disclosure may be used in diagnostic methods or imaging methods, including methods used in relation to the indications or conditions identified herein.

In some embodiments, a method comprises administering a GSI in combination (e.g., concurrently, separately, or sequentially) with a BCMA-specific binding protein that may comprise, for example, a BCMA-specific antibody or antigen-binding portion thereof, such as antibody-drug conjugate, or a bispecific or a multispecific binding protein, such as those useful for pre-targeted radiation immunotherapy (see, e.g., Green et al., *Blood* 131:611 (2018)).

EXAMPLES

Example 1

Design and Testing of BCMA-Specific Chimeric Antigen Receptors

Anti-BCMA CARs were prepared to examine their usefulness for immunotherapy of multiple myeloma and other disorders. Anti-BCMA CARs were constructed with scFvs comprised of the $V_H$ and $V_L$ regions from C115 D5.3 ("C11") antibody and A7D12.2 ("A7") antibody, which included an IgG4 hinge region (spacer), a CD28 transmembrane domain, a 4-1BB costimulatory domain, and a CD3ζ effector domain. The scFvs were produced in both the "HL" and "LH" orientations (see FIG. 1A). Human T cells were transduced with expression constructs encoding the anti-BCMA CARs and examined for functional characteristics. As shown in FIG. 1B, T cells expressing the C11 CARs and A7 CARs proliferated when co-cultured with BCMA-expressing target cells, although the C11 CARs appeared to proliferate slightly more robustly than the A7 CAR-expressing T cells. The C11 CAR-T cells also produced more cytokines in response to target cell lines (either antigen-transfected K562 cells or BCMA-expressing MM cell lines; FIG. 1C) and had greater specific killing activity against target cells as compared to the A7 LH CAR-T cells (FIG. 1D).

Additional A7 and C11 CARs were generated having different intracellular components, including CARs containing a 4-1BB costimulatory domain (FIG. 1E, upper illustration) and a CD28 costimulatory domain (FIG. 1E, lower illustration). The length of the extracellular spacer domain was also varied to improve interaction between the CAR expressing T cell and the BCMA⁺ target cell, including short (e.g., 12 amino acids, 48 amino acids, and 66 amino acids in length), intermediate (e.g., 157 amino acids in length), and long (e.g., 228 amino acids in length) spacers. The 48 amino acid and 157 amino acid spacer CARs each included two (2) Strep-Tag cassettes, while the 66 amino acid spacer included three (3) Strep-Tag cassettes (see FIG. 1F). Tagged chimeric antigen receptors such as the Strep-Tag cassette-containing CARs shown in FIGS. 1F and 1G are referred to herein as T-ChARMs.

Figure 1P:
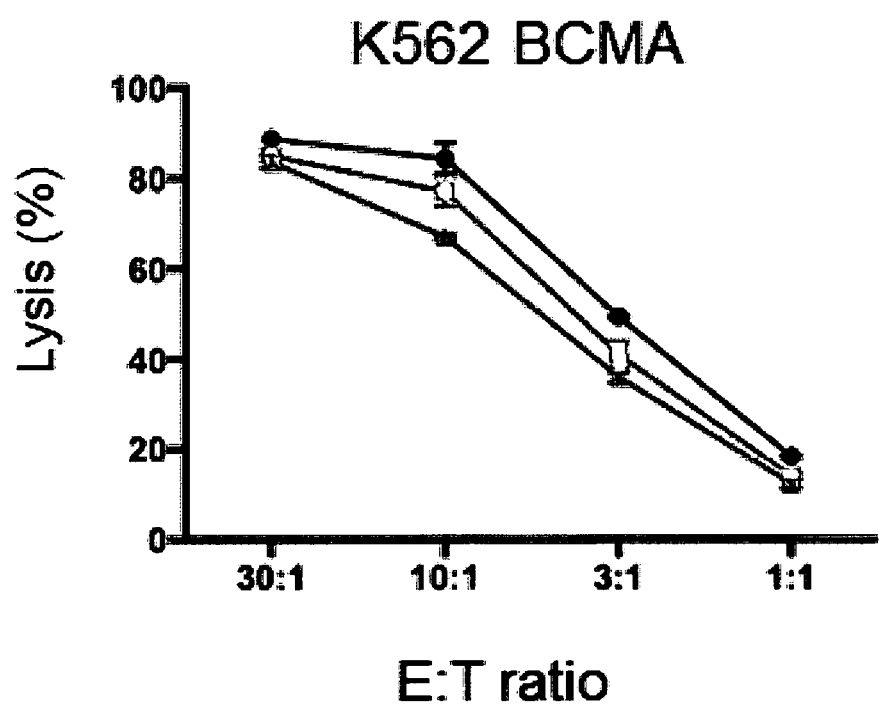

Human T cells were transduced to express the T-ChARMs (see Example 2) and analyzed for functionality. The length of the spacer had an effect on the T-ChARM constructs comprising a scFv derived from anti-BCMA antibody C11 D5.3, wherein intermediate (about 65 amino acids; see C11 3ST, C11 2STint and C11Lo of FIG. 1H) to long (about 200 amino acids) spacers worked best for this binding domain. C113ST_4-1BB and C113ST_CD28 were selected as best-performing constructs (FIGS. 1H-1J) and compared to a previously disclosed anti-BCMA CAR ("BCMA-2"; Carpenter et al. *Clin. Cancer Res.* 19:2048, 2013). Expression of EGFRt on primary T cells was similar for each T-ChARM/CAR construct and surface expression of the T-ChARM was confirmed for those containing STII sequences as shown by staining with anti-STII monoclonal antibody (FIG. 1K). T cells expressing either C113ST T-ChARM produced more cytokines (FIG. 1L, 1M) and proliferated more robustly (FIG. 1N) than T cells expressing BCMA-2 when co-cultured with target cells. It was also determined that T cells expressing either C113ST T-ChARM can recognize and lyse CD138⁺ patient MM cells (data not shown). The T cells expressing either C113ST T-ChARM or the BCMA-2 CAR did not have cytolytic activity against non-antigen-expressing K562 cells (FIG. 1O), but effectively lysed K562 cells transduced to express the BCMA antigen (FIG. 1P), demonstrating that the engineered T cells specifically recognize antigen.

Example 2

Production of Recombinant T Cells and Expression of BCMA-Specific T-ChARMs

CD8⁺ and CD4⁺ T cells were isolated from PBMC of normal human donors using CD8⁺/CD4⁺ T Cell Isolation Kit (Miltenyi Biotec), activated with anti-CD3/CD28 beads (Life Technologies) according to the manufacturer's instructions, and transduced with a CAR-encoding lentiviral (epHIB7) supernatant generated by transient transfection of HEK293T cells using PsPAX2 and pMD2G packaging plasmids (MOI=3) supplemented with 0.8 µg/mL polybrene (Millipore, Bedford, Mass.) on day 3 after activation by centrifugation at 2,100 rpm for 45 min at 32° C. T cells were expanded in RPMI, 10% human serum, 2 mM L-glutamine and 1% penicillin-streptomycin (CTL medium), supplemented with recombinant human (rh) IL-2 to a final concentration of 50 U/mL every 48 hours. After expansion, an aliquot of each transduced T cell line was stained with biotin-conjugated anti-EGFR antibody and streptavidin-PE (Miltenyi, Auburn, Calif.). The tEGFR$^+$ T cells were isolated by sorting on a FACS-Aria cell sorter (Becton Dickinson). The tEGFR$^+$ T cell subset was then stimulated with irradiated (8,000 rad) CD19$^+$ B-LCL at a T cell:LCL ratio of 1:7, and expanded for 8 days in CTL medium with addition of 50 U/mL rh IL-2 every 48 hours or using a rapid expansion protocol for cells expressing T-ChARMs (Riddell and Greenberg, *J. Immunol. Methods* 128:189, 1990), wherein the T-ChARM comprises a scFv derived from anti-BCMA antibody A7 or C11 D5.3.

The following conjugated antibodies were used for flow cytometric phenotyping and analysis: CD4, CD8, CD25, CD137, CD45, Annexin V, CD62L, CD27, CD28 (BD Biosciences), anti-Streptag II antibody (Genscript), EGFR antibody (ImClone Systems Incorporated, Branchburg, N.J.); strepTavidin-PE (BD Biosciences, San Jose, Calif.). Staining with propidium iodide (PI, BD Biosciences) was performed for live/dead cell discrimination as directed by the manufacturer. Flow analyses were done on a FACS Canto II, sort-purifications on a FACS AriaII (Becton Dickinson, Franklin Lakes, N.J.) and data analyzed using FlowJo software (Treestar, Ashland, Oreg.).

To examine cell surface expression of BCMA-specific T-ChARM, transduced T cells were sorted for EGFRt expression and evaluated by staining with fluorochrome labeled anti-Streptag mAb. The mean fluorescence intensity (MFI) of EGFR staining was similar on T cells transduced with each of the BCMA-specific T-ChARM and the CD19-Short CAR. The introduction of a tag into a CAR to produce a T-ChARM did not interfere with transgene expression (data not shown). An anti-StrepTag mAb specifically stained T cells transduced with the various BCMA-specific T-ChARMs, independent of the position or number of tag sequences in each T-ChARM.

Example 3

Soluble BCMA (sBCMA) Inhibits BCMA-Specific CAR T Cell Activity

The potential effectiveness of BCMA-targeted T cell therapies against most myelomas was examined. Because shedding of surface BCMA by myeloma cells may hinder T cell recognition, soluble BCMA levels were measured in the supernatants during culture of a myeloma cell line. U266 myeloma cells were washed and plated in culture media for 1, 3, 5 and 24 hours. The media supernatant was harvested and assayed for sBCMA by ELISA. The data shows a time-dependent increase in sBCMA levels in the supernatant (FIG. 2A). Next, the extent of BCMA expression on primary patient multiple myeloma (MM) cells and cytokine production by BCMA-specific T-ChARM T cells contacted with patient MM cells was examined. FIG. 2B shows surface BCMA expression by a reference cell line (RPMI, left panel) and samples from primary patient MM cells with differing levels of BCMA expression. The pie chart of FIG. 2C shows that BCMA expression on the surface of MM cells from nineteen (19) different patients was found to be positive for most patients, though there were some patient samples that showed intermediate to low/no surface BCMA expression (~25%). Furthermore, FIG. 2D shows that the T-ChARM T cells produced more IFN-γ when cultured with patient MM cells expressing high levels of surface BCMA, as compared to culture with low-BCMA patient MM cells.

Myeloma cells frequently express PD-L1, which is believed to inhibit T cell function by binding to PD-1 on T cells (Freeman et al. *J. Exp. Med.* 192(7):1027 (2000)). The possibility that PD-L affected BCMA-specific T-ChARM T cells was also investigated. Flow cytometry of patient samples showed that PD-L1 was also expressed on 79% of samples, with 47% PD-L1$^{hi}$, 32% PD-L1$^{int}$, and 21% PD-L1$^{low/neg}$ (FIGS. 2E and 2F). No correlation between BCMA and PD-L1 expression was observed. FIG. 2G shows that T-ChARM T cells produced more IFN-γ when cultured with patient MM cells expressing low levels of PD-L1 versus high levels of PD-L1, although this trend was not statistically significant.

The effect of sBCMA was examined as well by adding sBCMA to co-cultures of T cells expressing a BCMA-specific T-ChARM and K562 cells transduced with a polynucleotide encoding full-length BCMA (K562/BCMA$^+$). A dose-dependent inhibition of BCMA-specific T-ChARM T cell effector function was detected as a measure of IFN-γ release into the media supernatant upon administration of exogenous sBCMA (FIGS. 2H, 2I). Additionally, MM cell lines showed substantial increases in culture supernatant sBCMA within 24 hours (FIG. 2J).

To examine whether high levels of sBCMA might inhibit the activity of BCMA-specific T-ChARM T cells, patient bone marrow (BM) sera were examined for sBCMA levels. Patient BM was found to have high levels of sBCMA, which roughly correlated with disease burden as determined by the percentage of CD138$^+$ cells present (FIG. 2K). To test whether sBCMA would bind to the T-ChARM T cells, the T cells were incubated with increasing levels of recombinant BCMA and then stained using BCMA-Fc conjugated to APC. As shown in FIG. 2L, the staining decreased with higher levels of recombinant BCMA, which indicates that sBCMA could potentially have a detrimental effect BCMA-specific T-ChARM T cell function.

To confirm T-ChARM expression, C113ST T-ChARM T cells and control anti-CD19 CAR T cells ("FMC63") were incubated with Fc-BCMA and stained for EGFRt (CAR/T-ChARM transduction marker) and CD4, showing that T-ChARMs were expressed by the cells (FIG. 2M). Staining of EGFRt and other T cell surface molecules was unaffected (data not shown).

To determine whether shedding and binding of sBCMA to the T-ChARMs inhibits T cell function, BCMA-Fc was added to T cell/target cell line co-cultures, resulting in much-reduced recognition (IFN-γ production and CD4 expression) by the BCMA-targeting T-ChARM T cells, but not by control anti-CD19 CAR T cells (cultured with K562 cells expressing the CD19 antigen (FIG. 2N). The effect on the BCMA T-ChARM T cells was dose-dependent (FIGS. 2O, 2P). Addition of recombinant BCMA not fused to the Fc also inhibited IFN-γ production in a dose-dependent fashion, but did not inhibit lysis of K562 BCMA$^+$ cells by T-ChARM T cells (FIG. 2Q), which may be due to high antigen density on the surface of the target cells.

Example 4

Effect of γ-Secretase Inhibitor on MM BCMA Levels

To examine the effect of γ-secretase inhibition on BCMA levels on myeloma cells, γ-secretase inhibitor (GSI) RO4929097 was used. BCMA is rapidly upregulated on various myeloma cell lines when incubated with γ-secretase inhibitor (GSI) RO4929097 (concentration used ranged from 0.001 µM to 1.0 µM) (FIGS. 3A-3D).

To examine the effect of GSI on surface BCMA expression kinetics, U266 myeloma cells were incubated for 1, 3, 5 and 24 hours in the presence of various concentrations of GSI RO429097 (0.01 µM, 0.1 µM and 1.0 µM) and evaluated for cell surface BCMA expression by flow cytometry. BCMA expression increased in a dose-dependent manner in the presence of a GSI (FIG. 3E). The upregulation persisted over 7 days of culture in in 1.0 µM GSI (FIG. 3F).

To test the effect of GSI on BCMA shedding in MM, three different myeloma cell lines (MM1.R, U266 and 8226) were washed and plated in culture media for 24 hours in the presence of various concentrations of GSI RO429097 (0.01 µM, 0.1 µM and 1.0 µM). The media supernatant was harvested and assayed for sBCMA by ELISA. sBCMA levels decreased in the supernatant in the presence of a GSI in a dose dependent manner (FIGS. 3G & 3H).

To examine the effect on soluble BCMA (sBCMA) levels over time, U266 cells were washed and plated in culture media for 1, 3, 5 and 24 hours in the presence of various concentrations of GSI RO429097 (0.01 µM, 0.1 µM and 1.0 µM). The media supernatant was harvested and assayed for soluble BCMA (sBCMA) by ELISA. The data shows a dose-dependent decrease in soluble BCMA levels in the supernatant when a GSI is present (FIG. 3I).

Next, the effect of removing GSI from MM cell culture was examined. As shown in FIGS. 3J and 3K, surface BCMA levels decreased following removal of 1.0 µM RO429097, while supernatant sBCMA increased when the GSI was removed, but did not increase when the GSI remained. These data indicate a reversible inhibitory effect of GSI on surface BCMA shedding. Finally, the viability of the tested MM cell lines was not affected by addition of 1.0 µM RO429097 to culture (FIG. 3L).

The effect of GSI on BCMA expression was then tested on primary myeloma samples from patients. CD138$^+$ myeloma cells were enriched from patient bone marrow samples, incubated for 3 hours in the presence of various concentrations of GSI RO429097 (0.01 µM to 10 µM) and evaluated for surface BCMA expression by flow cytometry (FIGS. 3M and 3R). BCMA mean fluorescence intensity (MFI) on tumor cells is presented as fold increase over tumor cells incubated without RO4929097. There is an observed dose-dependent upregulation of BCMA on tumor cells (FIG. 3N), while there was no effect on the levels of several other cell surface molecules, including CS1, CD86, PD-L1, CD80 and CD38 (FIGS. 3O-3Q).

Example 5

γ-Secretase Inhibitor Improves Recognition of BCMA$^+$ Myeloma Cells by T Cells Expressing BCMA-Specific T-Charm To examine the effect of a GSI on CAR T cell activity against BCMA$^+$ multiple myeloma, IL-2 production by BCMA CAR-T cells (BCMA-specific T-ChARM C11 3ST-CD28 and BCMA-specific T-ChARM C11 3ST-41BB) or control CD19sh CAR (short spacer)-T cells was measured after co-culture with primary human myeloma tumor cells for 24 hours in media containing at various concentrations of GSI RO429097 (0.003 µM to 3.0 µM) (FIG. 4A). Treatment with GSI resulted in a dose dependent increase in IL-2 production by BCMA T-ChARM T cells. Also, IFNγ production by BMCA T-ChARM T cells co-cultured with myeloma cells at various concentrations of RO429097 was measured and was also increased in the presence of GSI (FIG. 4B). These data show that multiple myeloma cells stimulate BCMA-specific T-ChARM T cells better when pre-treated with a γ-secretase inhibitor that upregulates BCMA expression on the tumor cell. Finally, proliferation of CFSE-labeled BCMA-specific T-ChARM T cells was increased in a dose dependent manner after co-culture for 3 days with primary human myeloma tumor cells in presence of GSI RO492097 (FIG. 4C).

Without wishing to be bound by theory, a potential caveat of using GSI to augment BCMA on myeloma cells to improve CAR-T cell recognition is that high concentrations of GSI may inhibit T-cell signaling and effector functions. See Eagar et al., *Immunity* 20(4):407, 2004. To evaluate potential effects of GSI on CAR T cells in a setting where target ligand expression remains stable, CD19 CAR-T cells were co-cultured with Raji or K562/CD19$^+$ target cells in the presence of GSI (0.01 µM to 100 µM) and measured viability and effector function. Over this concentration range there was no effect on CD19 antigen expression (FIG. 5A) or on CAR-T cell viability after 24 hours (FIG. 5B). GSI RO4929097 was found to inhibit CD19 CAR-T cell effector function at concentrations≥1 µM when co-cultured with K562 CD19$^+$ cells, as determined by measuring IL-2 (FIG. 5C, upper panel) and IFNγ (FIG. 5C, lower panel) production (see also FIG. 5D-5F). However, the ability of the CD19 CAR-T cells to specifically kill target cells was not affected by GSI concentration (FIG. 5G). The CD19 CAR-T cells also proliferated in response to target cell stimulation in the presence of 10 µM GSI RO4929097, though less effectively than in the absence of GSI RO4929097 (FIG. 5H). To further investigate the dosage effect of GSI on CAR-T cell division, a dose titration of GSI RO4929097 was added to co-cultures of CD19 CAR-T and target cells. CAR-T cell division was essentially unaffected or only slightly affected by the addition of therapeutic doses of GSI (0.01 µM-1 µM), whereas GSI at a higher, non-therapeutic dose (10 µM) did detectably inhibit proliferation (FIG. 5I). CD19 CAR-T cells cultured in the presence of GSI did not show a decrease in expansion over 8 days in culture with (FIG. 5J) or without exogenous IL-2 (FIG. 5K). Also, T cells that were expanded in the presence of 5 µM, 0.5 µM, or absence of GSI did not show a significant difference in IFN-γ production when subsequently re-stimulated with target cells after expansion in the presence (FIG. 5L) or absence (FIG. 5M) of exogenous IL-2. IL-2 production between the CAR-T cell groups was also not markedly different (FIG. 5N). Overall, GSI at therapeutic levels does not affect T cell function, including cytokine production, cell lysis activity, and proliferation.

Next, the effect of GSI on T cell functionality of T cells containing a BCMA-specific T-ChARM was examined. GSI treatment of primary myeloma tumor samples greatly improved IFN-γ production (FIGS. 5O, 5P, and 5Q) and CD8 expression (FIG. 5O) by co-cultured T-ChARM T cells, with effects seen following treatment with 0.1 µM GSI or higher, and also increased proliferation of the T cells (FIG. 5R).

These data indicate the clinical utility of combining BCMA-specific CAR-T cells and a GSI in order to increase the levels of BCMA on multiple myeloma cells. This may provide an advantage or even have a synergistic effect on treating multiple myeloma by facilitating elimination of tumor cells that express low levels of BCMA. The data also show that a range of concentrations of a γ-secretase inhibitor promoted BCMA expression of tumor cells without affecting T cell activity.

Example 6

In Vivo Study of GSI Activity in a MM Xenograft Model

To investigate whether the sBCMA-inhibiting effects of GSI RO4929097 described in Example 4 could be replicated in vivo, a mouse xenograft model of human MM was tested as illustrated in FIG. 6A. Briefly, immunodeficient NOD/SCID gamma (NSG) mice (The Jackson Laboratory) received sublethal irradiation (275 rad) at day −1, followed by $5 \times 10^6$ MM.1R cells the next day (day 0). GSI RO4929097 (30 mg/kg) was administered by oral gavage at day 19 and day 20. Mice were sacrificed at different times after the second gavage administration of the GSI and blood and bone marrow samples were taken for analysis. GSI dosing was followed by a rapid increase (>3-fold by 4 hours post-second gavage) in surface BCMA expression on the tumor cells (FIG. 6B) and a concurrent decrease in sBCMA (FIG. 6C). The observed effects were generally reduced within 48 hours following the second gavage treatment.

Example 7

In Vivo Study of GSI+CAR T Cell Combination Therapy Targeting MM

Figure 7C:
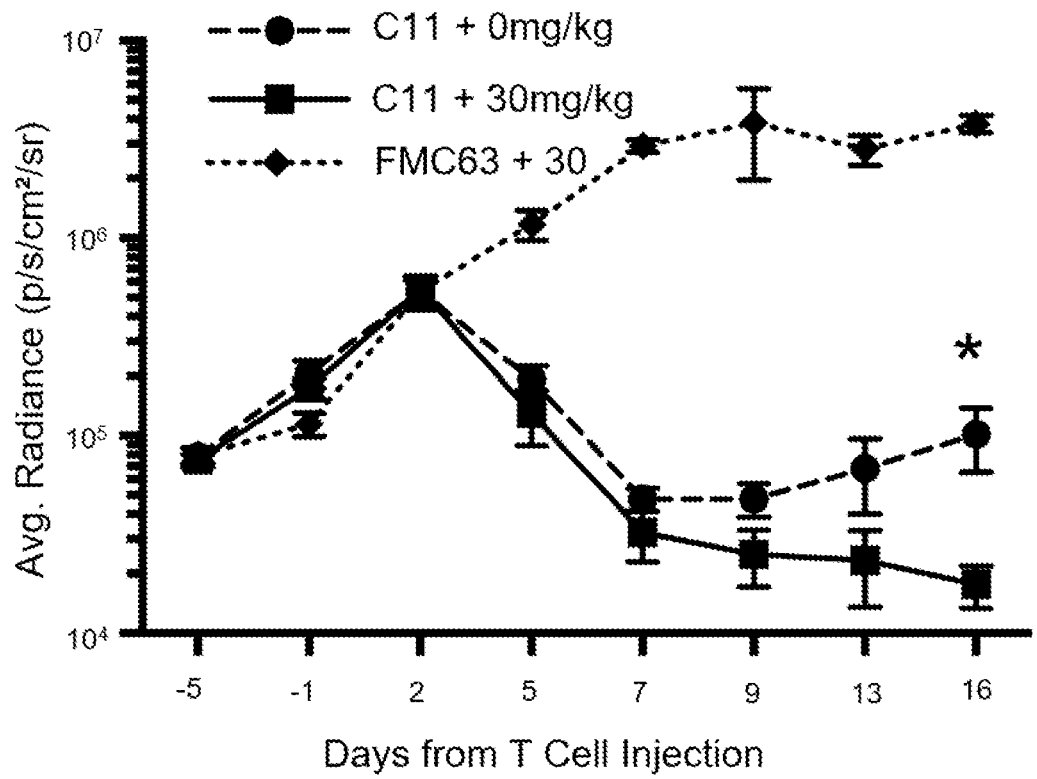
Figure 7D:
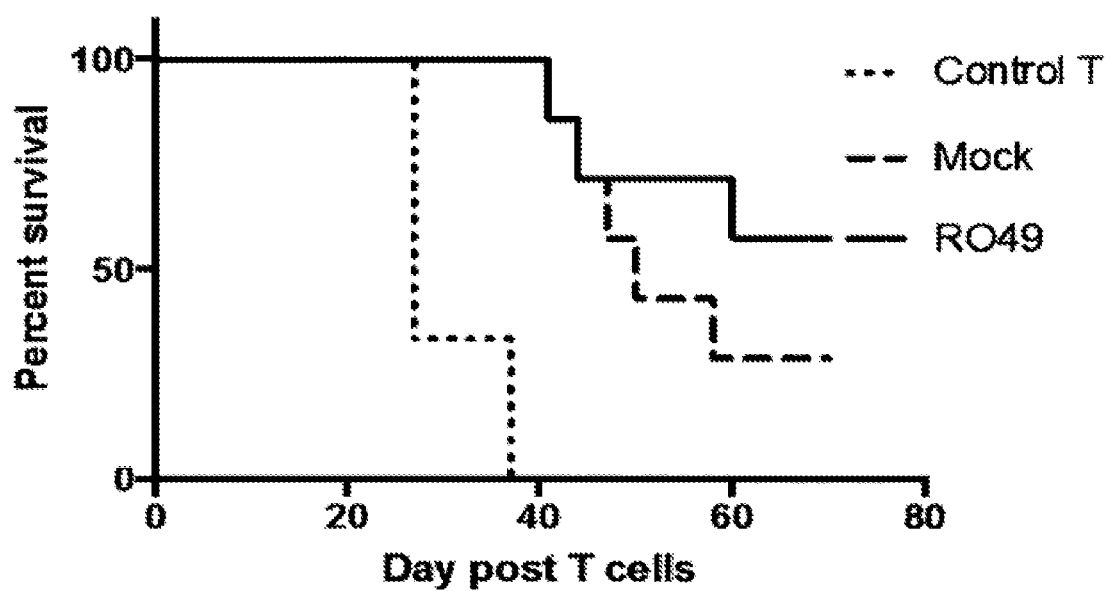
Figure 7E:
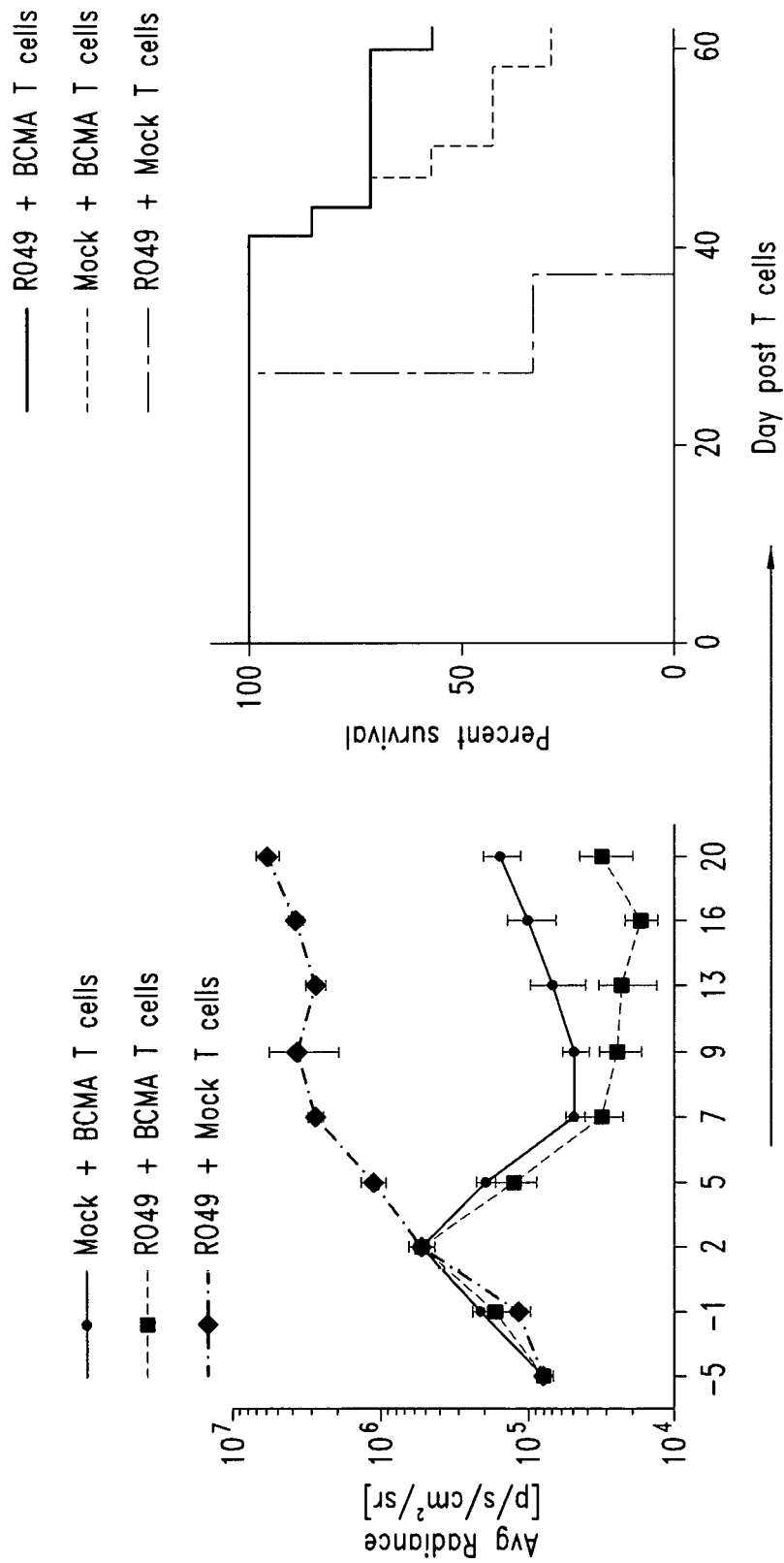

The ability of GSI therapy to improve anti-BCMA CAR T cell therapy in vivo was investigated. In a similar experiment to the one described in Example 6, NSG mice were sublethally irradiated at day −21, followed by administration of human MM cells ($5 \times 10^6$ MM.1R$^{ffluc}$) at day −20 (see FIG. 7A). A first dose of GSI (30 mg/kg RO4929097) was administered by oral gavage at day −1. At day 0, the mice were injected with a suboptimal dose of C11 3ST T-ChARM T cells ($0.33 \times 10^6$ cells; CD4:CD8 1:1) and received a second dose of the GSI. Further doses of GSI were administered at day +1, day +8, and day +9. Bioluminescence imaging (BLI) was performed throughout the experiment and mice were monitored for survival. As shown in FIGS. 7B, 7C, and 7E (left-hand graph), the group receiving GSI+T cells had reduced luminescence and more mice with no detectable tumors as compared to the group receiving the T cells only (BLI data from T cell only group not shown). The quantified luminescence data (FIGS. 7C and 7E (left-hand graph)) indicated that the initial T-ChARM T cell effect began reversing at approximately day 9, when the tumors began growing out ("Mock+BCMA T cells"). The anti-tumor effect was prolonged by combination with GSI RO4929097 ("RO49+BCMA T cells"), but the tumors in that treatment group also eventually grew out. The imaging data was consistent with survival of the mice (FIGS. 7D and 7E (right-hand graph)), with the mice receiving the combination therapy surviving longer than the group receiving T cells only before succumbing. In certain embodiments, GSI treatments are repeated (at least 2 to at least about 5 times up to at least about 25 times) when used in combination with anti-BCMA CAR T cells, which GSI treatments may be administered concurrently with, before, or after administration of the anti-BCMA CAR T cells.

Example 8

GSI Improves Binding to BCMA+MM Cells by a Bispecific Anti-BCMA Fusion Protein A bispecific fusion protein having specificity for BCMA and for another antigen, and with a YFP (yellow fluorescent protein) tag, was constructed. The bispecific fusion protein was added to BCMA-expressing H929 MM cells in culture ($0.5 \times 10^6$ cells) either with or without GSI. Binding was assessed by flow cytometry. As shown in FIG. 8, the addition of GSI improved binding by the BCMA-binding bispecific fusion protein, but had no effect on binding by a control bispecific fusion protein that does not target BCMA. These data show that immunotherapies involving bispecific molecules that target BCMA can be augmented or improved with GSI.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

What is claimed is:

1. A method of treating multiple myeloma in a subject, comprising administering to the subject (i) a therapeutically effective amount of a T cell expressing a BCMA-specific chimeric antigen receptor (CAR), wherein the CAR comprises a hydrophobic portion disposed between an extracellular component and an intracellular component, wherein the extracellular component comprises a BCMA-specific binding domain, and (ii) a therapeutically effective amount of a γ-secretase inhibitor.

2. The method of claim 1, wherein the BCMA-specific binding domain comprises a BCMA-specific scFv, a BCMA-specific scTCR, a BCMA-specific domain antibody, or a BCMA ligand or binding portion thereof.

3. The method of claim 2, wherein the BCMA-specific binding domain comprises a scFv comprising heavy chain and light chain variable regions based on BCMA antibody J6M0, J6M1, J6M2, J9M0, J9M1, J9M2, CA8, A7D12.2, C11 D5.3, C12A3.2, or C13F12.1.

4. The method of claim 1, wherein the intracellular component of the CAR comprises an effector domain or functional portion thereof, a costimulatory domain or functional portion thereof, or any combination thereof.

5. The method of claim 1, wherein:
(i) the intracellular component of the CAR comprises an effector domain from CD3ζ;
(ii) the intracellular component of the CAR comprises a costimulatory domain from 4-1BB;
(iii) the intracellular component of the CAR comprises a costimulatory domain from CD28;
(iv) the extracellular component of the CAR further comprises a hinge region comprising a cluster of differentiation molecule stalk region or a functional variant thereof;
(v) the extracellular component of the CAR further comprises a spacer region comprising a hinge, wherein the spacer region has a length of from about 15 to about 100 amino acids; or
(vi) any combination of (i)-(v).

6. The method of claim 1, wherein the T cell is a CD4+ T cell, a CD8+ T cell, a CD4− CD8− double negative T cell, a γδ T cell, or any combination thereof.

7. The method of claim 6, wherein the T cell comprises a CD8+ T cell, a CD4+ T cell, or both.

8. The method of claim 1, wherein the γ-secretase inhibitor comprises a small molecule, a peptidomimetic compound, LY411575, semagacestat, avagacestat, DAPT, BMS-906024, BMS-986115, MK-0752, PF-03084014, R04929097, or YO-01027.

9. The method of claim 1, wherein the γ-secretase inhibitor is a nicastrin-specific binding protein.

10. The method of claim 1, wherein the method further comprises pre-conditioning the subject with an immunosuppressive regimen prior to or concurrent with the T cell and the γ-secretase inhibitor.

11. The method of claim 10, wherein the immunosuppressive regimen is a non-myeloablative treatment or a myeloablative treatment.

12. The method of claim 1, wherein the T cell and the γ-secretase inhibitor are administered sequentially.

13. The method of claim 1, wherein the T cell and the γ-secretase inhibitor are administered concurrently.

14. The method of claim 13, wherein the T cell and the γ-secretase inhibitor are formulated together.

15. The method of claim 1, wherein the intracellular component of the CAR comprises:

(i) an effector domain from CD3ζ; and
(ii) a costimulatory domain from 4-1BB, CD28, or both.

16. The method of claim 15, wherein the extracellular component of the CAR further comprises:
(iii) a hinge region comprising a cluster of differentiation molecule stalk region or a functional variant thereof; and/or
(iv) a spacer region comprising a hinge, wherein the spacer region has a length of from about 15 to about 100 amino acids.

17. The method of claim 1, wherein the γ-secretase inhibitor is administered to the subject at least once subsequent to a first administration of the T cell.

18. A method of treating multiple myeloma in a subject, comprising administering to the subject a therapeutically effective amount of a T cell expressing a BCMA-specific chimeric antigen receptor (CAR), wherein the CAR comprises a hydrophobic portion disposed between an extracellular component and an intracellular component, wherein the extracellular component comprises a BCMA-specific binding domain,
wherein the subject has received a therapeutically effective amount of a γ-secretase inhibitor.

19. A method of treating multiple myeloma in a subject, comprising administering to the subject a therapeutically effective amount of a γ-secretase inhibitor,
wherein the subject has received therapeutically effective amount of a T cell expressing a BCMA-specific chimeric antigen receptor (CAR), wherein the CAR comprises a hydrophobic portion disposed between an extracellular component and an intracellular component, wherein the extracellular component comprises a BCMA-specific binding domain.

20. The method of claim 1, wherein:
(i) the CAR comprises (1) a BCMA-specific binding domain comprising a BCMA-specific scFv, a BCMA-specific scTCR, a BCMA-specific domain antibody, or a BCMA ligand or binding portion thereof, (2) an intracellular component comprising a costimulatory domain from 4-1BB and/or CD28, and an effector domain from CD3ζ, and/or (3) an extracellular spacer region comprising a hinge, wherein the spacer region has a length from about 15 to about 100 amino acids; and
(ii) the γ-secretase inhibitor comprises a small molecule.

21. The method of claim 18, wherein the intracellular component of the CAR comprises:
(i) an effector domain from CD3ζ; and
(ii) a costimulatory domain from 4-1BB, CD28, or both.

22. The method of claim 18, wherein:
(i) the CAR comprises (1) a BCMA-specific binding domain comprising a BCMA-specific scFv, a BCMA-specific scTCR, a BCMA-specific domain antibody, or a BCMA ligand or binding portion thereof, (2) an intracellular component comprising a costimulatory domain from 4-1BB and/or CD28, and an effector domain from CD3ζ, and/or (3) an extracellular spacer region comprising a hinge, wherein the spacer region has a length from about 15 to about 100 amino acids;
(ii) the γ-secretase inhibitor comprises a small molecule; or
(iii) (i) and (ii).

23. The method of claim 22, wherein the CAR comprises (1) a BCMA-specific binding domain comprising a BCMA-specific scFv, a BCMA-specific scTCR, a BCMA-specific domain antibody, or a BCMA ligand or binding portion thereof, and (2) an intracellular component comprising a costimulatory domain from 4-1BB and/or CD28, and an effector domain from CD3ζ.

24. The method of claim 19, wherein the intracellular component of the CAR comprises:
   (i) an effector domain from CD3ζ; and
   (ii) a costimulatory domain from 4-1BB, CD28, or both.

25. The method of claim 19, wherein:
   (i) the CAR comprises (1) a BCMA-specific binding domain comprising a BCMA-specific scFv, a BCMA-specific scTCR, a BCMA-specific domain antibody, or a BCMA ligand or binding portion thereof, (2) an intracellular component comprising a costimulatory domain from 4-1BB and/or CD28, and an effector domain from CD3ζ, and/or (3) an extracellular spacer region comprising a hinge, wherein the spacer region has a length from about 15 to about 100 amino acids;
   (ii) the γ-secretase inhibitor comprises a small molecule; or
   (iii) (i) and (ii).

26. The method of claim 25, wherein the CAR comprises (1) a BCMA-specific binding domain comprising a BCMA-specific scFv, a BCMA-specific scTCR, a BCMA-specific domain antibody, or a BCMA ligand or binding portion thereof, and (2) an intracellular component comprising a costimulatory domain from 4-1BB and/or CD28, and an effector domain from CD3ζ.

27. The method of claim 18, wherein the T cell comprises a CD8+ T cell, a CD4+ T cell, or both.

28. The method of claim 19, wherein the T cell comprises a CD8+ T cell, a CD4+ T cell, or both.

29. The method of claim 5, wherein the T cell comprises a CD8+ T cell, a CD4+ T cell, or both.

30. The method of claim 20, wherein the T cell comprises a CD8+ T cell, a CD4+ T cell, or both.

31. The method of claim 21, wherein the T cell comprises a CD8+ T cell, a CD4+ T cell, or both.

32. The method of claim 23, wherein the T cell comprises a CD8+ T cell, a CD4+ T cell, or both.

33. The method of claim 26, wherein the T cell comprises a CD8+ T cell, a CD4+ T cell, or both.

* * * * *